(12) United States Patent
Fan et al.

(10) Patent No.: US 11,397,882 B2
(45) Date of Patent: Jul. 26, 2022

(54) MOLECULAR LABEL COUNTING ADJUSTMENT METHODS

(71) Applicant: Becton, Dickinson And Company, Franklin Lakes, NJ (US)

(72) Inventors: Jue Fan, Menlo Park, CA (US); Jennifer Tsai, Menlo Park, CA (US); Eleen Shum, Menlo Park, CA (US); Lisha Deng, Menlo Park, CA (US); Glenn K. Fu, Menlo Park, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 976 days.

(21) Appl. No.: 15/605,874

(22) Filed: May 25, 2017

(65) Prior Publication Data

US 2017/0344866 A1    Nov. 30, 2017

Related U.S. Application Data

(60) Provisional application No. 62/401,720, filed on Sep. 29, 2016, provisional application No. 62/381,945, (Continued)

(51) Int. Cl.
*G06K 19/06* (2006.01)
*G16B 40/00* (2019.01)
(Continued)

(52) U.S. Cl.
CPC ....... *G06K 19/06028* (2013.01); *G16B 30/00* (2019.02); *G16B 40/00* (2019.02); *G16B 40/10* (2019.02)

(58) Field of Classification Search
CPC ............ C12Q 2563/179; C12Q 1/6869; C12Q 2525/191; C12Q 1/6806; C12Q 2525/161;
(Continued)

(56) References Cited

U.S. PATENT DOCUMENTS 4,510,244 A    4/1985  Parks et al.
4,725,536 A    2/1988  Fritsch et al.
(Continued)

FOREIGN PATENT DOCUMENTS

CN    102576020    7/2012
CN    105492627    4/2016
(Continued)

OTHER PUBLICATIONS

Peng et al. Aug. 7, 2015 Reducing amplification artifacts in high multiplex amplicon sequencing by using Molecular Barcodes. BMC Bioinformatics vol. 16:589, 12 pages.*
(Continued)

*Primary Examiner* — Mary K Zeman
(74) *Attorney, Agent, or Firm* — Knobbe, Martens, Olson & Bear, LLP

(57) ABSTRACT

Disclosed herein are methods and systems for determining the numbers of targets. In some embodiments, the method comprise: stochastically barcoding targets using stochastic barcodes; obtaining sequencing data; for one or more of the targets: counting the number of molecular labels with distinct sequences associated with the target in the sequencing data; identifying clusters of molecular labels of the target using directional adjacency; collapsing the sequencing data using the clusters of molecular labels of the target identified; and estimating the number of the target.

16 Claims, 53 Drawing Sheets

Specification includes a Sequence Listing.

Related U.S. Application Data filed on Aug. 31, 2016, provisional application No. 62/342,137, filed on May 26, 2016.

(51) Int. Cl.
*G16B 30/00* (2019.01)
*G16B 40/10* (2019.01)

(58) Field of Classification Search
CPC ............ C12Q 1/6809; C12Q 2565/514; C12Q 1/6876; C12Q 2525/173; C12Q 2537/159; C12Q 2525/179; C12Q 2525/185; C12Q 1/6851; C12Q 2537/16; C12Q 1/68; C12Q 2537/165; C12Q 1/6827; C12Q 2549/10; C12Q 1/6874; C12Q 2535/122; C12Q 2531/113; C12Q 1/686; C12Q 2537/157; C12Q 1/6844; C12Q 2545/114; C12Q 2525/197; C12Q 1/6858; C12Q 2600/158; C12N 15/1093; C12N 15/1065; C12N 15/1096; C12N 15/1089; C12N 15/11; G06F 19/00; G06F 16/2246; G06F 17/18; G06F 16/283; G06F 2221/033; G06K 9/6267; G06K 19/06028; G06K 9/6232; G06K 9/6278; G06N 20/00; G06N 7/005; G06N 3/082; G06N 3/0454; G06N 3/0472; G06N 3/084; G06T 2207/30072; G06T 2207/30242; G06T 7/277; G16C 20/70; G16B 25/00; G16B 30/00; G16B 25/10; G16B 40/00; G16B 45/00; G16B 50/00; G16B 30/10; G16B 20/00; G16B 25/20; G16B 50/30; G16B 99/00; G16B 5/00; C40B 40/06; C40B 70/00; C40B 50/04; G01N 2458/10; G01N 2015/1402

See application file for complete search history.

(56) References Cited

U.S. PATENT DOCUMENTS

| | | | |
|---|---|---|---|
| 5,119,316 A | 6/1992 | Dam et al. | |
| 5,124,246 A | 6/1992 | Urdea et al. | |
| 5,149,625 A | 9/1992 | Church et al. | |
| 5,200,314 A | 4/1993 | Urdea | |
| 5,424,186 A | 6/1995 | Fodor et al. | |
| 5,424,413 A | 6/1995 | Hogan et al. | |
| 5,445,934 A | 8/1995 | Fodor et al. | |
| 5,604,097 A | 2/1997 | Brenner | |
| 5,635,352 A | 6/1997 | Urdea et al. | |
| 5,635,400 A | 6/1997 | Brenner | |
| 5,648,245 A | 7/1997 | Fire et al. | |
| 5,654,413 A | 8/1997 | Brenner | |
| 5,656,731 A | 8/1997 | Urdea | |
| 5,658,737 A | 8/1997 | Nelson et al. | |
| 5,714,330 A | 2/1998 | Brenner et al. | |
| 5,744,305 A | 4/1998 | Fodor et al. | |
| 5,759,778 A | 6/1998 | Li et al. | |
| 5,763,175 A | 6/1998 | Brenner | |
| 5,800,992 A | 9/1998 | Fodor et al. | |
| 5,846,719 A | 12/1998 | Brenner et al. | |
| 5,854,033 A | 12/1998 | Lizardi | |
| 5,871,928 A | 2/1999 | Fodor et al. | |
| 5,925,525 A | 7/1999 | Fodor et al. | |
| 5,935,793 A | 8/1999 | Wong | |
| 5,962,271 A | 10/1999 | Chenchick et al. | |
| 5,962,272 A | 10/1999 | Chenchick et al. | |
| 5,968,740 A | 10/1999 | Fodor et al. | |
| 5,981,176 A | 11/1999 | Wallace | |
| 5,981,179 A | 11/1999 | Lorinez et al. | |
| 6,013,445 A | 1/2000 | Albrecht et al. | |
| 6,040,138 A | 3/2000 | Lockhart et al. | |
| 6,046,005 A | 4/2000 | Ju et al. | |
| 6,060,596 A | 5/2000 | Lerner et al. | |
| 6,064,755 A | 5/2000 | Some | |
| 6,114,149 A | 9/2000 | Fry et al. | |
| 6,117,631 A | 9/2000 | Nilsen | |
| 6,124,092 A | 9/2000 | O'neill et al. | |
| 6,138,077 A | 10/2000 | Brenner | |
| 6,140,489 A | 10/2000 | Brenner | |
| 6,172,214 B1 | 1/2001 | Brenner | |
| 6,197,506 B1 | 3/2001 | Fodor et al. | |
| 6,197,554 B1 | 3/2001 | Lin et al. | |
| 6,235,475 B1 | 5/2001 | Brenner et al. | |
| 6,235,483 B1 | 5/2001 | Wolber et al. | |
| 6,265,163 B1 | 7/2001 | Albrecht et al. | |
| 6,268,152 B1 | 7/2001 | Fodor et al. | |
| 6,284,460 B1 | 9/2001 | Fodor et al. | |
| 6,309,822 B1 | 10/2001 | Fodor et al. | |
| 6,309,823 B1 | 10/2001 | Cronin et al. | |
| 6,326,148 B1 | 12/2001 | Pauletti et al. | |
| 6,355,431 B1 | 3/2002 | Chee et al. | |
| 6,355,432 B1 | 3/2002 | Fodor et al. | |
| 6,395,491 B1 | 5/2002 | Fodor et al. | |
| 6,406,848 B1 | 6/2002 | Bridgham et al. | |
| 6,440,667 B1 | 8/2002 | Fodor et al. | |
| 6,440,706 B1 | 8/2002 | Vogelstein et al. | |
| 6,451,536 B1 | 9/2002 | Fodor et al. | |
| 6,458,530 B1 | 10/2002 | Morris et al. | |
| 6,468,744 B1 | 10/2002 | Cronin et al. | |
| 6,480,791 B1 | 11/2002 | Strathmann | |
| 6,489,114 B2 | 12/2002 | Laayoun et al. | |
| 6,492,121 B2 | 12/2002 | Kurane et al. | |
| 6,512,105 B1 | 1/2003 | Hogan et al. | |
| 6,514,699 B1 | 2/2003 | O'neill et al. | |
| 6,544,739 B1 | 4/2003 | Fodor et al. | |
| 6,551,784 B2 | 4/2003 | Fodor et al. | |
| 6,576,424 B2 | 6/2003 | Fodor et al. | |
| 6,600,996 B2 | 7/2003 | Webster et al. | |
| 6,629,040 B1 | 9/2003 | Goodlett et al. | |
| 6,653,077 B1 | 11/2003 | Brenner | |
| 6,753,147 B2 | 6/2004 | Vogelstein et al. | |
| 6,787,308 B2 | 9/2004 | Balasubramanian et al. | |
| 6,849,404 B2 | 2/2005 | Park et al. | |
| 6,852,488 B2 | 2/2005 | Fodor et al. | |
| 6,858,412 B2 | 2/2005 | Willis et al. | |
| 7,155,050 B1 | 12/2006 | Sloge | |
| 7,393,665 B2 | 7/2008 | Brenner | |
| 7,424,368 B2 | 9/2008 | Huang et al. | |
| 7,476,786 B2 | 1/2009 | Chan et al. | |
| 7,537,897 B2 | 5/2009 | Brenner et al. | |
| 7,544,473 B2 | 6/2009 | Brenner | |
| 7,635,566 B2 | 12/2009 | Brenner | |
| 7,822,555 B2 | 10/2010 | Huang et al. | |
| 7,824,856 B2 | 11/2010 | Monforte | |
| 7,824,889 B2 | 11/2010 | Vogelstein et al. | |
| 7,915,015 B2 | 3/2011 | Vogelstein et al. | |
| 7,985,546 B2 | 7/2011 | Church et al. | |
| 8,148,068 B2 | 4/2012 | Brenner | |
| 8,168,385 B2 | 5/2012 | Brenner | |
| 8,241,850 B2 | 8/2012 | Brenner | |
| 8,298,767 B2 | 10/2012 | Brenner et al. | |
| 8,318,433 B2 | 11/2012 | Brenner | |
| 8,445,205 B2 | 5/2013 | Brenner | |
| 8,470,996 B2 | 6/2013 | Brenner | |
| 8,476,018 B2 | 7/2013 | Brenner | |
| 8,481,292 B2 | 7/2013 | Casbon et al. | |
| 8,535,889 B2 | 9/2013 | Larson et al. | |
| 8,563,274 B2 | 10/2013 | Brenner et al. | |
| 8,603,749 B2 | 12/2013 | Gillevet | |
| 8,679,756 B1 | 3/2014 | Brenner et al. | |
| 8,685,678 B2 | 4/2014 | Casbon et al. | |
| 8,715,967 B2 | 5/2014 | Casbon et al. | |
| 8,722,368 B2 | 5/2014 | Casbon et al. | |
| 8,728,766 B2 | 5/2014 | Casbon et al. | |
| 8,741,606 B2 | 6/2014 | Casbon et al. | |
| 8,835,358 B2 | 9/2014 | Fodor et al. | |
| 8,841,071 B2 | 9/2014 | Link | |
| 8,856,410 B2 | 10/2014 | Park | |
| 9,150,852 B2 | 10/2015 | Samuels et al. | |
| 9,175,303 B2 | 11/2015 | Sanz Molinero | |
| 9,228,229 B2 | 1/2016 | Olson et al. | |

(56) References Cited

U.S. PATENT DOCUMENTS

| | | |
|---|---|---|
| 9,290,808 B2 | 3/2016 | Fodor et al. |
| 9,290,809 B2 | 3/2016 | Fodor et al. |
| 9,315,857 B2 | 4/2016 | Fu et al. |
| 9,567,645 B2 | 2/2017 | Fan et al. |
| 9,567,646 B2 | 2/2017 | Fan et al. |
| 9,582,877 B2 | 2/2017 | Fu et al. |
| 9,598,736 B2 | 3/2017 | Fan et al. |
| 9,637,799 B2 | 5/2017 | Fan et al. |
| 9,708,657 B2 | 7/2017 | Asbury et al. |
| 9,708,659 B2 | 7/2017 | Fodor et al. |
| 9,787,810 B1 | 8/2017 | Fodor et al. |
| 9,951,386 B2 | 4/2018 | Hindson et al. |
| 10,002,316 B2 | 6/2018 | Fodor et al. |
| 2002/0065609 A1 | 5/2002 | Ashby |
| 2002/0072058 A1 | 6/2002 | Voelker et al. |
| 2002/0168665 A1 | 11/2002 | Okawa |
| 2003/0003490 A1 | 1/2003 | Fan et al. |
| 2003/0049616 A1 | 3/2003 | Brenner et al. |
| 2003/0082818 A1 | 5/2003 | Bahnson et al. |
| 2003/0104436 A1 | 6/2003 | Morris et al. |
| 2003/0175908 A1 | 9/2003 | Linnarson |
| 2003/0186251 A1 | 10/2003 | Dunn et al. |
| 2003/0207300 A1 | 11/2003 | Matray et al. |
| 2004/0096368 A1 | 5/2004 | Davis |
| 2004/0096892 A1 | 5/2004 | Wang et al. |
| 2004/0146901 A1 | 7/2004 | Morris et al. |
| 2004/0157243 A1 | 8/2004 | Huang et al. |
| 2004/0259118 A1 | 12/2004 | Macevicz |
| 2005/0019776 A1 | 1/2005 | Callow et al. |
| 2005/0053952 A1 | 3/2005 | Hong et al. |
| 2005/0105077 A1 | 5/2005 | Padmanabhan |
| 2005/0170373 A1 | 8/2005 | Monforte |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0041385 A1 | 2/2006 | Bauer |
| 2006/0073506 A1 | 4/2006 | Christians et al. |
| 2006/0078941 A1 | 4/2006 | Santin |
| 2006/0141493 A1 | 6/2006 | West et al. |
| 2006/0211030 A1 | 9/2006 | Brenner |
| 2006/0211036 A1 | 9/2006 | Chou |
| 2006/0263709 A1 | 11/2006 | Matsumura et al. |
| 2006/0263789 A1 | 11/2006 | Kincaid |
| 2006/0280352 A1 | 12/2006 | Muschler |
| 2006/0286570 A1 | 12/2006 | Rowlen et al. |
| 2007/0020640 A1 | 1/2007 | Mccloskey et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0065823 A1 | 3/2007 | Dressman et al. |
| 2007/0105090 A1 | 5/2007 | Cassidy et al. |
| 2007/0117121 A1 | 5/2007 | Hutchison |
| 2007/0117134 A1 | 5/2007 | Kou |
| 2007/0133856 A1 | 6/2007 | Dutta-Choudhury |
| 2007/0172873 A1 | 7/2007 | Brenner et al. |
| 2007/0178478 A1 | 8/2007 | Dhallan et al. |
| 2008/0010304 A1 | 1/2008 | Vempala |
| 2008/0038727 A1 | 2/2008 | Spier |
| 2008/0070303 A1 | 3/2008 | West et al. |
| 2008/0119736 A1 | 5/2008 | Dentinger |
| 2008/0194414 A1 | 8/2008 | Albert et al. |
| 2008/0261204 A1 | 10/2008 | Lexow |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0061513 A1 | 3/2009 | Andersson et al. |
| 2009/0105959 A1 | 4/2009 | Braverman et al. |
| 2009/0137407 A1 | 5/2009 | Church et al. |
| 2009/0170075 A1 | 7/2009 | Petrovics |
| 2009/0220385 A1 | 9/2009 | Brown |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0290151 A1 | 11/2009 | Agrawal |
| 2009/0298709 A1 | 12/2009 | Ma |
| 2010/0069250 A1 | 3/2010 | White, III |
| 2010/0105049 A1 | 4/2010 | Ehrich et al. |
| 2010/0105886 A1 | 4/2010 | Woudenberg et al. |
| 2010/0120630 A1 | 5/2010 | Huang et al. |
| 2010/0145893 A1 | 6/2010 | Semizarov |
| 2010/0159533 A1 | 6/2010 | Lipson et al. |
| 2010/0255471 A1 | 10/2010 | Clarke |
| 2010/0267028 A1 | 10/2010 | Pasche |
| 2010/0291666 A1 | 11/2010 | Collier et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0059556 A1 | 3/2011 | Strey et al. |
| 2011/0070584 A1 | 3/2011 | Wohlgemuth et al. |
| 2011/0072889 A1 | 3/2011 | Albitar et al. |
| 2011/0160078 A1* | 6/2011 | Fodor ............... C12N 15/1065 506/9 |
| 2011/0201507 A1 | 8/2011 | Rava et al. |
| 2011/0230358 A1 | 9/2011 | Rava |
| 2011/0244455 A1 | 10/2011 | Larson et al. |
| 2011/0294689 A1 | 12/2011 | Namsaraev |
| 2012/0010091 A1 | 1/2012 | Linnarson |
| 2012/0014977 A1 | 1/2012 | Furihata et al. |
| 2012/0034607 A1 | 2/2012 | Rothberg |
| 2012/0040843 A1 | 2/2012 | Ducree et al. |
| 2012/0045844 A1 | 2/2012 | Rothberg et al. |
| 2012/0065081 A1 | 3/2012 | Chee |
| 2012/0071331 A1 | 3/2012 | Casbon |
| 2012/0149603 A1 | 6/2012 | Cooney |
| 2012/0156675 A1 | 6/2012 | Lueerssen et al. |
| 2012/0163681 A1 | 6/2012 | Lohse |
| 2012/0165219 A1 | 6/2012 | Van Der Zaag et al. |
| 2012/0173159 A1 | 7/2012 | Davey et al. |
| 2012/0190020 A1 | 7/2012 | Oliphant et al. |
| 2012/0220022 A1 | 8/2012 | Ehrlich et al. |
| 2012/0220494 A1 | 8/2012 | Samuels |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0116130 A1* | 5/2013 | Fu ................... C12Q 1/6809 506/4 |
| 2013/0190206 A1 | 7/2013 | Leonard |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0225623 A1 | 8/2013 | Buxbaum et al. |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0143186 A1 | 5/2014 | Fan |
| 2014/0147860 A1 | 5/2014 | Kaduchak |
| 2014/0155274 A1* | 6/2014 | Xie .................. C12N 15/1065 506/2 |
| 2014/0155295 A1 | 6/2014 | Hindson et al. |
| 2014/0178438 A1 | 6/2014 | Sahin et al. |
| 2014/0206079 A1 | 7/2014 | Malinoski |
| 2014/0206547 A1 | 7/2014 | Wang |
| 2014/0216128 A1 | 8/2014 | Neat |
| 2014/0227684 A1 | 8/2014 | Hindson et al. |
| 2014/0227705 A1 | 8/2014 | Vogelstein et al. |
| 2014/0228255 A1 | 8/2014 | Hindson et al. |
| 2014/0235506 A1 | 8/2014 | Hindson et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0344013 A1 | 11/2014 | Karty |

(56) References Cited

U.S. PATENT DOCUMENTS

| | | |
|---|---|---|
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005185 A1 | 1/2015 | Fodor et al. |
| 2015/0005199 A1 | 1/2015 | Hindson et al. |
| 2015/0005200 A1 | 1/2015 | Hindson et al. |
| 2015/0066385 A1 | 3/2015 | Schnall-levin et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0225778 A1 | 8/2015 | Hindson et al. |
| 2015/0298091 A1 | 10/2015 | Weitz |
| 2015/0299784 A1* | 10/2015 | Fan .................. C12Q 1/6876 506/4 |
| 2015/0307874 A1 | 10/2015 | Jaitin |
| 2015/0376609 A1 | 12/2015 | Hindson et al. |
| 2016/0026758 A1 | 1/2016 | Jabara et al. |
| 2016/0046986 A1 | 2/2016 | Eltoukhy et al. |
| 2016/0122753 A1 | 5/2016 | Mikkelsen |
| 2016/0222378 A1 | 8/2016 | Fodor et al. |
| 2016/0244828 A1 | 8/2016 | Mason |
| 2016/0257993 A1 | 9/2016 | Fu et al. |
| 2016/0289669 A1 | 10/2016 | Fan et al. |
| 2016/0289740 A1 | 10/2016 | Fu et al. |
| 2016/0312276 A1 | 10/2016 | Fu et al. |
| 2016/0320720 A1 | 11/2016 | Fan et al. |
| 2016/0326584 A1 | 11/2016 | Fodor et al. |
| 2016/0376583 A1 | 12/2016 | Fodor et al. |
| 2016/0376648 A1 | 12/2016 | Fodor et al. |
| 2017/0073730 A1 | 3/2017 | Betts et al. |
| 2017/0154421 A1 | 6/2017 | Fu et al. |
| 2017/0204406 A1 | 7/2017 | Kato et al. |
| 2017/0247689 A1* | 8/2017 | Brown .................. G16B 30/00 |
| 2017/0314067 A1 | 11/2017 | Shum et al. |
| 2017/0342405 A1 | 11/2017 | Fu et al. |
| 2017/0342465 A1 | 11/2017 | Shum et al. |
| 2018/0002764 A1 | 1/2018 | Fan et al. |
| 2018/0037942 A1 | 2/2018 | Fu et al. |
| 2018/0127744 A1 | 5/2018 | Hu et al. |
| 2018/0137242 A1 | 5/2018 | Fan et al. |
| 2018/0276332 A1 | 9/2018 | Fan et al. |
| 2019/0095578 A1 | 3/2019 | Shum |
| 2019/0218276 A1 | 7/2019 | Regev |

FOREIGN PATENT DOCUMENTS

| | | |
|---|---|---|
| DE | 102008025656 | 12/2009 |
| EP | 0 799 897 | 10/1997 |
| EP | 1 473 080 | 11/2004 |
| EP | 1 647 600 | 4/2006 |
| EP | 1 845 160 | 10/2007 |
| EP | 2 623 613 | 8/2013 |
| EP | 2 805 769 | 11/2014 |
| WO | WO 89/01050 | 2/1989 |
| WO | WO 97/10365 | 3/1997 |
| WO | WO 99/15702 | 4/1999 |
| WO | WO 99/28505 | 6/1999 |
| WO | WO 00/58516 | 10/2000 |
| WO | WO 02/056014 | 7/2002 |
| WO | WO 02/059355 | 8/2002 |
| WO | WO 02/070684 | 9/2002 |
| WO | WO 04/017374 | 2/2004 |
| WO | WO 05/042759 | 5/2005 |
| WO | WO 05/071110 | 8/2005 |
| WO | WO 05/080604 | 9/2005 |
| WO | WO 05/111242 | 11/2005 |
| WO | WO 06/071776 | 7/2006 |
| WO | WO 06/102264 | 9/2006 |
| WO | WO 07/087310 | 8/2007 |
| WO | WO 07/087312 | 8/2007 |
| WO | WO 07/147079 | 12/2007 |
| WO | WO 08/096318 | 8/2008 |
| WO | WO 08/150432 | 12/2008 |
| WO | WO 09/148560 | 12/2009 |
| WO | WO 09/152928 | 12/2009 |
| WO | WO 10/117620 | 10/2010 |
| WO | WO 11/123246 | 10/2011 |
| WO | WO 11/143659 | 11/2011 |
| WO | WO 11/155833 | 12/2011 |
| WO | WO 12/038839 | 3/2012 |
| WO | WO 12/042374 | 4/2012 |
| WO | WO 12/047297 | 4/2012 |
| WO | WO 12/048341 | 4/2012 |
| WO | WO 12/083225 | 6/2012 |
| WO | WO 12/108864 | 8/2012 |
| WO | WO 12/129363 | 9/2012 |
| WO | WO 12/140224 | 10/2012 |
| WO | WO 12/142213 | 10/2012 |
| WO | WO 12/148477 | 11/2012 |
| WO | WO 12/149042 | 11/2012 |
| WO | WO 12/162267 | 11/2012 |
| WO | WO 13/019075 | 2/2013 |
| WO | WO 13/117595 | 8/2013 |
| WO | WO 13/130674 | 9/2013 |
| WO | WO 13/173394 | 11/2013 |
| WO | WO 13/176767 | 11/2013 |
| WO | WO 13/177206 | 11/2013 |
| WO | WO 13/188831 | 12/2013 |
| WO | WO 13/188872 | 12/2013 |
| WO | WO 13/191775 | 12/2013 |
| WO | WO 14/015084 | 1/2014 |
| WO | WO 14/015098 | 1/2014 |
| WO | WO 14/018460 | 1/2014 |
| WO | WO 14/028537 | 2/2014 |
| WO | WO 14/071361 | 5/2014 |
| WO | WO 14/093676 | 6/2014 |
| WO | WO 14/108850 | 7/2014 |
| WO | WO 14/124336 | 8/2014 |
| WO | WO 14/124338 | 8/2014 |
| WO | WO 14/126937 | 8/2014 |
| WO | WO 14/144495 | 9/2014 |
| WO | WO 14/201273 | 12/2014 |
| WO | WO 14/210353 | 12/2014 |
| WO | WO 15/002908 | 1/2015 |
| WO | WO 15/031691 | 3/2015 |
| WO | WO 15/035087 | 3/2015 |
| WO | WO 15/044428 | 4/2015 |
| WO | WO 15/047186 | 4/2015 |
| WO | WO 15/103339 | 7/2015 |
| WO | WO 15/134787 | 9/2015 |
| WO | WO 15/177570 | 11/2015 |
| WO | WO 15/200869 | 12/2015 |
| WO | Wo 16/040476 | 3/2016 |
| WO | WO 16/118915 | 7/2016 |
| WO | WO 16/138500 | 9/2016 |
| WO | WO 16/149418 | 9/2016 |
| WO | WO 16/162309 | 10/2016 |
| WO | WO 17/205691 | 11/2017 |
| WO | WO 18/225293 | 12/2018 |

OTHER PUBLICATIONS

Peng et al. Aug. 7, 2015 Supplemental Material BMC Bioinformatics 16:589.*

Shiroguchi et al. (2012) Digital RNA sequencing minimizes sequence-dependent bias and amplification noise with optimized single molecule barcodes. PNAS vol. 109 No. 4 p. 1347-1352.*

Shiroguchi et al. (2012) Supplemental Material PNAS 109 4.*

Zorita et al. Jan. 31, 2015 Starcode: sequence clustering based on all pairs search. Bioinformatics vol. 13 No. 12 pp. 1913-1919.*

Tung et al. (Jan. 3, 2017) Batch effects and the effective design of single-cell gene expression studies. Nature Scientific Reports, 7:39921, 15 pages.*

Smith et al. (Jan. 18, 2017) UMI-tools: modeling sequencing errors in Unique Molecular identifiers to improve quantification accuracy Genome Research, vol. 27 p. 491-499.*

(56) References Cited

OTHER PUBLICATIONS

Fu, Glenn, PhD (Oct. 2015) Molecular indexing with precise assays: Technique enables single-cell gene analysis eliminating amplification bias. Genetic Engineering & biotechnology news vol. 35 No. 18 pp. 28-29. (Year: 2015).*
Becton Dickenson BD (tm) Precise Assays pamphlet, 2016. www.bdbiosciences.com p. 1-2. (Year: 2016).*
Wang et al. (2016) A complete workflow from single cell isolation to mRNA sequencing analysis. Becton Dickenson/genomics White Paper. www.bd.com /genomics p. 1-7. (Year: 2016).*
Achim et al., May 2015, High-throughput spatial mapping of single-cell RNA-seq data to tissue of origin. Nature Biotechnology, 33(5):503-511.
Alkan et al., Oct. 2009, Personalized copy number and segmental duplication maps using next-generation sequencing. Nat Genet., 41(10):1061-1067.
Anderson, Feb. 11, 2014, Study describes RNA sequencing applications for molecular indexing methods, genomeweb.com, 5 pages.
Ansorge, 2009, Next-generation DNA sequencing techniques. New Biotechnology, 25(4):195-203.
Atanur et al., Jun. 2010, The genome sequence of the spontaneously hypertensive rat: Analysis and functional significance. Genome Res., 20(6):791-803.
Audic et al., 1997, The Significance of Digital Gene Expression Profiles. Genome Research, 7:986-995.
Bendall et al., May 6, 2011, Single-cell mass cytometry of differential immune and drug responses across a human hematopoietic continuum. Science, 332(6030):687-696.
Bionumbers, Aug. 21, 2010, Useful fundamental numbers in molecular biology, http://bionumbers.hms.harvard.edu/KeyNumbers/aspx, 4 pages.
Bioscribe, Feb. 5, 2015, Massively parallel sequencing technology for single-cell gene expression published (press release), 3 pp.
Blainey, May 2013, The future is now: single-cell genomics of bacteria and archaea, FEMS Microbiol Rev., 37(3):407-427.
Bogdanova et al., Jan. 2008, Normalization of full-length enriched cDNA, Molecular Biosystems, 4(3):205.
Bonaldo et al., Sep. 1996, Normalization and subtraction: two approaches to facilitate gene discovery. Genome Res., 6(9):791-806.
Braha et al., 2000, Simultaneous stochastic sensing of divalent metal ions. Nature Biotechnology, 18:1005-1007.
Bratke et al., Sep. 2005, Differential expression of human granzymes A, B, and K in natural killer cells and during CD8+ T cell differentiation in peripheral blood. Eur J Immunol., 35(9):2608-2616.
Brenner et al., 2000, Gene expression analysis by massively parallel signature sequencing (MPSS) on microbead arrays. Nature Biotechnology, 18:630-634.
Brenner et al., Feb. 15, 2000, In vitro cloning of complex mixtures of DNA on microbeads: physical separation of differentially expressed cDNAs. Proc Natl Acad Sci, 97(4):1665-1670.
Brisco et al., Jun. 25, 2012, Quantification of RNA integrity and its use for measurement of transcript number, Nucleic Acids Research, 40(18):e144.
Brodin et al., 2015, Challenges with using primer IDs to improve accuracy of next generation sequencing, 19(3):1-12.
Butkus, Feb. 6, 2014, Cellular research set to launch first gene expression platform using 'molecular indexing' technology, genomeweb.com, 5 pages.
Cai, Mar. 2013, Turning single cells in microarrays by super-resolution bar-coding, Brief Funct Genomics, 12(2):75-80.
Carr et al., Dec. 15, 2009, Inferring relative proportions of DNA variants from sequencing electropherograms. Bioinformatics, 25(24):3244-3250.
Casbon et al., Jul. 2011, A method for counting PCR template molecules with application to next-generation sequencing. Nucleic Acids Res., 39(12):e81.
Castellarnau et al., Jan. 2015, Stochastic particle barcoding for single-cell tracking and multiparametric analysis, Small, 11(4):489-498.
Castle et al., Apr. 16, 2010, DNA copy number, including telomeres and mitochondria, assayed using next-generation sequencing. BMC Genomics, 11:244. doi: 10.1186/1471-2164-11-244.
Chamberlain et al., Dec. 9, 1988, Deletion screening of the Duchenne muscular dystrophy locus via multiplex DNA amplification. Nucleic Acids Res., 16(23):11141-11156.
Chang et al., Aug. 2002, Detection of allelic imbalance in ascitic supernatant by digital single nucleotide polymorphism analysis. Clin Cancer Res., 8(8):2580-2585.
Chee et al., 1996, Accessing genetic information with high-density DNA arrays, Science, 274:610-614.
Chee, 1991, Enzymatic multiplex DNA sequencing. Nucleic Acids Research, 19(12): 3301-3305.
Chen et al., Apr. 9, 2015, Spatially resolved, highly multiplexed RNA profiling in single cells. Science Express, pp. 1-21.
Church et al., 1988, Multiplex DNA sequencing. Science, 240:185-188.
Costello et al., Apr. 1, 2013, Discovery and characterization of artefactual mutations in deep coverage targeted capture sequencing data due to oxidative DNA damage during sample preparation. Nucleic Acids Res, 41(6):e67.
Cox. May 2001, Bar coding objects with DNA. Analyst, 126(5):545-547.
Craig et al., Oct. 2008, Identification of genetic variants using bar-coded multiplexed sequencing. Nat Methods, 5(10):887-893.
Cusanovich et al., May 7, 2014, Multiplex single-cell profiling of chromatin accessibility by combinatorial cellular indexing. Science Express, pp. 1-9.
Daines et al., Aug. 2009, High-throughput multiplex sequencing to discover copy number variants in *Drosophila*. Genetics, 182(4):935-941.
Dalerba et al., 2011, Single-cell dissection of transcriptional heterogeneity in human colon tumors, Nat Biotechnol., 29(12):1120-1127 and Supplementary Material.
D'Antoni et al., May 1, 2006, Rapid quantitative analysis using a single molecule counting approach. Anal Biochem. 352(1):97-109.
Daser et al., 2006, Interrogation of genomes by molecular copy-number counting (MCC). Nature Methods, 3(6):447-453.
De Saizieu et al., 1998, Bacterial transcript imaging by hybridization of total RNA to oligonucleotide arrays. Nature Biotechnology, 16:45-48.
Dirks et al., Oct. 26, 2004, Triggered amplification by hybridization chain reaction., Proc Natl Acad Sci U S A, 101(43), 15275-15278.
Fan et al., Feb. 6, 2015, Combinatorial labeling of single cells for gene expression cytometry. Science, 347(6222):1258367-8.
Fan et al., 2000, Parallel Genotyping of Human SNPs Using Generic High-density Oligonucleotide Tag Arrays. Genome Research, 10:853-860.
Fan et al., 2009, Microfluidic digital PCR enables rapid prenatal diagnosis of fetal aneuploidy. Am Obstet Gynecol. 200:543.e1-543.e7.
Fan et al., Jul. 19, 2012, Non-invasive prenatal measurement of the fetal genome. Nature, 487(7407):320-324.
Fan, Nov. 2010, Molecular counting: from noninvasive prenatal diagnostics to whole-genome haplotyping, doctoral dissertation, Stanford University, 185 pp.
Feldhaus et al., Jan. 15, 2000, Oligonucleotide-conjugated beads for transdominant genetic experiments, Nucleic Acids Res., 28(2):534-543.
Fox-Walsh et al., Oct. 2011, A multiplex RNA-seq strategy to profile poly(A+) RNA: application to analysis of transcription response and 3' end formation., Genomics, 98(4),266-271.
Fu et al., Marcy 18, 2014, Digital encoding of cellular mRNAs enabling precise and absolute gene expression measurement by single-molecule counting. Anal Chem., 86(6):2867-2870.
Fu et al., May 31, 2011, Counting individual DNA molecules by the stochastic attachment of diverse labels. Proc Natl Acad Sci, 108(22):9026-9031.

(56) References Cited

OTHER PUBLICATIONS

Gerry et al., 1999, Universal DNA microarray method for multiplex detection of low abundance point mutations. Journal of Molecular Biology, 292(2): 251-262.
Gillespie, 1977, Exact stochastic simulation of coupled chemical reactions. The Journal of Physical Chemistry, 81(25):2340-2361.
Gong et al., 2010, Massively parallel detection of gene expression in single cells using subnanolitre wells, Lab Chip, 10:2334-2337.
Grant et al., Nov. 15, 2002, SNP genotyping on a genome-wide amplified DOP-PCR template. Nucleic Acids Res, 30(22):e125.
Gunderson et al., May 2004, Decoding randomly ordered DNA arrays. Genome Res. 14(5):870-877.
Gundry et al., Jan. 3, 2012, Direct mutation analysis by high-throughput sequencing: from germline to low-abundant, somatic variants. Mutat Res. 729(1-2):1-15.
Gundry et al., Mar. 2012, Direct, genome-wide assessment of DNA mutations in single cells. Nucleic Acids Res., 40(5):2032-40.
Hacia et al., 1999, Determination of ancestral alleles for human single-nucleotide polymorphisms using high-density oligonucleotide arrays. Nature Genetics, 22:164-167.
Haff, 1994, Improved quantitative PCR using nested primers, PCR Methods and Applications, 3:332-337.
Hamady et al., Mar. 2008, Error-correcting barcoded primers for pyrosequencing hundreds of samples in multiplex. Nat Methods, 5(3):235-237.
Harrington et al., 2009, Cross-sectional characterization of HIV-1 env compartmentalization in cerebrospinal fluid over the full disease course, AIDS, 23(8) 907-915.
Hashimshony et al., Sep. 27, 2012, CEL-Seq: single-cell RNA-Seq by multiplexed linear amplification Cell Rep. 2(3):666-673.
Hensel et al., Jul. 21, 1995, Simultaneous identification of bacterial virulence genes by negative selection. Science. 269(5222):400-403.
Hiatt et al., Feb. 2010, Parallel, tag-directed assembly of locally derived short sequence reads. Nat Methods, 7(2):119-122.
Hiatt et al., May 2013, Single molecule molecular inversion probes for targeted, high-accuracy detection of low-frequency variation. Genome Res., 23(5):843-854.
Hollas et al., 2003, A stochastic approach to count RNA molecules using DNA sequencing methods. Lecture Notes in Computer Science, 2812:55-62.
Hug et al., 2003, Measure of the number of molecular of a single mRNA species in a complex mRNA preparation, Journal of Theoretical Biology, 221:615-624.
Ingolia et al., Apr. 10, 2009, Genome-wide analysis in vivo of translation with nucleotide resolution using ribosome profiling. Science, 324(5924):218-223.
Islam et al., 2011, Characterization of the single-cell transcriptional landscape by highly multiplex RNA-seq. Genome Research, 21:1160-1167.
Islam et al., 2014, Quantitative single-cell RNA-seq with unique molecular identifiers, Nature Methods, 11(2):163-168.
Jabara et al., Dec. 3, 2011, Accurate sampling and deep sequencing of the HIV-1 protease gene using a Primer ID, PNAS, 108(50):20166-20171.
Jabara, Apr. 23, 2010, Capturing the cloud: High throughput sequencing of multiple individual genomes from a retroviral population. Biology Lunch Bunch Series, Training Initiatives in Biomedical & Biological Sciences of the University of North Carolina at Chapel Hill.
Junker et al., May 21, 2015, Single-cell transcriptomics enters the age of mass production, Molecular Cell, 58:563-564.
Kanagawa, 2003, Bias and artifacts in multitemplate polymerase chain reactions (PCR), Journal of Bioscience and Bioengineering, 96(4):317-323.
Kebschull et al., Jul. 17, 2015, Sources of PCR-induced distortions in high-throughput sequencing data sets, Nucleic Acids Research, 15 pp.
Keys et al., Jun. 2015, Primer ID informs next-generation sequencing platforms and reveals preexisting drug resistance mutations in the HIV-1 reverse transcriptase coding domain, AIDS Research and Human Retroviruses, 31(6):658-668.
Kim et al., Jun. 8, 2007, Polony multiplex analysis of gene expression (PMAGE) in mouse hypertrophic cardiomyopathy, Science, 316(5830):1481-1484.
Kinde et al., Jun. 7, 2011, Detection and quantification of rare mutations with massively parallel sequencing, Proc. Natl Acad Sci, 108(23):9530-0535.
Kivioja et al., Jan. 2012, Counting absolute numbers of molecules using unique molecular identifiers. Nature Methods, 9(1):72-76.
Klein et al., May 21, 2015, Droplet barcoding for single-cell transcriptomics applied to embryonic stem cells, Cell, 161:1187-1201.
Koboldt et al., Sep. 1, 2009, VarScan: variant detection in massively parallel sequencing of individual and pooled samples. Bioinformatics. 25(17):2283-2285.
Kolodziejczyk et al., May 21, 2015, The technology and biology of single-cell RNA sequencing, Molecular Cell, 58:610-620.
Konig et al., Jul. 2010, iCLIP reveals the function of hnRNAP particles in splicing at individual nucleotide resolution, Nature Structural & Molecular Biology, 17(7):909-916.
Kotake et al., 1996, A simple nested RT-PCR method for quantitation of the relative amounts of multiple cytokine mRNAs in small tissue samples, Journal of Immunological Methods, 199:193-203.
Kurimoto et al., Mar. 17, 2006, An improved single-cell cDNA amplification method for efficient high-density oligonucleotide microarray analysis, Nucleic Acids Res., 34(5):e42.
Lambie et al., Nov. 20, 2013, Improved workflows for high throughput library preparation using thetransposome-based nextera system, BMC Biotechnology, 13(1):104.
Larson et al., Nov. 2009, A single molecule view of gene expression. Trends Cell Biol. 19(11):630-637.
Leamon et al., Nov. 2003, A massively parallel PicoTiterPlate based platform for discrete picoliter-scale polymerase chain reactions, Electrophoresis, 24(21):3769-3777.
Lee et al., 2010, Large-scale arrays of picolitre chambers for single-cell analysis of large cell populations, Lab Chip, 10:2952-2958.
Lee et al., Mar. 21, 2014, Highly multiplexed subcellular RNA sequencing in situ. Science. 343(6177):1360-1363.
Liu et al., Single-cell transcriptome sequencing: recent advances and remaining challenges, F1000Research 2016, 5(F1000 Faculty Rev):182, 9 pp.
Lizardi et al., Jul. 1998, Mutation detection and single-molecule counting using isothermal rolling-circle amplification. Nat Genet. 19(3):225-32.
Lockhart et al., 1996, Expression monitoring by hybridization to high-density oligonucleotide arrays. Nature Biotechnology, 14:1675-1680.
Lovatt et al., Feb. 2014, Transcriptome in vivo analysis (TIVA) of spatially defined single cells in live tissue. Nat Methods. 11(2):190-196.
Lucito et al., 1996, Representational Oligonucleotide Microarray Analysis: A High-Resolution Method to Detect Genome Copy Number Variation. Genome Research, 13: 2291-2305.
Maamar et al., 2007, Noise in Gene Expression Determines Cell Fate in Bacillus subtilis. Science, 317:526-529.
Macaulay et al., 2015, G&T-seq: parallel sequencing of single-cell genomes and transcriptomes. Nature Methods, pp. 1-7.
Macosko et al., 2015, Highly parallel genome-wide expression profiling of individual cells using nanoliter droplets, Cell 161:1202-1214 (and supplemental information).
Makrigiorgos et al., Sep. 2002, A PCR-Based amplification method retaining quantities difference between two complex genomes. Nature Biotech, 20(9):936-939.
Marcus et a., 2006, Microfluidic single-cell mRNA isolation and analysis, Ana. Chem. 78:3084-3089.
Margulies et al., Sep. 15, 2005 Genome sequencing in microfabricated high-density picolitre reactors, Nature, 437:376-380.
Martinez et al., Jul. 2012, A microfluidic approach to encapsulate living cells in uniform alginate hydrogel microparticles, Macromol. Biosci, 12(7):946-951.

(56) References Cited

OTHER PUBLICATIONS

McCloskey et al., Dec. 2007, Encoding PCR products with batch-stamps and barcodes. Biochem Genet. 45(11-12):761-767.
Medvedev et al., Nov. 2010, Detecting copy number variation with mated short reads. Genome Res. 20(11):1613-1622.
Mei et al., Mar. 22, 2010, Identification of recurrent regions of Copy-Number Variants across multiple individuals. BMC Bioinformatics. 11:147.
Merriam-Webster, definition of associate,: http://www.merriam-webster.com/dictionary/associate, accessed Apr. 5, 2016.
Miller et al., 2006, Directed evolution by in vitro compartmentalization, Nature Methods, 3:561-570.
Miner et al., 2004, Molecular barcodes detect redundancy and contamination in hairpin-bisulfite PCR, Nucleic Acids Research, 32(17):e135.
Mortazavi et al., 2008, Mapping and quantifying mammalian transcriptomes by RNA-Seq. Nat. Methods. 5:621-628.
Nadai et al., 2008, Protocol for nearly full-length sequencing of HIV-1 RNA from plasma, PLoS One, 3(1):e1420.
Nagai et al., 2001, Development of a microchamber array for picoleter PCR, Anal. Chem., 73:1043-1047.
Navin et al., 2015, The first five years of single-cell cancer genomics and beyond, Genome Research, 25(10):1499-1507.
Newell et al., Jan. 27, 2012, Cytometry by time-of-flight shows combinatorial cytokine expression and virus-specific cell niches within a continuum of CD8+ T cell phenotypes. Immunity. 36(1):142-152.
Novak et al., Jan. 20, 2011, Single-cell multiplex gene detection and sequencing with microfluidically generated agarose emulsions, Angew Chem Int Ed Engl., 50(2):390-395.
Ogino et al., Nov. 2002, Quantification of PCR bias caused by a single nucleotide polymorphism in SMN gene dosage analysis. J Mol Diagn. 4(4):185-190.
Parameswaran et al., 2007, A pyrosequencing-tailored nucleotide barcode design unveils opportunities for large-scale sample multiplexing. Nucleic Acids Res. 35(19):e130.
Park et al., May 2010, Discovery of common Asian copy number variants using integrated high-resolution array CGH and massively parallel DNA sequencing. Nat Genet. 42(5):400-405.
Patanjali et al., Mar. 1991, Construction of a uniform-abundance (normalized) CNDA library, Proceedings of the National Academy of Sciences, 88(5):1943-1947.
Peng et al., Mar. 11, 2016, Reducing amplification artifacts in high multiplex amplicon sequencing by using molecular barcodes, BMC Genomics, retrieved from the internet: url:http://bmcgenomics.biomedcentral.com/articles/0.1186/s12864-015-1806-8, 14 pp.
Pfaffl et al., Mar. 2004, Determination of stable housekeeping genes, differentially regulated target genes and sample integrity: BestKeeper—Excel-based tool using pair-wise correlations, Biotechnology Letters, 26(6):505-515.
Picelli et al., Jul. 30, 2014, Tn5 transposase and tagmentation procedures for massively scaled sequencing projects, Genome Research 24(12):2033-2040.
Pihlak et al., 2008, Rapid genome sequencing with short universal tiling probes. Nature Biotechnology, 26:676-684.
Pinkel et al., 2005, Comparative Genomic Hybridization. Annual Review of Genomics and Human Genetics, 6:331-354.
Pleasance et al., Jan. 14, 2010, A small-cell lung cancer genome with complex signatures of tobacco exposure. Nature. 463(7278):184-190.
Plessy et al., Feb. 2013, Population transcriptomics with single-cell resolution: a new field made possible by microfluidics: a technology for high throughput transcript counting and data-driven definition of cell types, Bioessays, 35(2):131-140.
Qiu et al., Oct. 2003, DNA sequence-based "bar codes" for tracking the origins of expressed sequence tags from a maize cDNA library constructed using multiple mRNA sources. Plant Physiol. 133(2):475-481.
Rajeevan et al., Oct. 2003, Global amplification of sense RNA: a novel method to replicate and archive mRNA for gene expression analysis, Genomics, 82(4):491-497.
Roche Diagnostics GmbH, 2006, Genome Sequencer 20 System: First to the Finish (product brochure), 40 pp.
Sasagawa et al., 2013, Quartz-Seq: a highly reproducible and sensitive single-cell RNA sequencing method, reveals non-genetic gene-expression heterogeneity. Genome Biology, 14:R31.
Sasuga et al., Dec. 2008, Single-cell chemical lysis method for analyses of intracellular molecules using an array of picoliter-scale microwells, Anal Chem, 80(23):9141-9149.
Satija et al., May 2015, Spatial reconstruction of single-cell gene expression data. Nature Biotechnology, 33(5):495-508.
Schmitt et al., Sep. 4, 2012, Detection of ultra-rare mutations by next-generation sequencing. Proc Natl Acad Sci U S A. 109(36):14508-14513.
Sebat et al., 2004, Large-Scale Copy Number Polymorphism in the Human Genome. Science, 305:525-528.
Shalek et al., Jun. 13, 2013, Single-cell transcriptomics reveals bimodality in expression and splicing in immune cells. Nature. 498(7453):236-240.
Shiroguchi et al., Jan. 24, 2012, Digital RNA sequencing minimizes sequence-dependent bias and amplification noise with optimized single-molecule barcodes. Proc Natl Acad Sci U S A. 109(4):1347-1352.
Shoemaker et al., 1996, Quantitative phenotypic analysis of yeast deletion mutants using a highly parallel molecular bar-coding strategy. Nature Genetics, 14:450-456.
Simpson et al., Feb. 15, 2010, Copy number variant detection in inbred strains from short read sequence data. Bioinformatics. 26(4):565-567.
Smith et al., 2010, Highly-multiplexed barcode sequencing: an efficient method for parallel analysis of pooled samples. Nucleic Acids Research, 38(13):e142.
Soumillon et al., Mar. 5, 2014, Characterization of directed differentiation by high-throughput single-cell RNA-Seq, bioRxiv preprint, http://biorxiv.org/content/early/2014/03/05/003236.full.pdf, 13 pp.
Speicher et al., Oct. 2005, The new cytogenetics: blurring the boundaries with molecular biology, Nature Reviews Genetics, 6(10):782-792.
Stratagene 1998 Catalog, Gene Characterization Kits, p. 39.
Takahashi et al., Mar. 2006, Novel technique of quantitative nested real-time PCR assay for *Mycobacterium tuberculosis* DNA, Journal of Clinical Microbiology, 44(3):1029-1039.
Tan et al., Apr. 2013, Genome-wide comparison of DNA hydroxymethylation in mouse embryonic stem cells and neural progenitor cells by a new comparative hMeDIP-seq method. Nucleic Acids Res. 41(7):e84.
Taudien et al., Apr. 19, 2010, Haplotyping and copy number estimation of the highly polymorphic human beta-defensin locus on 8p23 by 454 amplicon sequencing. BMC Genomics. 11:252.
The Tibbs Times, UNC bioscience newsletter, Apr. 2010, 17 pp.
Tomaz et al., Aug. 2010, Differential methylation as a cause of allele dropout at the imprinted GNAS locus. Genet Test Mol Biomarkers. 14(4):455-460.
Treutlein et al., May 15, 2014, Reconstructing lineage hierarchies of the distal lung epithelium using single-cell RNA-seq. Nature. 509(7500):371-375.
Vandesompele et al., Jun. 18, 2002, Accurate normalization of real-time quantitative RT-PCR data by geometric averaging of multiple internal control genes, Genome Biology, 3(7).
Velculescu et al., 1995, Serial Analysis of Gene Expression. Science, 270:484-487.
Velculescu et al., 1997, Characterization of the Yeast Transcriptome. Cell, 88:243-251.
Vogelstein et al., 1999, Digital PCR. Proc. Natl. Acad. Sci., 96(16):9236-9241.
Walker et al., Jan. 1, 1992, Isothermal in vitro amplification of DNA by a restriction enzyme/DNA polymerase system. Proc Natl Acad Sci U S A., 89(1):392-396.

(56) References Cited

OTHER PUBLICATIONS

Walsh et al., Jul. 13, 2010, Detection of inherited mutations for breast and ovarian cancer using genomic capture and massively parallel sequencing. Proc Natl Acad Sci U S A. 107(28):12629-12633.
Wang et al., 2009, RNA-Seq: a revolutionary tool for transcriptomics. Nature Reviews Genetics, 10:57-63.
Wang et al., May 21, 2015, Advances and applications of single-cell sequencing technologies, Molecular Cell, 58(4):598-609.
Wang et al., Oct. 2010, iCLIP predicts the dual splicing effects of TIA-RNA interactions, PLoS Biol, 8(10):e1000530.
Warren et al., Nov. 21, 2006, Transcription factor profiling in individual hematopoietic progenitors by digital RT-PCR, PNAS, 103(47):17807-17812.
Weber et al., Sep. 15, 2003, A real-time polymerase chain reaction assay for quantification of allele ratios and correction of amplification bias. Anal Biochem. 320(2):252-258.
Weiner et al., Apr. 2008, Kits and their unique role in molecular biology: a brief retrospective, BioTechniques, 44:701-704.
White et al., Aug. 23, 2011, High-throughput microfluidic single-cell RT-qPCR, PNAS, 108(34):13999-14004.
Wittes et al., 1999, Searching for Evidence of Altered Gene Expression: a Comment on Statistical Analysis of Microarray Data. Journal of the National Cancer Institute, 91(5):400-401.
Wodicka et al., 1997, Genome-wide expression monitoring in *Saccharomyces cerevisiae*. Nature Biotechnology, 15:1359-1367.
Wojdacz et al., May 16, 2009, Primer design versus PCR bias in methylation independent PCR amplifications. Epigenetics. 4(4):231-234.
Wood et al., Aug. 2010, Using next-generation sequencing for high resolution multiplex analysis of copy number variation from nanogram quantities of DNA from formalin-fixed paraffin-embedded specimens. Nucleic Acids Res. 38(14):e151.
Wu et al., Jan. 2014, Quantitative assessment of single-cell RNA-sequencing methods. Nat Methods. 11(1):41-46.
Yandell et al., Sep. 2011, A probabilistic disease-gene finder for personal genomes. Genome Res. 21(9):1529-1542.
Ye et al., 2001, Fluorescent microsphere-based readout technology for multiplexed human single nucleotide polymorphism analysis and bacterial identification. Human Mutation, 17(4):305-316.
Yoon et al., Sep. 2009, Sensitive and accurate detection of copy number variants using read depth of coverage. Genome Res. 19(9):1586-1592.
Zhang et al., Jun. 19, 2012, DNA-based hybridization chain reaction for amplified bioelectronic signal and ultrasensitive detection of proteins. Anal Chem., 84(12),5392-5399.
Zhang et al., Mar. 20, 2011, The impact of next-generation sequencing on genomics. J Genet Genomics. 38(3):95-109.
Zhao et al., 2005, Homozygous Deletions and Chromosome Amplifications in Human Lung Carcinomas Revealed by Single Nucleotide Polymorphism Array Analysis. Cancer Research, 65:5561-5570.
Zheng et al., Feb. 2016, Haplotyping germline and cancer genomes with high-throughput linked-read sequencing, Nature Biotechnology, 34(3):303-311.
Zhou et al., 2001, Counting alleles reveals a connection between chromosome 18q loss and vascular invasion. Nature Biotechnology, 19:78-81.
International Search Report and Written Opinion dated May 3, 2016 in PCT/US16/018354.
Office action dated Oct. 3, 2013 for U.S. Appl. No. 12/969,581.
Response with allowed claims dated Mar. 4, 2014 for U.S. Appl. No. 12/969,581.
Notice of allowance dated Mar. 21, 2014 for U.S. Appl. No. 12/969,581.
Notice of allowance dated Jun. 19, 2014 for U.S. Appl. No. 12/969,581.
Notice of allowance dated Aug. 22, 2014 for U.S. Appl. No. 12/969,581.
Office action dated Dec. 3, 2015 for U.S. Appl. No. 14/281,706.
Office action dated Jul. 20, 2016 for U.S. Appl. No. 14/281,706.
Office Action dated Oct. 11, 2016 in U.S. Appl. No. 15/224,460.
Office Action dated May 8, 2017 in U.S. Appl. No. 15/224,460.
Office Action dated May 7, 2015 for U.S. Appl. No. 13/327,526.
Notice of allowance dated Jan. 21, 2016 for U.S. Appl. No. 13/327,526.
Office action dated Feb. 18, 2015 for U.S. Appl. No. 14/540,007.
Office action dated Sep. 24, 2015 for U.S. Appl. No. 14/540,007.
Notice of allowance dated Dec. 15, 2015 for U.S. Appl. No. 14/540,007.
Office action dated Mar. 19, 2015 for U.S. Appl. No. 14/540,018.
Office action dated Oct. 6, 2015 for U.S. Appl. No. 14/540,018.
Notice of allowance dated Dec. 21, 2015 for U.S. Appl. No. 14/540,018.
Office Action dated Feb. 26, 2015 for U.S. Appl. No. 14/540,029.
Office action dated Sep. 1, 2015 for U.S. Appl. No. 14/540,029.
Office Action dated Jul. 28, 2017 in U.S. Appl. No. 14/975,441.
International Search Report and Written Opinion dated Jun. 6, 2012 in PCT/US11/065291.
Restriction Requirement dated Mar. 15, 2016 in U.S. Appl. No. 14/381,488.
Office Action dated May 10, 2016 in U.S. Appl. No. 14/381,488.
Office Action dated Aug. 12, 2016 in U.S. Appl. No. 14/381,488.
Office Action dated Feb. 13, 2017 in U.S. Appl. No. 14/381,488.
Office Action dated Jun. 7, 2017 in U.S. Appl. No. 14/381,488.
International Search Report and Written Opinion dated Septembers, 2013 in PCT/US13/028103.
Office Action dated Feb. 17, 2017 in Canadian patent application No. 2,865,575.
Second Office Action dated Jun. 6, 2016 in Chinese patent application No. 201380022187.9.
Third Office Action dated Dec. 27, 2016 in Chinese patent application No. 201380022187.9.
Fourth Office Action dated Jul. 14, 2017 in Chinese patent application No. 201380022187.9.
European search report and search opinion dated Jul. 17, 2015 for European patent application No. 13755319.4.
Examination report dated Jul. 12, 2016 in European patent application No. 13755319.4.
Search and Examination Report dated Aug. 6, 2014 for GB patent application No. 1408829.8.
Search and Examination Report dated Jan. 27, 2016 in GB patent application No. 1408829.8.
Examination Report dated Jun. 8, 2016 in GB patent application No. 1408829.8.
Official Action dated Dec. 28, 2016 in Japanese patent application No. 2014-558975.
Search Report and Written Opinion dated Mar. 1, 2016 in Singapore patent application No. 11201405274W.
Written Opinion dated May 26, 2017 in Singapore patent application No. 11201405274W.
International search report and written opinion dated Aug. 16, 2013 for PCT/US2013/027891.
Extended European Search Report dated Dec. 15, 2015 in European patent application No. 13754428.4.
Restriction Requirement dated Mar. 17, 2016 in U.S. Appl. No. 14/472,363.
Office Action dated Apr. 11, 2016 in U.S. Appl. No. 14/472,363.
Office action dated Dec. 31, 2015 for U.S. Appl. No. 14/800,526.
Office action dated Apr. 11, 2016 for U.S. Appl. No. 14/800,526.
Office action dated Aug. 17, 2016 for U.S. Appl. No. 14/800,526.
Office Action dated Oct. 25, 2016 in U.S. Appl. No. 14/872,337.
Office action dated Sep. 26, 2016 in U.S. Appl. No. 15/167,807.
International Search Report and Written Opinion dated Feb. 3, 2015 in PCT/US14/053301.
Examination Report dated Apr. 10, 2017 in European patent application No. 14761937.3.
Search and Examination Report dated Aug. 26, 2015 in GB patent application No. 1511591.8.
Examination Report dated Feb. 19, 2016 in Great Britain patent application No. GB1511591.8.
Examination Report dated Jun. 15, 2016 in Great Britain patent application No. GB1511591.8.

(56) References Cited

OTHER PUBLICATIONS

Combined Search and Examination Report dated Feb. 21, 2017 in GB patent application No. 1609740.4.
Office Action dated May 13, 2016 in U.S. Appl. No. 14/508,911.
Office Action dated Mar. 24, 2017 in U.S. Appl. No. 15/409,355.
International search report and written opinion dated Dec. 19, 2014 for PCT Application No. US2014/059542.
International Search Report and Written Opinion dated Jun. 20, 2016 in PCT/US16/14612.
Office Action dated Jan. 19, 2017 in U.S. Appl. No. 15/055,445.
International Search Report and Written Opinion dated Jun. 17, 2016 in PCT/US16/019962.
Written Opinion dated Jul. 5, 2016 in PCT/US16/019962.
Written Opinion dated Sep. 27, 2016 in PCT/US16/019962.
Invitation to Pay Additional Search Fees dated Jun. 2, 2016 in PCT/US16/019971.
International Search Report and Written Opinion dated Aug. 9, 2016 in PCT/US16/019971.
International Search Report and Written Opinion dated Jun. 9, 2016 in PCT/US16/022712.
International Search Report and Written Opinion dated Dec. 5, 2016 in PCT/US16/024783.
International Search Report and Written Opinion dated Sep. 28, 2016 in PCT/US16/028694.
International Search Report and Written Opinion dated Sep. 27, 2016 in PCT/US16/034473.
International Search Report and Written Opinion dated Jan. 31, 2017 in PCT/US16/050694.
International Search Report and Written Opinion dated Aug. 7, 2017 in PCT/US2017/034576.
International search report and written opinion dated May 7, 2012 for PCT/IB2011/003160.
Notice of opposition dated Jul. 22, 2015 for European patent application No. 11810645.9.
Notice of opposition dated Jul. 9, 2015 for European patent application No. 11810645.9.
"SOLiD™ System Barcoding", Applied Biosystems (ABI) Application Note, (Apr. 2008), pp. 1-4.
"Super Smart™ PCR cDNA Synthesis Kit User Manual", Clontech Laboratories, Inc., (2007) pp. 1-39.
Algae, Wikipedia.org, accessed Mar. 4, 2016, 20 pp.
Archaea, Wikipedia.org, accessed May 11, 2016, 26 pp.
Bontoux et al., "Integrating whole transcriptome assays on a lab-on-a-chip for single cell gene profiling", Lab on a Chip, (2008) vol. 8, No. 3, pp. 443-450.
Brady et al., "Construction of cDNA libraries form single cells", Methods in Enzymology, Academic Press, US, (1993) vol. 225, doi:10.1016/0076-6879(93)25039-5, ISSN 0076-6879, pp. 611-623.
Buschmann et al., Aug. 7, 2014, Enhancing the detection of barcoded reads in high throughput DNA sequencing DNA by controlling the false discovery rate, BMC Bioinformatics, 15(1):264.
Cloonan et al., "Stem cell transcriptome profiling via massive-scale mRNA sequencing", Nature Methods, (Jul. 2008) vol. 5, No. 7, pp. 613-619.
Costa et al., Aug. 22, 2012, Single-tube nested real-time PCR as a new highly sensitive approach to trace hazelnut, J. Agric Food Chem, 60(33):8103-8110.
Custom Antibody Services, Precision Antibody, accessed Apr. 16, 2014, 2 pp.
Eberwine et al., "Analysis of gene expression in single live neurons", Proc. Natl. Acad. Sci. USA, (Apr. 1992) vol. 89, No. 7, pp. 3010-3014.
Fish, Wikipedia.org, accessed Nov. 2, 2014, 11 pp.
Fungus, Wikipedia.org, accessed Jun. 3, 2013, 28 pp.
Harbers, "The current status of cDNA cloning", Genomics, (2008) vol. 91, No. 3, pp. 232-242.
Hartmann, "Gene expression profiling of single cells on large-scale oligonucleotide arrays", Nucleic Acids Research, (Oct. 2006) vol. 34, No. 21, p. e143.

How many species of bacteria are there? Wisegeek.org, accessed Jan. 21, 2014, 2 pp.
Islam et al., "Highly multiplexed and strand specific single-cell RNA 5' end sequencing", Nature Protocols, (2012) vol. 7, No. 5, pp. 813-828.
Karrer et al., "In situ isolation of mRNA from individual plant cells: creation of cell-specific cDNA libraries.", Proc. Natl. Acad. Sci. USA, (Apr. 1995) vol. 92, No. 9, pp. 3814-3818.
Ko et al., "RNA-conjugated template-switching RT-PCR method for generating an *Escherichia coli* cDNA library for small RNAs", Journal of Microbiological Methods, (2006) vol. 64, No. 3, pp. 297-304.
Kurimoto et al., "Global single-cell cDNA amplification to provide a template for representative high-density oligonucleotide microarray analysis", Nature Protocols, (2007) vol. 2, No. 3, pp. 739-752.
List of sequenced bacterial genomes, Wikipedia.org, accessed Jan. 24, 2014, 57 pp.
Maeda et al., "Development of a DNA barcode tagging method for monitoring dynamic changes in gene expression by using an ultra high-throughput sequencer", BioTechniques, (Jul. 2008), vol. 45, No. 1, pp. 95-97.
Mammal, Wikipedia.org, accessed Sep. 22, 2011, 16 pp.
Mardis, "Next-generation DNA sequencing methods", Annu. Rev. Genomics Hum. Genet., (2008) vol. 9, pp. 387-402.
Marguerat et al., "Next-generation sequencing: applications beyond genomes", Biochemical Society Transactions, (2008) vol. 36, No. 5, pp. 1091-1096.
Meyer et al., "Parallel tagged sequencing on the 454 platform", Nature Protocols, (2008) vol. 3, No. 2, pp. 267-278.
Murinae, Wikipedia.org, accessed Mar. 18, 2013, 21 pp.
Ozkumur et al., Apr. 3, 2013, Inertial focusing for tumor antigen-dependent and -independent sorting of rare circulating tumor cells, Sci Transl Med, 5(179):1-20.
Plant, Wikipedia.org, accessed Aug. 28, 2015, 14 pp.
Protozoa, Wikipedia.org, accessed May 11, 2016, 10 pp.
Shendure et al., "Next-generation DNA sequencing", Nature Biotechnology, (Oct. 2008) vol. 26, No. 10, pp. 1135-1145.
Sommer et al., Nov. 16, 1989, Minimal homology requirements for PGR primers, Nucleic Acids Research, 17(16):6749.
Song et al., 2013, Design rules for size-based cell sorting and sheathless cell focusing by hydrophoresis, Journal of Chromatography A, 1302:191-196.
Subkhankulova et al., "Comparative evaluation of linear and exponential amplification techniques for expression profiling at the single cell level", Genome Biology, (Mar. 2006) vol. 7, No. R18, pp. 1-16.
Tang et al, "RNA-Seq analysis to capture the transcriptome landscape of a single cell", Nature Protocols, (2010) vol. 5, No. 3, pp. 516-535.
Virus, Wikipedia.org, accessed Nov. 24, 2012, 34 pp.
Zhu et al., "Reverse transcriptase template switching: a SMART approach for full-length cDNA library construction.", BioTechniques, (Apr. 2001) vol. 30, No. 4, pp. 892-897.
Office Action dated Sep. 8, 2017 in U.S. Appl. No. 15/046,225.
Office Action dated May 3, 2018 in U.S. Appl. No. 15/046,225.
Office action dated Jan. 9, 2018 in U.S. Appl. No. 15/217,896.
Office action dated Jan. 12, 2018 in U.S. Appl. No. 15/217,886.
Office Action dated Nov. 16, 2017 in U.S. Appl. No. 14/381,488.
Office Action dated May 10, 2018 in U.S. Appl. No. 14/381,488.
Examination Report No. 1 for standard patent application, dated Oct. 24, 2017, Australian patent application No. 2013226081.
Office Action dated Feb. 15, 2018 in Canadian patent application No. 2,865,575.
Extended European Search Report dated Feb. 8, 2018 in patent application No. 17202409.3.
Final Decision dated Aug. 30, 2017 in Japanese patent application No. 2014-558975.
Notice of Reasons for Rejection dated Apr. 2, 2018 in Japanese patent application No. 2014-558975.
Examination Report dated Mar. 16, 2018 in European patent application No. 13754428.4.
Examination Report dated Oct. 10, 2017 in European patent application No. 14761937.3.

(56) References Cited

OTHER PUBLICATIONS

Examination Report dated Jan. 3, 2018 in GB patent application No. 1609740.4.
Office Action dated Oct. 16, 2017 in U.S. Appl. No. 15/409,355.
First Office Action dated Dec. 19, 2017 in Chinese patent application No. 201480061859.1.
Office Action dated Nov. 9, 2017 in U.S. Appl. No. 15/004,618.
Office Action dated Nov. 1, 2017 in U.S. Appl. No. 15/667,125.
Office Action dated Sep. 8, 2017 in U.S. Appl. No. 15/134,967.
Office Action dated Mar. 8, 2018 in U.S. Appl. No. 15/608,780.
International Search Report and Written Opinion dated Sep. 8, 2017 in PCT/US2017/030097.
Statement of Opposition of Strawman Limited filed against European Patent No. EP2414548B1 on Jul. 19, 2016.
Statement of Opposition filed against European Patent No. EP2414548B1 on Jul. 26, 2016.
Statement of Opposition filed against European Patent No. EP2414548B1 on Jul. 21, 2016.
Submission dated Jan. 15, 2018 by Strawman Limited in preparation for upcoming oral proceedings in opposition against European Patent No. EP2414548B1.
Submission dated Jan. 15, 2018 by Vossius & Partner in preparation for upcoming oral proceedings in opposition against European Patent No. EP2414548B1.
Third-Party Pre-Issuance Submission filed on Jun. 16, 2018 for U.S. Appl. No. 15/847,752.
Third-Party Pre-Issuance Submission filed on Jun. 6, 2018 for U.S. Appl. No. 15/847,752.
Third-Party Pre-Issuance Submission filed on May 21, 2018 for U.S. Appl. No. 15/847,752.
D'haeseleer, Dec. 2005, How does gene expression clustering work?, Nature Biotechnology, pp. 1499-1501.
Di Carlo et al., Dec. 1, 2008, Dynamic single-cell analysis for quantitative biology, Analytical Chemistry, 78(23):7918-7925.
Lau et al., Sep. 21, 2017, Single molecule counting and assessment of random molecular tagging errors with transposable giga-scale error-correcting barcodes, BMC Genomics, 18(1):1-13.
Peng et al. Aug. 7, 2015 Supplementary Material BMC Bioinformatics 16:589.
Smith et al., Jan. 18, 2017, UMI-tools: modeling sequencing errors in unique molecular identifiers to improve quantification accuracy, Genome Research, 27(3):491-499.
Sorlie et al., Sep. 11, 2001, Gene expression patterns of breast carcinomas distinguish tumor subclasses with clinical implications, Proceedings National Academy of Sciences PNAS, 98(19):10869-10874.
Tung et al., Jan. 3, 2017, Batch effects and the effective design of single-cell gene expression studies. Nature Scientific Reports, 7:39921, 15 pp.
Zorita et al., Jan. 31, 2015 Starcode: sequence clustering based on all pairs search. Bioinformatics, 13(12):1913-1919.
Office Action dated May 8, 2020 in U.S. Appl. No. 15/806,174.
Examination Report dated Apr. 2, 2020 in European patent application No. 17805040.7.
Written Opinion dated Oct. 7, 2020 in Singapore patent application No. 11201903158R.
International Search Report and Written Opinion dated Jan. 18, 2018 in PCT/US2017/060447.
Office Action dated Apr. 15, 2020 in U.S. Appl. No. 15/806,223.
Written Opinion dated Oct. 8, 2020 in Singapore patent application No. 11201903139S.

International Search Report and Written Opinion dated Feb. 22, 2018 in PCT/US2017/060451.
International Search Report and Written Opinion dated Jul. 18, 2018 in PCT/US2018/023387.
International Search Report and Written Opinion dated Feb. 28, 2019 in PCT/US2018/052365.
Third Party Observation dated Jun. 14, 2018 in Japanese patent application No. 2016-537867.
Official Action dated Jul. 30, 2018 in Japanese patent application No. 2016-537867.
Office Action dated Jan. 6, 2021 in U.S. Appl. No. 15/605,874.
Johnson, Sep. 1967, Hierarchical clustering schemes, Psychometrika, 32(3):241-254.
Murtagh et al., 2012, Algorithms for hierarchical clustering: an overview, WIREs Data Mining and Knowledge Discovery, 2:86-97.
First Office Action dated Jun. 18, 2021 in Chinese patent application No. 201780028283.2.
Examination report dated Dec. 22, 2020 in European patent application No. 17728398.3.
Notice of Reasons for Rejection dated Jul. 8, 2021 in Japanese patent application No. 2018-561218.
Examination Report dated May 27, 2021 in European patent application No. 17805040.7.
Office Action dated Oct. 30, 2020 in U.S. Appl. No. 15/806,223.
Examination report dated Apr. 15, 2021 in European patent application No. 17805344.3.
Examination Report dated Nov. 5, 2020 in European patent application No. 18716453.8.
Office action dated Mar. 2, 2022 in U.S. Appl. No. 16/139,699.
Anders et al., Jan. 7, 2010, Differential expression analysis for sequence count data. Nature Precedings, pp. 1-13.
Bolotin et al., 2015. MiXCR software for comprehensive adaptive immunity profiling. MiXCR Documentation, pp. 1-3.
Bolotin et al., 2015. MiXCR software for comprehensive adaptive immunity profiling. Nature methods Supplemental, 12(5), pp. 1-14.
Bolotin, D.A., Poslavsky, S., Mitrophanov, I., Shugay, M., Mamedov, I.Z. Putintseva, E.V. and Chudakov, D.M., 2015. MiXCR software comprehensive adaptive immunity profiling. Nature methods, 12(5), pp. 380-381. (Year: 2015).
Edgar, 2016. UNOISE2: improved error-correction for Illumina 16S and ITS amplicon sequencing. BioRxiv, p. 081257, pp. 1-21.
Grun et al., Nov. 5, 2015, Design and analysis of single-cell sequencing experiments, Cell, 163:799-810.
Ilicic et al., 2016, Classification of low quality cells from single-cell RNA-seq data, Genome Bioloigy, 127:29.
Jaitin et al., 2015, Each cell counts: hematopoiesis and immunity research in the era of single cell genomics, Seminars in Immunology, 27:67-71.
Smyth et al., 2010, Reducing chimera formation during PCR amplification to ensure accurate genotyping. Gene, 469(1-2):45-51.
Wagner et al., 2013, A model based criterion for gene expression calls using RNA-seq data, Theory in Biosciences, 132(3):159-164.
Notification of Reasons for Refusal with English Translation dated Oct. 4, 2021 in Japanese patent application No. 2019-523874.
Examination Report No. 1 dated Oct. 29, 2021 in Australian patent application No. 2017359048.
Notice of Reasons for Rejection with English Translation) dated Dec. 15, 2021 in Japanese patent application No. 2019-523873.
Office action dated Nov. 23, 2021 in U.S. Appl. No. 15/926,977.
Notice of Reasons for Rejection with English Translation dated Nov. 29, 2021 in Japanese patent application No. 2019-552517.
Final Office Action dated Apr. 26, 2022 in U.S. Appl. No. 15/926,977 in 20 pages.

\* cited by examiner

Raw Reads

FIG. 36

| | SEQ ID NO: 47-66 | | | SEQ ID NO: 67-86 | | | SEQ ID NO: 87-106 | |
|---|---|---|---|---|---|---|---|---|
| Gene ID | Adjusted ML | Number of Reads Per ML | Gene ID | Adjusted ML | Number of Reads Per ML | Gene ID | Adjusted ML | Number of Reads Per ML |
| GAPDH | GGGGGGGG | 1417 | ACTB | TTTTTTTA | 5395 | HSP90AB1 | TTTTTTGA | 982 |
| GAPDH | GGTTGGTA | 702 | ACTB | GGGCGGGG | 4014 | HSP90AB2 | TTTGGGGG | 432 |
| GAPDH | GCGGCGGG | 630 | ACTB | GGGGGGCG | 3890 | HSP90AB3 | GGGTGGCG | 359 |
| GAPDH | GGTGGGGG | 626 | ACTB | GGGGTTCG | 3749 | HSP90AB4 | CGTTTTTA | 348 |
| GAPDH | TGCGCCTC | 598 | ACTB | GGGGGGGG | 3660 | HSP90AB5 | TGTTGTTA | 335 |
| GAPDH | GGCGGGGA | 598 | ACTB | TTTTTTTA | 3435 | HSP90AB6 | TTTGGGGC | 313 |
| GAPDH | CTTTTTTA | 581 | ACTB | GGCGGGGG | 3430 | HSP90AB7 | TTCTTTTA | 305 |
| GAPDH | GGCGGGGG | 575 | ACTB | GGGCGGCG | 3347 | HSP90AB8 | TGGTTCGC | 300 |
| GAPDH | CGGGGGGC | 563 | ACTB | GTGGGGGG | 3282 | HSP90AB9 | TTTTTTTG | 291 |
| GAPDH | CGGGTCGG | 551 | ACTB | TGGCGGGG | 3170 | HSP90AB10 | CGTGGTGC | 283 |
| GAPDH | GGCGTGGG | 515 | ACTB | GGGGGGGG | 3070 | HSP90AB11 | GGGCGCGA | 270 |
| GAPDH | GTGTTGTA | 511 | ACTB | TTCGGTTG | 2913 | HSP90AB12 | TGGCTGGC | 268 |
| GAPDH | TTTGGGGG | 479 | ACTB | GTCGGGGA | 2861 | HSP90AB13 | GTGGGTGA | 264 |
| GAPDH | GTGTGTGA | 474 | ACTB | GGGGGTGG | 2817 | HSP90AB14 | TTTTTGCG | 252 |
| GAPDH | GGGGGGGG | 444 | ACTB | TTTTTTTG | 2734 | HSP90AB15 | GGCGGGGG | 252 |
| GAPDH | TGCGGGGG | 442 | ACTB | TTGGGCGC | 2692 | HSP90AB16 | TGTCCTTG | 249 |
| GAPDH | TTTTTTGC | 430 | ACTB | TGGCGGGG | 2667 | HSP90AB17 | TGGGGGGG | 245 |
| GAPDH | GGGGGGTC | 430 | ACTB | GTGTGTTG | 2642 | HSP90AB18 | GGGGTTTG | 244 |
| GAPDH | GGTGGGGG | 423 | ACTB | TTGGTTTG | 2540 | HSP90AB19 | TTGGTTTA | 243 |
| GAPDH | TGCGCGGA | 419 | ACTB | GGGGTTGG | 2508 | HSP90AB20 | GGGGTGCC | 241 |

(a) Raw ML

SEQUENCE LISTING

```
<160> NUMBER OF SEQ ID NOS: 106

<210> SEQ ID NO 1
<211> LENGTH: 20
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 1
aaaaaaaaaa aaaaaaaaaa                                              20

<210> SEQ ID NO 2
<211> LENGTH: 20
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 2
tttttttttt tttttttttt                                              20
```

```
<210> SEQ ID NO 3
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 3 tgtgcgtg                                                                    8

<210> SEQ ID NO 4
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 4 tgtgcgcg                                                                    8

<210> SEQ ID NO 5
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 5 tgtgcggg                                                                    8

<210> SEQ ID NO 6
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 6 ggtgcgtg                                                                    8

<210> SEQ ID NO 7
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 7 tgggcgtg                                                                    8

<210> SEQ ID NO 8
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 8 cgtgtctg                                                                    8
```

```
<210> SEQ ID NO 9
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 9 gggggcga                                                                  8

<210> SEQ ID NO 10
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 10 gctgctgg                                                                  8

<210> SEQ ID NO 11
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 11 tcgggcga                                                                  8

<210> SEQ ID NO 12
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 12 cgcgttca                                                                  8

<210> SEQ ID NO 13
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 13 cgcgttta                                                                  8

<210> SEQ ID NO 14
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 14 tgggcttg                                                                  8
```

```
<210> SEQ ID NO 15
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 15 ccgctctg                                                              8

<210> SEQ ID NO 16
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 16 cggtgttc                                                              8

<210> SEQ ID NO 17
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 17 cgggggtg                                                              8

<210> SEQ ID NO 18
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 18 cccccttg                                                              8

<210> SEQ ID NO 19
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 19 cggggggg                                                              8

<210> SEQ ID NO 20
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 20 cggggggcg                                                             8

<210> SEQ ID NO 21
```

```
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 21 ccgcgctg                                                                  8

<210> SEQ ID NO 22
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 22 cggcgttc                                                                  8

<210> SEQ ID NO 23
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 23 cggtgtcc                                                                  8

<210> SEQ ID NO 24
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 24 tggtgttc                                                                  8

<210> SEQ ID NO 25
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 25 ctgctctg                                                                  8

<210> SEQ ID NO 26
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 26 ggccgtgg                                                                  8

<210> SEQ ID NO 27
<211> LENGTH: 8
```

```
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 27 tcgctctg                                                                 8

<210> SEQ ID NO 28
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 28 ccgccctg                                                                 8

<210> SEQ ID NO 29
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 29 cccgcttg                                                                 8

<210> SEQ ID NO 30
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 30 ccgttctg                                                                 8

<210> SEQ ID NO 31
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 31 gggtgttc                                                                 8

<210> SEQ ID NO 32
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 32 cgttgttc                                                                 8

<210> SEQ ID NO 33
<211> LENGTH: 8
<212> TYPE: DNA
```

<213> ORGANISM: Artificial Sequence
<220> FEATURE:
<223> OTHER INFORMATION: note="Description of Artificial Sequence: Synthetic Oligonucleotide"

<400> SEQUENCE: 33 gggggtgg                                                                8

<210> SEQ ID NO 34
<211> LENGTH: 8
<212> TYPE: DNA
<213> ORGANISM: Artificial Sequence
<220> FEATURE:
<223> OTHER INFORMATION: note="Description of Artificial Sequence: Synthetic Oligonucleotide"

<400> SEQUENCE: 34 gggtccgg                                                                8

<210> SEQ ID NO 35
<211> LENGTH: 8
<212> TYPE: DNA
<213> ORGANISM: Artificial Sequence
<220> FEATURE:
<223> OTHER INFORMATION: note="Description of Artificial Sequence: Synthetic Oligonucleotide"

<400> SEQUENCE: 35 cggctctg                                                                8

<210> SEQ ID NO 36
<211> LENGTH: 8
<212> TYPE: DNA
<213> ORGANISM: Artificial Sequence
<220> FEATURE:
<223> OTHER INFORMATION: note="Description of Artificial Sequence: Synthetic Oligonucleotide"

<400> SEQUENCE: 36 cggcgtcc                                                                8

<210> SEQ ID NO 37
<211> LENGTH: 8
<212> TYPE: DNA
<213> ORGANISM: Artificial Sequence
<220> FEATURE:
<223> OTHER INFORMATION: note="Description of Artificial Sequence: Synthetic Oligonucleotide"

<400> SEQUENCE: 37 ccgctccg                                                                8

<210> SEQ ID NO 38
<211> LENGTH: 8
<212> TYPE: DNA
<213> ORGANISM: Artificial Sequence
<220> FEATURE:
<223> OTHER INFORMATION: note="Description of Artificial Sequence: Synthetic Oligonucleotide"

<400> SEQUENCE: 38 gtcaaatt                                                                8

<210> SEQ ID NO 39
<211> LENGTH: 8
<212> TYPE: DNA
<213> ORGANISM: Artificial Sequence

```
<220> FEATURE:
<223> OTHER INFORMATION: note="Description of Artificial Sequence:
      Synthetic Oligonucleotide"

<400> SEQUENCE: 39 gtcaaaat                                                                  8

<210> SEQ ID NO 40
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 40 gtcaaaaa                                                                  8

<210> SEQ ID NO 41
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 41 ttcaaaaa                                                                  8

<210> SEQ ID NO 42
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 42 ttcagaaa                                                                  8

<210> SEQ ID NO 43
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 43 ctcaaaaa                                                                  8

<210> SEQ ID NO 44
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 44 ttcaaact                                                                  8

<210> SEQ ID NO 45
<211> LENGTH: 8
<212> TYPE: DNA
<213> ORGANISM: Artificial Sequence
<220> FEATURE:
```

```
<223> OTHER INFORMATION: note="Description of Artificial Sequence:
      Synthetic Oligonucleotide"

<400> SEQUENCE: 45 ttcaaaat                                                              8

<210> SEQ ID NO 46
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 46 ttcaaaca                                                              8

<210> SEQ ID NO 47
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 47 gggggggg                                                              8

<210> SEQ ID NO 48
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 48 ggttggta                                                              8

<210> SEQ ID NO 49
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 49 gcggcggg                                                              8

<210> SEQ ID NO 50
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 50 ggtggggg                                                              8

<210> SEQ ID NO 51
<211> LENGTH: 8
<212> TYPE: DNA
<213> ORGANISM: Artificial Sequence
<220> FEATURE:
<223> OTHER INFORMATION: note="Description of Artificial Sequence:
```

Synthetic Oligonucleotide"

<400> SEQUENCE: 51 tgcgcctc                                                             8

<210> SEQ ID NO 52
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 52 ggcgggga                                                             8

<210> SEQ ID NO 53
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 53 ctttttta                                                             8

<210> SEQ ID NO 54
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 54 ggcggggg                                                             8

<210> SEQ ID NO 55
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 55 cgggggc                                                              8

<210> SEQ ID NO 56
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 56 cgggtcgg                                                             8

<210> SEQ ID NO 57
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

```
<400> SEQUENCE: 57 ggcgtggg                                                              8

<210> SEQ ID NO 58
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 58 gtgttgta                                                              8

<210> SEQ ID NO 59
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 59 tttggggg                                                              8

<210> SEQ ID NO 60
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 60 gtgtgtga                                                              8

<210> SEQ ID NO 61
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 61 gggggggg                                                              8

<210> SEQ ID NO 62
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 62 tgcggggg                                                              8

<210> SEQ ID NO 63
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"
```

```
<400> SEQUENCE: 63 tttttttgc                                                             8

<210> SEQ ID NO 64
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 64 gggggtc                                                               8

<210> SEQ ID NO 65
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 65 ggtggggg                                                              8

<210> SEQ ID NO 66
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 66 tgcgcgga                                                              8

<210> SEQ ID NO 67
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 67 tttttta                                                               8

<210> SEQ ID NO 68
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 68 gggcgggg                                                              8

<210> SEQ ID NO 69
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 69
``` ggggggcg                                                                8

<210> SEQ ID NO 70
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 70 ggggttcg                                                                8

<210> SEQ ID NO 71
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 71 gggggggg                                                                8

<210> SEQ ID NO 72
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 72 tttttttta                                                               8

<210> SEQ ID NO 73
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 73 ggcggggg                                                                8

<210> SEQ ID NO 74
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 74 gggcggcg                                                                8

<210> SEQ ID NO 75
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 75 gtgggggg 8

<210> SEQ ID NO 76
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 76 tggcgggg 8

<210> SEQ ID NO 77
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 77 gggggggg 8

<210> SEQ ID NO 78
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 78 ttcggttg 8

<210> SEQ ID NO 79
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 79 gtcgggga 8

<210> SEQ ID NO 80
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 80 gggggtgg 8

<210> SEQ ID NO 81
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 81 tttttttg 8

<210> SEQ ID NO 82
<211> LENGTH: 8
<212> TYPE: DNA
<213> ORGANISM: Artificial Sequence
<220> FEATURE:
<223> OTHER INFORMATION: note="Description of Artificial Sequence: Synthetic Oligonucleotide"

<400> SEQUENCE: 82 ttgggcgc                                                                8

<210> SEQ ID NO 83
<211> LENGTH: 8
<212> TYPE: DNA
<213> ORGANISM: Artificial Sequence
<220> FEATURE:
<223> OTHER INFORMATION: note="Description of Artificial Sequence: Synthetic Oligonucleotide"

<400> SEQUENCE: 83 tggctggg                                                                8

<210> SEQ ID NO 84
<211> LENGTH: 8
<212> TYPE: DNA
<213> ORGANISM: Artificial Sequence
<220> FEATURE:
<223> OTHER INFORMATION: note="Description of Artificial Sequence: Synthetic Oligonucleotide"

<400> SEQUENCE: 84 gtgtgttg                                                                8

<210> SEQ ID NO 85
<211> LENGTH: 8
<212> TYPE: DNA
<213> ORGANISM: Artificial Sequence
<220> FEATURE:
<223> OTHER INFORMATION: note="Description of Artificial Sequence: Synthetic Oligonucleotide"

<400> SEQUENCE: 85 ttggtttg                                                                8

<210> SEQ ID NO 86
<211> LENGTH: 8
<212> TYPE: DNA
<213> ORGANISM: Artificial Sequence
<220> FEATURE:
<223> OTHER INFORMATION: note="Description of Artificial Sequence: Synthetic Oligonucleotide"

<400> SEQUENCE: 86 ggggttgg                                                                8

<210> SEQ ID NO 87
<211> LENGTH: 8
<212> TYPE: DNA
<213> ORGANISM: Artificial Sequence
<220> FEATURE:
<223> OTHER INFORMATION: note="Description of Artificial Sequence: Synthetic Oligonucleotide"

<400> SEQUENCE: 87 tttttga                                                                 8

```
<210> SEQ ID NO 88
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 88 tttggggg                                                            8

<210> SEQ ID NO 89
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 89 gggtggcg                                                            8

<210> SEQ ID NO 90
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 90 cgttttta                                                            8

<210> SEQ ID NO 91
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 91 tgttgtta                                                            8

<210> SEQ ID NO 92
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 92 tttggggc                                                            8

<210> SEQ ID NO 93
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 93 ttcttta                                                             8
```

```
<210> SEQ ID NO 94
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 94 tggttcgc                                                              8

<210> SEQ ID NO 95
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 95 tttttttg                                                              8

<210> SEQ ID NO 96
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 96 cgtggtgc                                                              8

<210> SEQ ID NO 97
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 97 gggcgcga                                                              8

<210> SEQ ID NO 98
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 98 tggctggc                                                              8

<210> SEQ ID NO 99
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 99 gtgggtga                                                              8

<210> SEQ ID NO 100
```

```
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 100 tttttgcg                                                                  8

<210> SEQ ID NO 101
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 101 ggcggggg                                                                  8

<210> SEQ ID NO 102
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 102 tgtccttg                                                                  8

<210> SEQ ID NO 103
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 103 tggggggg                                                                  8

<210> SEQ ID NO 104
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 104 ggggtttg                                                                  8

<210> SEQ ID NO 105
<211> LENGTH: 8
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 105 ttggttta                                                                  8

<210> SEQ ID NO 106
<211> LENGTH: 8
```

```
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 106 ggggtgcc                                                                  8
```

MOLECULAR LABEL COUNTING ADJUSTMENT METHODS

RELATED APPLICATIONS

The present application claims priority under 35 U.S.C. § 119(e) to U.S. Provisional Application No. 62/342,137, filed on May 26, 2016; U.S. Provisional Application No. 62/381,945, filed on Aug. 31, 2016; and U.S. Provisional Application No. 62/401,720, filed on Sep. 29, 2016; the content of each is herein expressly incorporated by reference in its entirety.

BACKGROUND

Field

The present disclosure relates generally to the field of molecular barcoding and more particularly correcting PCR and sequencing errors using molecular labels.

Description of the Related Art

Methods and techniques such as stochastic barcoding are useful for cell analysis, in particular deciphering gene expression profiles to determine the states of cells using, for example, reverse transcription, polymerase chain reaction (PCR) amplification, and next generation sequencing (NGS). However, these methods and techniques can introduce errors such as substitution errors (including one or more bases) and non-substitution errors, if uncorrected, may result in over-estimated molecular counts. Thus, there is a need for methods and techniques capable of correcting various errors in order to attain accurate molecular counts estimated using stochastic barcoding.

SUMMARY

Disclosed herein are methods for determining the numbers of targets. In some embodiments, the method comprises: (a) stochastically barcoding a plurality of targets using a plurality of stochastic barcodes to create a plurality of stochastically barcoded targets, wherein each of the plurality of stochastic barcodes comprises a molecular label; (b) obtaining sequencing data of the stochastically barcoded targets; and (c) for one or more of the plurality of targets: (i) counting the number of molecular labels with distinct sequences associated with the target in the sequencing data; (ii) determining a quality status of the target in the sequencing data obtained in (b); (iii) determining one or more sequencing data errors in the sequencing data obtained in (b), wherein determining the one or more sequencing data errors in the sequencing data comprises determining one or more of: the number of the molecular labels with distinct sequences associated with the target in the sequencing data, the quality status of the target in the sequencing data, and the number of molecular labels with distinct sequences in the plurality of stochastic barcodes; and (iv) estimating the number of the target, wherein the number of the target estimated correlates with the number of molecular labels with distinct sequences associated with the target in the sequencing data counted in (i) adjusted according to the one or more sequencing data errors determined in (iii). Steps (i), (ii), (iii), and (iv) can be performed for each of the plurality of targets. The method can be multiplexed.

In some embodiments, the method further comprises: collapsing the sequencing data obtained in (b) prior to determining the one or more sequencing data errors. Collapsing the sequencing data obtained in (b) comprises: attributing copies of the target with similar molecular labels and with occurrences fewer than a predetermined collapsing occurrence threshold as having the same molecular label for the plurality of targets, wherein two copies of a target have similar molecular labels if the molecular labels of the two copies of the target differ by at least one base in sequence.

In some embodiments, the predetermined collapsing occurrence threshold can be 7 if the stochastic barcodes comprise about 6561 molecular labels with distinct sequences. The predetermined collapsing occurrence threshold can be 17 if the stochastic barcodes comprise about 65536 molecular labels with distinct sequences. Two copies of the target have similar molecular labels if the molecular labels of the two copies of the target differ by at least one base in sequence. In some embodiments, the molecular label comprises 5-20 nucleotides. The molecular labels of different stochastic barcodes can be different from one another. The plurality of stochastic barcodes comprises about 6561 molecular labels with distinct sequences. The plurality of stochastic barcodes comprises about 65536 molecular labels with distinct sequences.

In some embodiments the sequencing data comprises sequences of the plurality of targets with read lengths of 50 or more nucleotides. The sequencing data comprises sequences of the plurality of targets with read lengths of 75 or more nucleotides. The sequencing data comprises sequences of the plurality of targets with read lengths of 100 or more nucleotides. The sequencing data obtained in (b) can be generated by performing polymerase chain reaction (PCR) amplification on the plurality of stochastically barcoded targets.

In some embodiments, the one or more sequencing data errors can be a PCR-introduced error, a sequencing-introduced error, an error caused by barcode contamination, a library preparation error, or any combination thereof. The PCR-introduced error can be a result of a PCR amplification error, PCR amplification bias, insufficient PCR amplification, or any combination thereof. The sequencing-introduced error can be a result of inaccurate base calling, insufficient sequencing, or any combination thereof.

In some embodiments, the quality status of the target in the sequencing data can be complete sequencing, incomplete sequencing, or saturated sequencing. The quality status of the target in the sequencing data can be determined by the number of molecular labels with distinct sequences in the plurality of stochastic barcodes and the number of molecular labels with distinct sequences associated with the target in the sequencing data counted. The quality status of the target in the sequencing data can be classified as incomplete sequencing if the quality status of the target in the sequencing data obtained in (b) is not complete sequencing and not saturated sequencing.

In some embodiments, the complete sequencing quality status can be determined by a dispersion index relative to the Poisson distribution greater than or equal to a predetermined complete sequencing dispersion threshold, wherein the predetermined complete sequencing dispersion threshold can be 0.9, 1, or 4. The complete sequencing quality status can be further determined by a molecular label with an occurrence greater than or equal to a predetermined complete sequencing occurrence threshold in the sequencing data obtained in (b), wherein the predetermined complete sequencing occurrence threshold can be 10 or 18.

In some embodiments, the saturated sequencing quality status can be determined by the target having a number of molecular labels with distinct sequences been greater than a predetermined saturation threshold. The saturated sequencing quality status can be further determined by one other target of the plurality of targets having a number of molecular labels with distinct sequences to be greater than the predetermined saturation threshold. The predetermined saturation threshold can be 6557 if the stochastic barcodes comprise about 6561 molecular labels with distinct sequences. The predetermined saturation threshold can be 65532 if the stochastic barcodes comprise about 65536 molecular labels with distinct sequences.

In some embodiments, the number of molecular labels with distinct sequences associated with the target in the sequencing data counted in (i) is adjusted in (iv) by, if the target has the complete sequencing quality status, determining all children molecular labels for one or more parent molecular labels; performing a first statistical analysis for at least one child molecular label and the parent molecular label; and attributing the occurrence of the child molecular label to the parent molecular label if the null hypothesis of the first statistical analysis is accepted.

In some embodiments, the one or more parent molecular labels comprise molecular labels with occurrences greater than or equal to a predetermined complete sequencing parent threshold, wherein the predetermined complete sequencing parent threshold equals to the predetermined complete sequencing occurrence threshold. The children molecular labels comprise molecular labels that differ from the parent molecular label by one base and have occurrences smaller than or equal to a predetermined complete sequencing child threshold, wherein the predetermined complete sequencing child threshold can be 3 or 5. The null hypothesis of the first statistical analysis can be accepted if the probability of the null hypothesis being true is below the false discovery rates, wherein the false discovery rate is 5% or 10%. The first statistical analysis can be a multiple binomial test.

In some embodiments, the number of molecular labels with distinct sequences associated with the target in the sequencing data counted in (i) is adjusted in (iv) by, if the target has the complete sequencing quality status, thresholding molecular labels of the target to determine true molecular labels and false molecular labels associated with the target in the sequencing data obtained in (b). Thresholding the molecular labels of the target comprises performing a second statistical analysis on the molecular labels of the target.

In some embodiments, performing the second statistical analysis comprises: fitting the distribution of the molecular labels of the target and their occurrences to two Poisson distributions; determining the number of true molecular labels n using the two Poisson distributions; and removing the false molecular labels from the sequencing data obtained in (b), wherein the false molecular labels comprise molecular labels with occurrences lower than the occurrence of the nth most abundant molecular label, and wherein the true molecular labels comprise molecular labels with occurrences greater than or equal to the occurrence of the nth most abundant molecular label. The two Poisson distributions comprise a first Poisson distribution corresponding for the true molecular labels and a second Poisson distribution for the false molecular labels.

In some embodiments, the number of molecular labels with distinct sequences associated with the target in the sequencing data counted in (i) can be adjusted in (iv) by, if the quality status of the target in the sequencing data obtained in (b) is the incomplete sequencing quality status, determining if the target is noisy in the sequencing data obtained in (b); and removing the noisy target from the sequencing data obtained in (b). The target can be noisy if the occurrence of the molecular labels of the noisy targets is smaller than or equal to an incomplete sequencing noisy target threshold, wherein the incomplete sequencing noisy gene threshold is 5. The incomplete sequencing noisy target threshold can equal the median or mean occurrence of the molecular labels of the plurality of targets with quality statuses of complete sequencing.

In some embodiments, the number of molecular labels with distinct sequences associated with the target in the sequencing data counted in (i) can be adjusted in (iv) by, if the quality status of the target in the sequencing data obtained in (b) is the incomplete sequencing quality status, thresholding the molecular labels of the target to determine true molecular labels and false molecular labels in the sequencing data obtained in (b).

In some embodiments, thresholding the molecular labels of the target comprises performing a third statistical analysis on the molecular labels. Performing the third statistical analysis on the molecular labels comprises: determining the number of true molecular labels n using a Zero-Truncated Poisson model; and removing the false molecular labels from the sequencing data obtained in (b), wherein the false molecular labels comprise molecular labels with occurrences lower than the occurrence of the nth most abundant molecular label, and wherein the true molecular labels comprise molecular labels with occurrences greater than or equal to the occurrence of the nth most abundant molecular label.

In some embodiments, at least 50% or 80% of the molecular labels in the sequencing data obtained in (b) can be retained after the sequencing data counted in (i) is adjusted according to the one or more sequencing data errors determined in (iii).

In some embodiments, stochastically barcoding the plurality of targets comprises hybridizing the plurality of stochastic barcodes with the plurality of targets to create the stochastically barcoded targets. Stochastically barcoding the plurality of targets comprises generating an indexed library of the stochastically barcoded targets. Generating an indexed library of the stochastically barcoded targets can be performed with a solid support comprising the plurality of stochastic barcodes. The solid support comprises a plurality of synthetic particles associated with the plurality of stochastic barcodes. The solid support comprises the plurality of stochastic barcodes in two dimensions or three dimensions. The solid support comprises a polymer, a matrix, a hydrogel, a needle array device, an antibody, or any combination thereof.

In some embodiments, each of the plurality of stochastic barcodes comprises one or more of a sample label, a universal label and a cell label, wherein the sample label can be the same for the plurality of stochastic barcodes on the solid support, wherein universal labels are the same for the plurality of stochastic barcodes on the solid support and cell labels can be the same for the plurality of stochastic barcodes on the solid support. The sample label comprises 5-20 nucleotides. The universal label comprises 5-20 nucleotides. The cell label comprises 5-20 nucleotides.

In some embodiments, the synthetic particles can be beads. The beads can be silica gel beads, controlled pore glass beads, magnetic beads, Dynabeads, Sephadex/Sepharose beads, cellulose beads, polystyrene beads, or any combination thereof.

In some embodiments, the plurality of targets can be comprised in a sample. The sample comprises one or more cells. The sample can be a single cell. The one or more cells comprise one or more cell types. At least one of the one or more cell types is brain cell, heart cell, cancer cell, circulating tumor cell, organ cell, epithelial cell, metastatic cell, benign cell, primary cell, circulatory cell, or any combination thereof.

In some embodiments, the plurality of targets comprise ribonucleic acids (RNAs), messenger RNAs (mRNAs), microRNAs, small interfering RNAs (siRNAs), RNA degradation products, RNAs each comprising a poly(A) tail, or any combination thereof.

In some embodiments, the method can further comprise lysing the one or more cells. Lysing the one or more cells comprises heating the sample, contacting the sample with a detergent, changing the pH of the sample, or any combination thereof.

Disclosed herein are methods for determining the numbers of targets. In some embodiments, the method comprises: (a) stochastically barcoding a plurality of targets using a plurality of stochastic barcodes to create a plurality of stochastically barcoded targets, wherein each of the plurality of stochastic barcodes comprises a molecular label; (b) obtaining sequencing data of the stochastically barcoded targets; and (c) for one or more of the plurality of targets: (i) counting the number of molecular labels with distinct sequences associated with the target in the sequencing data; (ii) identifying clusters of molecular labels of the target using directional adjacency; (iii) collapsing the sequencing data obtained in (b) using the clusters of molecular labels of the target identified in (ii); and (iv) estimating the number of the target, wherein the number of the target estimated correlates with the number of molecular labels with distinct sequences associated with the target in the sequencing data counted in (i) after collapsing the sequencing data in (ii). The plurality of targets comprises targets of the whole transcriptome of a cell.

In some embodiments, molecular labels of the target within a cluster are within a predetermined directional adjacency threshold of one another. The directional adjacency threshold is a Hamming distance of one. The molecular labels of the target within the cluster comprise one or more parent molecular labels and children molecular labels of the one or more parent molecular labels, wherein the occurrence of the parent molecular label is greater than or equal to a predetermined directional adjacency occurrence threshold. The predetermined directional adjacency occurrence threshold can be twice the occurrence of a child molecular label less one.

In some embodiments, collapsing the sequencing data obtained in (b) using the clusters of molecular labels of the target identified in (ii) comprises: attributing the occurrence of the child molecular label to the parent molecular label.

In some embodiments, the method can further comprise: determining a sequencing depth of the target. Estimating the number of the target, if the sequencing depth of the target is above a predetermined sequencing depth threshold, comprises adjusting the sequencing data counted in (i). The predetermined sequencing depth threshold can be between 15 and 20. Adjusting the sequencing data counted in (i) comprises: thresholding molecular labels of the target to determine true molecular labels and false molecular labels associated with the target in the sequencing data obtained in (b). Thresholding the molecular labels of the target comprises performing a statistical analysis on the molecular labels of the target. Performing the statistical analysis comprises: fitting the distribution of the molecular labels of the target and their occurrences to two Poisson distributions; determining the number of true molecular labels n using the two Poisson distributions; and removing the false molecular labels from the sequencing data obtained in (b), wherein the false molecular labels comprise molecular labels with occurrences lower than the occurrence of the nth most abundant molecular label, and wherein the true molecular labels comprise molecular labels with occurrences greater than or equal to the occurrence of the nth most abundant molecular label.

Disclosed herein are computer systems for determining the number of targets. In some embodiments, the computer system comprises: a computer-readable memory storing executable instructions; and one or more computer processors in communication with the computer readable memory, wherein the one or more computer processors are programmed by the executable instructions to perform (a) stochastically barcoding a plurality of targets using a plurality of stochastic barcodes to create a plurality of stochastically barcoded targets, wherein each of the plurality of stochastic barcodes comprises a molecular label; (b) obtaining sequencing data of the stochastically barcoded targets; and (c) for one or more of the plurality of targets: (i) counting the number of molecular labels with distinct sequences associated with the target in the sequencing data; (ii) determining a quality status of the target in the sequencing data obtained in (b); (iii) determining one or more sequencing data errors in the sequencing data obtained in (b), wherein determining the one or more sequencing data errors in the sequencing data comprises determining one or more of: the number of the molecular labels with distinct sequences associated with the target in the sequencing data, the quality status of the target in the sequencing data, and the number of molecular labels with distinct sequences in the plurality of stochastic barcodes; and (iv) estimating the number of the target, wherein the number of the target estimated correlates with the number of molecular labels with distinct sequences associated with the target in the sequencing data counted in (i) adjusted according to the one or more sequencing data errors determined in (iii). Steps (i), (ii), (iii), and (iv) for each of the plurality of targets. The steps (a), (b), (c), (i), (ii), (iii), and (iv) can be multiplexed.

In some embodiments, the executable instructions can further program the one or more computer processors to perform: collapsing the sequencing data obtained in (b) prior to determining the one or more sequencing data errors. Collapsing the sequencing data obtained in (b) comprises: attributing copies of the target with similar molecular labels and with occurrences fewer than a predetermined collapsing occurrence threshold as having the same molecular label for the plurality of targets, wherein two copies of a target have similar molecular labels if the molecular labels of the two copies of the target differ by at least one base in sequence.

In some embodiments, the predetermined collapsing occurrence threshold can be 7 if the stochastic barcodes comprise about 6561 molecular labels with distinct sequences. The predetermined collapsing occurrence threshold can be 17 if the stochastic barcodes comprise about 65536 molecular labels with distinct sequences. Two copies of the target have similar molecular labels if the molecular labels of the two copies of the target differ by at least one base in sequence. In some embodiments, the molecular label comprises 5-20 nucleotides. The molecular labels of different stochastic barcodes can be different from one another. The plurality of stochastic barcodes comprises about 6561 molecular labels with distinct sequences. The plurality of stochastic barcodes comprises about 65536 molecular labels with distinct sequences.

In some embodiments the sequencing data comprises sequences of the plurality of targets with read lengths of 50 or more nucleotides. The sequencing data comprises sequences of the plurality of targets with read lengths of 75 or more nucleotides. The sequencing data comprises sequences of the plurality of targets with read lengths of 100 or more nucleotides. The sequencing data obtained in (b) can be generated by performing polymerase chain reaction (PCR) amplification on the plurality of stochastically barcoded targets.

In some embodiments, the one or more sequencing data errors can be a PCR-introduced error, a sequencing-introduced error, an error caused by barcode contamination, a library preparation error, or any combination thereof. The PCR-introduced error can be a result of a PCR amplification error, PCR amplification bias, insufficient PCR amplification, or any combination thereof. The sequencing-introduced error can be a result of inaccurate base calling, insufficient sequencing, or any combination thereof.

In some embodiments, the executable instructions can further program the one or more computer processors to determine the quality status of the target in the sequencing data to be complete sequencing, incomplete sequencing, or saturated sequencing. The quality status of the target in the sequencing data can be determined by the number of molecular labels with distinct sequences in the plurality of stochastic barcodes and the number of molecular labels with distinct sequences associated with the target in the sequencing data counted. The quality status of the target in the sequencing data can be classified as incomplete sequencing if the quality status of the target in the sequencing data obtained in (b) is not complete sequencing and not saturated sequencing.

In some embodiments, the executable instructions can further program the one or more computer processors to determine the complete sequencing quality status by a dispersion index relative to the Poisson distribution greater than or equal to a predetermined complete sequencing dispersion threshold, wherein the predetermined complete sequencing dispersion threshold can be 0.9, 1, or 4. The complete sequencing quality status can be further determined by a molecular label with an occurrence greater than or equal to a predetermined complete sequencing occurrence threshold in the sequencing data obtained in (b), wherein the predetermined complete sequencing occurrence threshold can be 10 or 18.

In some embodiments, the executable instructions can further program the one or more computer processors to determine the saturated sequencing quality status by the target having a number of molecular labels with distinct sequences been greater than a predetermined saturation threshold. The saturated sequencing quality status can be further determined by one other target of the plurality of targets having a number of molecular labels with distinct sequences to be greater than the predetermined saturation threshold. The predetermined saturation threshold can be 6557 if the stochastic barcodes comprise about 6561 molecular labels with distinct sequences. The predetermined saturation threshold can be 65532 if the stochastic barcodes comprise about 65536 molecular labels with distinct sequences.

In some embodiments, the executable instructions can further program the one or more computer processors to adjust in (iv) the number of molecular labels with distinct sequences associated with the target in the sequencing data counted in (i) by, if the target has the complete sequencing quality status, determining all children molecular labels for one or more parent molecular labels; performing a first statistical analysis for at least one child molecular label and the parent molecular label; and attributing the occurrence of the child molecular label to the parent molecular label if the null hypothesis of the first statistical analysis is accepted.

In some embodiments, the one or more parent molecular labels comprise molecular labels with occurrences greater than or equal to a predetermined complete sequencing parent threshold, wherein the predetermined complete sequencing parent threshold equals to the predetermined complete sequencing occurrence threshold. The children molecular labels comprise molecular labels that differ from the parent molecular label by one base and have occurrences smaller than or equal to a predetermined complete sequencing child threshold, wherein the predetermined complete sequencing child threshold can be 3 or 5. The null hypothesis of the first statistical analysis can be accepted if the probability of the null hypothesis being true is below the false discovery rates, wherein the false discovery rate is 5% or 10%. The first statistical analysis can be a multiple binomial test.

In some embodiments, the executable instructions can further program the one or more computer processors to adjust in (iv) the number of molecular labels with distinct sequences associated with the target in the sequencing data counted in (i) by, if the target has the complete sequencing quality status, thresholding molecular labels of the target to determine true molecular labels and false molecular labels associated with the target in the sequencing data obtained in (b). Thresholding the molecular labels of the target comprises performing a second statistical analysis on the molecular labels of the target.

In some embodiments, the executable instructions can further program the one or more computer processors to perform the second statistical analysis by: fitting the distribution of the molecular labels of the target and their occurrences to two Poisson distributions; determining the number of true molecular labels n using the two Poisson distributions; and removing the false molecular labels from the sequencing data obtained in (b), wherein the false molecular labels comprise molecular labels with occurrences lower than the occurrence of the nth most abundant molecular label, and wherein the true molecular labels comprise molecular labels with occurrences greater than or equal to the occurrence of the nth most abundant molecular label. The two Poisson distributions comprise a first Poisson distribution corresponding for the true molecular labels and a second Poisson distribution for the false molecular labels.

In some embodiments, the executable instructions can further program the one or more computer processors to adjust in (iv) the number of molecular labels with distinct sequences associated with the target in the sequencing data counted in (i) by, if the quality status of the target in the sequencing data obtained in (b) is the incomplete sequencing quality status, determining if the target is noisy in the sequencing data obtained in (b); and removing the noisy target from the sequencing data obtained in (b). The target can be noisy if the occurrence of the molecular labels of the noisy targets is smaller than or equal to an incomplete sequencing noisy target threshold, wherein the incomplete sequencing noisy gene threshold is 5. The incomplete sequencing noisy target threshold can equal the median or mean occurrence of the molecular labels of the plurality of targets with quality statuses of complete sequencing.

In some embodiments, the executable instructions can further program the one or more computer processors to adjust in (iv) the number of molecular labels with distinct sequences associated with the target in the sequencing data counted in (i) by, if the quality status of the target in the sequencing data obtained in (b) is the incomplete sequencing quality status, thresholding the molecular labels of the target to determine true molecular labels and false molecular labels in the sequencing data obtained in (b).

In some embodiments, the executable instructions can further program the one or more computer processors to threshold the molecular labels of the target by performing a third statistical analysis on the molecular labels. Performing the third statistical analysis on the molecular labels comprises: determining the number of true molecular labels n using a Zero-Truncated Poisson model; and removing the false molecular labels from the sequencing data obtained in (b), wherein the false molecular labels comprise molecular labels with occurrences lower than the occurrence of the nth most abundant molecular label, and wherein the true molecular labels comprise molecular labels with occurrences greater than or equal to the occurrence of the nth most abundant molecular label.

In some embodiments, at least 50% or 80% of the molecular labels in the sequencing data obtained in (b) can be retained after the sequencing data counted in (i) is adjusted according to the one or more sequencing data errors determined in (iii).

Disclosed herein are computer systems for determining the number of targets. In some embodiments, the computer system comprises: a computer-readable memory storing executable instructions; and one or more computer processors in communication with the computer readable memory, wherein the one or more computer processors are programmed by the executable instructions to perform: (a) stochastically barcoding a plurality of targets using a plurality of stochastic barcodes to create a plurality of stochastically barcoded targets, wherein each of the plurality of stochastic barcodes comprises a molecular label; (b) obtaining sequencing data of the stochastically barcoded targets; and (c) for one or more of the plurality of targets: (i) counting the number of molecular labels with distinct sequences associated with the target in the sequencing data; (ii) identifying clusters of molecular labels of the target using directional adjacency; (iii) collapsing the sequencing data obtained in (b) using the clusters of molecular labels of the target identified in (ii); and (iv) estimating the number of the target, wherein the number of the target estimated correlates with the number of molecular labels with distinct sequences associated with the target in the sequencing data counted in (i) after collapsing the sequencing data in (ii). The plurality of targets comprises targets of the whole transcriptome of a cell.

In some embodiments, molecular labels of the target within a cluster are within a predetermined directional adjacency threshold of one another. The directional adjacency threshold is a Hamming distance of one. The molecular labels of the target within the cluster comprise one or more parent molecular labels and children molecular labels of the one or more parent molecular labels, wherein the occurrence of the parent molecular label is greater than or equal to a predetermined directional adjacency occurrence threshold. The predetermined directional adjacency occurrence threshold can be twice the occurrence of a child molecular label less one.

In some embodiments, collapsing the sequencing data obtained in (b) using the clusters of molecular labels of the target identified in (ii) comprises: attributing the occurrence of the child molecular label to the parent molecular label.

In some embodiments, the executable instructions can further program the one or more computer processors to: determining a sequencing depth of the target. Estimating the number of the target, if the sequencing depth of the target is above a predetermined sequencing depth threshold, comprises adjusting the sequencing data counted in (i). The predetermined sequencing depth threshold can be between 15 and 20. Adjusting the sequencing data counted in (i) comprises: thresholding molecular labels of the target to determine true molecular labels and false molecular labels associated with the target in the sequencing data obtained in (b). Thresholding the molecular labels of the target comprises performing a statistical analysis on the molecular labels of the target. Performing the statistical analysis comprises: fitting the distribution of the molecular labels of the target and their occurrences to two Poisson distributions; determining the number of true molecular labels n using the two Poisson distributions; and removing the false molecular labels from the sequencing data obtained in (b), wherein the false molecular labels comprise molecular labels with occurrences lower than the occurrence of the nth most abundant molecular label, and wherein the true molecular labels comprise molecular labels with occurrences greater than or equal to the occurrence of the nth most abundant molecular label.

Disclosed herein are one or more non-transitory computer readable media comprising executable codes that, when executed, cause one or more computing devices to determine the number of targets. In some embodiments, the executable codes, when executed, cause the one or more computing devices to perform a process comprising: (a) stochastically barcoding a plurality of targets using a plurality of stochastic barcodes to create a plurality of stochastically barcoded targets, wherein each of the plurality of stochastic barcodes comprises a molecular label; (b) obtaining sequencing data of the stochastically barcoded targets; and (c) for one or more of the plurality of targets: (i) counting the number of molecular labels with distinct sequences associated with the target in the sequencing data; (ii) determining a quality status of the target in the sequencing data obtained in (b); (iii) determining one or more sequencing data errors in the sequencing data obtained in (b), wherein determining the one or more sequencing data errors in the sequencing data comprises determining one or more of: the number of the molecular labels with distinct sequences associated with the target in the sequencing data, the quality status of the target in the sequencing data, and the number of molecular labels with distinct sequences in the plurality of stochastic barcodes; and (iv) estimating the number of the target, wherein the number of the target estimated correlates with the number of molecular labels with distinct sequences associated with the target in the sequencing data counted in (i) adjusted according to the one or more sequencing data errors determined in (iii). Steps (i), (ii), (iii), and (iv) can be performed for each of the plurality of targets. The method can be multiplexed.

In some embodiments, the process further comprises: collapsing the sequencing data obtained in (b) prior to determining the one or more sequencing data errors. Collapsing the sequencing data obtained in (b) comprises: attributing copies of the target with similar molecular labels and with occurrences fewer than a predetermined collapsing occurrence threshold as having the same molecular label for the plurality of targets, wherein two copies of a target have similar molecular labels if the molecular labels of the two copies of the target differ by at least one base in sequence.

In some embodiments, the predetermined collapsing occurrence threshold can be 7 if the stochastic barcodes comprise about 6561 molecular labels with distinct sequences. The predetermined collapsing occurrence threshold can be 17 if the stochastic barcodes comprise about 65536 molecular labels with distinct sequences. Two copies of the target have similar molecular labels if the molecular labels of the two copies of the target differ by at least one base in sequence. In some embodiments, the molecular label comprises 5-20 nucleotides. The molecular labels of different stochastic barcodes can be different from one another. The plurality of stochastic barcodes comprises about 6561 molecular labels with distinct sequences. The plurality of stochastic barcodes comprises about 65536 molecular labels with distinct sequences.

In some embodiments the sequencing data comprises sequences of the plurality of targets with read lengths of 50 or more nucleotides. The sequencing data comprises sequences of the plurality of targets with read lengths of 75 or more nucleotides. The sequencing data comprises sequences of the plurality of targets with read lengths of 100 or more nucleotides. The sequencing data obtained in (b) can be generated by performing polymerase chain reaction (PCR) amplification on the plurality of stochastically barcoded targets.

In some embodiments, the one or more sequencing data errors can be a PCR-introduced error, a sequencing-introduced error, an error caused by barcode contamination, a library preparation error, or any combination thereof. The PCR-introduced error can be a result of a PCR amplification error, PCR amplification bias, insufficient PCR amplification, or any combination thereof. The sequencing-introduced error can be a result of inaccurate base calling, insufficient sequencing, or any combination thereof.

In some embodiments, the quality status of the target in the sequencing data can be complete sequencing, incomplete sequencing, or saturated sequencing. The quality status of the target in the sequencing data can be determined by the number of molecular labels with distinct sequences in the plurality of stochastic barcodes and the number of molecular labels with distinct sequences associated with the target in the sequencing data counted. The quality status of the target in the sequencing data can be classified as incomplete sequencing if the quality status of the target in the sequencing data obtained in (b) is not complete sequencing and not saturated sequencing.

In some embodiments, the complete sequencing quality status can be determined by a dispersion index relative to the Poisson distribution greater than or equal to a predetermined complete sequencing dispersion threshold, wherein the predetermined complete sequencing dispersion threshold can be 0.9, 1, or 4. The complete sequencing quality status can be further determined by a molecular label with an occurrence greater than or equal to a predetermined complete sequencing occurrence threshold in the sequencing data obtained in (b), wherein the predetermined complete sequencing occurrence threshold can be 10 or 18.

In some embodiments, the saturated sequencing quality status can be determined by the target having a number of molecular labels with distinct sequences been greater than a predetermined saturation threshold. The saturated sequencing quality status can be further determined by one other target of the plurality of targets having a number of molecular labels with distinct sequences to be greater than the predetermined saturation threshold. The predetermined saturation threshold can be 6557 if the stochastic barcodes comprise about 6561 molecular labels with distinct sequences. The predetermined saturation threshold can be 65532 if the stochastic barcodes comprise about 65536 molecular labels with distinct sequences.

In some embodiments, the number of molecular labels with distinct sequences associated with the target in the sequencing data counted in (i) is adjusted in (iv) by, if the target has the complete sequencing quality status, determining all children molecular labels for one or more parent molecular labels; performing a first statistical analysis for at least one child molecular label and the parent molecular label; and attributing the occurrence of the child molecular label to the parent molecular label if the null hypothesis of the first statistical analysis is accepted.

In some embodiments, the one or more parent molecular labels comprise molecular labels with occurrences greater than or equal to a predetermined complete sequencing parent threshold, wherein the predetermined complete sequencing parent threshold equals to the predetermined complete sequencing occurrence threshold. The children molecular labels comprise molecular labels that differ from the parent molecular label by one base and have occurrences smaller than or equal to a predetermined complete sequencing child threshold, wherein the predetermined complete sequencing child threshold can be 3 or 5. The null hypothesis of the first statistical analysis can be accepted if the probability of the null hypothesis being true is below the false discovery rates, wherein the false discovery rate is 5% or 10%. The first statistical analysis can be a multiple binomial test.

In some embodiments, the number of molecular labels with distinct sequences associated with the target in the sequencing data counted in (i) is adjusted in (iv) by, if the target has the complete sequencing quality status, thresholding molecular labels of the target to determine true molecular labels and false molecular labels associated with the target in the sequencing data obtained in (b). Thresholding the molecular labels of the target comprises performing a second statistical analysis on the molecular labels of the target.

In some embodiments, performing the second statistical analysis comprises: fitting the distribution of the molecular labels of the target and their occurrences to two Poisson distributions; determining the number of true molecular labels n using the two Poisson distributions; and removing the false molecular labels from the sequencing data obtained in (b), wherein the false molecular labels comprise molecular labels with occurrences lower than the occurrence of the nth most abundant molecular label, and wherein the true molecular labels comprise molecular labels with occurrences greater than or equal to the occurrence of the nth most abundant molecular label. The two Poisson distributions comprise a first Poisson distribution corresponding for the true molecular labels and a second Poisson distribution for the false molecular labels.

In some embodiments, the number of molecular labels with distinct sequences associated with the target in the sequencing data counted in (i) can be adjusted in (iv) by, if the quality status of the target in the sequencing data obtained in (b) is the incomplete sequencing quality status, determining if the target is noisy in the sequencing data obtained in (b); and removing the noisy target from the sequencing data obtained in (b). The target can be noisy if the occurrence of the molecular labels of the noisy targets is smaller than or equal to an incomplete sequencing noisy target threshold, wherein the incomplete sequencing noisy gene threshold is 5. The incomplete sequencing noisy target threshold can equal the median or mean occurrence of the molecular labels of the plurality of targets with quality statuses of complete sequencing.

In some embodiments, the number of molecular labels with distinct sequences associated with the target in the sequencing data counted in (i) can be adjusted in (iv) by, if the quality status of the target in the sequencing data obtained in (b) is the incomplete sequencing quality status, thresholding the molecular labels of the target to determine true molecular labels and false molecular labels in the sequencing data obtained in (b).

In some embodiments, thresholding the molecular labels of the target comprises performing a third statistical analysis on the molecular labels. Performing the third statistical analysis on the molecular labels comprises: determining the number of true molecular labels n using a Zero-Truncated Poisson model; and removing the false molecular labels from the sequencing data obtained in (b), wherein the false molecular labels comprise molecular labels with occurrences lower than the occurrence of the nth most abundant molecular label, and wherein the true molecular labels comprise molecular labels with occurrences greater than or equal to the occurrence of the nth most abundant molecular label.

In some embodiments, at least 50% or 80% of the molecular labels in the sequencing data obtained in (b) can be retained after the sequencing data counted in (i) is adjusted according to the one or more sequencing data errors determined in (iii).

Disclosed herein are herein are one or more non-transitory computer readable media comprising executable codes that, when executed, cause one or more computing devices to determine the number of targets. In some embodiments, the executable codes, when executed, cause the one or more computing devices to perform a process comprising: (a) stochastically barcoding a plurality of targets using a plurality of stochastic barcodes to create a plurality of stochastically barcoded targets, wherein each of the plurality of stochastic barcodes comprises a molecular label; (b) obtaining sequencing data of the stochastically barcoded targets; and (c) for one or more of the plurality of targets: (i) counting the number of molecular labels with distinct sequences associated with the target in the sequencing data; (ii) identifying clusters of molecular labels of the target using directional adjacency; (iii) collapsing the sequencing data obtained in (b) using the clusters of molecular labels of the target identified in (ii); and (iv) estimating the number of the target, wherein the number of the target estimated correlates with the number of molecular labels with distinct sequences associated with the target in the sequencing data counted in (i) after collapsing the sequencing data in (ii). The plurality of targets comprises targets of the whole transcriptome of a cell.

In some embodiments, molecular labels of the target within a cluster are within a predetermined directional adjacency threshold of one another. The directional adjacency threshold is a Hamming distance of one. The molecular labels of the target within the cluster comprise one or more parent molecular labels and children molecular labels of the one or more parent molecular labels, wherein the occurrence of the parent molecular label is greater than or equal to a predetermined directional adjacency occurrence threshold. The predetermined directional adjacency occurrence threshold can be twice the occurrence of a child molecular label less one.

In some embodiments, collapsing the sequencing data obtained in (b) using the clusters of molecular labels of the target identified in (ii) comprises: attributing the occurrence of the child molecular label to the parent molecular label.

In some embodiments, the method can further comprise: determining a sequencing depth of the target. Estimating the number of the target, if the sequencing depth of the target is above a predetermined sequencing depth threshold, comprises adjusting the sequencing data counted in (i). The predetermined sequencing depth threshold can be between 15 and 20. Adjusting the sequencing data counted in (i) comprises: thresholding molecular labels of the target to determine true molecular labels and false molecular labels associated with the target in the sequencing data obtained in (b). Thresholding the molecular labels of the target comprises performing a statistical analysis on the molecular labels of the target. Performing the statistical analysis comprises: fitting the distribution of the molecular labels of the target and their occurrences to two Poisson distributions; determining the number of true molecular labels n using the two Poisson distributions; and removing the false molecular labels from the sequencing data obtained in (b), wherein the false molecular labels comprise molecular labels with occurrences lower than the occurrence of the nth most abundant molecular label, and wherein the true molecular labels comprise molecular labels with occurrences greater than or equal to the occurrence of the nth most abundant molecular label.

Disclosed herein are methods for correcting PCR or sequencing errors. In some embodiments, the method can comprise: (a) obtaining sequencing data of the stochastically barcoded targets; and (b) for one or more of the plurality of targets: (i) counting the number of molecular labels with distinct sequences associated with the target in the sequencing data; (ii) identifying clusters of molecular labels of the target using directional adjacency; (iii) collapsing the sequencing data obtained in (a) using the clusters of molecular labels of the target identified in (ii); and (iv) estimating the number of the target, wherein the number of the target estimated correlates with the number of molecular labels with distinct sequences associated with the target in the sequencing data counted in (i) after collapsing the sequencing data in (ii). The plurality of targets comprises targets of the whole transcriptome of a cell. In some embodiments, the method can be used to determine the number of targets. The method can further comprise (c) stochastically barcoding the plurality of targets using the plurality of stochastic barcodes to create the plurality of stochastically barcoded targets; and (d) sequencing the stochastically barcoded targets to generate the sequencing data of stochastically barcoded targets received.

In some embodiments, molecular labels of the target within a cluster are within a predetermined directional adjacency threshold of one another. The directional adjacency threshold is a Hamming distance of one. The molecular labels of the target within the cluster comprise one or more parent molecular labels and children molecular labels of the one or more parent molecular labels, wherein the occurrence of the parent molecular label is greater than or equal to a predetermined directional adjacency occurrence threshold. The predetermined directional adjacency occurrence threshold can be twice the occurrence of a child molecular label less one.

In some embodiments, collapsing the sequencing data obtained in (b) using the clusters of molecular labels of the target identified in (ii) comprises: attributing the occurrence of the child molecular label to the parent molecular label.

In some embodiments, the method further comprises: determining a sequencing depth of the target. Estimating the number of the target, if the sequencing depth of the target is above a predetermined sequencing depth threshold, comprises adjusting the sequencing data counted in (i). The predetermined sequencing depth threshold can be between 15 and 20. Adjusting the sequencing data counted in (i)

comprises: thresholding molecular labels of the target to determine true molecular labels and false molecular labels associated with the target in the sequencing data obtained in (b). Thresholding the molecular labels of the target comprises performing a statistical analysis on the molecular labels of the target. Performing the statistical analysis comprises: fitting the distribution of the molecular labels of the target and their occurrences to two negative binomial distributions; determining the number of true molecular labels n using the two negative binomial distributions; and removing the false molecular labels from the sequencing data obtained in (b), wherein the false molecular labels comprise molecular labels with occurrences lower than the occurrence of the nth most abundant molecular label, and wherein the true molecular labels comprise molecular labels with occurrences greater than or equal to the occurrence of the nth most abundant molecular label.

Disclosed herein are computer systems for determining the number of targets. In some embodiments, the computer system comprises: a computer-readable memory storing executable instructions; and one or more computer processors in communication with the computer readable memory, wherein the one or more computer processors are programmed by the executable instructions to perform: (a) stochastically barcoding a plurality of targets using a plurality of stochastic barcodes to create a plurality of stochastically barcoded targets, wherein each of the plurality of stochastic barcodes comprises a molecular label; (b) obtaining sequencing data of the stochastically barcoded targets; and (c) for one or more of the plurality of targets: (i) counting the number of molecular labels with distinct sequences associated with the target in the sequencing data; (ii) identifying clusters of molecular labels of the target using directional adjacency; (iii) collapsing the sequencing data obtained in (b) using the clusters of molecular labels of the target identified in (ii); and (iv) estimating the number of the target, wherein the number of the target estimated correlates with the number of molecular labels with distinct sequences associated with the target in the sequencing data counted in (i) after collapsing the sequencing data in (ii). The plurality of targets comprises targets of the whole transcriptome of a cell.

In some embodiments, molecular labels of the target within a cluster are within a predetermined directional adjacency threshold of one another. The directional adjacency threshold is a Hamming distance of one. The molecular labels of the target within the cluster comprise one or more parent molecular labels and children molecular labels of the one or more parent molecular labels, wherein the occurrence of the parent molecular label is greater than or equal to a predetermined directional adjacency occurrence threshold. The predetermined directional adjacency occurrence threshold can be twice the occurrence of a child molecular label less one.

In some embodiments, collapsing the sequencing data obtained in (b) using the clusters of molecular labels of the target identified in (ii) comprises: attributing the occurrence of the child molecular label to the parent molecular label.

In some embodiments, the executable instructions further program the one or more computer processors to: determining a sequencing depth of the target. Estimating the number of the target, if the sequencing depth of the target is above a predetermined sequencing depth threshold, comprises adjusting the sequencing data counted in (i). The predetermined sequencing depth threshold can be between 15 and 20. Adjusting the sequencing data counted in (i) comprises: thresholding molecular labels of the target to determine true molecular labels and false molecular labels associated with the target in the sequencing data obtained in (b). Thresholding the molecular labels of the target comprises performing a statistical analysis on the molecular labels of the target. Performing the statistical analysis comprises: fitting the distribution of the molecular labels of the target and their occurrences to two negative binomial distributions; determining the number of true molecular labels n using the two negative binomial distributions; and removing the false molecular labels from the sequencing data obtained in (b), wherein the false molecular labels comprise molecular labels with occurrences lower than the occurrence of the nth most abundant molecular label, and wherein the true molecular labels comprise molecular labels with occurrences greater than or equal to the occurrence of the nth most abundant molecular label.

Disclosed herein are methods for correcting PCR or sequencing errors. In some embodiments, the method comprises: (a) obtaining sequencing data of the stochastically barcoded targets; and (b) for one or more of the plurality of targets: (i) counting the number of molecular labels with distinct sequences associated with the target in the sequencing data; (ii) determining a number of noise molecular labels with distinct sequences associated with the target in the sequencing data; and (iii) estimating the number of the target, wherein the number of the target estimated correlates with the number of molecular labels with distinct sequences associated with the target in the sequencing data counted in (i) adjusted according to the number of noise molecular labels determined in (ii). In some embodiments, the method further comprises determining a sequencing status of the target in the sequencing data. The sequencing status of the target in the sequencing data is saturated sequencing, under sequencing, or over sequencing. In some embodiments, the method can be used to determine the number of targets. The method can further comprise (c) stochastically barcoding the plurality of targets using the plurality of stochastic barcodes to create the plurality of stochastically barcoded targets; and (d) sequencing the stochastically barcoded targets to generate the sequencing data of stochastically barcoded targets received.

In some embodiments, the saturated sequencing status is determined by the target having a number of molecular labels with distinct sequences greater than a predetermined saturation threshold. The predetermined saturation threshold is about 6557 if the stochastic barcodes comprise about 6561 molecular labels with distinct sequences. The predetermined saturation threshold is about 65532 if the stochastic barcodes comprise about 65536 molecular labels with distinct sequences. If the sequencing status of the target in the sequencing data is the saturated sequencing status, the number of noise molecular labels determined in (ii) is zero.

In some embodiments, the under sequencing status can be determined by the target having a depth (e.g., an average, a minimum, or a maximum depth) smaller than a predetermined under sequencing threshold. The under sequencing threshold is about four. The under sequencing threshold can be independent of the number molecular labels with distinct sequences. If the sequencing status of the target in the sequencing data is the under sequencing status, the number of noise molecular labels determined in (ii) is zero.

In some embodiments, the over sequencing status is determined by the target having a number of molecular labels with distinct sequences greater than a predetermined over sequencing threshold. For example, the over sequencing threshold can be about 250 if the stochastic barcodes comprise about 6561 molecular labels with distinct sequences. The method comprises, if the sequencing status of the target in the sequencing data is the over sequencing status: subsampling the number of molecular labels with distinct sequences associated with the target in the sequencing data to about the predetermined over sequencing threshold.

In some embodiments, determining the number of noise molecular labels with distinct sequences associated with the target in the sequencing data comprises: if a negative binomial distribution fitting condition is satisfied, (iv) fitting a signal negative binomial distribution to the number of molecular labels with distinct sequences associated with the target in the sequencing data counted in (i), wherein the signal negative binomial distribution corresponds to a number of molecular labels with distinct sequences associated with the target in the sequencing data counted in (i) being signal molecular labels; (v) fitting a noise negative binomial distribution to the number of molecular labels with distinct sequences associated with the target in the sequencing data counted in (i), wherein the noise negative binomial distribution corresponds to a number of molecular labels with distinct sequences associated with the target in the sequencing data counted in (i) being noise molecular labels; and (vi) determining the number of noise molecular labels using the signal negative binomial distribution fitted in (v) and the noise negative binomial distribution fitted in (vi).

In some embodiments, the negative binomial distribution fitting condition comprises: the sequencing status of the target in the sequencing data is not the under sequencing status or the over sequencing status. Determining the number of noise molecular labels using the signal negative binomial distribution fitted in (v) and the noise negative binomial distribution fitted in (vi) comprises: for each of the distinct sequences associated with the target in the sequencing data: determining a signal probability of the distinct sequence to be in the signal negative binomial distribution; determining a noise probability of the distinct sequence to be in the noise negative binomial distribution; and determining the distinct sequence to be a noise molecular label if the signal probability is smaller than the noise probability.

In some embodiments, determining the number of noise molecular labels with distinct sequences associated with the target in the sequencing data comprises: adding pseudopoints to the number of molecular labels with distinct sequences associated with the target in the sequencing data prior to determining the number of noise molecular labels with distinct sequences associated with the target in the sequencing data in (ii), if the sequencing status of the target in the sequencing data is not the under sequencing status or the over sequencing status and the number of molecular labels with distinct sequences associated with the target in the sequencing data counted in (i) is less than a pseudopoints threshold. The pseudopoints threshold is ten.

In some embodiments, determining the number of noise molecular labels with distinct sequences associated with the target in the sequencing data comprises: removing non-unique molecular labels when determining the number of noise molecular labels with distinct sequences associated with the target in the sequencing data in (ii), if the sequencing status of the target in the sequencing data is not the under sequencing status or the over sequencing status and the number of molecular labels with distinct sequences associated with the target in the sequencing data counted in (i) is not less than a pseudopoints threshold.

In some embodiments, removing the non-unique molecular labels comprises removing the non-unique molecular labels when determining the number of noise molecular labels with distinct sequences associated with the target in the sequencing data in (ii) if the number of molecular labels with distinct sequences associated with the target in the sequencing data is greater than a predetermined recycled molecular label threshold. For example, the recycled molecular label threshold can be about 650 if the stochastic barcodes comprise about 6561 molecular labels with distinct sequences.

In some embodiments, removing the non-unique molecular labels comprises: determining a theoretical number of non-unique molecular labels for the number of molecular labels with distinct sequences associated with the target in the sequencing data; and removing a molecular label with an occurrence greater than the nth most abundant molecular label of the molecular labels with distinct sequences associated with the target in the sequencing data, wherein n is the theoretical number of non-unique molecular labels.

Disclosed herein are computer systems for determining the number of targets. In some embodiments, the computer system comprises: a computer-readable memory storing executable instructions; and one or more computer processors in communication with the computer readable memory, wherein the one or more computer processors are programmed by the executable instructions to perform: (a) stochastically barcoding a plurality of targets using a plurality of stochastic barcodes to create a plurality of stochastically barcoded targets, wherein each of the plurality of stochastic barcodes comprises a molecular label; (b) obtaining sequencing data of the stochastically barcoded targets; and (c) for one or more of the plurality of targets: (i) counting the number of molecular labels with distinct sequences associated with the target in the sequencing data; (ii) determining a number of noise molecular labels with distinct sequences associated with the target in the sequencing data; and (iii) estimating the number of the target, wherein the number of the target estimated correlates with the number of molecular labels with distinct sequences associated with the target in the sequencing data counted in (i) adjusted according to the number of noise molecular labels determined in (ii). In some embodiments, the method further comprises determining a sequencing status of the target in the sequencing data. The sequencing status of the target in the sequencing data is saturated sequencing, under sequencing, or over sequencing.

In some embodiments, the saturated sequencing status is determined by the target having a number of molecular labels with distinct sequences greater than a predetermined saturation threshold. For example, the predetermined saturation threshold can be about 6557 if the stochastic barcodes comprise about 6561 molecular labels with distinct sequences. The predetermined saturation threshold can be about 65532 if the stochastic barcodes comprise about 65536 molecular labels with distinct sequences. If the sequencing status of the target in the sequencing data is the saturated sequencing status, the number of noise molecular labels determined in (ii) is zero.

In some embodiments, the under sequencing status can be determined by the target having a depth (e.g., an average, a minimum, or a maximum depth) smaller than a predetermined under sequencing threshold. The under sequencing threshold is about four. The under sequencing threshold can be independent of the number molecular labels with distinct sequences. If the sequencing status of the target in the sequencing data is the under sequencing status, the number of noise molecular labels determined in (ii) is zero.

In some embodiments, the over sequencing status is determined by the target having a number of molecular labels with distinct sequences greater than a predetermined over sequencing threshold. For example, the over sequencing threshold can be about 250 if the stochastic barcodes comprise about 6561 molecular labels with distinct sequences. The method comprises, if the sequencing status of the target in the sequencing data is the over sequencing status: subsampling the number of molecular labels with distinct sequences associated with the target in the sequencing data to about the predetermined over sequencing threshold.

In some embodiments, determining the number of noise molecular labels with distinct sequences associated with the target in the sequencing data comprises: if a negative binomial distribution fitting condition is satisfied, (iv) fitting a signal negative binomial distribution to the number of molecular labels with distinct sequences associated with the target in the sequencing data counted in (i), wherein the signal negative binomial distribution corresponds to a number of molecular labels with distinct sequences associated with the target in the sequencing data counted in (i) being signal molecular labels; (v) fitting a noise negative binomial distribution to the number of molecular labels with distinct sequences associated with the target in the sequencing data counted in (i), wherein the noise negative binomial distribution corresponds to a number of molecular labels with distinct sequences associated with the target in the sequencing data counted in (i) being noise molecular labels; and (vi) determining the number of noise molecular labels using the signal negative binomial distribution fitted in (v) and the noise negative binomial distribution fitted in (vi).

In some embodiments, the negative binomial distribution fitting condition comprises: the sequencing status of the target in the sequencing data is not the under sequencing status or the over sequencing status. Determining the number of noise molecular labels using the signal negative binomial distribution fitted in (v) and the noise negative binomial distribution fitted in (vi) comprises: for each of the distinct sequences associated with the target in the sequencing data: determining a signal probability of the distinct sequence to be in the signal negative binomial distribution; determining a noise probability of the distinct sequence to be in the noise negative binomial distribution; and determining the distinct sequence to be a noise molecular label if the signal probability is smaller than the noise probability.

In some embodiments, determining the number of noise molecular labels with distinct sequences associated with the target in the sequencing data comprises: adding pseudopoints to the number of molecular labels with distinct sequences associated with the target in the sequencing data prior to determining the number of noise molecular labels with distinct sequences associated with the target in the sequencing data in (ii), if the sequencing status of the target in the sequencing data is not the under sequencing status or the over sequencing status and the number of molecular labels with distinct sequences associated with the target in the sequencing data counted in (i) is less than a pseudopoints threshold. The pseudopoints threshold is ten.

In some embodiments, determining the number of noise molecular labels with distinct sequences associated with the target in the sequencing data comprises: removing non-unique molecular labels when determining the number of noise molecular labels with distinct sequences associated with the target in the sequencing data in (ii), if the sequencing status of the target in the sequencing data is not the under sequencing status or the over sequencing status and the number of molecular labels with distinct sequences associated with the target in the sequencing data counted in (i) is not less than a pseudopoints threshold.

In some embodiments, removing the non-unique molecular labels comprises removing the non-unique molecular labels when determining the number of noise molecular labels with distinct sequences associated with the target in the sequencing data in (ii) if the number of molecular labels with distinct sequences associated with the target in the sequencing data is greater than a predetermined recycled molecular label threshold. For example, the recycled molecular label threshold can be about 650 if the stochastic barcodes comprise about 6561 molecular labels with distinct sequences.

Disclosed herein are one or more non-transitory computer readable media comprising executable codes that, when executed, perform any of the methods disclosed herein.

BRIEF DESCRIPTION OF THE DRAWINGS

FIG. 36 shows exemplary results of recycling of G-rich molecular labels for high expressor genes.

DETAILED DESCRIPTION

Figure 1:
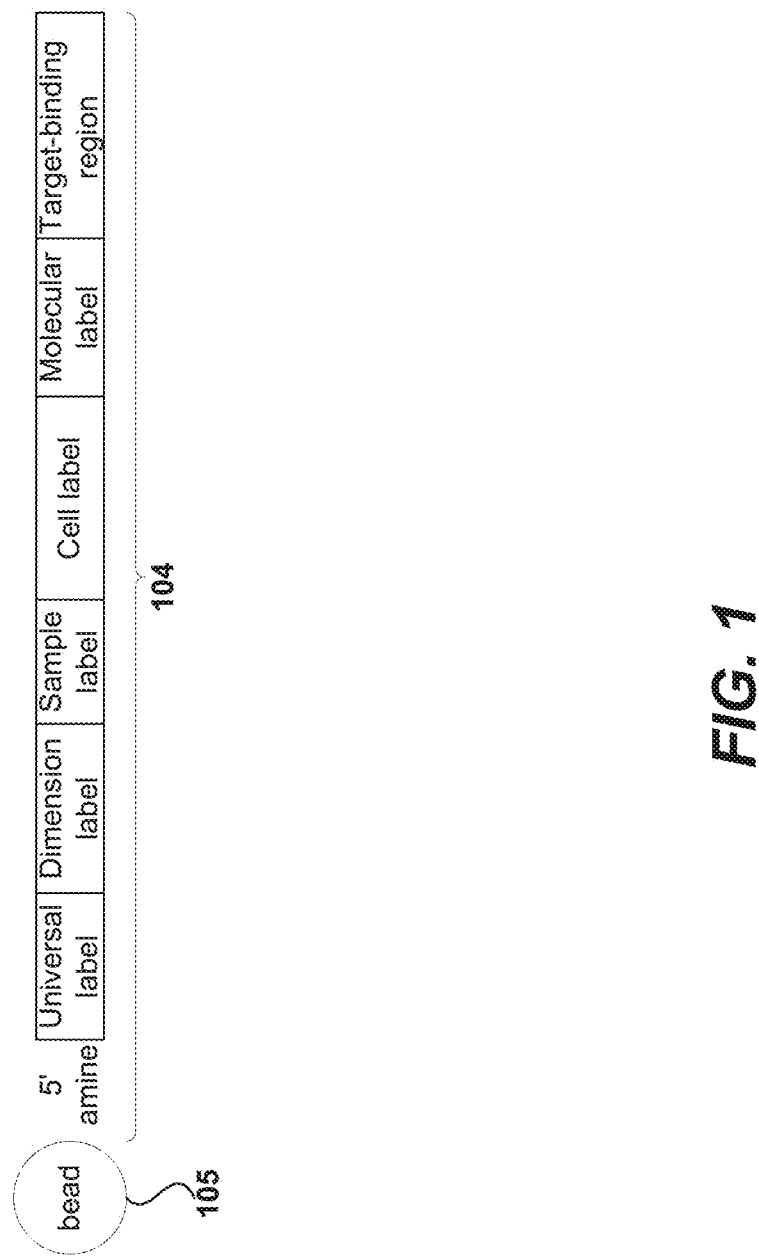
FIG. 1 illustrates a non-limiting exemplary stochastic barcode.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Quantifying small numbers of nucleic acids, for example messenger ribonucleotide acid (mRNA) molecules, is clinically important for determining, for example, the genes that are expressed in a cell at different stages of development or under different environmental conditions. However, it can also be very challenging to determine the absolute number of nucleic acid molecules (e.g., mRNA molecules), especially when the number of molecules is very small. One method to determine the absolute number of molecules in a sample is digital polymerase chain reaction (PCR). Ideally, PCR produces an identical copy of a molecule at each cycle. However, PCR can have disadvantages such that each molecule replicates with a stochastic probability, and this probability varies by PCR cycle and gene sequence, resulting in amplification bias and inaccurate gene expression measurements. Stochastic barcodes with unique molecular labels (also referred to as molecular indexes (MIs)) can be used to count the number of molecules and correct for amplification bias. Stochastic barcoding such as the Precise™ assay (Cellular Research, Inc. (Palo Alto, Calif.)) can correct for bias induced by PCR and library preparation steps by using molecular labels (MLs) to label mRNAs during reverse transcription (RT).

The Precise™ assay can utilize a non-depleting pool of stochastic barcodes with large number, for example 6561 to 65536, unique molecular labels on poly(T) oligonucleotides to hybridize to all poly(A)-mRNAs in a sample during the RT step. In addition to molecular labels, sample label (also referred to as a sample index (SI)) of stochastic barcodes can be used to identify each well of the Precise™ plate. A stochastic barcode can comprise a universal PCR priming site. During RT, target gene molecules react randomly with stochastic barcodes. Each target molecule can hybridize to a stochastic barcode resulting to generate stochastically barcoded complementary ribonucleotide acid (cDNA) molecules). After labeling, stochastically barcoded cDNA molecules from microwells of a microwell plate can be pooled into a single tube for PCR amplification and sequencing. Raw sequencing data can be analyzed to produce the number of reads, the number of stochastic barcodes with unique molecular labels, and the numbers of mRNA molecules based on a Poisson correction or a correction method based on two negative binomial distributions.

In addition to bias correction, molecular labels can provide a better understanding of the statistical quality of the results by revealing the starting number of cDNA molecules present in the observed sequencing reads. For example, a large number of reads may indicate a statistically accurate answer, but if the reads are derived from just a small number of starting mRNA molecules, then the measurement accuracy may be compromised.

Although amplification bias induced by PCR and library preparation steps can be remedied, for example, by molecular labels, the quantification of the absolute number of molecules can still be challenging due to several other factors. First, estimation of the number of mRNA molecules may be limited by the total diversity of the molecular labels. During stochastic barcoding, mRNA molecules can react randomly with available stochastic barcodes. Thus, each mRNA molecule can hybridize to a stochastic barcode; however his molecular label might not necessarily be unique for any given gene. When the number of mRNA molecules is small relative to the number of stochastic barcodes, each mRNA molecule will likely hybridize to a stochastic barcode with a unique molecular label, and counting the number of molecules can be equivalent to counting the number of molecular labels.

As the number of mRNA molecules increase, multiple mRNA molecules become increasing likely to hybridize to stochastic barcodes with the same molecular labels. Hence using counts of unique molecular labels may underestimate the number of molecules. In some cases, the number of mRNA molecules can be estimated based on a Poisson correction or a correction based on two negative binomial distributions of the number of unique molecular labels observed in total. However, at the extreme where the entire collection of 6561 stochastic barcodes is observed, a Poisson correction or a correction based on two negative binomial distributions may no longer be possible. For example, regardless of 65000 or 100000 starting mRNA molecules, a maximum of 6561 saturated stochastic barcodes is expected in either case.

Second, PCR errors (that is, errors occurred during PCR amplification), may introduce artificial stochastic barcodes and arbitrarily inflate molecular label counts. Third, PCR amplification bias and inefficient PCR may generate low copies of barcoded molecules that are indistinguishable from errors. Fourth, sequencing errors, the inaccurate calling of stochastic barcode sequences, may introduce artificial stochastic barcodes and inflate molecular label counts. Additionally, sequencing depth may be important, especially when sequencing is too shallow to detect all of the stochastically barcoded mRNAs present in a sample library.

Methods and systems for determining the numbers of targets with one or more of PCR or sequencing errors corrected or adjusted are disclosed herein. In some embodiments, the method comprises: (a) stochastically barcoding a plurality of targets using a plurality of stochastic barcodes to create a plurality of stochastically barcoded targets, wherein each of the plurality of stochastic barcodes comprises a molecular label; (b) obtaining sequencing data of the stochastically barcoded targets; and (c) for one or more of the plurality of targets: (i) counting the number of molecular labels with distinct sequences associated with the target in the sequencing data; (ii) determining a quality status of the target in the sequencing data obtained in (b); (iii) determining one or more sequencing data errors in the sequencing data obtained in (b), wherein determining the one or more sequencing data errors in the sequencing data comprises determining one or more of: the number of the molecular labels with distinct sequences associated with the target in the sequencing data, the quality status of the target in the sequencing data, and the number of molecular labels with distinct sequences in the plurality of stochastic barcodes; and (iv) estimating the number of the target, wherein the number of the target estimated correlates with the number of molecular labels with distinct sequences associated with the target in the sequencing data counted in (i) adjusted according to the one or more sequencing data errors determined in (iii).

Methods for determining the number of targets with one or more PCR or sequencing errors corrected or adjusted based on directional adjacency are disclosed. In some embodiments, the method comprises: (a) stochastically barcoding a plurality of targets using a plurality of stochastic barcodes to create a plurality of stochastically barcoded targets, wherein each of the plurality of stochastic barcodes comprises a molecular label; (b) obtaining sequencing data of the stochastically barcoded targets; (c) for one or more of the plurality of targets: (i) counting the number of molecular labels with distinct sequences associated with the target in the sequencing data; (ii) identifying clusters of molecular labels of the target using directional adjacency; (iii) collapsing the sequencing data obtained in (b) using the clusters of molecular labels of the target identified in (ii); (iv) estimating the number of the target, wherein the number of the target estimated correlates with the number of molecular labels with distinct sequences associated with the target in the sequencing data counted in (i) after collapsing the sequencing data in (ii).

Computer systems for determining the numbers of targets with one or more of PCR or sequencing errors corrected or adjusted are disclosed. A non-transitory computer readable media containing executable codes, when executed, cause one or more computing devices to determine the number of targets with one or more of PCR or sequencing errors corrected or adjusted is disclosed.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present disclosure, the following terms are defined below.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, barcodes, stochastic barcodes, or molecular labels. The adapters can be linear. The adaptors can be pre-adenylated adapters. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adapter can, in some embodiments, comprise a universal sequence. A universal sequence can be a region of nucleotide sequence that is common to two or more nucleic acid molecules. The two or more nucleic acid molecules can also have regions of different sequence. Thus, for example, the 5' adapters can comprise identical and/or universal nucleic acid sequences and the 3' adapters can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adapters (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some embodiments, two or more associated species are "tethered", "attached", or "immobilized" to one another or to a common solid or semisolid surface. An association may refer to covalent or non-covalent means for attaching labels to solid or semisolid supports such as beads. An association may be a covalent bond between a target and a label.

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This stochastic methodology transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of stochastic barcodes made up of many different labels. A non-depleting reservoir can comprise large numbers of different stochastic barcodes such that when the non-depleting reservoir is associated with a pool of targets each target is likely to be associated with a unique stochastic barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of stochastic barcodes detected then allows calculation of the number of target molecules present in the original collection or sample. When the ratio of the number of copies of a target molecule present to the number of unique stochastic barcodes is low, the labeled target molecules are highly unique (i.e. there is a very low probability that more than one target molecule will have been labeled with a given label).

As used herein, the term "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene (—CH2), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions.

As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',':4,5)pyrrolo[2,3-d]pyrimidin-2-one).

As used herein, the term "sample" can refer to a composition comprising targets. Suitable samples for analysis by the disclosed methods, devices, and systems include cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of stochastic barcodes may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A plurality of solid supports spaced in an array may not comprise a substrate. A solid support may be used interchangeably with the term "bead."

A solid support can refer to a "substrate." A substrate can be a type of solid support. A substrate can refer to a continuous solid or semi-solid surface on which the methods of the disclosure may be performed. A substrate can refer to an array, a cartridge, a chip, a device, and a slide, for example.

As used here, the term, "spatial label" can refer to a label which can be associated with a position in space.

As used herein, the term "stochastic barcode" can refer to a polynucleotide sequence comprising labels. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "gene-specific stochastic barcode" can refer to a polynucleotide sequence comprising labels and a target-binding region that is gene-specific. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "gene-specific stochastic barcoding."

As used here, the term "target" can refer to a composition which can be associated with a stochastic barcode. Exemplary suitable targets for analysis by the disclosed methods, devices, and systems include oligonucleotides, DNA, RNA, mRNA, microRNA, tRNA, and the like. Targets can be single or double stranded. In some embodiments targets can be proteins. In some embodiments targets are lipids.

As used herein, the term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transciptases, and group II intron reverse transcriptases. Examples of group II intron reverse transcriptases include the *Lactococcus lactis* Ll.LtrB intron reverse transcriptase, the *Thermosynechococcus* elongates TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

The terms "universal adaptor primer," "universal primer adaptor" or "universal adaptor sequence" are used interchangeably to refer to a nucleotide sequence that can be used to hybridize stochastic barcodes to generate gene-specific stochastic barcodes. A universal adaptor sequence can, for example, be a known sequence that is universal across all stochastic barcodes used in methods of the disclosure. For example, when multiple targets are being labeled using the methods disclosed herein, each of the target-specific sequences may be linked to the same universal adaptor sequence. In some embodiments, more than one universal adaptor sequences may be used in the methods disclosed herein. For example, when multiple targets are being labeled using the methods disclosed herein, at least two of the target-specific sequences are linked to different universal adaptor sequences. A universal adaptor primer and its complement may be included in two oligonucleotides, one of which comprises a target-specific sequence and the other comprises a stochastic barcode. For example, a universal adaptor sequence may be part of an oligonucleotide comprising a target-specific sequence to generate a nucleotide sequence that is complementary to a target nucleic acid. A second oligonucleotide comprising a stochastic barcode and a complementary sequence of the universal adaptor sequence may hybridize with the nucleotide sequence and generate a target-specific stochastic barcode. In some embodiments, a universal adaptor primer has a sequence that is different from a universal PCR primer used in the methods of this disclosure.

Disclosed herein are methods and system for detecting and/or correcting errors occurred during PCR and/or sequencing. The types of errors can vary, for example, include but not limited to, substitution errors (one or more bases) and non-substitution errors. Amongst the substitution errors, one-base substitution errors can occur much more frequently than those further than one-base apart. The methods and systems can be used, for example, to provide accurate counting of molecular targets by stochastic barcoding.

Stochastic Barcodes

Stochastic barcoding has been described in, for example, US20150299784, WO2015031691, and Fu et al, Proc Natl Acad Sci U.S.A. 2011 May 31; 108(22):9026-31, the content of these publications is incorporated hereby in its entirety. Briefly, a stochastic barcode can be a polynucleotide sequence that may be used to stochastically label (e.g., barcode, tag) a target. A stochastic barcode can comprise one or more labels. Exemplary labels can include a universal label, a cell label, a molecular label, a sample label, a plate label, a spatial label, and/or a pre-spatial label. FIG. 1 illustrates an exemplary stochastic barcode 104 with a spatial label. The stochastic barcode 104 can comprise a 5' amine that may link the stochastic barcode to a solid support 105. The stochastic barcode can comprise a universal label, a dimension label, a spatial label, a cell label, and/or a molecular label. The order of different labels (including but not limited to the universal label, the dimension label, the spatial label, the cell label, and the molecule label) in the stochastic barcode can vary. For example, as shown in FIG. 1, the universal label may be the 5'-most label, and the molecular label may be the 3'-most label. The spatial label, dimension label, and the cell label may be in any order. In some embodiments, the universal label, the spatial label, the dimension label, the cell label, and the molecular label are in any order.

A label, for example the cell label, can comprise a unique set of nucleic acid sub-sequences of defined length, e.g. seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

The stochastic barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, or any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the stochastic barcode (e.g., the universal label, the dimension label, the spatial label, the cell label, and the molecular label) can be separated by a spacer from another one or two of the remaining labels of the stochastic barcode. The spacer can be, for example, 1, 2, 3, 4, 5, 6, 7, 8, 9, 10, 11, 12, 13, 14, 15, 16, 17, 18, 19, or 20 or more nucleotides. In some embodiments, none of the labels of the stochastic barcode is separated by spacer.

Universal Labels

A stochastic barcode can comprise one or more universal labels. In some embodiments, the one or more universal labels can be the same for all stochastic barcodes in the set of stochastic barcodes attached to a given solid support. In some embodiments, the one or more universal labels can be the same for all stochastic barcodes attached to a plurality of beads. In some embodiments, a universal label can comprise a nucleic acid sequence that is capable of hybridizing to a sequencing primer. Sequencing primers can be used for sequencing stochastic barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the stochastic barcode. A universal label can comprise a sequence that can be used for extension of the stochastic barcode or a region within the stochastic barcode. A universal label can be, or be about, 1, 2, 3, 4, 5, 10, 15, 20, 25, 30, 35, 40, 45, 50, or a number or a range between any two of these values, nucleotides in length. For example, a universal label can comprise at least about 10 nucleotides. A universal label can be at least, or at most, 1, 2, 3, 4, 5, 10, 15, 20, 25, 30, 35, 40, 45, 50, 100, 200, or 300 nucleotides in length. In some embodiments, a cleavable linker or modified nucleotide can be part of the universal label sequence to enable the stochastic barcode to be cleaved off from the support.

Dimension Labels

A stochastic barcode can comprise one or more dimension labels. In some embodiments, a dimension label can comprise a nucleic acid sequence that provides information about a dimension in which the stochastic labeling occurred. For example, a dimension label can provide information about the time at which a target was stochastically barcoded. A dimension label can be associated with a time of stochastic barcoding in a sample. A dimension label can be activated at the time of stochastic labeling. Different dimension labels can be activated at different times. The dimension label provides information about the order in which targets, groups of targets, and/or samples were stochastically barcoded. For example, a population of cells can be stochastically barcoded at the G0 phase of the cell cycle. The cells can be pulsed again with stochastic barcodes at the G1 phase of the cell cycle. The cells can be pulsed again with stochastic barcodes at the S phase of the cell cycle, and so on. Stochastic barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be stochastically labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, or 10 or more times. The dimension label can be reversibly activatable, for example, at least 1, 2, 3, 4, 5, 6, 7, 8, 9, or 10 or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all stochastic barcodes attached to a given solid support (e.g., bead), but different for different solid supports (e.g., beads). In some embodiments, at least 60%, 70%, 80%, 85%, 90%, 95%, 97%, 99% or 100% of stochastic barcodes on the same solid support can comprise the same dimension label. In some embodiments, at least 60% of stochastic barcodes on the same solid support can comprise the same dimension label. In some embodiments, at least 95% of stochastic barcodes on the same solid support can comprise the same dimension label.

There can be as many as $10^6$ or more unique dimension label sequences represented in a plurality of solid supports (e.g., beads). A dimension label can be, or be about 1, 2, 3, 4, 5, 10, 15, 20, 25, 30, 35, 40, 45, 50, or a number or a range between any two of these values, nucleotides in length. A dimension label can be at least, or at most, 1, 2, 3, 4, 5, 10, 15, 20, 25, 30, 35, 40, 45, 50, 100, 200, or 300 nucleotides in length. A dimension label can comprise between about 5 to about 200 nucleotides. A dimension label can comprise between about 10 to about 150 nucleotides. A dimension label can comprise between about 20 to about 125 nucleotides in length.

Spatial Labels

A stochastic barcode can comprise one or more spatial labels. In some embodiments, a spatial label can comprise a nucleic acid sequence that provides information about the spatial orientation of a target molecule which is associated with the stochastic barcode. A spatial label can be associated with a coordinate in a sample. The coordinate can be a fixed coordinate. For example a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g. a well, a container, or a droplet). In some embodiments, multiple spatial labels are used together to encode one or more positions in space.

The spatial label can be identical for all stochastic barcodes attached to a given solid support (e.g., bead), but different for different solid supports (e.g., beads). In some embodiments, the percentage of stochastic barcodes on the same solid support comprising the same spatial label can be, or be about, 60%, 70%, 80%, 85%, 90%, 95%, 97%, 99%, 100%, or a number or a range between any two of these values. In some embodiments, the percentage of stochastic barcodes on the same solid support comprising the same spatial label can be at least, or at most, 60%, 70%, 80%, 85%, 90%, 95%, 97%, 99%, or 100%. In some embodiments, at least 60% of stochastic barcodes on the same solid support can comprise the same spatial label. In some embodiments, at least 95% of stochastic barcodes on the same solid support can comprise the same spatial label.

There can be as many as $10^6$ or more unique spatial label sequences represented in a plurality of solid supports (e.g., beads). A spatial label can be, or be about, 1, 2, 3, 4, 5, 10, 15, 20, 25, 30, 35, 40, 45, 50, or a number or a range between any two of these values, nucleotides in length. A spatial label can be at least or at most 1, 2, 3, 4, 5, 10, 15, 20, 25, 30, 35, 40, 45, 50, 100, 200, or 300 nucleotides in length. A spatial label can comprise between about 5 to about 200 nucleotides. A spatial label can comprise between about 10 to about 150 nucleotides. A spatial label can comprise between about 20 to about 125 nucleotides in length.

Cell Labels

A stochastic barcodes can comprise one or more cell labels. In some embodiments, a cell label can comprise a nucleic acid sequence that provides information for determining which target nucleic acid originated from which cell. In some embodiments, the cell label is identical for all stochastic barcodes attached to a given solid support (e.g., bead), but different for different solid supports (e.g., beads). In some embodiments, the percentage of stochastic barcodes on the same solid support comprising the same cell label can be, or be about 60%, 70%, 80%, 85%, 90%, 95%, 97%, 99%, 100%, or a number or a range between any two of these values. In some embodiments, the percentage of stochastic barcodes on the same solid support comprising the same cell label can be, or be about 60%, 70%, 80%, 85%, 90%, 95%, 97%, 99%, or 100%. For example, at least 60% of stochastic barcodes on the same solid support can comprise the same cell label. As another example, at least 95% of stochastic barcodes on the same solid support can comprise the same cell label.

There can be as many as $10^6$ or more unique cell label sequences represented in a plurality of solid supports (e.g., beads). A cell label can be, or be about, 1, 2, 3, 4, 5, 10, 15, 20, 25, 30, 35, 40, 45, 50, or a number or a range between any two of these values, nucleotides in length. A cell label can be at least, or at most, 1, 2, 3, 4, 5, 10, 15, 20, 25, 30, 35, 40, 45, 50, 100, 200, or 300 nucleotides in length. For example, a cell label can comprise between about 5 to about 200 nucleotides. As another example, a cell label can comprise between about 10 to about 150 nucleotides. As yet another example, a cell label can comprise between about 20 to about 125 nucleotides in length.

Molecular Labels

A stochastic barcodes can comprise one or more molecular labels. In some embodiments, a molecular label can comprise a nucleic acid sequence that provides identifying information for the specific type of target nucleic acid species hybridized to the stochastic barcode. A molecular label can comprise a nucleic acid sequence that provides a counter for the specific occurrence of the target nucleic acid species hybridized to the stochastic barcode (e.g., target-binding region).

In some embodiments, a diverse set of molecular labels are attached to a given solid support (e.g., bead). In some embodiments, there can be, or be about, $10^2$, $10^3$, $10^4$, $10^5$, $10^6$, $10^7$, $10^8$, $10^9$, or a number or a range of unique molecular label sequences. For example, a plurality of stochastic barcodes can comprise about 6561 molecular labels with distinct sequences. As another example, a plurality of stochastic barcodes can comprise about 65536 molecular labels with distinct sequences. In some embodiments, there can be at least, or at most, $10^2$, $10^3$, $10^4$, $10^5$, $10^6$, $10^7$, $10^8$, or $10^9$, unique molecular label sequences. The unique molecular label sequences attached to a given solid support (e.g., bead).

A molecular label can be, or be about, 1, 2, 3, 4, 5, 10, 15, 20, 25, 30, 35, 40, 45, 50, or a number or a range between any two of these values, nucleotides in length. A molecular label can be at least, or at most, 1, 2, 3, 4, 5, 10, 15, 20, 25, 30, 35, 40, 45, 50, 100, 200, or 300 nucleotides in length.

Target-Binding Region

A stochastic barcodes can comprise one or more target binding regions. In some embodiments, a target-binding region can hybridize with a target of interest. In some embodiments, the target binding regions can comprise a nucleic acid sequence that hybridizes specifically to a target (e.g. target nucleic acid, target molecule, e.g., a cellular nucleic acid to be analyzed), for example to a specific gene sequence. In some embodiments, a target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction enzyme site overhang (e.g. an EcoRI sticky-end overhang). The stochastic barcode can then ligate to any nucleic acid molecule comprising a sequence complementary to the restriction site overhang.

In some embodiments, a target binding region can comprise a non-specific target nucleic acid sequence. A non-specific target nucleic acid sequence can refer to a sequence that can bind to multiple target nucleic acids, independent of the specific sequence of the target nucleic acid. For example, target binding region can comprise a random multimer sequence, or an oligo(dT) sequence that hybridizes to the poly(A) tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all stochastic barcodes attached to a given bead. In some embodiments, the target binding regions for the plurality of stochastic barcodes attached to a given bead can comprise two or more different target binding sequences. A target binding region can be, or be about, 5, 10, 15, 20, 25, 30, 35, 40, 45, 50, or a number or a range between any two of these values, nucleotides in length. A target binding region can be at most about 5, 10, 15, 20, 25, 30, 35, 40, 45, 50 or more nucleotides in length.

In some embodiments, a target-binding region can comprise an oligo(dT) which can hybridize with mRNAs comprising poly-adenylated ends. A target-binding region can be gene-specific. For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a stochastic barcode comprises a gene-specific target-binding region, the stochastic barcode can be referred to as a gene-specific stochastic barcode.

Orientation Property

A stochastic barcode can comprise one or more orientation properties which can be used to orient (e.g., align) the stochastic barcodes. A stochastic barcode can comprise a moiety for isoelectric focusing. Different stochastic barcodes can comprise different isoelectric focusing points. When these stochastic barcodes are introduced to a sample, the sample can undergo isoelectric focusing in order to orient the stochastic barcodes into a known way. In this way, the orientation property can be used to develop a known map of stochastic barcodes in a sample. Exemplary orientation properties can include, electrophoretic mobility (e.g., based on size of the stochastic barcode), isoelectric point, spin, conductivity, and/or self-assembly. For example, stochastic barcodes with an orientation property of self-assembly, can self-assemble into a specific orientation (e.g., nucleic acid nanostructure) upon activation.

Affinity Property

A stochastic barcode can comprise one or more affinity properties. For example, a spatial label can comprise an affinity property. An affinity property can include a chemical and/or biological moiety that can facilitate binding of the stochastic barcode to another entity (e.g., cell receptor). For example, an affinity property can comprise an antibody, for example, an antibody specific for a specific moiety (e.g., receptor) on a sample. In some embodiments, the antibody can guide the stochastic barcode to a specific cell type or molecule. Targets at and/or near the specific cell type or molecule can be stochastically labeled. The affinity property can, in some embodiments, provide spatial information in addition to the nucleotide sequence of the spatial label because the antibody can guide the stochastic barcode to a specific location. The antibody can be a therapeutic antibody, for example a monoclonal antibody or a polyclonal antibody. The antibody can be humanized or chimeric. The antibody can be a naked antibody or a fusion antibody.

The antibody can be a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody fragment can be, for example, a portion of an antibody such as F(ab')2, Fab', Fab, Fv, sFv and the like.

In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (CD8, CD34, CD45), and therapeutic antibodies.

Universal Adaptor Primer

A stochastic barcode can comprise one or more universal adaptor primers. For example, a gene-specific stochastic barcode can comprise a universal adaptor primer. A universal adaptor primer can refer to a nucleotide sequence that is universal across all stochastic barcodes. A universal adaptor primer can be used for building gene-specific stochastic barcodes. A universal adaptor primer can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these nucleotides in length. A universal adaptor primer can be at least, or at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 nucleotides in length. A universal adaptor primer can be from 5-30 nucleotides in length.

Solid Supports

Stochastic barcodes disclosed herein can, in some embodiments, be associated with a solid support. The solid support can be, for example, a synthetic particle. In some embodiments, some or all of the molecular labels (e.g., the first molecular labels) of a plurality of stochastic barcodes (e.g., the first plurality of stochastic barcodes) on a solid support differ by at least one nucleotide. The cell labels of the stochastic barcodes on the same solid support can be the same. The cell labels of the stochastic barcodes on different solid supports can differ by at least one nucleotide. For example, first cell labels of a first plurality of stochastic barcodes on a first solid support can have the same sequence, and second cell labels of a second plurality of stochastic barcodes on a second solid support can have the same sequence. The first cell labels of the first plurality of stochastic barcodes on the first solid support and the second cell labels of the second plurality of stochastic barcodes on the second solid support can differ by at least one nucleotide. A cell label can be, for example, about 5-20 nucleotides long. A molecular label can be, for example, about 5-20 nucleotides long. The synthetic particle can be, for example, a bead.

The bead can be, for example, a silica gel bead, a controlled pore glass bead, a magnetic bead, a Dynabead, a Sephadex/Sepharose bead, a cellulose bead, a polystyrene bead, or any combination thereof. The bead can comprise a material such as polydimethylsiloxane (PDMS), polystyrene, glass, polypropylene, agarose, gelatin, hydrogel, paramagnetic, ceramic, plastic, glass, methyl styrene, acrylic polymer, titanium, latex, sepharose, cellulose, nylon, silicone, or any combination thereof.

In some embodiments, the bead can be a polymeric bead, for example a deformable bead or a gel bead, functionalized with stochastic barcodes (such as gel beads from 10× Genomics (San Francisco, Calif.). In some implementation, a gel bead can comprise a polymer based gels. Gel beads can be generated, for example, by encapsulating one or more polymeric precursors into droplets. Upon exposure of the polymeric precursors to an accelerator (e.g., tetramethylethylenediamine (TEMED)), a gel bead may be generated.

In some embodiments, the polymeric bead can dissolve, melt, or degrade, for example, under a desired condition. The desired condition can include an environmental condition. The desired condition may result in the polymeric bead dissolving, melting, or degrading in a controlled manner. A gel bead may dissolve, melt, or degrade due to a chemical stimulus, a physical stimulus, a biological stimulus, a thermal stimulus, a magnetic stimulus, an electric stimulus, a light stimulus, or any combination thereof.

Analytes and/or reagents, such as oligonucleotide barcodes, for example, may be coupled/immobilized to the interior surface of a gel bead (e.g., the interior accessible via diffusion of an oligonucleotide barcode and/or materials used to generate an oligonucleotide barcode) and/or the outer surface of a gel bead or any other microcapsule described herein. Coupling/immobilization may be via any form of chemical bonding (e.g., covalent bond, ionic bond) or physical phenomena (e.g., Van der Waals forces, dipole-dipole interactions, etc.). In some cases, coupling/immobilization of a reagent to a gel bead or any other microcapsule described herein may be reversible, such as, for example, via a labile moiety (e.g., via a chemical cross-linker, including chemical cross-linkers described herein). Upon application of a stimulus, the labile moiety may be cleaved and the immobilized reagent set free. In some cases, the labile moiety is a disulfide bond. For example, in the case where an oligonucleotide barcode is immobilized to a gel bead via a disulfide bond, exposure of the disulfide bond to a reducing agent can cleave the disulfide bond and free the oligonucleotide barcode from the bead. The labile moiety may be included as part of a gel bead or microcapsule, as part of a chemical linker that links a reagent or analyte to a gel bead or microcapsule, and/or as part of a reagent or analyte.

In some embodiments, a gel bead can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption or degradation of the beads. Examples of these chemical changes may include, but are not limited to pH-mediated changes to the bead wall, disintegration of the bead wall via chemical cleavage of crosslink bonds, triggered depolymerization of the bead wall, and bead wall switching reactions. Bulk changes may also be used to trigger disruption of the beads.

Bulk or physical changes to the microcapsule through various stimuli also offer many advantages in designing capsules to release reagents. Bulk or physical changes occur on a macroscopic scale, in which bead rupture is the result of mechano-physical forces induced by a stimulus. These processes may include, but are not limited to pressure induced rupture, bead wall melting, or changes in the porosity of the bead wall.

Biological stimuli may also be used to trigger disruption or degradation of beads. Generally, biological triggers resemble chemical triggers, but many examples use biomolecules, or molecules commonly found in living systems such as enzymes, peptides, saccharides, fatty acids, nucleic acids and the like. For example, beads may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the beads are released. In other cases, the proteases may be heat-activated. In another example, beads comprise a shell wall comprising cellulose. Addition of the hydrolytic enzyme chitosan serves as biologic trigger for cleavage of cellulosic bonds, depolymerization of the shell wall, and release of its inner contents.

The beads may also be induced to release their contents upon the application of a thermal stimulus. A change in temperature can cause a variety changes to the beads. A change in heat may cause melting of a bead such that the bead wall disintegrates. In other cases, the heat may increase the internal pressure of the inner components of the bead such that the bead ruptures or explodes. In still other cases, the heat may transform the bead into a shrunken dehydrated state. The heat may also act upon heat-sensitive polymers within the wall of a bead to cause disruption of the bead.

Inclusion of magnetic nanoparticles to the bead wall of microcapsules may allow triggered rupture of the beads as well as guide the beads in an array. A device of this disclosure may comprise magnetic beads for either purpose. In one example, incorporation of $Fe_3O_4$ nanoparticles into polyelectrolyte containing beads triggers rupture in the presence of an oscillating magnetic field stimulus.

A bead may also be disrupted or degraded as the result of electrical stimulation. Similar to magnetic particles described in the previous section, electrically sensitive beads can allow for both triggered rupture of the beads as well as other functions such as alignment in an electric field, electrical conductivity or redox reactions. In one example, beads containing electrically sensitive material are aligned in an electric field such that release of inner reagents can be controlled. In other examples, electrical fields may induce redox reactions within the bead wall itself that may increase porosity.

A light stimulus may also be used to disrupt the beads. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the bead wall. In yet another example, photo switchable materials such as azobenzene groups may be incorporated in the bead wall. Upon the application of UV or visible light, chemicals such as these undergo a reversible cis-to-trans isomerization upon absorption of photons. In this aspect, incorporation of photon switches result in a bead wall that may disintegrate or become more porous upon the application of a light trigger.

Figure 2:
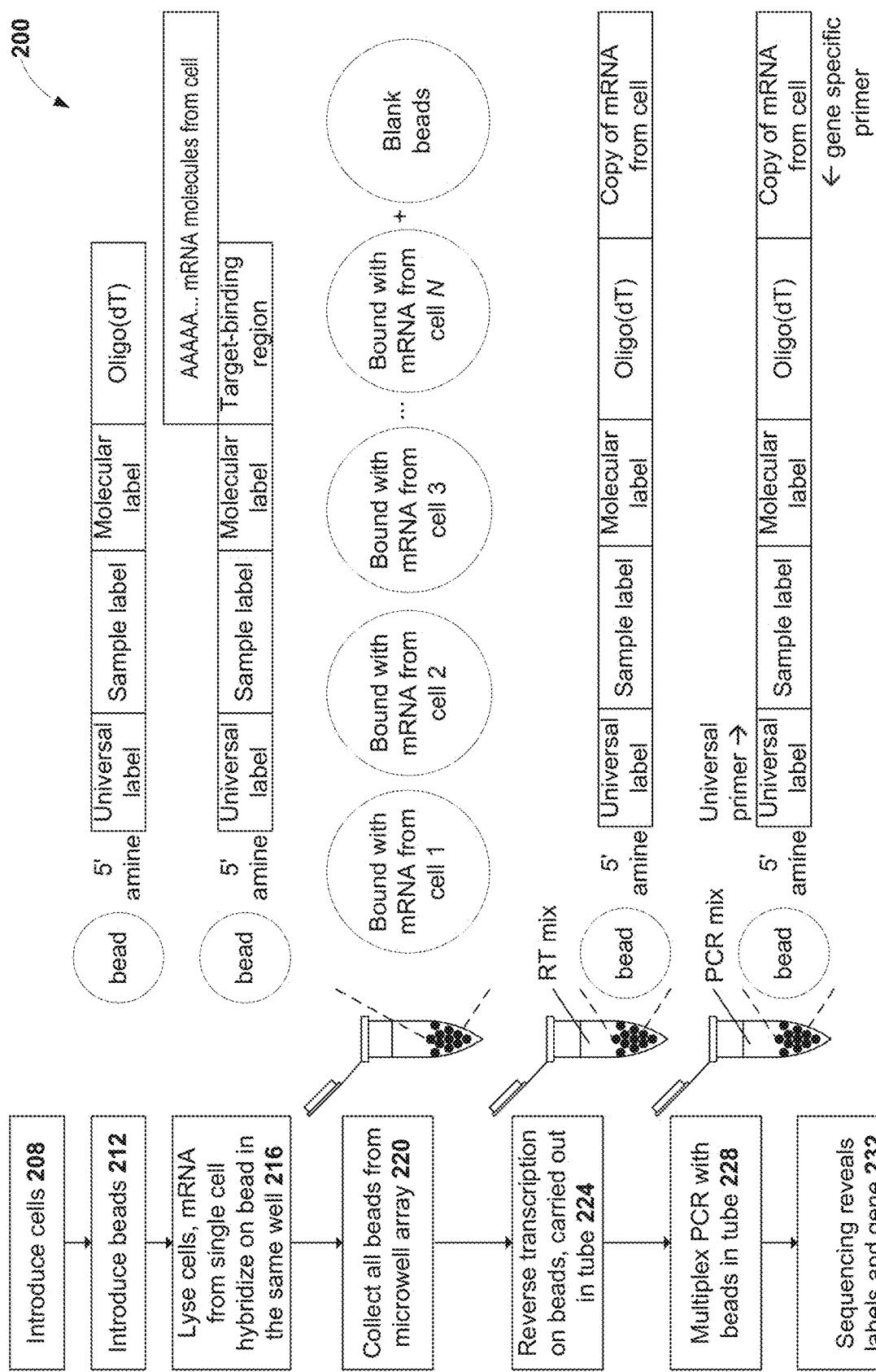
FIG. 2 shows a non-limiting exemplary workflow of stochastic barcoding and digital counting.

For example, in a non-limiting example of stochastic barcoding illustrated in FIG. 2, after introducing cells such as single cells onto a plurality of microwells of a microwell array at block 208, beads can be introduced onto the plurality of microwells of the microwell array at block 212. Each microwell can comprise one bead. The beads can comprise a plurality of stochastic barcodes. A stochastic barcode can comprise a 5' amine region attached to a bead. The stochastic barcode can comprise a universal label, a molecular label, a target-binding region, or any combination thereof.

The stochastic barcodes disclosed herein can be associated with (e.g., attached to) a solid support (e.g., a bead). The stochastic barcodes associated with a solid support can each comprise a molecular label selected from a group comprising at least 100 or 1000 molecular labels with unique sequences. In some embodiments, different stochastic barcodes associated with a solid support can comprise molecular labels of different sequences. In some embodiments, a percentage of stochastic barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or at most 60%, 70%, 80%, 85%, 90%, 95%, 97%, 99%, or 100%. In some embodiments, stochastic barcodes associated with a solid support can have the same cell label. The stochastic barcodes associated with different solid supports can have different cell labels selected from a group comprising at least 100 or 1000 cell labels with unique sequences.

The stochastic barcodes disclosed herein can be associated to (e.g., attached to) a solid support (e.g., a bead). In some embodiments, stochastically barcoding the plurality of targets in the sample can be performed with a solid support including a plurality of synthetic particles associated with the plurality of stochastic barcodes. In some embodiments, the solid support can include a plurality of synthetic particles associated with the plurality of stochastic barcodes. The spatial labels of the plurality of stochastic barcodes on different solid supports can differ by at least one nucleotide. The solid support can, for example, include the plurality of stochastic barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The stochastic barcodes may not be associated with solid supports. The stochastic barcodes can be individual nucleotides. The stochastic barcodes can be associated with a substrate.

As used herein, the terms "tethered", "attached", and "immobilized" are used interchangeably, and can refer to covalent or non-covalent means for attaching stochastic barcodes to a solid support. Any of a variety of different solid supports can be used as solid supports for attaching pre-synthesized stochastic barcodes or for in situ solid-phase synthesis of stochastic barcode.

In some embodiments, the solid support is a bead. The bead can comprise one or more types of solid, porous, or hollow sphere, ball, bearing, cylinder, or other similar configuration which a nucleic acid can be immobilized (e.g., covalently or non-covalently). The bead can be, for example, composed of plastic, ceramic, metal, polymeric material, or any combination thereof. A bead can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a bead can be non-spherical in shape.

Beads can comprise a variety of materials including, but not limited to, paramagnetic materials (e.g. magnesium, molybdenum, lithium, and tantalum), superparamagnetic materials (e.g. ferrite ($Fe_3O_4$; magnetite) nanoparticles), ferromagnetic materials (e.g. iron, nickel, cobalt, some alloys thereof, and some rare earth metal compounds), ceramic, plastic, glass, polystyrene, silica, methylstyrene, acrylic polymers, titanium, latex, sepharose, agarose, hydrogel, polymer, cellulose, nylon, or any combination thereof.

In some embodiments, the bead (e.g., the bead to which the stochastic labels are attached) is a hydrogel bead. In some embodiments, the bead comprises hydrogel.

Some embodiments disclosed herein include one or more particles (for example beads). Each of the particles can comprise a plurality of oligonucleotides (e.g., stochastic barcodes). Each of the plurality of oligonucleotides can comprise a molecular label sequence, a cell label sequence, and a target-binding region (e.g., an oligo dT sequence, a gene-specific sequence, a random multimer, or a combination thereof). The cell label sequence of each of the plurality of oligonucleotides can be the same. The cell label sequences of oligonucleotides on different particles can be different such that the oligonucleotides on different particles can be identified. The number of different cell label sequences can be different in different implementations. In some embodiments, the number of cell label sequences can be, or about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell label sequences can be at least, or at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles include oligonucleotides with the same cell sequence. In some embodiment, the plurality of particles that include oligonucleotides with the same cell sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10% or more. In some embodiments, none of the plurality of the particles has the same cell label sequence.

The plurality of oligonucleotides on each particle can comprise different molecular label sequences. In some embodiments, the number of molecular label sequences can be, or about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of molecular label sequences can be at least, or at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. For example, at least 100 of the plurality of oligonucleotides comprise different molecular label sequences. As another example example, in a single particle, at least 100, 500, 1000, 5000, 10000, 15000, 20000, 50000, a number or a range between any two of these values, or more of the plurality of oligonucleotides comprise different molecular label sequences. Some embodiments provide a plurality of the particles comprising stochastic barcodes. In some embodiments, the ratio of an occurrence (or a copy or a number) of a target to be labeled and the different molecular label sequences can be at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or more. In some embodiments, each of the plurality of oligonucleotides further comprises a sample label, a universal label, or both. The particle can be, for example, a nanoparticle or microparticle.

The size of the beads can vary. For example, the diameter of the bead can range from 0.1 micrometer to 50 micrometer. In some embodiments, the diameters of beads can be, or be about, 0.1, 0.5, 1, 2, 3, 4, 5, 6, 7, 8, 9, 10, 20, 30, 40, 50 micrometer, or a number or a range between any two of these values.

The diameters of the bead can be related to the diameter of the wells of the substrate. In some embodiments, the diameters of the bead can be, or be about, 10%, 20%, 30%, 40%, 50%, 60%, 70%, 80%, 90%, 100%, or a number or a range between any two of these values, longer or shorter than the diameter of the well. The diameter of the beads can be related to the diameter of a cell (e.g., a single cell entrapped by a well of the substrate). In some embodiments, the diameters of the beads can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell.

A bead can be attached to and/or embedded in a substrate. A bead can be attached to and/or embedded in a gel, hydrogel, polymer and/or matrix. The spatial position of a bead within a substrate (e.g., gel, matrix, scaffold, or polymer) can be identified using the spatial label present on the stochastic barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A bead can be associated with (e.g. impregnated with) quantum dots or fluorescent dyes to make it fluorescent in one fluorescence optical channel or multiple optical channels. A bead can be associated with iron oxide or chromium oxide to make it paramagnetic or ferromagnetic. Beads can be identifiable. For example, a bead can be imaged using a camera. A bead can have a detectable code associated with the bead. For example, a bead can comprise a stochastic barcode. A bead can change size, for example due to swelling in an organic or inorganic solution. A bead can be hydrophobic. A bead can be hydrophilic. A bead can be biocompatible.

A solid support (e.g., bead) can be visualized. The solid support can comprise a visualizing tag (e.g., fluorescent dye). A solid support (e.g., bead) can be etched with an identifier (e.g., a number). The identifier can be visualized through imaging the beads.

Substrates and Microwell Array

As used herein, a substrate can refer to a type of solid support. A substrate can refer to a solid support that can comprise stochastic barcodes of the disclosure. A substrate can, for example, comprise a plurality of microwells. For example, a substrate can be a well array comprising two or more microwells. In some embodiments, a microwell can comprise a small reaction chamber of defined volume. In some embodiments, a microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., bead).

Methods of Stochastic Barcoding

The disclosure provides for methods for estimating the number of distinct targets at distinct locations in a physical sample (e.g., tissue, organ, tumor, cell). The methods can comprise placing the stochastic barcodes in close proximity with the sample, lysing the sample, associating distinct targets with the stochastic barcodes, amplifying the targets and/or digitally counting the targets. The method can further comprise analyzing and/or visualizing the information obtained from the spatial labels on the stochastic barcodes. In some embodiments, a method comprises visualizing the plurality of targets in the sample. Mapping the plurality of targets onto the map of the sample can include generating a two dimensional map or a three dimensional map of the sample. The two dimensional map and the three dimensional map can be generated prior to or after stochastically barcoding the plurality of targets in the sample. Visualizing the plurality of targets in the sample can include mapping the plurality of targets onto a map of the sample. Mapping the plurality of targets onto the map of the sample can include generating a two dimensional map or a three dimensional map of the sample. The two dimensional map and the three dimensional map can be generated prior to or after stochastically barcoding the plurality of targets in the sample. in some embodiments, the two dimensional map and the three dimensional map can be generated before or after lysing the sample. Lysing the sample before or after generating the two dimensional map or the three dimensional map can include heating the sample, contacting the sample with a detergent, changing the pH of the sample, or any combination thereof.

In some embodiments, stochastically barcoding the plurality of targets comprises hybridizing a plurality of stochastic barcodes with a plurality of targets to create stochastically barcoded targets. Stochastically barcoding the plurality of targets can comprise generating an indexed library of the stochastically barcoded targets. Generating an indexed library of the stochastically barcoded targets can be performed with a solid support comprising the plurality of stochastic barcodes.

Contacting a Sample and a Stochastic Barcode

The disclosure provides for methods for contacting a sample (e.g., cells) to a substrate of the disclosure. A sample comprising, for example, a cell, organ, or tissue thin section, can be contacted to stochastic barcodes. The cells can be contacted, for example, by gravity flow wherein the cells can settle and create a monolayer. The sample can be a tissue thin section. The thin section can be placed on the substrate. The sample can be one-dimensional (e.g., form a planar surface). The sample (e.g., cells) can be spread across the substrate, for example, by growing/culturing the cells on the substrate.

When stochastic barcodes are in close proximity to targets, the targets can hybridize to the stochastic barcode. The stochastic barcodes can be contacted at a non-depletable ratio such that each distinct target can associate with a distinct stochastic barcode of the disclosure. To ensure efficient association between the target and the stochastic barcode, the targets can be crosslinked to the stochastic barcode.

Cell Lysis

Following the distribution of cells and stochastic barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g. SDS, Li dodecyl sulfate, Triton X-100, Tween-20, or NP-40), an organic solvent (e.g. methanol or acetone), or digestive enzymes (e.g. proteinase K, pepsin, or trypsin), or any combination thereof. To increase the association of a target and a stochastic barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about 0.01, 0.05, 0.1, 0.5, or 1 M or more Tris HCl. A lysis buffer can comprise at most about 0.01, 0.05, 0.1, 0.5, or 1 M or more Tris HCL. A lysis buffer can comprise about 0.1 M Tris HCl. The pH of the lysis buffer can be at least about 1, 2, 3, 4, 5, 6, 7, 8, 9, or 10 or more. The pH of the lysis buffer can be at most about 1, 2, 3, 4, 5, 6, 7, 8, 9, or 10 or more. In some embodiments, the pH of the lysis buffer is about 7.5. The lysis buffer can comprise a salt (e.g., LiCl). The concentration of salt in the lysis buffer can be at least about 0.1, 0.5, or 1 M or more. The concentration of salt in the lysis buffer can be at most about 0.1, 0.5, or 1 M or more. In some embodiments, the concentration of salt in the lysis buffer is about 0.5M. The lysis buffer can comprise a detergent (e.g., SDS, Li dodecyl sufate, triton X, tween, NP-40). The concentration of the detergent in the lysis buffer can be at least about 0.0001%, 0.0005%, 0.001%, 0.005%, 0.01%, 0.05%, 0.1%, 0.5%, 1%, 2%, 3%, 4%, 5%, 6%, or 7% or more. The concentration of the detergent in the lysis buffer can be at most about 0.0001%, 0.0005%, 0.001%, 0.005%, 0.01%, 0.05%, 0.1%, 0.5%, 1%, 2%, 3%, 4%, 5%, 6%, or 7% or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1, 5, 10, 15, or 20 mM or more. The concentration of the reducing reagent in the lysis buffer can be at most about 1, 5, 10, 15, or 20 mM or more. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, or 20 or more minutes. A lysed cell can comprise at least about 100000, 200000, 300000, 400000, 500000, 600000, or 700000 or more target nucleic acid molecules. A lysed cell can comprise at most about 100000, 200000, 300000, 400000, 500000, 600000, or 700000 or more target nucleic acid molecules.

Attachment of Stochastic Barcodes to Target Nucleic Acid Molecules

Following lysis of the cells and release of nucleic acid molecules therefrom, the nucleic acid molecules can randomly associate with the stochastic barcodes of the co-localized solid support. Association can comprise hybridization of a stochastic barcode's target recognition region to a complementary portion of the target nucleic acid molecule (e.g., oligo(dT) of the stochastic barcode can interact with a poly(A) tail of a target). The assay conditions used for hybridization (e.g. buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, in a non-limiting example of stochastic barcoding illustrated in FIG. 2, at block 216, mRNA molecules can hybridize to stochastic barcodes on beads. For example, single-stranded nucleotide fragments can hybridize to the target-binding regions of stochastic barcodes.

Attachment can further comprise ligation of a stochastic barcode's target recognition region and a portion of the target nucleic acid molecule. For example, the target binding region can comprise a nucleic acid sequence that can be capable of specific hybridization to a restriction site overhang (e.g. an EcoRI sticky-end overhang). The assay procedure can further comprise treating the target nucleic acids with a restriction enzyme (e.g. EcoRI) to create a restriction site overhang. The stochastic barcode can then be ligated to any nucleic acid molecule comprising a sequence complementary to the restriction site overhang. A ligase (e.g., T4 DNA ligase) can be used to join the two fragments.

For example, in a non-limiting example of stochastic barcoding illustrated in FIG. 2, at block 220, the labeled targets from a plurality of cells (or a plurality of samples) (e.g., target-barcode molecules) can be subsequently pooled, for example, into a tube. The labeled targets can be pooled by, for example, retrieving the stochastic barcodes and/or the beads to which the target-barcode molecules are attached.

The retrieval of solid support-based collections of attached target-barcode molecules can be implemented by use of magnetic beads and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Reverse Transcription

The disclosure provides for a method to create a stochastic target-barcode conjugate using reverse transcription (e.g., at block 224 of FIG. 2). The stochastic target-barcode conjugate can comprise the stochastic barcode and a complementary sequence of all or a portion of the target nucleic acid (i.e. a stochastically barcoded cDNA molecule). Reverse transcription of the associated RNA molecule can occur by the addition of a reverse transcription primer along with the reverse transcriptase. The reverse transcription primer can be an oligo(dT) primer, a random hexanucleotide primer, or a target-specific oligonucleotide primer. Oligo (dT) primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of the labeled-RNA molecule can occur by the addition of a reverse transcription primer. In some embodiments, the reverse transcription primer is an oligo(dT) primer, random hexanucleotide primer, or a target-specific oligonucleotide primer. Generally, oligo(dT) primers are 12-18 nucleotides in length and bind to the endogenous poly(A)+ tail at the 3' end of mammalian mRNA. Random hexanucleotide primers can bind to mRNA at a variety of complementary sites. Target-specific oligonucleotide primers typically selectively prime the mRNA of interest.

Reverse transcription can occur repeatedly to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, or 20 reverse transcription reactions. The method can comprise conducting at least about 25, 30, 35, 40, 45, 50, 55, 60, 65, 70, 75, 80, 85, 90, 95, or 100 reverse transcription reactions.

Amplification

One or more nucleic acid amplification reactions (e.g., at block 228 of FIG. 2) can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cellular and/or molecular label. The amplification reactions can comprise amplifying at least a portion of a sample tag, a cell label, a spatial label, a molecular label, a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cell label, a spatial label, and/or a molecular label.

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a stochastically labeled-amplicon. The labeled-amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cell label, and/or a molecular label. The stochastically labeled-amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise, for example, 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of stochastically labeled targets. The one or more primers can anneal to the 3' end or 5' end of the plurality of stochastically labeled targets. The one or more primers can anneal to an internal region of the plurality of stochastically labeled targets. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of stochastically labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cell label, a molecular label, a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total stochastically labeled targets in one or more samples. The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the bead using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and molecular label on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonucelase digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photo-labile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by polymerase chain reaction (PCR). PCR can refer to a reaction for the in vitro amplification of specific DNA sequences by the simultaneous primer extension of complementary strands of DNA. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), a Qβ replicase (Qβ), use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and/or ramification extension amplification (RAM).

In some embodiments, the methods disclosed herein further comprise conducting a nested polymerase chain reaction on the amplified amplicon (e.g., target). The amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids of the present invention can comprise synthetic or altered nucleic acids.

In some embodiments, the method comprises repeatedly amplifying the labeled nucleic acid to produce multiple amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, stochastically barcoding the plurality of targets in the sample further comprises generating an indexed library of the stochastically barcoded fragments. The molecular labels of different stochastic barcodes can be different from one another. Generating an indexed library of the stochastically barcoded targets includes generating a plurality of indexed polynucleotides from the plurality of targets in the sample. For example, for an indexed library of the stochastically barcoded targets comprising a first indexed target and a second indexed target, the label region of the first indexed polynucleotide can differ from the label region of the second indexed polynucleotide by, by about, by at least, or by at most, 1, 2, 3, 4, 5, 6, 7, 8, 9, 10, 20, 30, 40, 50, or a number or a range between any two of these values, nucleotides. In some embodiments, generating an indexed library of the stochastically barcoded targets includes contacting a plurality of targets, for example mRNA molecules, with a plurality of oligonucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligonucleotides includes at least two oligonucleotides of different sequences. Generating an indexed library of the stochastically barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Stochastic barcoding can use nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS). The sequencing results can be used to determine cell labels, molecular labels, and sequences of nucleotide fragments of the one or more copies of the targets, for example at block 232 of FIG. 2.

Figure 3:
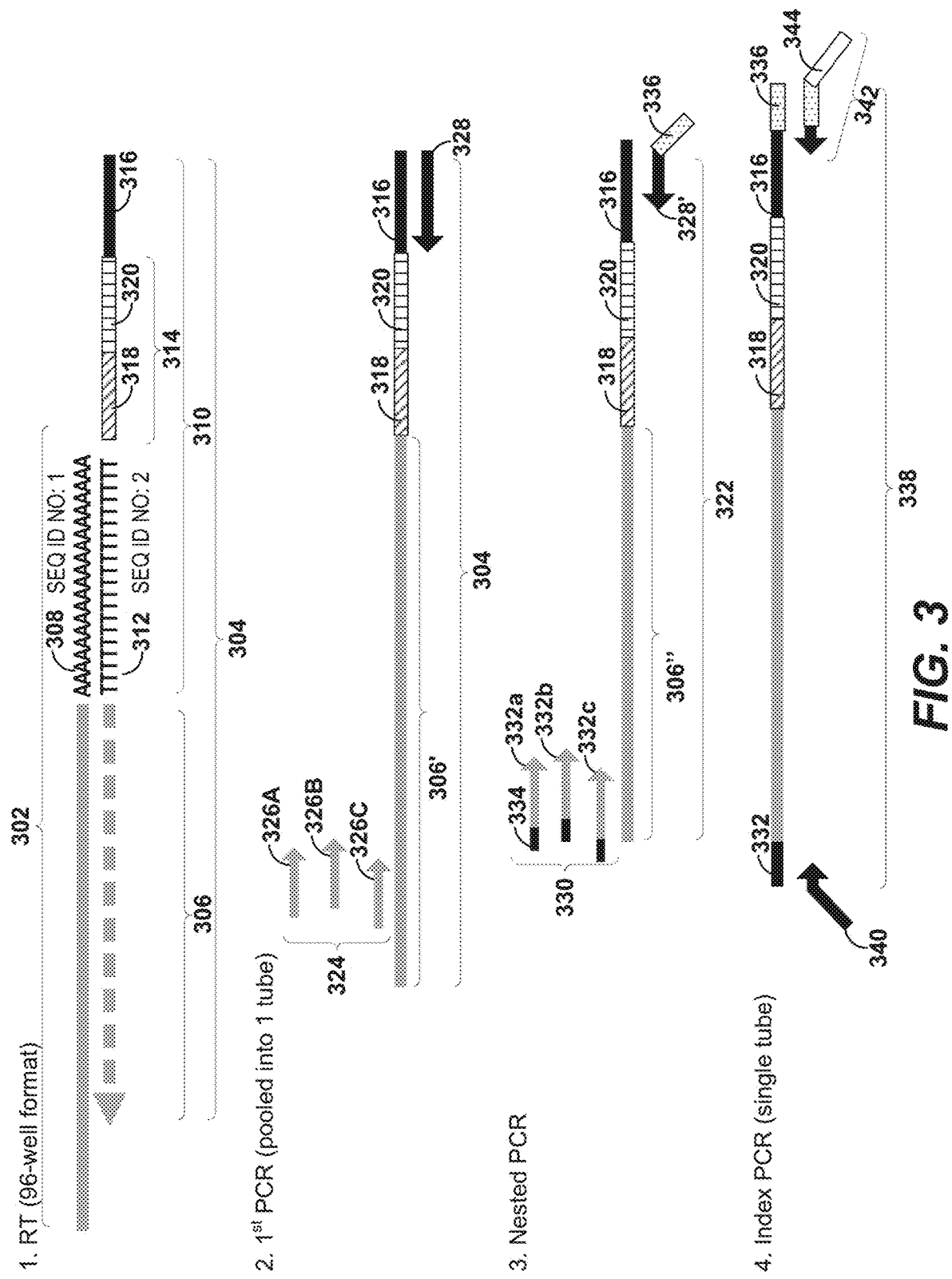
FIG. 3 is a schematic illustration showing a non-limiting exemplary process for generating an indexed library of the stochastically barcoded targets from a plurality of targets.

FIG. 3 is a schematic illustration showing a non-limiting exemplary process of generating an indexed library of the stochastically barcoded targets, for example mRNAs. As shown in step 1, the reverse transcription process can encode each mRNA molecule with a unique molecular label, a cell label, and a universal PCR site. In particular, RNA molecules 302 can be reverse transcribed to produce labeled cDNA molecules 304, including a cDNA region 306, by the stochastic hybridization of a set of molecular identifier labels 310 to the poly(A) tail region 308 of the RNA molecules 302. Each of the molecular identifier labels 310 can comprise a target-binding region, for example a poly (dT) region 312, a label region 314, and a universal PCR region 316.

In some embodiments, the cell label can include 3 to 20 nucleotides. In some embodiments, the molecular label can include 3 to 20 nucleotides. In some embodiments, each of the plurality of stochastic barcodes further comprises one or more of a universal label and a cell label, wherein universal labels are the same for the plurality of stochastic barcodes on the solid support and cell labels are the same for the plurality of stochastic barcodes on the solid support. In some embodiments, the universal label can include 3 to 20 nucleotides. In some embodiments, the cell label comprises 3 to 20 nucleotides.

In some embodiments, the label region 314 can include a molecular label 318 and a cell label 320. In some embodiments, the label region 314 can include one or more of a universal label, a dimension label, and a cell label. The molecular label 318 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The cell label 320 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The universal label can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cell labels are the same for the plurality of stochastic barcodes on the solid support. The dimension label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 314 can comprise, comprise about, comprise at least, or comprise at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a molecular label 318 and a cell label 320. Each label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length. A set of molecular identifier labels 310 can contain, contain about, contain at least, or can be at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, molecular identifier labels 310. And the set of molecular identifier labels 310 can, for example, each contain a unique label region 314. The labeled cDNA molecules 304 can be purified to remove excess molecular identifier labels 310. Purification can comprise Ampure bead purification.

As shown in step 2, products from the reverse transcription process in step 1 can be pooled into 1 tube and PCR amplified with a $1^{st}$ PCR primer pool and a $1^{st}$ universal PCR primer. Pooling is possible because of the unique label region 314. In particular, the labeled cDNA molecules 304 can be amplified to produce nested PCR labeled amplicons 322. Amplification can comprise multiplex PCR amplification. Amplification can comprise a multiplex PCR amplification with 96 multiplex primers in a single reaction volume. In some embodiments, multiplex PCR amplification can utilize, utilize about, utilize at least, or utilize at most, 10, 20, 40, 50, 70, 80, 90, $10^2$, $10^3$, $10^4$, $10^5$, $10^6$, $10^7$, $10^8$, $10^9$, $10^{10}$, $10^{10}$, $10^{12}$, $10^{13}$, $10^{14}$, $10^{15}$, $10^{20}$, or a number or a range between any of these values, multiplex primers in a single reaction volume. Amplification can comprise $1^{st}$ PCR primer pool 324 of custom primers 326A-C targeting specific genes and a universal primer 328. The custom primers 326 can hybridize to a region within the cDNA portion 306' of the labeled cDNA molecule 304. The universal primer 328 can hybridize to the universal PCR region 316 of the labeled cDNA molecule 304.

As shown in step 3 of FIG. 3, products from PCR amplification in step 2 can be amplified with a nested PCR primers pool and a $2^{nd}$ universal PCR primer. Nested PCR can minimize PCR amplification bias. In particular, the nested PCR labeled amplicons 322 can be further amplified by nested PCR. The nested PCR can comprise multiplex PCR with nested PCR primers pool 330 of nested PCR primers 332a-c and a $2^{nd}$ universal PCR primer 328' in a single reaction volume. The nested PCR primer pool 328 can contain, contain about, contain at least, or contain at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 330. The nested PCR primers 332 can contain an adaptor 334 and hybridize to a region within the cDNA portion 306" of the labeled amplicon 322. The universal primer 328' can contain an adaptor 336 and hybridize to the universal PCR region 316 of the labeled amplicon 322. Thus, step 3 produces adaptor-labeled amplicon 338. In some embodiments, nested PCR primers 332 and the $2^{nd}$ universal PCR primer 328' may not contain the adaptors 334 and 336. The adaptors 334 and 336 can instead be ligated to the products of nested PCR to produce adaptor-labeled amplicon 338.

As shown in step 4, PCR products from step 3 can be PCR amplified for sequencing using library amplification primers. In particular, the adaptors 334 and 336 can be used to conduct one or more additional assays on the adaptor-labeled amplicon 338. The adaptors 334 and 336 can be hybridized to primers 340 and 342. The one or more primers 340 and 342 can be PCR amplification primers. The one or more primers 340 and 342 can be sequencing primers. The one or more adaptors 334 and 336 can be used for further amplification of the adaptor-labeled amplicons 338. The one or more adaptors 334 and 336 can be used for sequencing the adaptor-labeled amplicon 338. The primer 342 can contain a plate index 344 so that amplicons generated using the same set of molecular identifier labels 318 can be sequenced in one sequencing reaction using next generation sequencing (NGS).

Correcting PCR and Sequencing Errors

Disclosed herein are methods for determining the numbers of targets. In some embodiments, the method comprises: (a) stochastically barcoding a plurality of targets using a plurality of stochastic barcodes to create a plurality of stochastically barcoded targets, wherein each of the plurality of stochastic barcodes comprises a molecular label; (b) obtaining sequencing data of the stochastically barcoded targets; and (c) for one or more of the plurality of targets: (i) counting the number of molecular labels with distinct sequences associated with the target in the sequencing data; (ii) determining a quality status of the target in the sequencing data; (iii) determining one or more sequencing data errors in the sequencing data, wherein determining the one or more sequencing data errors in the sequencing data comprises determining one or more of: the number of the molecular labels with distinct sequences associated with the target in the sequencing data, the quality status of the target in the sequencing data, and the number of molecular labels with distinct sequences in the plurality of stochastic barcodes; and (iv) estimating the number of the target, wherein the number of the target estimated correlates with the number of molecular labels with distinct sequences associated with the target in the sequencing data counted adjusted according to the one or more sequencing data errors. Steps (i), (ii), (iii), and (iv) can be performed for each of the plurality of targets. The method can be multiplexed.

In some embodiments, the methods further comprise: collapsing the sequencing data prior to determining the one or more sequencing data errors. Collapsing the sequencing data comprises: attributing copies of the target with similar molecular labels and with occurrences fewer than a predetermined collapsing occurrence threshold as having the same molecular label for the plurality of targets, wherein two copies of a target have similar molecular labels if the molecular labels of the two copies of the target differ by at least one base in sequence.

The percentage of the molecular labels in the sequencing data retained after the sequencing data is adjusted according to the one or more sequencing data errors can vary. In some embodiments, the percentage of the molecular labels in the sequencing data retained after the sequencing data is adjusted according to the one or more sequencing data errors can be, or be about, 50%, 60%, 70%, 80%, 90%, 95%, 99%, 99.9%, or a number or a range between any two of these values. In some embodiments, the percentage of the molecular labels in the sequencing data retained after the sequencing data is adjusted according to the one or more sequencing data errors can be at least, or at most, 50%, 60%, 70%, 80%, 90%, 95%, 99%, or 99.9%.

Determine Molecular Label Counts

Figure 5:
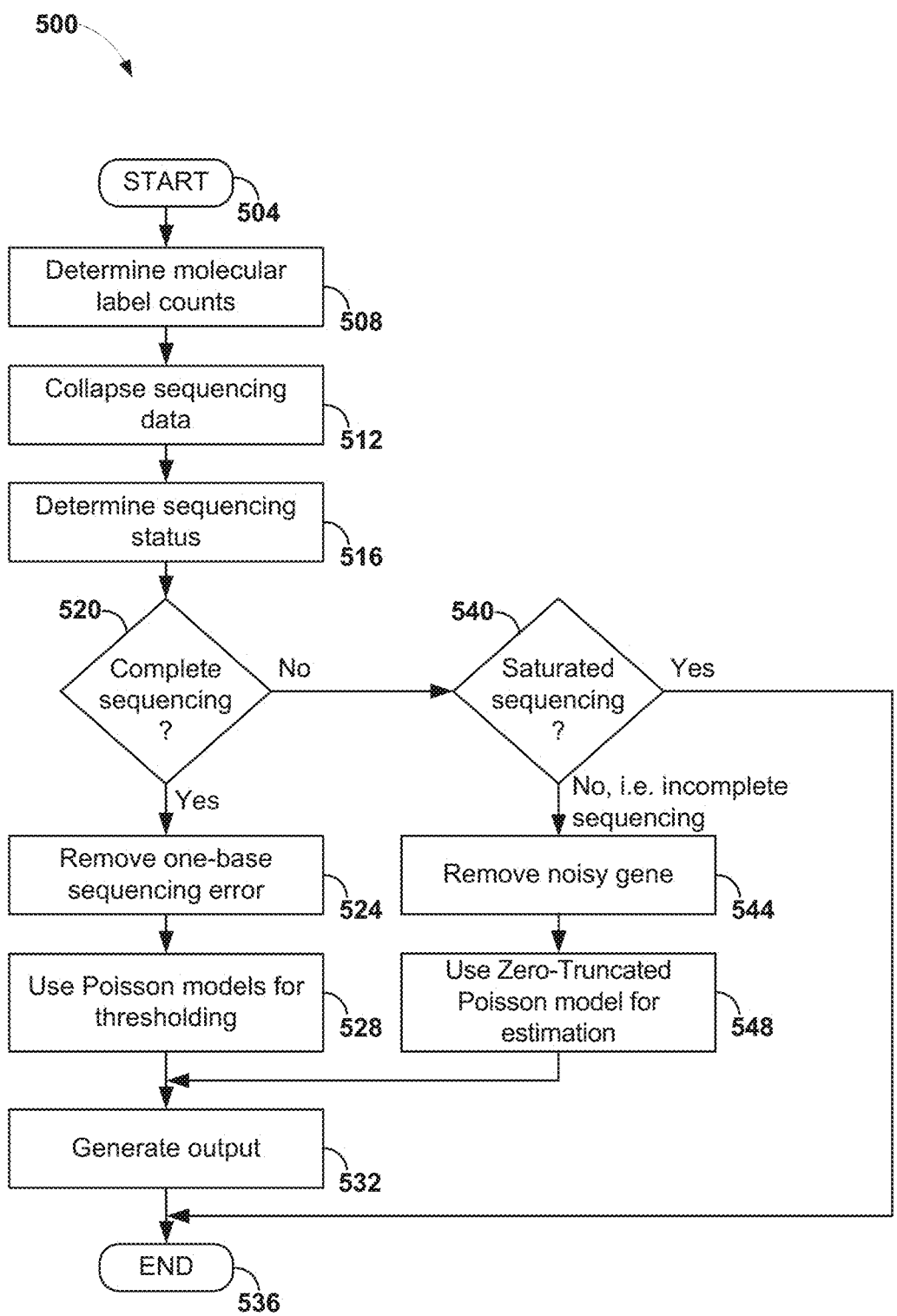
FIG. 5 is a flowchart showing a non-limiting exemplary embodiment of correcting PCR and sequencing errors using molecular labels.

FIG. 5 is a flowchart showing a non-limiting exemplary embodiment 500 of correcting PCR and sequencing errors using molecular labels. The embodiment 500 starts at beginning block 504 after stochastically barcoding a plurality of targets using a plurality of stochastic barcodes to create a plurality of stochastically barcoded targets, wherein each of the plurality of stochastic barcodes comprises a molecular label, and after obtaining sequencing data of the stochastically barcoded targets.

For a target, for example a gene originating from a cell in a microwell of a microwell array, the number of molecular labels with distinct sequences associated with the target in the sequencing data can be counted at block 508. In the sequencing data, two copies of the target may have similar molecular labels, for example the molecular labels of the two copies of the target may differ by one base in sequence. The two copies of the target may both be true, one copy of the target may be true and the other copy of the target may be a result of a sequencing error or a PCR error, or both copies of the target may be results of sequencing errors or PCR errors.

Collapsing Sequencing Data

At block 512, sequencing data can be collapsed. Collapsing the sequencing data can comprise attributing copies of the target with similar molecular labels and with occurrences fewer than a predetermined collapsing occurrence threshold as having the same molecular label for the plurality of targets. The predetermined collapsing occurrence threshold can vary, ranging from 1 to 100. In some embodiments, the predetermined collapsing occurrence threshold can be, or be about, 1, 2, 3, 4, 5, 6, 7, 8, 9, 10, 20, 30, 40, 50, 60, 70, 80, 90, 100, or a number or a range between any two of these values if the stochastic barcodes comprise about 6561 molecular labels with distinct sequences. In some embodiments, the predetermined collapsing occurrence threshold can be at least, or at most, 1, 2, 3, 4, 5, 6, 7, 8, 9, 10, 20, 30, 40, 50, 60, 70, 80, 90, or 100, if the stochastic barcodes comprise about 6561 molecular labels with distinct sequences. For example, the molecular labels can be 8 nucleotides in length, and each nucleotide position can have three possibilities such as adenine (A), cytosine (C), guanine (G); C, G, thymine (T); A, G, T; or A, C, T, giving rise to $3^8=6561$ unique molecular labels.

In some embodiments, the predetermined collapsing occurrence threshold can be, or be about, 1, 2, 3, 4, 5, 6, 7, 8, 9, 10, 17, 20, 30, 40, 50, 60, 70, 80, 90, 100, or a number or a range between any two of these values if the stochastic barcodes comprise about 65536 molecular labels with distinct sequences. In some embodiments, the predetermined collapsing occurrence threshold can be at least, or at most, 1, 2, 3, 4, 5, 6, 7, 8, 9, 10, 17, 20, 30, 40, 50, 60, 70, 80, 90, or 100, if the stochastic barcodes comprise about 65536 molecular labels with distinct sequences. For example, the molecular labels can be 8 nucleotides in length, and each nucleotide position can have four possibilities A, C, G, T, resulting in $3^4=65536$ unique molecular labels.

For example, there may be five copies of the target. The five copies of the target can have molecular labels of TGTGCGTG, TGTGCGCG, TGTGCGGG, GGTGCGTG, and TGGGCGTG (SEQ ID NO: 3-7) with numbers of reads per molecular label being 261, 2, 2, 1, and 1 respectively. The molecular labels TGTGCGCG, TGTGCGGG, GGTGCGTG, and TGGGCGTG (SEQ ID NO: 4-6) are similar to the molecular label TGTGCGTG (SEQ ID NO: 3) because they differ from the molecular label TGTGCGTG by one nucleotide (underlined). If there are 6561 molecular labels with distinct sequences, and the predetermined collapsing occurrence threshold is 7, then the occurrences of the molecular labels TGTGCGCG, TGTGCGGG, GGTGCGTG, and TGGGCGTG (SEQ ID NO: 4-6) can be attributed to the molecular label TGTGCGTG (SEQ ID NO: 3).

As another example, there may be seven copies of the target. The seven copies of the target can have molecular labels of CGTGTCTG, GGGGGCGA, GCTGCTGG, TCGGGCGA, CGCGTTCA, CGCGTTTA, and TGGGCTTG (SEQ ID NO: 8-14) with numbers of reads per molecular label being 10, 7, 5, 4, 1, 1, and 1 respectively. The molecular label CGCGTTTA (SEQ ID NO: 13) is similar to the molecular label CGCGTTCA (SEQ ID NO: 12) because they differ from each other by one nucleotide (underlined). If there are 6561 molecular labels with distinct sequences, and the predetermined collapsing occurrence threshold is 7, then the occurrence of the molecular label CGCGTTTA (SEQ ID NO: 13) can be attributed to the molecular label CGCGTTCA (SEQ ID NO: 12).

Sequencing Data Errors

Methods disclosed herein can be used for identifying and/or correcting sequencing data errors, for example the errors occurring in the methods for counting one or more target nucleic acids. In some embodiments, a sequencing data error can comprise, or be, a PCR-introduced error, a sequencing-introduced error, an error caused by barcode contamination, a library preparation error, or any combination thereof. The PCR-introduced error can comprise, or be, be a result of a PCR amplification error, PCR amplification bias, insufficient PCR amplification, or any combination thereof. The sequencing-introduced error can comprise, or be, a result of inaccurate base calling, insufficient sequencing, or any combination thereof. The error can comprise, or be, a deletion of one or more nucleotides, a substitution of one or more nucleotides, an addition of one or more nucleotides, or any combination thereof.

Determine Sequencing Status

As described above, a plurality of targets can be stochastically barcoded using a plurality of stochastic barcodes to create a plurality of stochastically barcoded targets, and each of the plurality of stochastic barcodes can comprise a molecular label and obtaining sequencing data of the stochastically barcoded targets. For a target, for example a gene originating from a cell in a microwell of a microwell array, the number of molecular labels with distinct sequences associated with the target in the sequencing data can be counted. The counted sequencing data can be collapsed by, for example, attributing copies of the target with similar molecular labels and with occurrences fewer than a predetermined collapsing occurrence threshold as having the same molecular label for the plurality of targets. After collapsing the sequencing data, a quality status of the target can be determined.

Referring to FIG. 5, in some embodiments, at block 516, a quality status of the target in the sequencing data can be determined to be complete sequencing, incomplete sequencing, or saturated sequencing. The quality status of the target can depend on whether all of the true or real molecular labels have been observed in the depth of the sequencing run. True or real molecular labels can refer to molecule labels that are not error or false molecular labels. Error or false molecular labels can refer to molecular labels having sequences resulting from PCR errors, artifacts, or sequencing errors. The quality status of the target in the sequencing data can be determined by the number of molecular labels with distinct sequences in the plurality of stochastic barcodes and the number of molecular labels with distinct sequences associated with the target in the sequencing data counted.

Figure 6:
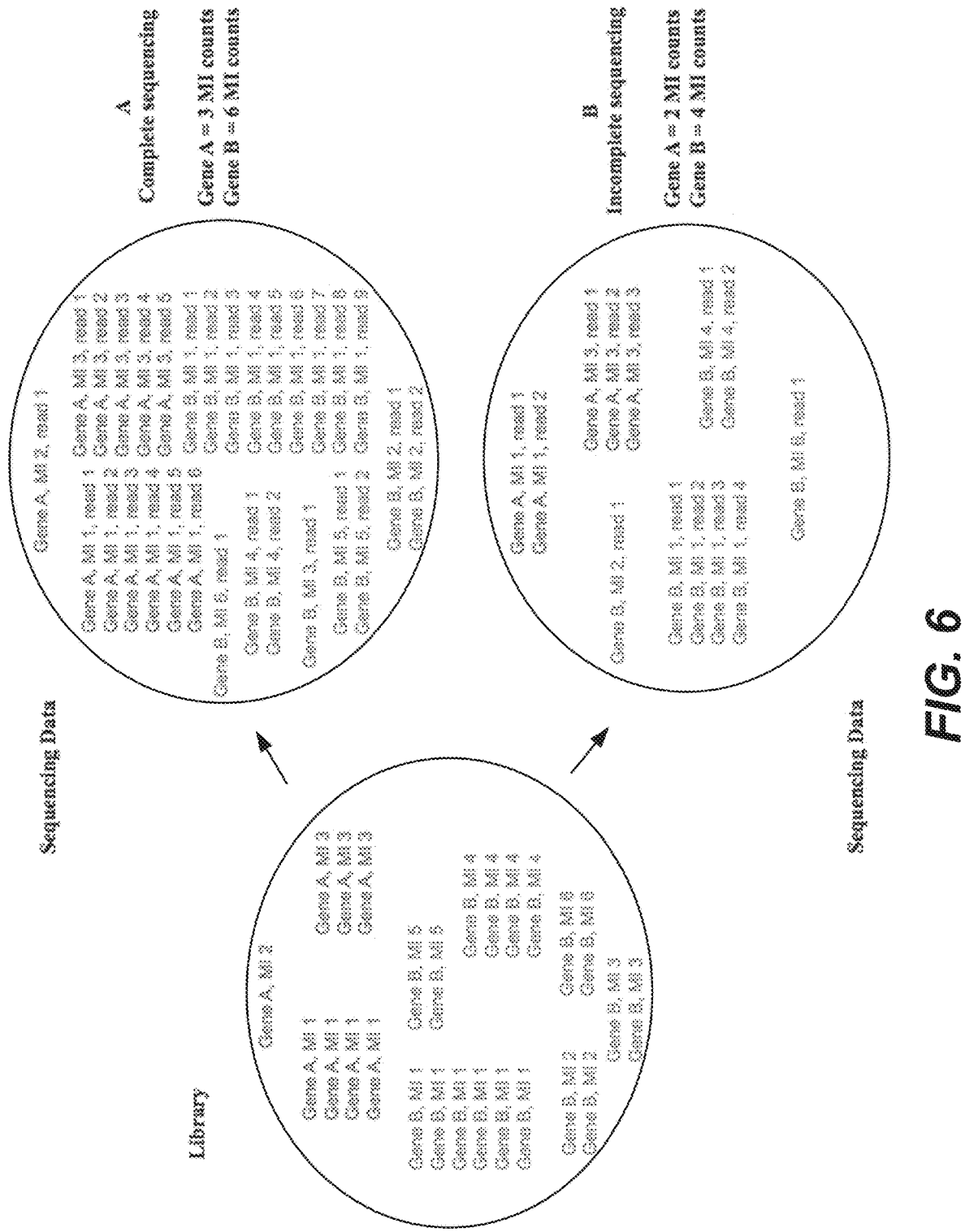
FIG. 6 is a schematic illustration showing sequence data obtained by complete sequencing and incomplete sequencing.

In some embodiments, the complete sequencing quality status can be determined by a dispersion index relative to the Poisson distribution greater than or equal to a predetermined complete sequencing dispersion threshold. The dispersion index can be defined as variance/mean for a target. FIG. 6 is a schematic illustration showing sequence data obtained by complete sequencing and incomplete sequencing. FIG. 6 shows three copies of Gene A and six copies of Gene B in the library (left circle). If the three copies of Gene A had sequencing reads of six times, five times, and once in the sequencing data (top right circle), the variance is 7, the mean is 4, and the dispersion index is 1.75. If the six copies of Gene B had sequencing reads of nine times, twice, twice, twice, once, and once in the sequencing data (top right circle), the variance is 9.36, the mean is 2.83, and the dispersion index is 3.31. With these sequencing data, Gene A and Gene B can be considered to have the complete sequencing status if the predetermined complete sequencing dispersion threshold is, for example, 0.9 for complete sequencing.

If one copy of Gene A was not observed and the other two copies of Gene A had sequencing reads of twice and three times in the sequencing data (bottom right circle), the variance is 0.5, the mean is 2.5, and the dispersion index is 0.2. If two copies of Gene B were not observed and the other four copies of Gene B had sequencing reads of four times, twice, once, and once in the sequencing data (bottom right circle), the variance is 2, the mean is 2, and the dispersion index is 2. With these sequencing data, Gene A and Gene B can be considered to have the incomplete sequencing status if the predetermined complete sequencing dispersion threshold is, for example, 1.1 for complete sequencing.

The predetermined complete sequencing dispersion threshold can vary, ranging from 0.5 to 5. In some embodiments, the predetermined complete sequencing dispersion threshold can be, or be about, 0.5, 0.6, 0.7, 0.8, 0.9, 1, 2, 3, 4, 5, 6, or a number or a range between any two of these values. In some embodiments, the predetermined complete sequencing dispersion threshold can be at least, or at most 0.5, 0.6, 0.7, 0.8, 0.9, 1, 2, 3, 4, 5, or 6

In some embodiments, the complete sequencing quality status can be further determined by a molecular label with an occurrence greater than or equal to a predetermined complete sequencing occurrence threshold in the sequencing data. The predetermined complete sequencing occurrence threshold can vary, ranging from 8 to 20. In some embodiments, the complete sequencing occurrence threshold can be, or be about, 8, 9, 10, 11, 12, 13, 14, 15, 16, 17, 18, 19, 20, or a number or a range between any two of these values. In some embodiments, the complete sequencing occurrence threshold can be at least, or at most, 8, 9, 10, 11, 12, 13, 14, 15, 16, 17, 18, 19, or 20.

In some embodiments, the saturated sequencing quality status can be determined by the target having a number of molecular labels with distinct sequences been greater than a predetermined saturation threshold. The saturated sequencing quality status can be further determined by one other target of the plurality of targets having a number of molecular labels with distinct sequences to be greater than the predetermined saturation threshold.

The predetermined saturation threshold can vary. In some embodiments, the predetermined saturation threshold can be, or be about, 6000, 6100, 6200, 6300, 6400, 6500, 6557, 6558, 6559, 6560, 6561 or a number or a range between any two of these values if the stochastic barcodes comprise about 6561 molecular labels with distinct sequences. In some embodiments, the predetermined saturation threshold can be at least, or at most, 6000, 6100, 6200, 6300, 6400, 6500, 6557, 6558, 6559, 6560, or 6561 if the stochastic barcodes comprise about 6561 molecular labels with distinct sequences. In some embodiments, the predetermined saturation threshold can be, or be about, 64000, 64100, 64200, 64300, 64400, 64500, 64600, 64700, 64800, 64900, 65000, 65100, 65200, 65300, 65400, 65500, 65510, 65520, 65530, 65532, 65533, 65534, 65535, or a number or a range between any two of these values if the stochastic barcodes comprise about 65536 molecular labels with distinct sequences. In some embodiments, the predetermined saturation threshold can be at least, or at most, 64000, 64100, 64200, 64300, 64400, 64500, 64600, 64700, 64800, 64900, 65000, 65100, 65200, 65300, 65400, 65500, 65510, 65520, 65530, 65532, 65533, 65534, or 65535 if the stochastic barcodes comprise about 65536 molecular labels with distinct sequences.

In some embodiments, the quality status of the target in the sequencing data can be classified as incomplete sequencing if the quality status of the target in the sequencing data is not complete sequencing and not saturated sequencing.

Complete Sequencing Quality Status

The methods disclosed herein can provide an estimate of the number of a target in a sequencing library if the target has the complete sequencing quality status. When the target in the sequencing library has the complete sequencing quality status, a threshold can be established through separate Poisson models for sequencing reads of true and error stochastic barcodes. The quality status of the target can depend on whether all of the true or real molecular labels have been observed in the depth of the sequencing run. True or real molecular labels can refer to molecule labels that are not error or false molecular labels. Error or false molecular labels can refer to molecular labels having sequences resulting from PCR errors, artifacts, or sequencing errors.

Referring to FIG. 5, at decision state 520, if a target molecule has the complete sequencing status, the embodiment 500 proceeds to block 524. At block 524, one-base sequencing errors can be removed by the following steps. Step (1), select the molecular label associated with the most abundance sequencing read as the first parent molecular label if its sequencing read is bigger than 25. For example, after counting the number of molecular labels with distinct sequences associated with the target in the sequencing data, select the molecular label associated with the target in the sequencing data with the highest sequencing read.

Step (2), identify children molecular labels: molecular labels with sequencing reads ≤3 and are one-base apart from the first parent molecular label; if no child molecular label or no one-base children molecular labels are found, go to step (5). Step (3), perform multiple Binomial tests on all children molecular labels and parent molecular labels, and remove those children molecular labels whose null hypothesis is accepted and attributing their sequencing reads to their parents. If none of the null hypotheses is accepted, which implies that all children molecular labels are not one-base sequencing errors of the parent molecular label, no read correction needs to be performed. Step (4), update molecular label sequences as well as sequencing reads. For example, the occurrence of the child molecular label can be attributed to the parent molecular label if the null hypothesis of the multiple Binomial test is accepted. Step (5), choose the molecular label with the next largest sequencing read as the parent molecular label and repeat the above steps until no qualified parental molecular label or no qualified child molecular label remain.

In some embodiments, the number of molecular labels with distinct sequences associated with the target in the sequencing data counted can be adjusted by, if the target has the complete sequencing quality status, determining all children molecular labels for one or more parent molecular labels; performing a statistical analysis such as a multiple Binomial test for at least one child molecular label and the parent molecular label; and attributing the occurrence of the child molecular label to the parent molecular label if the null hypothesis of the statistical analysis is accepted.

In some embodiments, the children molecular labels can comprise molecular labels that differ from the parent molecular label by one base and have occurrences smaller than or equal to a predetermined complete sequencing child threshold. The predetermined complete sequencing child threshold can vary. In some embodiments, the predetermined complete sequencing child threshold can be, or be about, 1, 2, 3, 4, 5, 6, 7, 8, 9, 10, or a number or a range between any two of these values. In some embodiments, the predetermined complete sequencing child threshold can be at least, or at most, 1, 2, 3, 4, 5, 6, 7, 8, 9, or 10.

In some embodiments, the one or more parent molecular labels comprise molecular labels with occurrences greater than or equal to a predetermined complete sequencing parent threshold, wherein the predetermined complete sequencing parent threshold equals to the predetermined complete sequencing occurrence threshold, for example 8. The null hypothesis of the first statistical analysis can be accepted if the probability of the null hypothesis being true is below the false discovery rates. The false discovery rates can vary. In some embodiments, the false discovery rate can be, or be about, 1%, 2%, 3%, 4%, 5%, 6%, 7%, 8%, 9%, 10%, 11%, 12%, 13%, 14%, 15%, 16%, 17%, 18%, 19%, 20%, or a number or a range between any two of these values. In some embodiments, the false discovery rate can be at least, or at most, 1%, 2%, 3%, 4%, 5%, 6%, 7%, 8%, 9%, 10%, 11%, 12%, 13%, 14%, 15%, 16%, 17%, 18%, 19%, or 20%. The first statistical analysis can be a multiple binomial test.

At block 528, Poisson models can be used for thresholding molecular labels of the target to determine true molecular labels and false molecular labels associated with the target in the sequencing data. For example, Poisson models can be applied to sequencing reads to distinguish "likely to be true" molecular labels from artifacts.

In some embodiments, the number of molecular labels with distinct sequences associated with the target in the sequencing data counted can be adjusted by, if the target has the complete sequencing quality status, thresholding molecular labels of the target to determine true molecular labels and false molecular labels associated with the target in the sequencing data. Thresholding the molecular labels of the target can comprise performing a statistical analysis on the molecular labels of the target.

In some embodiments, performing the statistical analysis comprises: fitting the distribution of the molecular labels of the target and their occurrences to two Poisson distributions; determining the number of true molecular labels n using the two Poisson distributions; and removing the false molecular labels from the sequencing data, wherein the false molecular labels comprise molecular labels with occurrences lower than the occurrence of the nth most abundant molecular label, and wherein the true molecular labels comprise molecular labels with occurrences greater than or equal to the occurrence of the nth most abundant molecular label. The two Poisson distributions can comprise a first Poisson distribution corresponding for the true molecular labels and a second Poisson distribution for the false molecular labels.

At block 532, the number of the target can be estimated to generate output after correcting or adjusting the sequencing data using multiple Binomial tests or the two Poisson distributions. The embodiment 500 ends at ending block 536.

Saturated Sequencing Quality Status

The methods disclosed herein may be unable to provide an estimate of the number of a target in a sequencing library if the target has the saturated sequencing quality status because of the large uncertainties in estimating the molecular label counts. Referring to FIG. 5, in some embodiments, at decision state 520, if the sequencing status is not the complete sequencing status, the embodiment 500 proceeds to decision state 540. At decision state 540, if the target has the saturated sequencing status, the embodiment 500 proceeds to the ending block 536. With the saturated sequencing status, the number of the target may not be determined because of the large uncertainties in estimating the molecular label counts.

Incomplete Sequencing Quality Status

The methods disclosed herein can provide an estimate of the number of a target in a sequencing library if the target has the incomplete sequencing quality status. When the target in the sequencing library has the incomplete sequencing quality status, a noisy target, for example a noisy gene, can be removed. A target can be noisy if its amplification rate (average reads per molecular label) is similar to the amplification rate of errors derived from completely sequenced genes in the same library containing the target. A Zero-Truncated Poisson model can be applied to the sequencing reads of the target with a quality status of incomplete sequencing to extrapolate an estimate of the number of stochastic barcodes comprising the target with distinct molecular labels present in the library The embodiment 500 can provide an estimate of the number of a target in a sequencing library if some of the true stochastic barcodes used to label the starting target were not observed due to inadequate sequencing depth. At decision state 540, if the target does not have the saturated sequencing status, then the target has the incomplete sequencing status, and the embodiment 500 proceeds to block 544 to remove a noisy target, for example a noisy gene.

If the dispersion index of a target is >4 and the maximum sequencing read for that target is >18, using Poisson modeling to derive the threshold to separate true and error barcodes can still provide a sensible estimate. If the sequencing data shows moderate over-dispersion, for example 1.5< dispersion index ≤4 and the maximum sequencing read for that target is ≤18, then using Poisson models to derive the threshold may underestimate true molecular label counts. The reason for underestimation may be because molecular labels with low reads may likely be a mixture of true and false molecular labels. Consequently those true molecular labels with low sequencing reads may be forced into the Poisson model for errors, and the Poisson model for true molecular labels may have fewer molecular labels than it should be. An ad-hoc method, for example using molecular label counts after removing molecular labels with low counts such as one, may be used. If the dispersion index is close to one, such as between 0.9 and 1.5, then the observed molecular label counts can produce in a sensible estimate. If the dispersion index is between 0.1 and 0.9, the Zero-Truncated-Poisson model featuring the under-dispersed Poisson model may produce sensible estimates; but if errors are present in the sequencing data, then this model may tend to overestimate.

In some embodiments, the number of molecular labels with distinct sequences associated with the target in the sequencing data can be adjusted by, if the quality status of the target in the sequencing data is the incomplete sequencing quality status, determining if the target is noisy in the sequencing data; and removing the noisy target from the sequencing data. The target can be noisy if the occurrence of the molecular labels of the noisy targets is smaller than or equal to an incomplete sequencing noisy target threshold. The incomplete sequencing noisy gene threshold can vary. In some embodiments, the incomplete sequencing noisy target threshold can equal the median or mean occurrence of the molecular labels of the plurality of targets with quality statuses of complete sequencing. In some embodiments, the incomplete sequencing noisy gene threshold can be, or be about, 1, 2, 3, 4, 5, 6, 7, 8, 9, 10, or a number or a range between any two of these values. In some embodiments, the incomplete sequencing noisy gene threshold can be at least, or at most, 1, 2, 3, 4, 5, 6, 7, 8, 9, or 10.

At block 548, a Zero-Truncated Poisson model is applied to the sequencing reads of the target with a quality status of incomplete sequencing to extrapolate an estimate of the number of stochastic barcodes comprising the target with distinct molecular labels present in the library. In some embodiments, the number of molecular labels with distinct sequences associated with the target in the sequencing data is adjusted by, if the quality status of the target in the sequencing data obtained is the incomplete sequencing quality status, determining if the target is noisy in the sequencing data; and removing the target that is noisy.

In some embodiments, the number of molecular labels with distinct sequences associated with the target in the sequencing data can be adjusted by, if the quality status of the target in the sequencing data is the incomplete sequencing quality status, thresholding the molecular labels of the target to determine true molecular labels and false molecular labels in the sequencing data. Thresholding the molecular labels of the target can comprise performing a statistical analysis on the molecular labels. Performing the statistical analysis on the molecular labels can comprise: determining the number of true molecular labels n using a Zero-Truncated Poisson model; and removing the false molecular labels from the sequencing data.

In some embodiments, the false molecular labels can comprise molecular labels with occurrences lower than the occurrence of the nth most abundant molecular label. The true molecular labels can comprise molecular labels with occurrences greater than or equal to the occurrence of the nth most abundant molecular label.

Sequencing Data Errors

Methods disclosed herein can be used for identifying and/or correcting sequencing data errors, for example the errors occurring in the methods for counting one or more target nucleic acids. In some embodiments, the error can comprise, or be, a deletion of one or more nucleotides, a substitution of one or more nucleotides, an addition of one or more nucleotides, or any combination thereof. The error can be present on a molecular label (ML), a sample label (SL), or another other label on a stochastic barcode. In some embodiments, a sequencing data error can comprise, or be, a PCR-introduced error, a sequencing-introduced error, a reverse transcription (RT) primer contamination error, or any combination thereof. The PCR-introduced error can comprise, or be, a result of a PCR amplification error, PCR amplification bias, insufficient PCR amplification, or any combination thereof. The sequencing-introduced error can comprise, or be, a result of inaccurate base calling, insufficient sequencing, or any combination thereof. The RT primer contamination error may be an error caused by a reverse transcription primer entering PCR.

As used herein, the term "coverage" or "sequencing depth" can refer to the number of reads of a barcoded target with a particular ML and a particular SL in sequencing data. For example, a barcoded target may be sequenced multiple times. Accordingly, the barcoded target with a particular ML and SL can be observed multiple times. As another example, a cell may contain multiple copies of a target (for example, multiple copies of mRNA molecules of a gene). These multiple copies of the target can be barcoded. After PCR amplification, there can be multiple copies of a barcoded target with a particular ML and SL. During sequencing, some or all of the multiple copies of the barcoded target with the particular ML and SL may be sequenced. The number of reads the barcoded target with the same ML and SL observed in sequencing data may be referred to as "coverage" or "sequencing depth."

In some embodiments, sequencing data errors can be identified and/or corrected. For example, copies of a target from a cell can be barcoded with different MLs and the same SL. The barcoded target with a ML can have multiple reads in sequencing data. The barcoded target with a different ML can have only a few reads (e.g., one read). The former barcoded target can be more likely to have a true ML (or real or signal ML), compared to the latter barcoded target. The latter barcoded target can include an error ML (or false or noise ML). This may be because that the two MLs can be expected to have similar coverages or sequencing depths. The latter barcoded target with only a few reads can be an artifact or error generated during sequencing or PCR.

As another example, a stochastic barcode entering PCR can result in a RT primer contamination error. In some embodiments, after reverse transcribing mRNA molecules into cDNA molecules, stochastic barcodes not incorporated into cDNA molecules can be removed by, for example, Ampure bead purification. The removal method, for example Ampure bead purification, may not completely remove the stochastic barcodes that are not extended by reverse transcription to be incorporated into stochastically barcoded cDNA molecules. For example, 15%, 10%, 9%, 8%, 7%, 6%, 5%, 4%, 3%, 2%, 1%, 0.5%, 0.1%, or a range between any of these two values of stochastic barcodes that are not extended by reverse transcription to be incorporated into stochastically barcoded cDNA molecules may not be removed by Ampure bead purification. These unremoved stochastic barcodes can result in sequencing data error during amplification of cDNA molecules. The stochastic barcodes between samples can be highly similar. For example, sample labels of stochastic barcodes can be identical for a sample. Thus, PCR cross over can occur because these unremoved stochastic barcodes can hybridize to other nucleic acid molecules from the same sample (for example, the SL regions of stochastically barcoded mRNA molecules) during PCR and can result in sequencing data errors referred to as SL errors.

Figure 4:
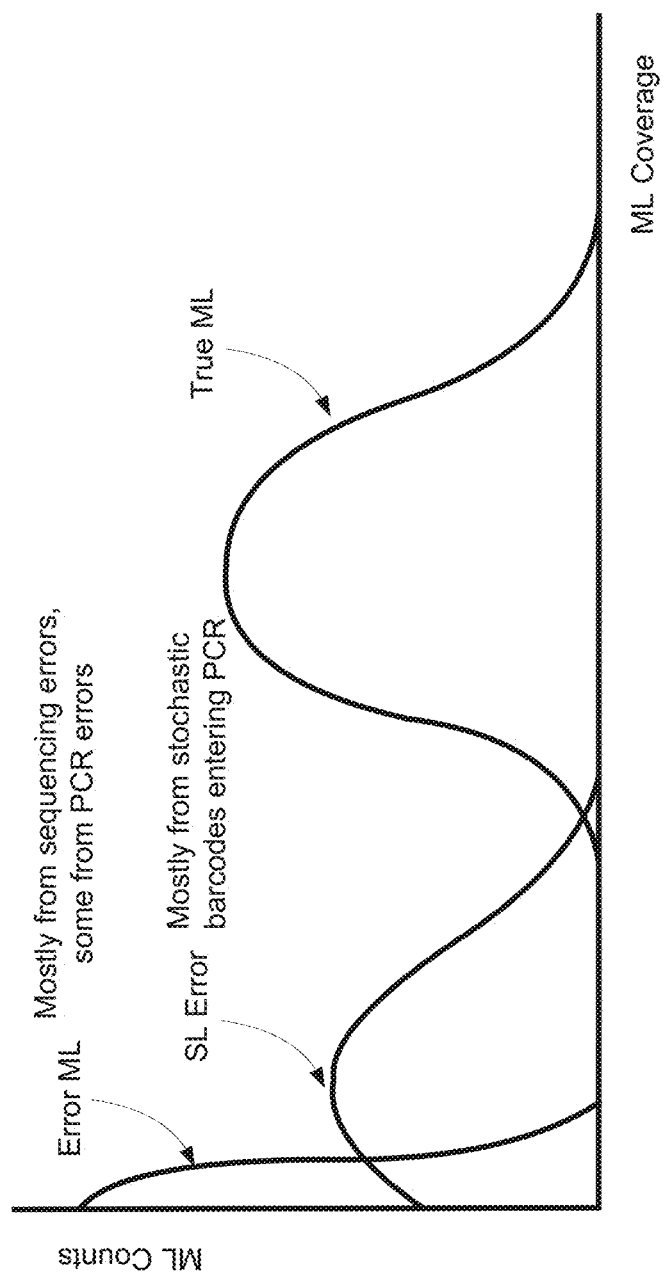
FIG. 4 is a schematic illustration showing non-limiting exemplary distributions of molecular label errors, sample label errors, and true molecular label signals.

True MLs, error MLs, and SL errors can have distinct distributions. FIG. 4 is a schematic illustration showing non-limiting exemplary distributions of molecular label errors, sample label errors, and true molecular label signals. As illustrated in FIG. 4, error MLs may be more likely to have lower ML coverage because error MLs may be results of PCR or sequencing errors. For example, error MLs may be results of mostly sequencing errors and some PCR errors. SL errors may be more likely to have lower ML coverage because SL errors may be results mostly from stochastic barcodes entering PCR.

Correcting PCR and Sequencing Errors Based on Directional Adjacency

Disclosed herein are methods for correcting PCR or sequencing errors. In some embodiments, the method comprises: (a) receiving sequencing data of stochastically barcoded targets. The stochastically barcoded targets can be obtained by stochastically barcoding a plurality of targets using a plurality of stochastic barcodes to create a plurality of stochastically barcoded targets, wherein each of the plurality of stochastic barcodes comprises a molecular label. In some embodiments, the method comprises: (b) for one or more of the plurality of targets: (i) counting the number of molecular labels with distinct sequences associated with the target in the sequencing data; (ii) identifying clusters of molecular labels of the target using directional adjacency; (iii) collapsing the sequencing data received in (b) using the clusters of molecular labels of the target identified in (ii); and (iv) estimating the number of the target, wherein the number of the target estimated correlates with the number of molecular labels with distinct sequences associated with the target in the sequencing data counted in (i) after collapsing the sequencing data in (ii). The plurality of targets can comprise targets of the whole transcriptome of a cell. In some embodiments, the method further comprises: (c) stochastically barcoding the plurality of targets using the plurality of stochastic barcodes to create the plurality of stochastically barcoded targets; and (d) sequencing the stochastically barcoded targets to generate the sequencing data of stochastically barcoded targets received.

Figure 7:
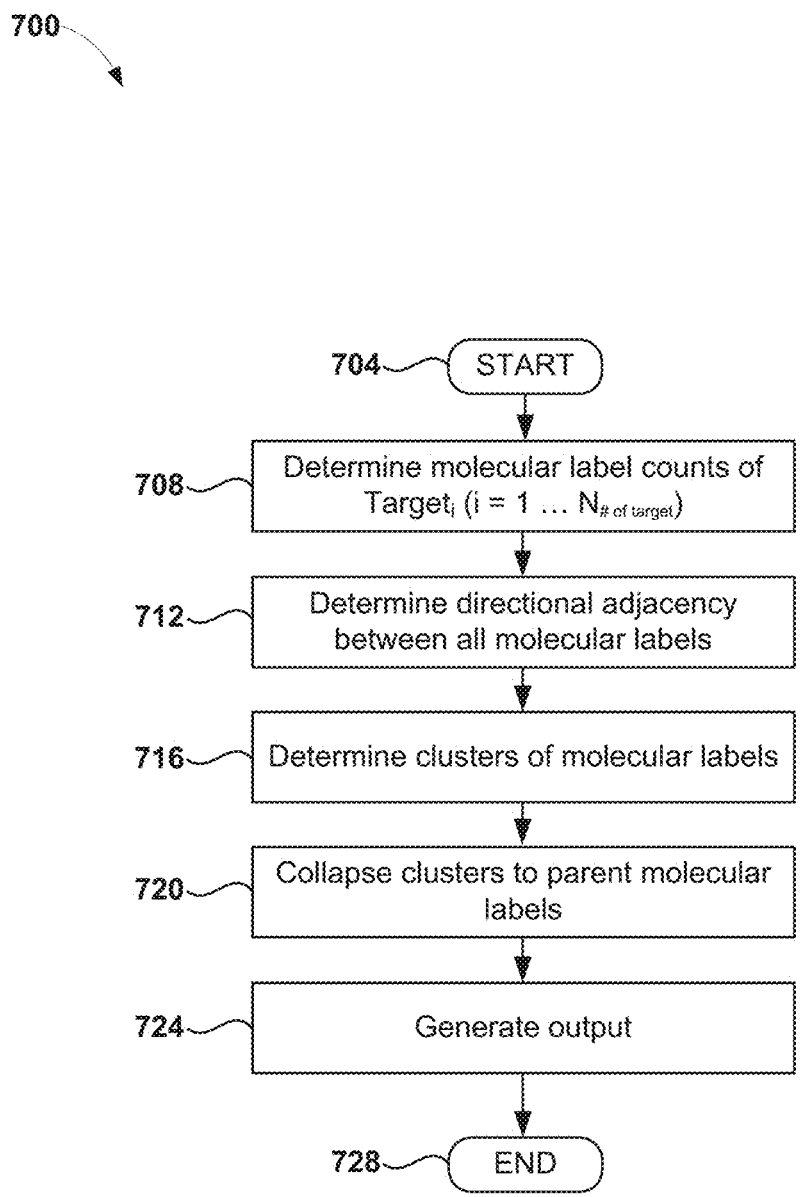
FIG. 7 is a flowchart showing a non-limiting exemplary embodiment of correcting PCR and sequencing errors using molecular labels based on directional adjacency.

FIG. 7 is a flowchart showing a non-limiting exemplary embodiment 700 of correcting PCR and sequencing errors using molecular labels based on directional adjacency. Correcting PCR and sequencing errors using molecular labels based on directional adjacency may be referred to as recursive substitution error correction (RSEC) The method 700 starts at block 704 after receiving sequencing data of a plurality of stochastically barcoded targets. In some embodiments, the method 700 further comprises stochastically barcoding a plurality of targets using a plurality of stochastic barcodes to create the plurality of stochastically barcoded targets, wherein each of the plurality of stochastic barcodes comprises a molecular label. In some embodiments, the method 700 further comprises sequencing the plurality of stochastically barcoded targets to obtain the sequencing data.

At block 708, for one or more of the plurality of targets: the number of molecular labels with distinct sequences associated with the target in the sequencing data can be counted. At block 712, clusters of molecular labels of the target can be identified using directional adjacency. Molecular labels of the target within a cluster can be within a predetermined directional adjacency threshold of one another. The directional adjacency threshold can vary. In some embodiments, the predetermined directional adjacency threshold can be, be about, be at least, or be at most, a Hamming distance of one or two.

In some embodiments, the molecular labels of the target within the cluster can comprise one or more parent molecular labels and children molecular labels of the one or more parent molecular labels. The occurrence of the parent molecular label can be greater than or equal to a predetermined directional adjacency occurrence threshold. In some embodiments, the predetermined directional adjacency occurrence threshold can be, be about, be at least, or be at most, twice the occurrence of a child molecular label less one. In some embodiments, the predetermined directional adjacency occurrence threshold can be, or be about 1.5 time, 2 times, 3 times, 4 times, 5 times, 6 times, 7 times, 8 times, 9 times, 10 times, or a number or a range between any two of these values, the occurrence of a child molecular label. In some embodiments, the predetermined directional adjacency occurrence threshold can be, at least or at most 1.5 time, 2 times, 3 times, 4 times, 5 times, 6 times, 7 times, 8 times, 9 times, or 10 times, the occurrence of a child molecular label.

At block 720, the sequencing data is collapsed using the clusters of molecular labels of the target. Collapsing the sequencing data can comprise attributing the occurrence of the child molecular label to the parent molecular label. At block 724, the number of the target can be estimated to generate output after collapsing the sequencing data. The method 700 ends at block 728.

In some embodiments, the methods further comprise: determining a sequencing depth of the target. Estimating the number of the target, if the sequencing depth of the target is above a predetermined sequencing depth threshold, comprises adjusting the sequencing data counted in (i). The predetermined sequencing depth threshold can be between 15 and 20. Adjusting the sequencing data counted in (i) comprises: thresholding molecular labels of the target to determine true molecular labels and false molecular labels associated with the target in the sequencing data obtained in (b). Thresholding the molecular labels of the target comprises performing a statistical analysis on the molecular labels of the target. Performing the statistical analysis comprises: fitting the distribution of the molecular labels of the target and their occurrences to two distributions such as two negative binomial distributions; determining the number of true molecular labels n using the two negative binomial distributions; and removing the false molecular labels from the sequencing data obtained in (b), wherein the false molecular labels comprise molecular labels with occurrences lower than the occurrence of the nth most abundant molecular label, and wherein the true molecular labels comprise molecular labels with occurrences greater than or equal to the occurrence of the nth most abundant molecular label.

Correcting PCR and Sequencing Errors Based on Directional Adjacency and Second Derivatives Disclosed herein are methods for determining the numbers of targets. In some embodiments, a method comprises: (a) stochastically barcoding a plurality of targets using a plurality of stochastic barcodes to create a plurality of stochastically barcoded targets, wherein each of the plurality of stochastic barcodes comprises a molecular label; (b) obtaining sequencing data of the stochastically barcoded targets; and (c) for one or more of the plurality of targets: (i) counting the number of molecular labels with distinct sequences associated with the target in the sequencing data; (ii) identifying clusters of molecular labels of the target using directional adjacency; (iii) collapsing the sequencing data obtained in (b) using the clusters of molecular labels of the target identified in (ii); and (iv) estimating the number of the target, wherein the number of the target estimated correlates with the number of molecular labels with distinct sequences associated with the target in the sequencing data counted in (i) after collapsing the sequencing data in (ii). The plurality of targets can comprise targets of the whole transcriptome of a cell.

In some embodiments, the method comprises determining a sequencing status of the target in the sequencing data. The sequencing status of the target in the sequencing data can include, or be, saturated sequencing. In some embodiments, if the sequencing status of the target in the sequencing data is the saturated sequencing status, the number of the target estimated in (iv) correlates with the number of molecular labels with distinct sequences associated with the target in the sequencing data counted in (i).

In some embodiments, the number of the target estimated correlates with the number of molecular labels with distinct sequences associated with the target in the sequencing data counted in (i) after correcting for SL errors. Correcting for SL errors can comprise generating a cumulative sum plot of the molecular labels with distinct sequences associated with the target in the sequencing data; determining second derivatives of the cumulative sum plot; and determining a ML read depth cutoff based on a minimum of the second derivatives of the cumulative sum plot. In some embodiments, correcting for the SL errors can include removing molecular labels with distinct sequences associated with the target in the sequencing data with read depths lower than the ML read depth cutoff determined.

Figure 8:
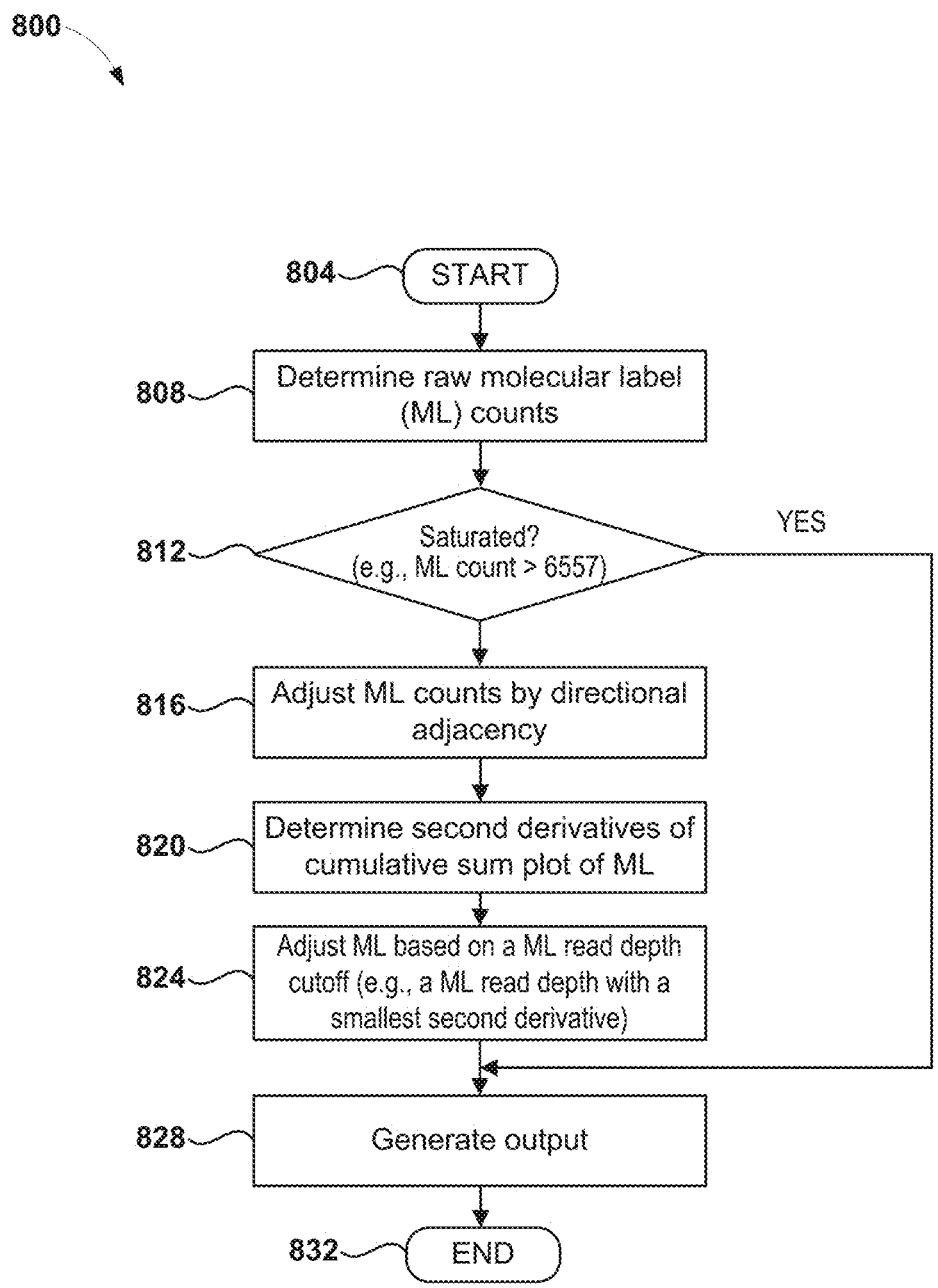
FIG. 8 is a flowchart showing a non-limiting exemplary embodiment of correcting PCR and sequencing errors based on recursive substitution error correction and second derivatives of molecular label depth change.

FIG. 8 is a flowchart showing a non-limiting exemplary embodiment 800 of correcting PCR and sequencing errors using molecular labels based on directional adjacency and second derivatives. The method 800 starts at block 804 after receiving sequencing data of a plurality of stochastically barcoded targets. In some embodiments, the method 800 further comprises stochastically barcoding a plurality of targets using a plurality of stochastic barcodes to create the plurality of stochastically barcoded targets, wherein each of the plurality of stochastic barcodes comprises a molecular label. In some embodiments, the method 800 further comprises sequencing the plurality of stochastically barcoded targets to obtain the sequencing data.

At block 808, for one or more of the plurality of targets: the number of molecular labels with distinct sequences associated with the target in the sequencing data can be counted. At decision block 812, whether the sequencing data has a saturated sequencing status can be determined. The saturated sequencing status can be determined by the target having a number of molecular labels with distinct sequences greater than a predetermined saturation threshold. The predetermined saturation threshold can be different in different implementations. For example, the predetermined saturation threshold can be about 6557 if the stochastic barcodes comprise about 6561 molecular labels with distinct sequences. As another example, the predetermined saturation threshold can be about 65532 if the stochastic barcodes comprise about 65536 molecular labels with distinct sequences.

If the sequencing data does not have a saturated sequencing status at decision block 812, the method 800 can proceed to block 816, wherein the molecular label counts can be adjusted based on directional adjacency. For example, the target can be considered to have the saturated sequencing status if it has a number of molecular labels with distinct sequences greater than 1000, 2000, 3000, 4000, 5000, 6000, 7000, 8000, 9000, 10000, 20000, 30000, 40000, 50000, 60000, 70000, 80000, 90000, 100000, or a number or a range between any two of these. As another example, the target can be considered to have the saturated sequencing status if it has a number of molecular labels with distinct sequences greater than 50%, 60%, 70%, 80%, 90%, 95%, 99%, 99.9%, or a number or a range between any two of these, of the molecular barcodes of the stochastic barcodes with distinct sequences. In some embodiments, adjusting the molecular counts based on directional adjacency can be as described with reference to FIG. 7. For example, adjusting the molecular counts based on dictionary can include identifying clusters of molecular labels of the target using directional adjacency; collapsing the sequencing data using the clusters of molecular labels of the target identified; and estimating the number of the target, wherein the number of the target estimated correlates with the number of molecular labels with distinct sequences associated with the target in the sequencing data counted after collapsing the sequencing data.

At block 820, second derivatives of a cumulative sum plot can be determined. Determining the second derivatives of the cumulative sum plot can include generating the cumulative sum plot of the molecular labels with distinct sequences associated with the target in the sequencing data.

At block 824, molecular labels can be adjusted based on a ML read depth cutoff. The ML read depth cutoff can be based on a minimum (such as a local minimum or a global minimum) of the second derivative of the cumulative sum plot. In some embodiments, correcting for the SL errors can include removing molecular labels with distinct sequences associated with the target in the sequencing data with read depths lower than the ML read depth cutoff determined.

At block 828, the number of the target can be estimated to generate output after collapsing the sequencing data and correcting for SL errors. At decision block 812, if the sequencing data has the saturated sequencing status, the method 800 can proceed to block 828 to generate output without collapsing the sequencing data and correcting for SL errors. The method 800 ends at block 832.

Correcting PCR and Sequencing Errors Based on Directional Adjacency and Distribution-Based Error Correction Disclosed herein are methods for correcting PCR or sequencing errors. The methods can be used to determine the number of targets. In some embodiments, the method comprises: (a) receiving sequencing data of stochastically barcoded targets. The stochastically barcoded targets can be obtained by stochastically barcoding a plurality of targets using a plurality of stochastic barcodes to create a plurality of stochastically barcoded targets, wherein each of the plurality of stochastic barcodes comprises a molecular label. In some embodiments, the method comprises (b) for one or more of the plurality of targets: (i) counting the number of molecular labels with distinct sequences associated with the target in the sequencing data; (ii) determining a number of noise molecular labels with distinct sequences associated with the target in the sequencing data; and (iii) estimating the number of the target, wherein the number of the target estimated correlates with the number of molecular labels with distinct sequences associated with the target in the sequencing data counted in (i) adjusted according to the number of noise molecular labels determined in (ii). In some embodiments, the method comprises determining a sequencing status of the target in the sequencing data. In some embodiments, the method further comprises: (c) stochastically barcoding the plurality of targets using the plurality of stochastic barcodes to create the plurality of stochastically barcoded targets; and (d) sequencing the stochastically barcoded targets to generate the sequencing data of stochastically barcoded targets received.

Figure 9:
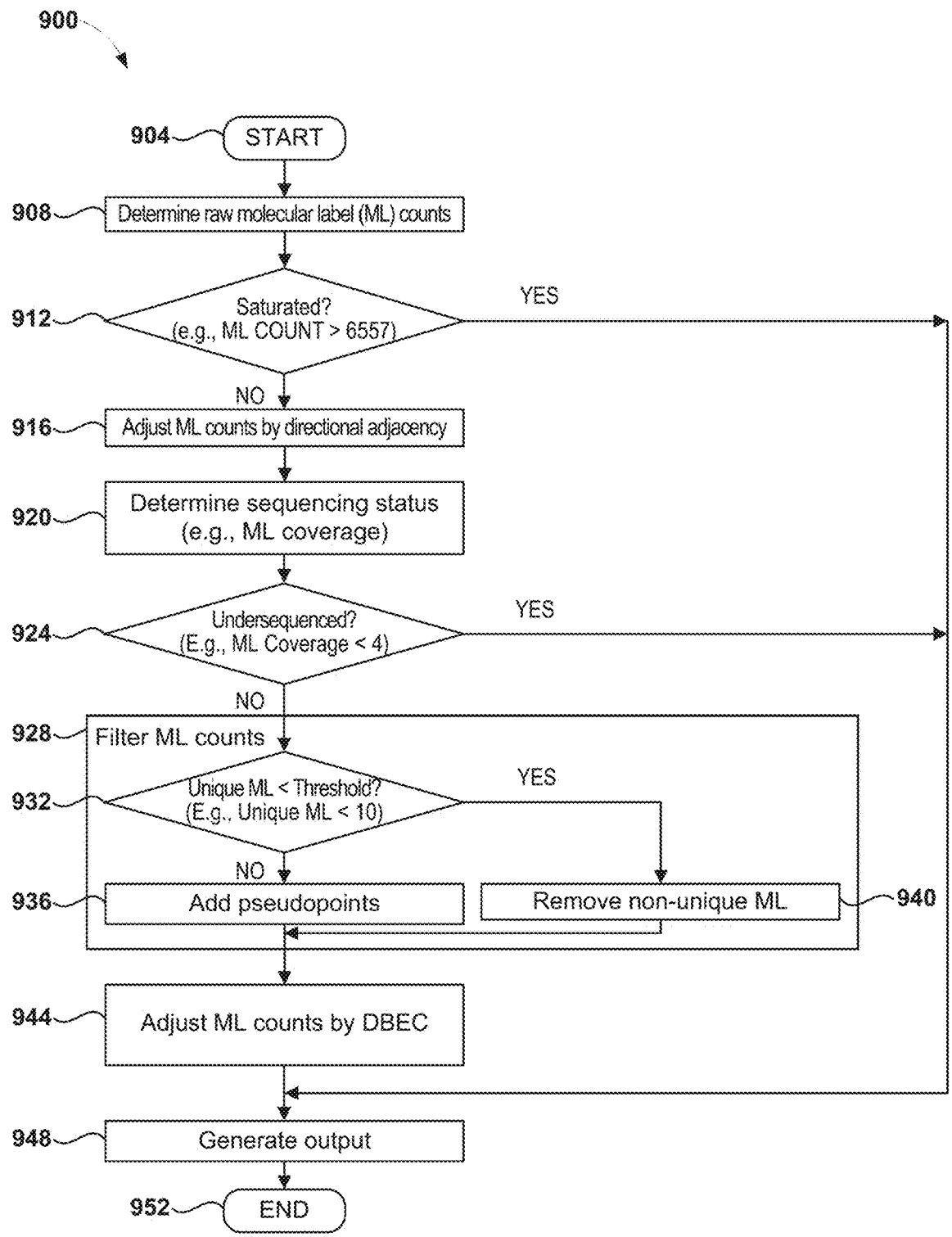
FIG. 9 is a flowchart showing a non-limiting exemplary embodiment of correcting PCR and sequencing errors based on recursive substitution error correction and distribution-based error correction.

FIG. 9 is a flowchart showing a non-limiting exemplary embodiment 900 of correcting PCR and sequencing errors based on recursive substitution error correction and distribution-based error correction. The method 900 starts at block 904 after receiving sequencing data of a plurality of stochastically barcoded targets. In some embodiments, the method 900 further comprises stochastically barcoding a plurality of targets using a plurality of stochastic barcodes to create the plurality of stochastically barcoded targets, wherein each of the plurality of stochastic barcodes comprises a molecular label. In some embodiments, the method 900 further comprises sequencing the plurality of stochastically barcoded targets to obtain the sequencing data.

At block 908, for one or more of the plurality of targets: the number of molecular labels with distinct sequences associated with the target in the sequencing data can be counted. At decision block 912, whether the sequencing data has a saturated sequencing status can be determined. For example, the target can be considered to have the saturated sequencing status if it has a number of molecular labels with distinct sequences greater than 1000, 2000, 3000, 4000, 5000, 6000, 7000, 8000, 9000, 10000, 20000, 30000, 40000, 50000, 60000, 70000, 80000, 90000, 100000, or a number or a range between any two of these. As another example, the target can be considered to have the saturated sequencing status if it has a number of molecular labels with distinct sequences greater than 50%, 60%, 70%, 80%, 90%, 95%, 99%, 99.9%, or a number or a range between any two of these, of the molecular barcodes of the stochastic barcodes with distinct sequences.

In some embodiments, the saturated sequencing status can be determined by the target having a number of molecular labels with distinct sequences greater than a predetermined saturation threshold. The predetermined saturation threshold can be different in different implementations. For example, the predetermined saturation threshold can be, or be about, 1000, 2000, 3000, 4000, 5000, 6000, 6557, 7000, 8000, 9000, 10000, 20000, 30000, 40000, 50000, 60000, 65532, 70000, 80000, 90000, 100000, or a number or a range between any two of these values. As another example, the predetermined saturation threshold can be at least, or at most, 1000, 2000, 3000, 4000, 5000, 6000, 6557, 7000, 8000, 9000, 10000, 20000, 30000, 40000, 50000, 60000, 65532, 70000, 80000, 90000, or 100000.

In some embodiments, the saturated sequencing status can depend on the number of molecular labels of the stochastic barcodes with distinct sequences. For example, the predetermined saturation threshold can be about 6557 if the stochastic barcodes comprise about 6561 molecular labels with distinct sequences. As another example, the predetermined saturation threshold can be about 65532 if the stochastic barcodes comprise about 65536 molecular labels with distinct sequences. In some embodiments, the saturated sequencing status may not depend on the number of molecular labels of the stochastic barcodes with distinct sequences.

If the sequencing data does not have a saturated sequencing status at decision block 912, the method 900 can proceed to block 916, where the molecular label counts can be adjusted based on directional adjacency. In some embodiments, adjusting the molecular counts based on directional adjacency can be as described with reference to FIG. 7. For example, adjusting the molecular counts based on dictionary can include identifying clusters of molecular labels of the target using directional adjacency; collapsing the sequencing data using the clusters of molecular labels of the target identified; and estimating the number of the target, wherein the number of the target estimated correlates with the number of molecular labels with distinct sequences associated with the target in the sequencing data counted after collapsing the sequencing data.

At block 920, the sequencing status of the target in the sequencing data can be determined. The sequencing status of the target in the sequencing data can include, or be, under sequencing. At decision block 924, whether the sequencing status of the target in the sequencing data is the under sequencing status can be determined. For example, the target can be considered to have the under sequencing status if its depth (e.g., an average, a minimum, or a maximum depth) is smaller than, or smaller than about, 1, 2, 3, 4, 5, 6, 7, 8, 9, 10, 20, 30, 40, 50, 60, 70, 80, 90, 100, or a number or a range between any two of these. As another example, the target can be considered to have the under sequencing status if its depth is smaller than at least, or at most, 1, 2, 3, 4, 5, 6, 7, 8, 9, 10, 20, 30, 40, 50, 60, 70, 80, 90, or 100.

In some embodiments, the under sequencing status can be determined by the target having a depth (e.g., an average, a minimum, or a maximum depth) smaller than a predetermined under sequencing threshold. The under sequencing threshold can be different in different implementations. For example, the under sequencing threshold can be, or be about, 1, 2, 3, 4, 5, 6, 7, 8, 9, 10, 20, 30, 40, 50, 60, 70, 80, 90, 100, or a number or a range between any two of these values. As another example, the under sequencing threshold can be at least, or at most, 1, 2, 3, 4, 5, 6, 7, 8, 9, 10, 20, 30, 40, 50, 60, 70, 80, 90, or 100.

In some embodiments, the under sequencing status may depend on the number of molecular labels of the stochastic barcodes with distinct sequences. For example, the under sequencing threshold can be 10 (or another threshold number) if the stochastic barcodes comprise, or about, 1000, 2000, 3000, 4000, 5000, 6000, 6561, 7000, 8000, 9000, 10000, 20000, 30000, 40000, 50000, 60000, 65532, 70000, 80000, 90000, 100000, or a number or range between any two of these values, molecular labels with distinct sequences. As another example, the under sequencing threshold can be 10 (or another threshold number) if the stochastic barcodes comprise at least, or at most, 1000, 2000, 3000, 4000, 5000, 6000, 6561, 7000, 8000, 9000, 10000, 20000, 30000, 40000, 50000, 60000, 65532, 70000, 80000, 90000, or 100000. In some embodiments, the under sequencing status may not depend on the number of molecular labels of the stochastic barcodes with distinct sequences.

At decision block 924, if the sequencing status of the target in the sequencing data is not the under sequencing status, the method 900 can proceed to block 928 to filter molecular label counts. Filtering molecular label counts can include, at decision block 932, determining the number of molecular labels with distinct sequences associated with the target in the sequencing data being less than a pseudopoints threshold. The pseudopoints threshold can be different in different implementations. For example, the pseudopoints threshold can be, or be about, 1, 2, 3, 4, 5, 6, 7, 8, 9, 10, 20, 30, 40, 50, 60, 70, 80, 90, 100, or a number or a range between any two of these values if the stochastic barcodes comprise about 6561 molecular labels with distinct sequences. As another example, the pseudopoints sequencing threshold can be at least, or at most, 1, 2, 3, 4, 5, 6, 7, 8, 9, 10, 20, 30, 40, 50, 60, 70, 80, 90, or 100, if the stochastic barcodes comprise about 6561 molecular labels with distinct sequences.

At decision block 932, if the number of molecular labels with distinct sequences associated with the target in the sequencing data is less than the pseudopoints threshold, the method 900 can optionally proceed to block 936, where pseudopoints can be added to the number of molecular labels with distinct sequences associated with the target in the sequencing data prior to determining the number of noise molecular labels with distinct sequences associated with the target in the sequencing data. The pseudopoints can have different molecular label counts in different implementations. For example, the molecular label count of a pseudopoint can be, or be about, 0.0001, 0.001, 0.01, 0.1, 1, 2, 3, 4, 5, 6, 7, 8, 9, 10, 20, 30, 40, 50, 60, 70, 80, 90, 100, or a number or a range between any two of these values. As another example, the molecular label count of a pseudopoint can be at least, or at most, 0.0001, 0.001, 0.01, 0.1, 1, 2, 3, 4, 5, 6, 7, 8, 9, 10, 20, 30, 40, 50, 60, 70, 80, 90, or 100. In some embodiments, if the number of molecular labels with distinct sequences associated with the target in the sequencing data is less than the pseudopoints threshold, the method 900 can proceed to block if the number of molecular labels with distinct sequences associated with the target in the sequencing data is less than the pseudopoints threshold, the method 944.

At decision block 932, if the number of molecular labels with distinct sequences associated with the target in the sequencing data is not less than the pseudopoints threshold, non-unique molecular labels can be removed at block 940. The non-unique molecular labels can be removed for determining the number of noise molecular labels with distinct sequences associated with the target in the sequencing data at block 944. The non-unique molecular labels can include molecular labels with distinct sequences associated with the target in the sequencing data being greater than a predetermined recycled molecular label threshold. The recycled molecular label threshold can be different in different implementations. For example, the recycled molecular label threshold can be, or be about, 100, 200, 300, 400, 500, 600, 650, 700, 900, 1000, 2000, or a number or a range between any two of these values, if the stochastic barcodes comprise about 6561 molecular labels with distinct sequences. As another example, the recycled molecular label threshold can be at least, or at most, 100, 200, 300, 400, 500, 600, 650, 700, 900, 1000, or 2000, if the stochastic barcodes comprise about 6561 molecular labels with distinct sequences.

In some embodiments, removing the non-unique molecular labels comprises: determining a theoretical number of non-unique molecular labels for the number of molecular labels with distinct sequences associated with the target in the sequencing data. Removing the non-unique molecular labels can comprise removing a molecular label with an occurrence greater than the nth most abundant molecular label of the molecular labels with distinct sequences associated with the target in the sequencing data. The number n can be the theoretical number of non-unique molecular labels.

At block 944, the molecular label counts can be adjusted using a distribution-based error correction method. The distribution-based error correction method can include determining the number of noise molecular labels with distinct sequences associated with the target in the sequencing data. Determining the number of noise molecular labels can comprise: fitting two negative binomial distributions to the number of molecular labels with distinct sequences associated with the target in the sequencing data. For example, determining the number of noise molecular labels can comprise: fitting a signal negative binomial distribution (one of the two negative binomial distributions) to the number of molecular labels with distinct sequences associated with the target in the sequencing data counted, wherein the signal negative binomial distribution corresponds to a number of molecular labels with distinct sequences associated with the target in the sequencing data counted being signal molecular labels. Determining the number of noise molecular labels can comprise: fitting a noise negative binomial distribution (the other of the two negative binomial distributions) to the number of molecular labels with distinct sequences associated with the target in the sequencing data counted, wherein the noise negative binomial distribution corresponds to a number of molecular labels with distinct sequences associated with the target in the sequencing data counted being noise molecular labels. Determining the number of noise molecular labels can comprise determining the number of noise molecular labels using the signal negative binomial distribution fitted and the noise negative binomial distribution fitted.

In some embodiments, determining the number of noise molecular labels using the signal negative binomial distribution fitted and the noise negative binomial distribution fitted comprises, for each of the distinct sequences associated with the target in the sequencing data: determining a signal probability of the distinct sequence to be in the signal negative binomial distribution. And a noise probability of the distinct sequence to be in the noise negative binomial distribution can be determined. Furthermore, the distinct sequence can be determined to be a noise molecular label if the signal probability is smaller than the noise probability. In some embodiments, adjusting the molecular label counts at block 944 can include removing singletons (e.g., single base substitutions) if fewer than two peaks are found (because two peaks may be required to determine the signal negative binomial distribution and the noise negative binomial distribution).

At block 948, the number of the target can be estimated to generate output after adjacency-based and distribution-based error corrections. At decision block 912, if the sequencing status of the target in the sequencing data is the saturated sequencing status, the method 900 can proceed to block 948 to generate output without adjusting molecular labels based on directional adjacency and distribution-based error correction. For example, the number of noise molecular labels determined can be zero.

At decision block 924, if the sequencing status of the target in the sequencing data is the under sequencing status, the method 900 can proceed to block 948 to generate output without adjusting molecular labels based on distribution-based error correction. For example, the number of noise molecular labels determined can be zero. The method 900 ends at block 952.

Figure 10:
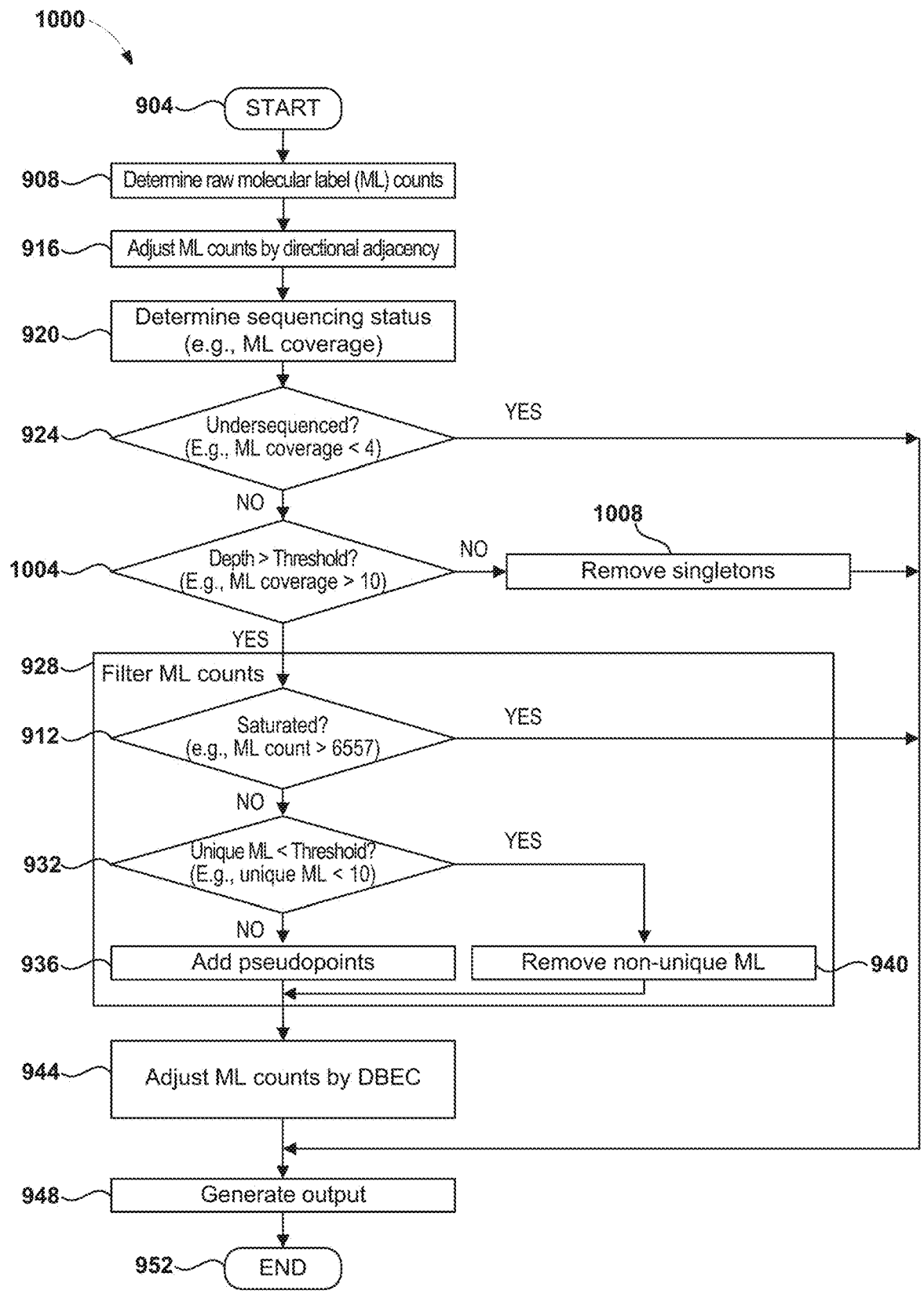
FIG. 10 is a flowchart showing a non-limiting exemplary embodiment of error correction using two negative binomial distributions.

FIG. 10 is a flowchart showing a non-limiting exemplary embodiment 1000 of error correction using two negative binomial distributions. Blocks of the method 1000 (such as blocks 904-952) have been described with reference to FIG. 9. Briefly, the method 1000 starts at block 904 after receiving sequencing data of a plurality of stochastically barcoded targets. In some embodiments, the method 1000 further comprises stochastically barcoding a plurality of targets using a plurality of stochastic barcodes to create the plurality of stochastically barcoded targets, wherein each of the plurality of stochastic barcodes comprises a molecular label. In some embodiments, the method 1000 further comprises sequencing the plurality of stochastically barcoded targets to obtain the sequencing data.

At block 908, for one or more of the plurality of targets: the number of molecular labels with distinct sequences associated with the target in the sequencing data can be counted. At block 916, the molecular label counts can be adjusted based on directional adjacency. In some embodiments, adjusting the molecular counts based on directional adjacency can be as described with reference to FIG. 7.

At block 920, the sequencing status of the target in the sequencing data can be determined. The sequencing status of the target in the sequencing data can include, or be, under sequencing. At decision block 924, whether the sequencing status of the target in the sequencing data is the under sequencing status can be determined.

At decision block 924, if the sequencing status of the target in the sequencing data is not the under sequencing status, the method 1000 can optionally proceed to decision block 1004. At decision block 1004, the sequencing depth of the target can be compared to a predetermined sequencing depth threshold. The sequencing depth threshold can be different in different implementations. For example, the sequencing depth of the target can be, or be about, 1, 2, 3, 4, 5, 6, 7, 8, 9, 10, 20, 30, 40, 50, 60, 70, 80, 90, 100, or a number or a range between any two of these values. As another example, the sequencing depth of the target can be at least, or at most, 1, 2, 3, 4, 5, 6, 7, 8, 9, 10, 20, 30, 40, 50, 60, 70, 80, 90, or 100.

If the sequencing depth of the target is greater than the sequencing depth threshold, the method 1000 proceeds to block 928. If the sequencing depth of the target is not greater than the sequencing depth threshold, the method 1000 proceeds to block 1008. At block 1008, singletons (e.g., single base substitutions) can be removed prior to generating output at block 948.

At block 928, molecular label counts can be filtered. Filtering molecular label counts can include, at decision block 912, determining whether the sequencing data has a saturated sequencing status. If the sequencing data does not have a saturated sequencing status at decision block 912, the method 1000 can proceed to decision block 932. At decision block 932, the number of molecular labels with distinct sequences associated with the target in the sequencing data being less than a pseudopoints threshold can be determined.

At decision block 932, if the number of molecular labels with distinct sequences associated with the target in the sequencing data is less than the pseudopoints threshold, the method 900 can optionally proceed to block 936, where pseudopoints can be added to the number of molecular labels with distinct sequences associated with the target in the sequencing data prior to determining the number of noise molecular labels with distinct sequences associated with the target in the sequencing data. In some embodiments, if the number of molecular labels with distinct sequences associated with the target in the sequencing data is less than the pseudopoints threshold, the method 900 can proceed to block if the number of molecular labels with distinct sequences associated with the target in the sequencing data is less than the pseudopoints threshold, the method 944.

At decision block 932, if the number of molecular labels with distinct sequences associated with the target in the sequencing data is not less than the pseudopoints threshold, non-unique molecular labels can be removed at block 940. The non-unique molecular labels can be removed for determining the number of noise molecular labels with distinct sequences associated with the target in the sequencing data at block 944. The non-unique molecular labels can include molecular labels with distinct sequences associated with the target in the sequencing data being greater than a predetermined recycled molecular label threshold.

At block 944, the molecular label counts can be adjusted using a distribution-based error correction method. The distribution-based error correction method can include determining the number of noise molecular labels with distinct sequences associated with the target in the sequencing data. Determining the number of noise molecular labels can comprise: fitting two negative binomial distributions, a signal negative binomial distribution and a noise negative binomial distribution, to the number of molecular labels with distinct sequences associated with the target in the sequencing data. The signal negative binomial distribution corresponds to a number of molecular labels with distinct sequences associated with the target in the sequencing data counted being signal molecular labels. The noise negative binomial distribution corresponds to a number of molecular labels with distinct sequences associated with the target in the sequencing data counted being noise molecular labels. Determining the number of noise molecular labels can comprise determining the number of noise molecular labels using the signal negative binomial distribution fitted and the noise negative binomial distribution fitted.

At block 948, the number of the target can be estimated to generate output after adjacency-based and distribution-based error corrections. At decision block 912, if the sequencing status of the target in the sequencing data is the saturated sequencing status, the method 1000 can proceed to block 948 to generate output without adjusting molecular labels based on directional adjacency and distribution-based error correction.

At decision block 924, if the sequencing status of the target in the sequencing data is the under sequencing status, the method 1000 can proceed to block 948 to generate output without adjusting molecular labels based on distribution-based error correction. For example, the number of noise molecular labels determined can be zero. The method 1000 ends at block 952.

Figure 11:
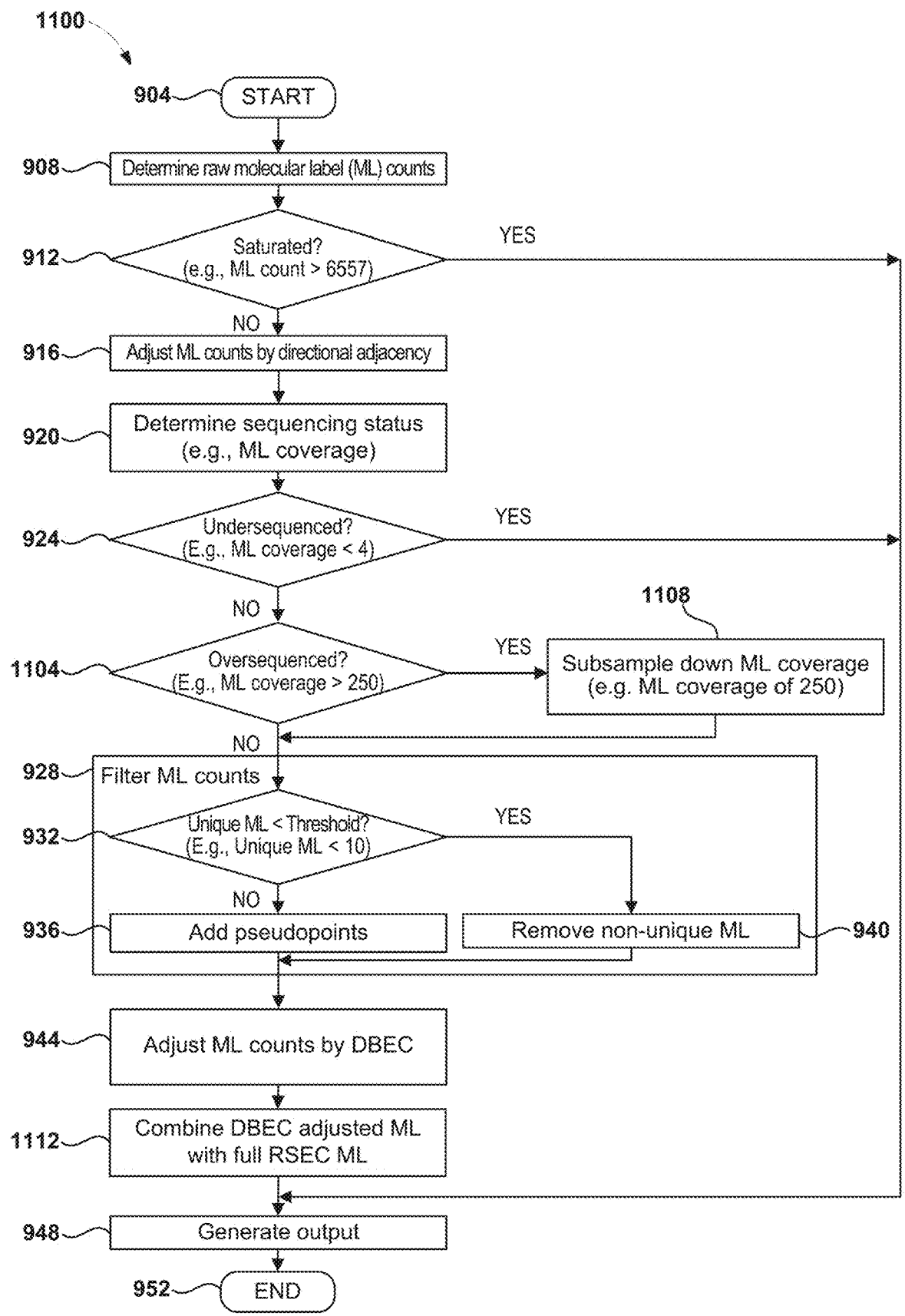
FIG. 11 is a flowchart showing a non-limiting exemplary embodiment of correcting PCR and sequencing errors based on recursive substitution error correction and distribution-based error correction by subsampling of microwell plate and mapping of molecular labels.

Correcting PCR and Sequencing Errors Based on Directional Adjacency, Distribution-Based Error Correction, and Subsampling FIG. 11 is a flowchart showing a non-limiting exemplary embodiment 1100 of error correction using two negative binomial distributions. Blocks of the method 1100 (such as blocks 904-952) have been described with reference to FIG. 9. Briefly, the method 1100 starts at block 904 after receiving sequencing data of a plurality of stochastically barcoded targets. In some embodiments, the method 1100 further comprises stochastically barcoding a plurality of targets using a plurality of stochastic barcodes to create the plurality of stochastically barcoded targets, wherein each of the plurality of stochastic barcodes comprises a molecular label. In some embodiments, the method 1100 further comprises sequencing the plurality of stochastically barcoded targets to obtain the sequencing data.

At block 908, for one or more of the plurality of targets: the number of molecular labels with distinct sequences associated with the target in the sequencing data can be counted. At decision block 912, whether the sequencing data has a saturated sequencing status can be determined. If the sequencing data does not have a saturated sequencing status at decision block 912, the method 1100 can proceed to block 916, where the molecular label counts can be adjusted based on directional adjacency. In some embodiments, adjusting the molecular counts based on directional adjacency can be as described with reference to FIG. 7.

At block 920, the sequencing status of the target in the sequencing data can be determined. The sequencing status of the target in the sequencing data can include, or be, under sequencing. At decision block 924, whether the sequencing status of the target in the sequencing data is the under sequencing status can be determined.

At decision block 924, if the sequencing status of the target in the sequencing data is not the under sequencing status, the method 1100 can optionally proceed to decision block 1104. At decision block 1104, whether the sequencing status of the target in the sequencing data is the over sequencing status can be determined. For example, the target can be considered to have the over sequencing status or a high expressor target, if its depth (e.g., an average, a minimum, or a maximum depth) is greater than, or greater than about, 50, 100, 200, 250, 300, 400, 500, 600, 700, 800, 900, 1000, or a number or a range between any two of these. As another example, the target can be considered to have the under sequencing status if its depth is greater than at least, or at most, 50, 100, 200, 250, 300, 400, 500, 600, 700, 800, 900, or 1000.

In some embodiments, the over sequencing status or the high expressor target can be determined by the target having a depth (e.g., an average, a minimum, or a maximum depth) greater than a predetermined over sequencing threshold. The over sequencing threshold can be different in different implementations. For example, the over sequencing threshold can be, or be about, 50, 100, 200, 250, 300, 400, 500, 600, 700, 800, 900, 1000, or a number or a range between any two of these. As another example, the over sequencing threshold can be at least, or at most, 50, 100, 200, 250, 300, 400, 500, 600, 700, 800, 900, 1000.

In some embodiments, the over sequencing status may depend on the number of molecular labels of the stochastic barcodes with distinct sequences. For example, the over sequencing threshold can be, or be about, 50, 100, 200, 250, 300, 400, 500, 600, 700, 800, 900, 1000, or a number or a range between any two of these values if the stochastic barcodes comprise about 6561 molecular labels with distinct sequences. As another example, the over sequencing threshold can be at least, or at most, 50, 100, 200, 250, 300, 400, 500, 600, 700, 800, 900, 1000, if the stochastic barcodes comprise about 6561 molecular labels with distinct sequences. In some embodiments, the under sequencing status may not depend on the number of molecular labels of the stochastic barcodes with distinct sequences.

At decision block 1104, if the target has the over sequencing status, the method 1100 proceeds to block 1108. At block 1108, the ML coverage of the target can be reduced by, for example, subsampling down the ML coverage for all targets. For example, the number of molecular labels with distinct sequences associated with the target in the sequencing data can be subsampled to about the predetermined over sequencing threshold for all targets (for example, 10). The method 1100 proceeds to block 928 from block 1108.

At decision block 1104, if the target does not have the over sequencing status, the method 1100 proceeds to block 928 to filter molecular label counts. Filtering molecular label counts can include, at decision block 932, the number of molecular labels with distinct sequences associated with the target in the sequencing data being less than a pseudopoints threshold can be determined.

At decision block 932, if the number of molecular labels with distinct sequences associated with the target in the sequencing data is less than the pseudopoints threshold, the method 900 can optionally proceed to block 936, where pseudopoints can be added to the number of molecular labels with distinct sequences associated with the target in the sequencing data prior to determining the number of noise molecular labels with distinct sequences associated with the target in the sequencing data. In some embodiments, if the number of molecular labels with distinct sequences associated with the target in the sequencing data is less than the pseudopoints threshold, the method 900 can proceed to block if the number of molecular labels with distinct sequences associated with the target in the sequencing data is less than the pseudopoints threshold, the method 944.

At decision block 932, if the number of molecular labels with distinct sequences associated with the target in the sequencing data is not less than the pseudopoints threshold, non-unique molecular labels can be removed at block 940. The non-unique molecular labels can be removed for determining the number of noise molecular labels with distinct sequences associated with the target in the sequencing data at block 944. The non-unique molecular labels can include molecular labels with distinct sequences associated with the target in the sequencing data being greater than a predetermined recycled molecular label threshold.

At block 944, the molecular label counts can be adjusted using a distribution-based error correction method. The distribution-based error correction method can include determining the number of noise molecular labels with distinct sequences associated with the target in the sequencing data. Determining the number of noise molecular labels can comprise: fitting two negative binomial distributions, a signal negative binomial distribution and a noise negative binomial distribution, to the number of molecular labels with distinct sequences associated with the target in the sequencing data. The signal negative binomial distribution corresponds to a number of molecular labels with distinct sequences associated with the target in the sequencing data counted being signal molecular labels. The noise negative binomial distribution corresponds to a number of molecular labels with distinct sequences associated with the target in the sequencing data counted being noise molecular labels. Determining the number of noise molecular labels can comprise determining the number of noise molecular labels using the signal negative binomial distribution fitted and the noise negative binomial distribution fitted.

After adjusting the molecular label counts using a distribution-based error correction method at block 944, the method 1100 optionally proceeds to block 1112. At block 1112, the adjusted molecular label counts from block 944 can be combined with molecular label counts adjusted based on directional adjacency determined at block 916. For example, non-unique molecular labels are removed at block 940 and are not used for distribution fitting at block 944. However, these molecular labels are still present in the molecular label counts adjusted based on directional adjacency determined at block 916. Accordingly, adjusted molecular label counts from block 944 and the molecular label counts adjusted at block 944 can be combined to generate output at block 948.

At decision block 912, if the sequencing status of the target in the sequencing data is the saturated sequencing status, the method 1100 can proceed to block 948 to generate output without adjusting molecular labels based on directional adjacency and distribution-based error correction. At decision block 924, if the sequencing status of the target in the sequencing data is the under sequencing status, the method 1100 can proceed to block 948 to generate output without adjusting molecular labels based on distribution-based error correction. For example, the number of noise molecular labels determined can be zero. The method 1100 can, for example, end at block 952.

Figure 12:
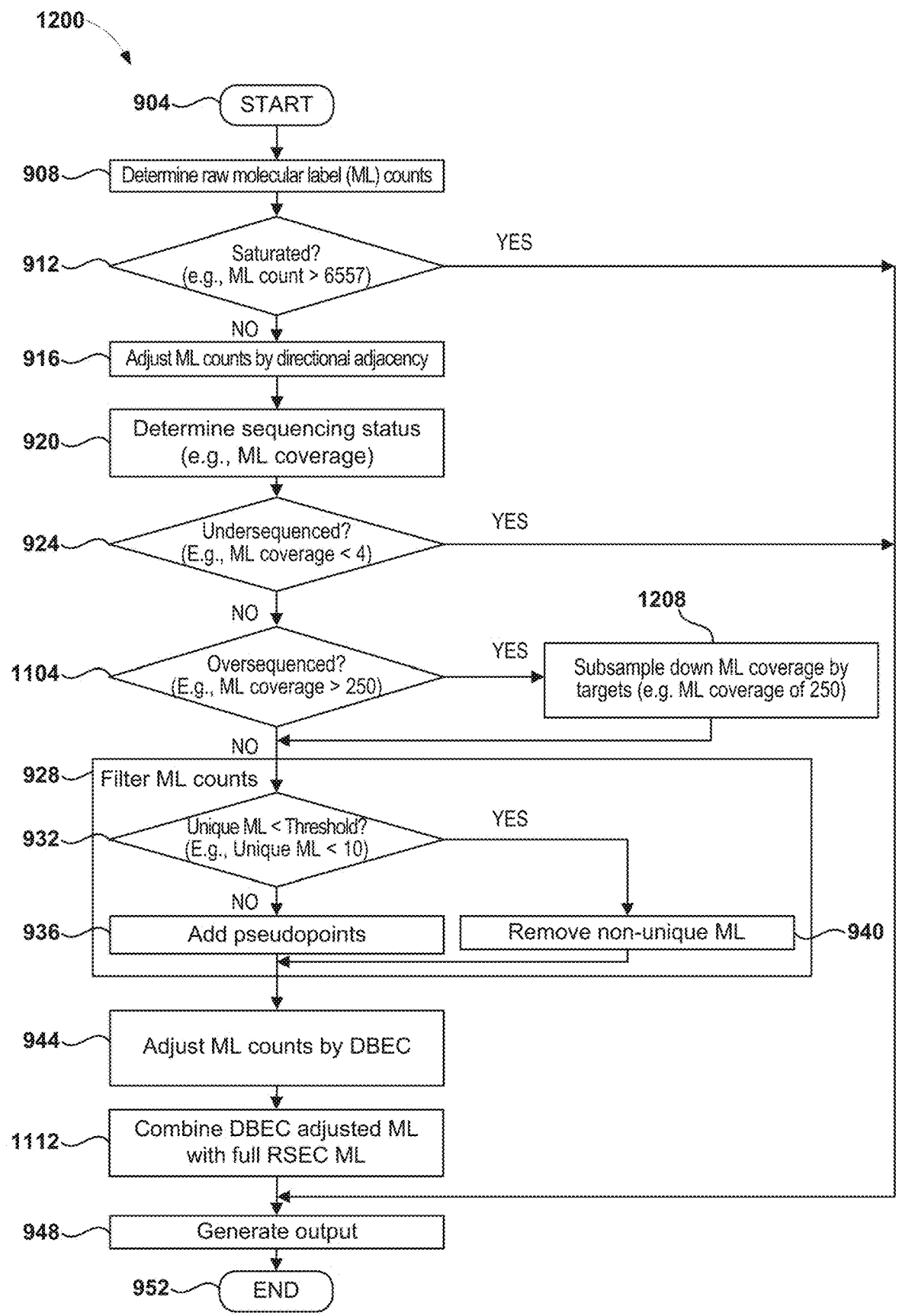
FIG. 12 is a flowchart showing a non-limiting exemplary embodiment of correcting PCR and sequencing errors based on recursive substitution error correction and distribution-based error correction by subsampling of genes and mapping of molecular labels.

FIG. 12 is a flowchart showing a non-limiting exemplary embodiment 1200 of error correction using two negative binomial distributions. Blocks of the method 1200 (such as blocks 904-952 and block 1104) have been described with reference to FIGS. 9 and 11. Briefly, the method 1200 starts at block 904 after receiving sequencing data of a plurality of stochastically barcoded targets. In some embodiments, the method 1200 further comprises stochastically barcoding a plurality of targets using a plurality of stochastic barcodes to create the plurality of stochastically barcoded targets, wherein each of the plurality of stochastic barcodes comprises a molecular label. In some embodiments, the method 1200 further comprises sequencing the plurality of stochastically barcoded targets to obtain the sequencing data.

At block 908, for one or more of the plurality of targets: the number of molecular labels with distinct sequences associated with the target in the sequencing data can be counted. At decision block 912, whether the sequencing data has a saturated sequencing status can be determined. If the sequencing data does not have a saturated sequencing status at decision block 912, the method 1200 can proceed to block 916, where the molecular label counts can be adjusted based on directional adjacency. In some embodiments, adjusting the molecular counts based on directional adjacency can be as described with reference to FIG. 7.

At block 920, the sequencing status of the target in the sequencing data can be determined. The sequencing status of the target in the sequencing data can include, or be, under sequencing. At decision block 924, whether the sequencing status of the target in the sequencing data is the under sequencing status can be determined.

At decision block 924, if the sequencing status of the target in the sequencing data is not the under sequencing status, the method 1200 can optionally proceed to decision block 1104. At decision block 1104, whether the sequencing status of the target in the sequencing data is the over sequencing status can be determined.

At decision block 1104, if the target has the over sequencing status or if the target is a high expressor target, the method 1200 optionally proceeds to block 1208. At block 1208, the ML coverage of the target can be reduced by, for example, subsampling down the ML coverage target by target. For example, the number of molecular labels with distinct sequences associated with the target in the sequencing data can be subsampled to about the predetermined over sequencing threshold target by target. The method 1200 proceeds to block 928 from block 1208.

At decision block 1104, if the target does not have the over sequencing status, the method 1200 proceeds to block 928 to filter molecular label counts. Filtering molecular label counts can include, at decision block 932, the number of molecular labels with distinct sequences associated with the target in the sequencing data being less than a pseudopoints threshold can be determined.

At decision block 932, if the number of molecular labels with distinct sequences associated with the target in the sequencing data is less than the pseudopoints threshold, the method 900 can optionally proceed to block 936, where pseudopoints can optionally be added to the number of molecular labels with distinct sequences associated with the target in the sequencing data prior to determining the number of noise molecular labels with distinct sequences associated with the target in the sequencing data. In some embodiments, if the number of molecular labels with distinct sequences associated with the target in the sequencing data is less than the pseudopoints threshold, the method 900 can proceed to block if the number of molecular labels with distinct sequences associated with the target in the sequencing data is less than the pseudopoints threshold, the method 944.

At decision block 932, if the number of molecular labels with distinct sequences associated with the target in the sequencing data is not less than the pseudopoints threshold, non-unique molecular labels can be removed at block 940. The non-unique molecular labels can be removed for determining the number of noise molecular labels with distinct sequences associated with the target in the sequencing data at block 944. The non-unique molecular labels can include molecular labels with distinct sequences associated with the target in the sequencing data being greater than a predetermined recycled molecular label threshold.

At block 944, the molecular label counts can be adjusted using a distribution-based error correction method. The distribution-based error correction method can include determining the number of noise molecular labels with distinct sequences associated with the target in the sequencing data. Determining the number of noise molecular labels can comprise: fitting two negative binomial distributions, a signal negative binomial distribution and a noise negative binomial distribution, to the number of molecular labels with distinct sequences associated with the target in the sequencing data. The signal negative binomial distribution corresponds to a number of molecular labels with distinct sequences associated with the target in the sequencing data counted being signal molecular labels. The noise negative binomial distribution corresponds to a number of molecular labels with distinct sequences associated with the target in the sequencing data counted being noise molecular labels. Determining the number of noise molecular labels can comprise determining the number of noise molecular labels using the signal negative binomial distribution fitted and the noise negative binomial distribution fitted.

After adjusting the molecular label counts using a distribution-based error correction method at block 944, the method 1200 optionally proceeds to block 1112. At block 1112, the adjusted molecular label counts from block 944 can be combined with molecular label counts adjusted based on directional adjacency determined at block 916. For example, non-unique molecular labels are removed at block 940 and are not used for distribution fitting at block 944. However, these molecular labels are still present in the molecular label counts adjusted based on directional adjacency determined at block 916. Accordingly, adjusted molecular label counts from block 944 and the molecular label counts adjusted at block 944 can be combined to generate output at block 948.

At decision block 912, if the sequencing status of the target in the sequencing data is the saturated sequencing status, the method 1200 can proceed to block 948 to generate output without adjusting molecular labels based on directional adjacency and distribution-based error correction. At decision block 924, if the sequencing status of the target in the sequencing data is the under sequencing status, the method 1200 can proceed to block 948 to generate output without adjusting molecular labels based on distribution-based error correction. For example, the number of noise molecular labels determined can be zero. The method 1200 ends at block 952.

Figure 13:
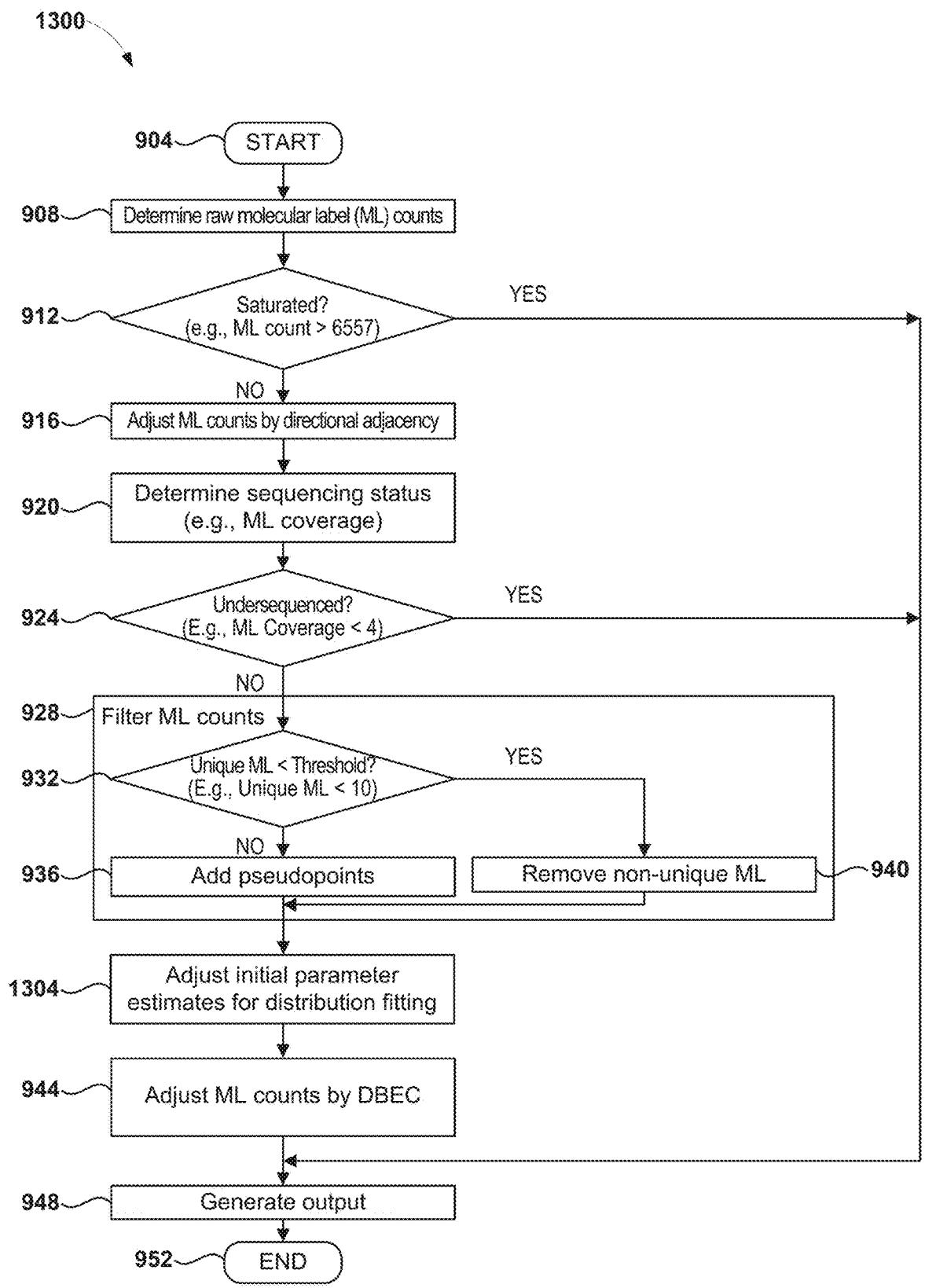
FIG. 13 is a flowchart showing a non-limiting exemplary embodiment of correcting PCR and sequencing errors based on recursive substitution error correction and distribution-based error correction by recursion.

Correcting PCR and Sequencing Errors Based on Directional Adjacency and Distribution-Based Error Correction with Initial Parameter Estimations for Distribution Fitting FIG. 13 is a flowchart showing a non-limiting exemplary embodiment 13 of correcting PCR and sequencing errors based on recursive substitution error correction and distribution-based error correction by recursion. Blocks of the method 1300 (such as blocks 904-952) have been described with reference to FIG. 9. Briefly, the method 1300 starts at block 904 after receiving sequencing data of a plurality of stochastically barcoded targets. In some embodiments, the method 1300 further comprises stochastically barcoding a plurality of targets using a plurality of stochastic barcodes to create the plurality of stochastically barcoded targets, wherein each of the plurality of stochastic barcodes comprises a molecular label. In some embodiments, the method 1300 further comprises sequencing the plurality of stochastically barcoded targets to obtain the sequencing data.

At block 908, for one or more of the plurality of targets: the number of molecular labels with distinct sequences associated with the target in the sequencing data can be counted. At decision block 912, whether the sequencing data has a saturated sequencing status can be determined. If the sequencing data does not have a saturated sequencing status at decision block 912, the method 1300 can proceed to block 916, where the molecular label counts can be adjusted based on directional adjacency. In some embodiments, adjusting the molecular counts based on directional adjacency can be as described with reference to FIG. 7.

At block 920, the sequencing status of the target in the sequencing data can be determined. The sequencing status of the target in the sequencing data can include, or be, under sequencing. At decision block 924, whether the sequencing status of the target in the sequencing data is the under sequencing status can be determined.

At decision block 924, if the sequencing status of the target in the sequencing data is not the under sequencing status, the method 1300 can proceed to block 928 to filter molecular label counts. Filtering molecular label counts can include, at decision block 932, the number of molecular labels with distinct sequences associated with the target in the sequencing data being less than a pseudopoints threshold can be determined.

At decision block 932, if the number of molecular labels with distinct sequences associated with the target in the sequencing data is less than the pseudopoints threshold, the method 900 can optionally proceed to block 936, where pseudopoints can be added to the number of molecular labels with distinct sequences associated with the target in the sequencing data prior to determining the number of noise molecular labels with distinct sequences associated with the target in the sequencing data. In some embodiments, if the number of molecular labels with distinct sequences associated with the target in the sequencing data is less than the pseudopoints threshold, the method 900 can proceed to block if the number of molecular labels with distinct sequences associated with the target in the sequencing data is less than the pseudopoints threshold, the method 944.

At decision block 932, if the number of molecular labels with distinct sequences associated with the target in the sequencing data is not less than the pseudopoints threshold, non-unique molecular labels can be removed at block 940.

Prior to adjusting molecular label counts at block 944, the initial parameters of the two negative binomial distributions can be optionally estimated at block 1304. The initial parameters of the two negative binomial distributions can be different in different implementations. In some embodiments, the mean and dispersion of each of the two negative binomial distributions can be one. In some embodiments, the mean and the dispersion of the two negative binomial distributions can be estimated to be the mean and the dispersion of a non-empty subset of the filtered molecular label counts from block 928. For example, the subset can be 25%-75% quantiles of the filtered molecular label counts from block 928. The upper or the lower range of the quantiles can be different in different implementations. In some embodiments, the upper or the lower range can be, or be about, 1%, 2%, 3%, 4%, 5%, 6%, 7%, 8%, 9%, 10%, 20%, 30%, 40%, 50%, 70%, 80%, 90%, 99%, or a number or a range between any two of these values. In some embodiments, the upper or the lower range can be at least, or at most, 1%, 2%, 3%, 4%, 5%, 6%, 7%, 8%, 9%, 10%, 20%, 30%, 40%, 50%, 70%, 80%, 90%, 99%, or 100%.

At block 944, the molecular label counts can be adjusted using a distribution-based error correction method. The distribution-based error correction method can include determining the number of noise molecular labels with distinct sequences associated with the target in the sequencing data. Determining the number of noise molecular labels can comprise: fitting two negative binomial distributions, a signal negative binomial distribution and a noise negative binomial distribution, to the number of molecular labels with distinct sequences associated with the target in the sequencing data. The signal negative binomial distribution corresponds to a number of molecular labels with distinct sequences associated with the target in the sequencing data counted being signal molecular labels. The noise negative binomial distribution corresponds to a number of molecular labels with distinct sequences associated with the target in the sequencing data counted being noise molecular labels. Determining the number of noise molecular labels can comprise determining the number of noise molecular labels using the signal negative binomial distribution fitted and the noise negative binomial distribution fitted.

At block 948, the number of the target can be estimated to generate output after adjacency-based and distribution-based error corrections. At decision block 912, if the sequencing status of the target in the sequencing data is the saturated sequencing status, the method 1300 can proceed to block 948 to generate output without adjusting molecular labels based on directional adjacency and distribution-based error correction.

At decision block 924, if the sequencing status of the target in the sequencing data is the under sequencing status, the method 1300 can proceed to block 948 to generate output without adjusting molecular labels based on distribution-based error correction. For example, the number of noise molecular labels determined can be zero. The method 1300 can, for example, end at block 952.

Figure 14:
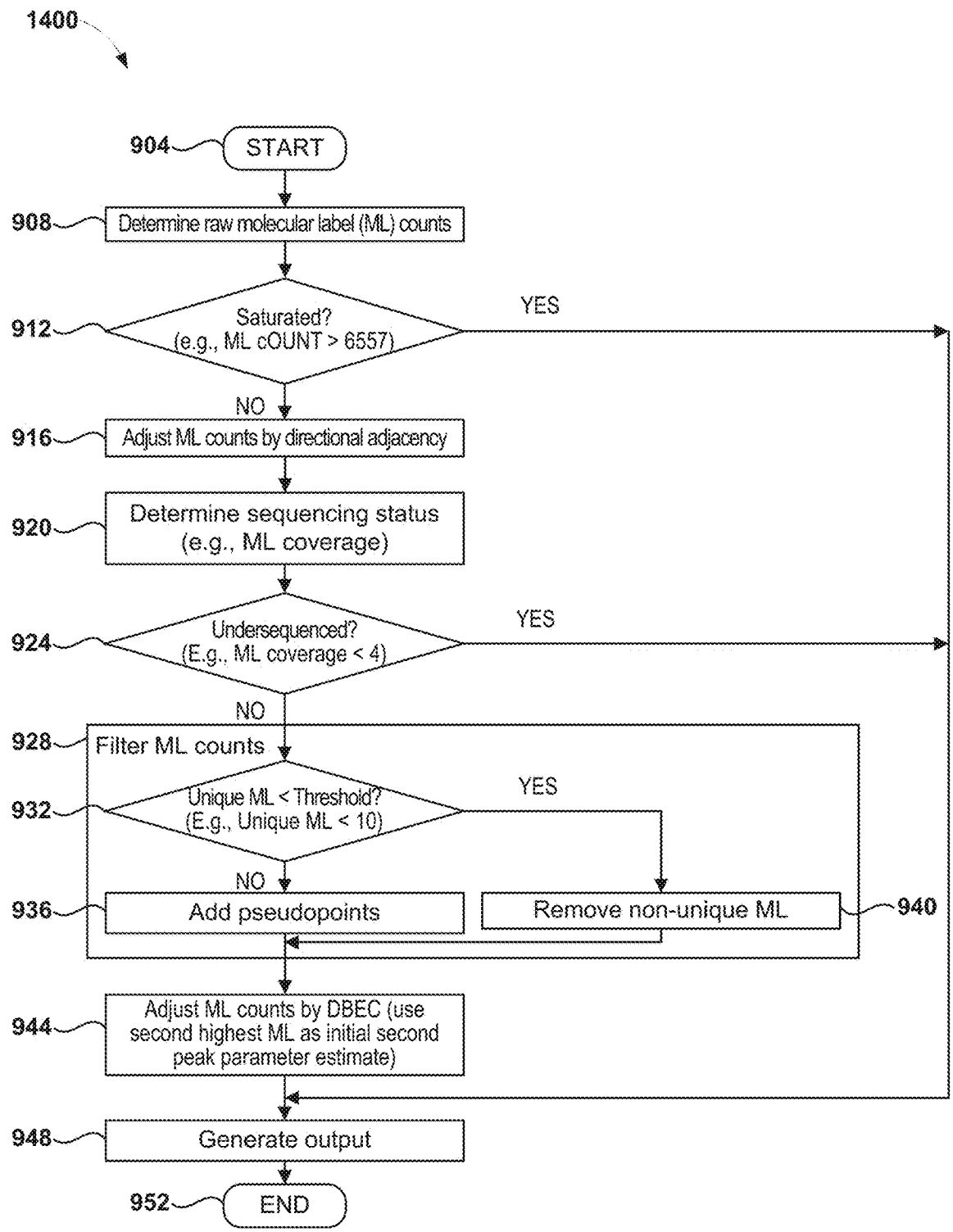
FIG. 14 is a flowchart showing a non-limiting exemplary embodiment of correcting PCR and sequencing errors based on recursive substitution error correction and distribution-based error correction by using the second highest molecular label for initial parameter estimates.

FIG. 14 is a flowchart showing a non-limiting exemplary embodiment of correcting PCR and sequencing errors based on recursive substitution error correction and distribution-based error correction by using the second highest molecular label for initial parameter estimates. Blocks of the method 1400 (such as blocks 904-952) have been described with reference to FIG. 9. Briefly, the method 1400 starts at block 904 after receiving sequencing data of a plurality of stochastically barcoded targets. In some embodiments, the method 1400 further comprises stochastically barcoding a plurality of targets using a plurality of stochastic barcodes to create the plurality of stochastically barcoded targets, wherein each of the plurality of stochastic barcodes comprises a molecular label. In some embodiments, the method 1400 further comprises sequencing the plurality of stochastically barcoded targets to obtain the sequencing data.

At block 908, for one or more of the plurality of targets: the number of molecular labels with distinct sequences associated with the target in the sequencing data can be counted. At decision block 912, whether the sequencing data has a saturated sequencing status can be determined. If the sequencing data does not have a saturated sequencing status at decision block 912, the method 1400 can proceed to block 916, where the molecular label counts can be adjusted based on directional adjacency. In some embodiments, adjusting the molecular counts based on directional adjacency can be as described with reference to FIG. 7.

At block 920, the sequencing status of the target in the sequencing data can be determined. The sequencing status of the target in the sequencing data can include, or be, under sequencing. At decision block 924, whether the sequencing status of the target in the sequencing data is the under sequencing status can be determined.

At decision block 924, if the sequencing status of the target in the sequencing data is not the under sequencing status, the method 1400 can proceed to block 928 to filter molecular label counts. Filtering molecular label counts can include, at decision block 932, the number of molecular labels with distinct sequences associated with the target in the sequencing data being less than a pseudopoints threshold can be determined.

At decision block 932, if the number of molecular labels with distinct sequences associated with the target in the sequencing data is less than the pseudopoints threshold, the method 900 can optionally proceed to block 936, where pseudopoints can be added to the number of molecular labels with distinct sequences associated with the target in the sequencing data prior to determining the number of noise molecular labels with distinct sequences associated with the target in the sequencing data.

At decision block 932, if the number of molecular labels with distinct sequences associated with the target in the sequencing data is not less than the pseudopoints threshold, non-unique molecular labels can be removed at block 940.

At block 944, the molecular label counts can be adjusted using a distribution-based error correction method. The initial parameters for the distribution-based error correction method can be based on the count of a molecular label. For example, the initial parameters (such as the mean and the dispersion) for one of the negative binomial distributions (e.g., the signal negative binomial distribution or the noise negative binomial distribution) can be based on the count of a molecular label or the mean or average or the counts of a number of molecular labels. This molecular label can be the molecular label with the second highest count or a molecular label with any ranking (e.g., with the 10th highest count). The ranking of the molecular label can be different in different implementations. In some embodiments, the ranking can be, or be about, 1, 2, 3, 4, 5, 6, 7, 8, 9, 10, 20, 30, 40, 50, 60, 70, 80, 90, 100, or a number or a range between any two of these values. In some embodiments, the ranking can be at least, or at most, 1, 2, 3, 4, 5, 6, 7, 8, 9, 10, 20, 30, 40, 50, 60, 70, 80, 90, or 100. The number of molecular labels can be different in different implementations. In some embodiments, the number of molecular labels can be, or be about, 1, 2, 3, 4, 5, 6, 7, 8, 9, 10, 20, 30, 40, 50, 60, 70, 80, 90, 100, or a number or a range between any two of these values. In some embodiments, the number of molecular labels can be at least, or at most, 1, 2, 3, 4, 5, 6, 7, 8, 9, 10, 20, 30, 40, 50, 60, 70, 80, 90, or 100.

At block 948, the number of the target can be estimated to generate output after adjacency-based and distribution-based error corrections. At decision block 912, if the sequencing status of the target in the sequencing data is the saturated sequencing status, the method 1400 can proceed to block 948 to generate output without adjusting molecular labels based on directional adjacency and distribution-based error correction.

At decision block 924, if the sequencing status of the target in the sequencing data is the under sequencing status, the method 1400 can proceed to block 948 to generate output without adjusting molecular labels based on distribution-based error correction. For example, the number of noise molecular labels determined can be zero. The method 1400 ends at block 952.

Sequencing

In some embodiments, estimating the number of different stochastically barcoded targets can comprise determining the sequences of the labeled targets, the spatial label, the molecular label, the sample label, the cell label, or any product thereof (e.g. labeled-amplicons, or labeled-cDNA molecules). An amplified target can be subjected to sequencing. Determining the sequence of the stochastically barcoded target or any product thereof can comprise conducting a sequencing reaction to determine the sequence of at least a portion of a sample label, a spatial label, a cell label, a molecular label, at least a portion of the stochastically labeled target, a complement thereof, a reverse complement thereof, or any combination thereof.

Determination of the sequence of a stochastically barcoded target (e.g. amplified nucleic acid, labeled nucleic acid, cDNA copy of a labeled nucleic acid, etc.) can be performed using variety of sequencing methods including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads, wobble sequencing, multiplex sequencing, polymerized colony (POLONY) sequencing; nanogrid rolling circle sequencing (ROLONY), allele-specific oligo ligation assays (e.g., oligo ligation assay (OLA), single template molecule OLA using a ligated linear probe and a rolling circle amplification (RCA) readout, ligated padlock probes, or single template molecule OLA using a ligated circular padlock probe and a rolling circle amplification (RCA) readout), and the like.

In some embodiments, determining the sequence of the stochastically barcoded target or any product thereof comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of the stochastically barcoded target or any product thereof can be determined by electron microscopy or a chemical-sensitive field effect transistor (chemFET) array.

High-throughput sequencing methods, such as cyclic array sequencing using platforms such as Roche 454, Illumina Solexa, ABI-SOLiD, ION Torrent, Complete Genomics, Pacific Bioscience, Helicos, or the Polonator platform, can also be utilized. In some embodiment, sequencing can comprise MiSeq sequencing. In some embodiment, sequencing can comprise HiSeq sequencing.

The stochastically labeled targets can comprise nucleic acids representing from about 0.01% of the genes of an organism's genome to about 100% of the genes of an organism's genome. For example, about 0.01% of the genes of an organism's genome to about 100% of the genes of an organism's genome can be sequenced using a target complimentary region comprising a plurality of multimers by capturing the genes containing a complimentary sequence from the sample. In some embodiments, the stochastically barcoded targets comprise nucleic acids representing from about 0.01% of the transcripts of an organism's transcriptome to about 100% of the transcripts of an organism's transcriptome. For example, about 0.501% of the transcripts of an organism's transcriptome to about 100% of the transcripts of an organism's transcriptome can be sequenced using a target complimentary region comprising a poly(T) tail by capturing the mRNAs from the sample.

Determining the sequences of the spatial labels and the molecular labels of the plurality of the stochastic barcodes can include sequencing 0.00001%, 0.0001%, 0.001%, 0.01%, 0.1%, 1%, 2%, 3%, 4%, 5%, 6%, 7%, 8%, 9%, 10%, 20%, 30%, 40%, 50%, 60%, 70%, 80%, 90%, 99%, 100%, or a number or a range between any two of these values, of the plurality of stochastic barcodes. Determining the sequences of the labels of the plurality of stochastic barcodes, for example the sample labels, the spatial labels, and the molecular labels, can include sequencing 1, 10, 20, 30, 40, 50, 60, 70, 80, 90, 100, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, or a number or a range between any two of these values, of the plurality of stochastic barcodes. Sequencing some or all of the plurality of stochastic barcodes can include generating sequences with read lengths of, of about, of at least, or of at most, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values, of nucleotides or bases.

Sequencing can comprise sequencing at least or at least about 10, 20, 30, 40, 50, 60, 70, 80, 90, 100 or more nucleotides or base pairs of the stochastically barcoded targets. For example, sequencing can comprise generating sequencing data with sequences with read lengths of 50, 75, or 100, or more nucleotides by performing polymerase chain reaction (PCR) amplification on the plurality of stochastically barcoded targets. Sequencing can comprise sequencing at least or at least about 200, 300, 400, 500, 600, 700, 800, 900, 1,000 or more nucleotides or base pairs of the stochastically barcoded targets. Sequencing can comprise sequencing at least or at least about 1500, 2000, 3000, 4000, 5000, 6000, 7000, 8000, 9000, or 10000 or more nucleotides or base pairs of the stochastically barcoded targets.

Sequencing can comprise at least about 200, 300, 400, 500, 600, 700, 800, 900, 1,000 or more sequencing reads per run. In some embodiments, sequencing comprises sequencing at least or at least about 1500, 2000, 3000, 4000, 5000, 6000, 7000, 8000, 9000, or 10000 or more sequencing reads per run. Sequencing can comprise less than or equal to about 1,600,000,000 sequencing reads per run. Sequencing can comprise less than or equal to about 200,000,000 reads per run.

Samples

In some embodiments, the plurality of targets can be comprised in one or more samples. A sample can comprise one or more cells, or nucleic acids from one or more cells. A sample can be a single cell or nucleic acids from a single cell. The one or more cells can be of one or more cell types. At least one of the one or more cell types can be brain cell, heart cell, cancer cell, circulating tumor cell, organ cell, epithelial cell, metastatic cell, benign cell, primary cell, circulatory cell, or any combination thereof.

A sample for use in the method of the disclosure can comprise one or more cells. A sample can refer to one or more cells. In some embodiments, the plurality of cells can include one or more cell types. At least one of the one or more cell types can be brain cell, heart cell, cancer cell, circulating tumor cell, organ cell, epithelial cell, metastatic cell, benign cell, primary cell, circulatory cell, or any combination thereof. In some embodiments, the cells are cancer cells excised from a cancerous tissue, for example, breast cancer, lung cancer, colon cancer, prostate cancer, ovarian cancer, pancreatic cancer, brain cancer, melanoma and non-melanoma skin cancers, and the like. In some embodiments, the cells are derived from a cancer but collected from a bodily fluid (e.g. circulating tumor cells). Non-limiting examples of cancers can include, adenoma, adenocarcinoma, squamous cell carcinoma, basal cell carcinoma, small cell carcinoma, large cell undifferentiated carcinoma, chondrosarcoma, and fibrosarcoma. The sample can include a tissue, a cell monolayer, fixed cells, a tissue section, or any combination thereof. The sample can include a biological sample, a clinical sample, an environmental sample, a biological fluid, a tissue, or a cell from a subject. The sample can be obtained from a human, a mammal, a dog, a rat, a mouse, a fish, a fly, a worm, a plant, a fungus, a bacterium, a virus, a vertebrate, or an invertebrate.

In some embodiments, the cells are cells that have been infected with virus and contain viral oligonucleotides. In some embodiments, the viral infection can be caused by a virus such as single-stranded (+ strand or "sense") DNA viruses (e.g. parvoviruses), or double-stranded RNA viruses (e.g. reoviruses). In some embodiments, the cells are bacteria. These can include either gram-positive or gram-negative bacteria. In some embodiments, the cells are fungi. In some embodiments, the cells are protozoans or other parasites.

As used herein, the term "cell" can refer to one or more cells. In some embodiments, the cells are normal cells, for example, human cells in different stages of development, or human cells from different organs or tissue types. In some embodiments, the cells are non-human cells, for example, other types of mammalian cells (e.g. mouse, rat, pig, dog, cow, or horse). In some embodiments, the cells are other types of animal or plant cells. In other embodiments, the cells can be any prokaryotic or eukaryotic cells.

In some embodiments the cells are sorted prior to associating a cell with a bead. For example the cells can be sorted by fluorescence-activated cell sorting or magnetic-activated cell sorting, or more generally by flow cytometry. The cells can be filtered by size. In some embodiments a retentate contains the cells to be associated with the bead. In some embodiments the flow through contains the cells to be associated with the bead.

A sample can refer to a plurality of cells. The sample can refer to a monolayer of cells. The sample can refer to a thin section (e.g., tissue thin section). The sample can refer to a solid or semi-solid collection of cells that can be place in one dimension on an array.

Data Analysis and Display Software

Data Analysis and Visualization of Spatial Resolution of Targets

The disclosure provides for methods for estimating the number and position of targets with stochastic barcoding and digital counting using spatial labels. The data obtained from the methods of the disclosure can be visualized on a map. A map of the number and location of targets from a sample can be constructed using information generated using the methods described herein. The map can be used to locate a physical location of a target. The map can be used to identify the location of multiple targets. The multiple targets can be the same species of target, or the multiple targets can be multiple different targets. For example a map of a brain can be constructed to show the digital count and location of multiple targets.

The map can be generated from data from a single sample. The map can be constructed using data from multiple samples, thereby generating a combined map. The map can be constructed with data from tens, hundreds, and/or thousands of samples. A map constructed from multiple samples can show a distribution of digital counts of targets associated with regions common to the multiple samples. For example, replicated assays can be displayed on the same map. At least 1, 2, 3, 4, 5, 6, 7, 8, 9, or 10 or more replicates can be displayed (e.g., overlaid) on the same map. At most 1, 2, 3, 4, 5, 6, 7, 8, 9, or 10 or more replicates can be displayed (e.g., overlaid) on the same map. The spatial distribution and number of targets can be represented by a variety of statistics.

Combining data from multiple samples can increase the locational resolution of the combined map. The orientation of multiple samples can be registered by common landmarks, wherein the individual locational measurements across samples are at least in part non-contiguous. A particular example is sectioning a sample using a microtome on one axis and then sectioning a second sample along a different access. The combined dataset will give three dimensional spatial locations associated with digital counts of targets. Multiplexing the above approach will allow for high resolution three dimensional maps of digital counting statistics.

In some embodiments of the instrument system, the system will comprise computer-readable media that includes code for providing data analysis for the sequence datasets generated by performing single cell, stochastic barcoding assays. Examples of data analysis functionality that can be provided by the data analysis software include, but are not limited to, (i) algorithms for decoding/demultiplexing of the sample label, cell label, spatial label, and molecular label, and target sequence data provided by sequencing the stochastic barcode library created in running the assay, (ii) algorithms for determining the number of reads per gene per cell, and the number of unique transcript molecules per gene per cell, based on the data, and creating summary tables, (iii) statistical analysis of the sequence data, e.g. for clustering of cells by gene expression data, or for predicting confidence intervals for determinations of the number of transcript molecules per gene per cell, etc., (iv) algorithms for identifying sub-populations of rare cells, for example, using principal component analysis, hierarchical clustering, k-mean clustering, self-organizing maps, neural networks etc., (v) sequence alignment capabilities for alignment of gene sequence data with known reference sequences and detection of mutation, polymorphic markers and splice variants, and (vi) automated clustering of molecular labels to compensate for amplification or sequencing errors. In some embodiments, commercially-available software can be used to perform all or a portion of the data analysis, for example, the Seven Bridges (https://www.sbgenomics.com/) software can be used to compile tables of the number of copies of one or more genes occurring in each cell for the entire collection of cells. In some embodiments, the data analysis software can include options for outputting the sequencing results in useful graphical formats, e.g. heatmaps that indicate the number of copies of one or more genes occurring in each cell of a collection of cells. In some embodiments, the data analysis software can further comprise algorithms for extracting biological meaning from the sequencing results, for example, by correlating the number of copies of one or more genes occurring in each cell of a collection of cells with a type of cell, a type of rare cell, or a cell derived from a subject having a specific disease or condition. In some embodiment, the data analysis software can further comprise algorithms for comparing populations of cells across different biological samples.

In some embodiments all of the data analysis functionality can be packaged within a single software package. In some embodiments, the complete set of data analysis capabilities can comprise a suite of software packages. In some embodiments, the data analysis software can be a standalone package that is made available to users independently of the assay instrument system. In some embodiments, the software can be web-based, and can allow users to share data.

In some embodiments all of the data analysis functionality can be packaged within a single software package. In some embodiments, the complete set of data analysis capabilities can comprise a suite of software packages. In some embodiments, the data analysis software can be a standalone package that is made available to users independently of the assay instrument system. In some embodiments, the software can be web-based, and can allow users to share data.

System Processors and Networks

Figure 15:
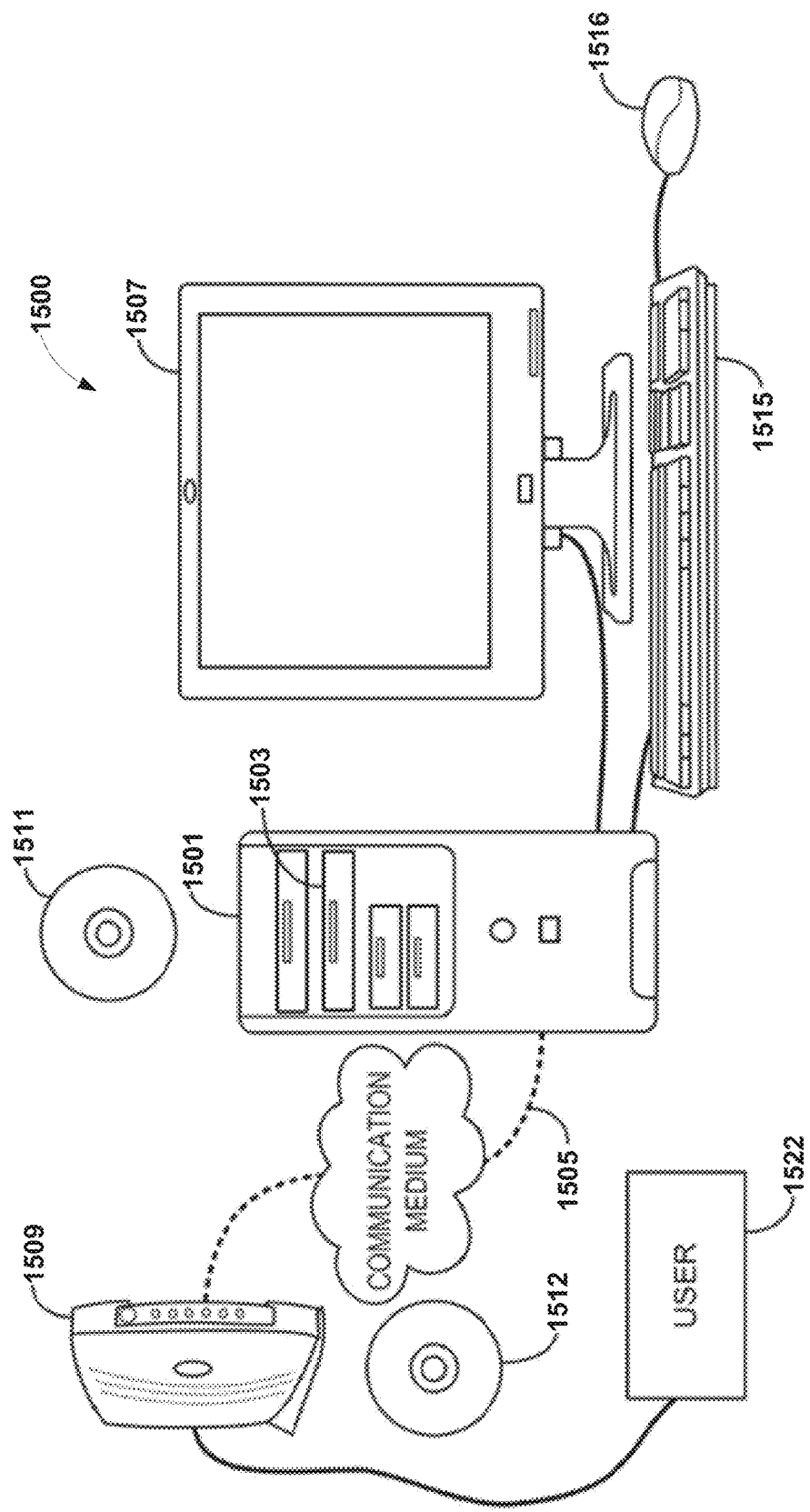
FIG. 15 shows a non-limiting exemplary instrument suitable to use in the methods of the disclosure.

In general, the computer or processor suitable for use in the methods of the presently disclosed instrument systems, as illustrated in FIG. 15, can be further understood as a logical apparatus that can read instructions from media 1511 or a network port 1505, which can optionally be connected to server 1509 having fixed media 1512. The system 1500, such as shown in FIG. 15 can include a CPU 1501, disk drives 1503, optional input devices such as keyboard 1515 or mouse 1516 and optional monitor 1507. Data communication can be achieved through the indicated communication medium to a server at a local or a remote location. The communication medium can include any means of transmitting or receiving data. For example, the communication medium can be a network connection, a wireless connection or an internet connection. Such a connection can provide for communication over the World Wide Web. It is envisioned that data relating to the present disclosure can be transmitted over such networks or connections for reception or review by a party 1522 as illustrated in FIG. 15.

Figure 16:
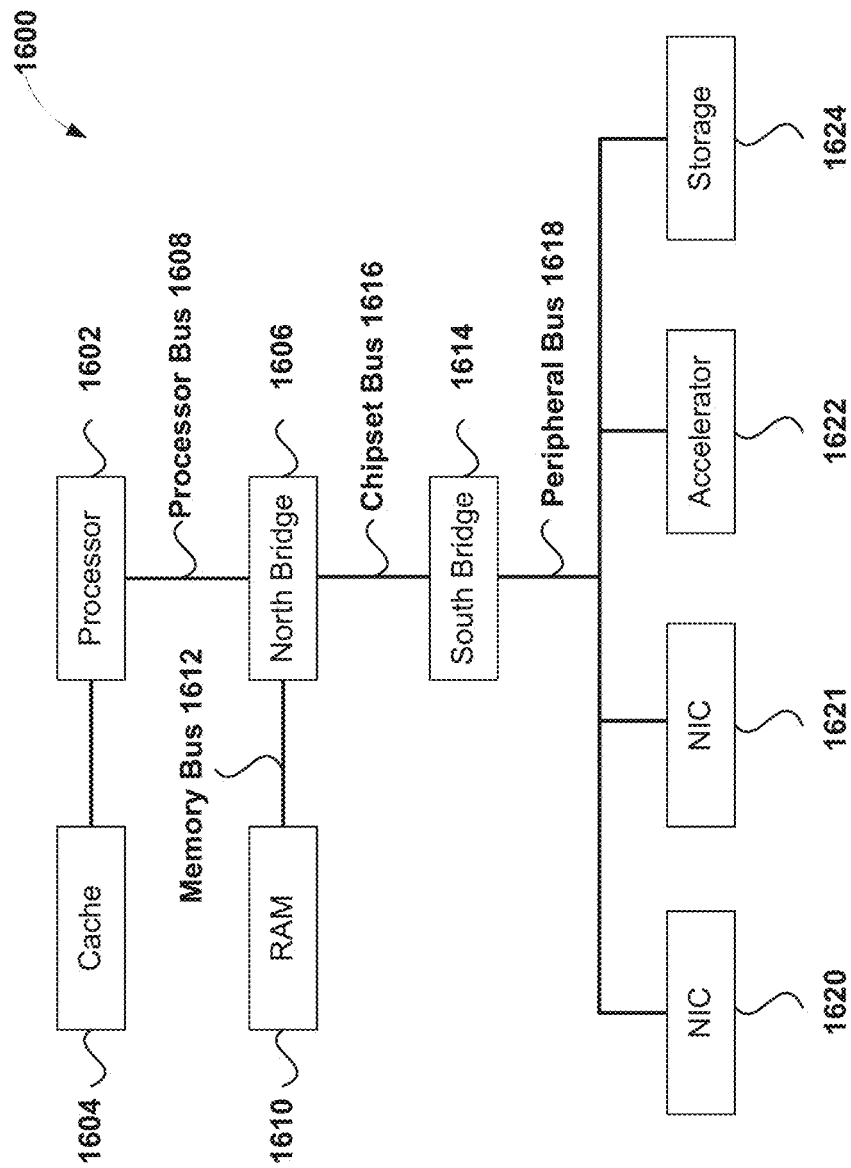
FIG. 16 illustrates a non-limiting exemplary architecture of a computer system that can be used in connection with embodiments of the present disclosure.

FIG. 16 illustrates an exemplary embodiment of a first example architecture of a computer system 1600 that can be used in connection with example embodiments of the present disclosure. As depicted in FIG. 16, the example computer system can include a processor 1602 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100TM processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, or personal data assistant devices.

As illustrated in FIG. 16, a high speed cache 1604 can be connected to, or incorporated in, the processor 1602 to provide a high speed memory for instructions or data that have been recently, or are frequently, used by processor 1602. The processor 1602 is connected to a north bridge 1606 by a processor bus 1608. The north bridge 1606 is connected to random access memory (RAM) 1610 by a memory bus 1612 and manages access to the RAM 1610 by the processor 1602. The north bridge 1606 is also connected to a south bridge 1614 by a chipset bus 1616. The south bridge 1614 is, in turn, connected to a peripheral bus 1618. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 1618. In some alternative architectures, the functionality of the north bridge can be incorporated into the processor instead of using a separate north bridge chip.

In some embodiments, system 1600 can include an accelerator card 1622 attached to the peripheral bus 1618. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 1624 and can be loaded into RAM 1610 or cache 1604 for use by the processor. The system 1600 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention.

In this example, system 1600 also includes network interface cards (NICs) 1620 and 1621 connected to the peripheral bus for providing network interfaces to external storage, such as Network Attached Storage (NAS) and other computer systems that can be used for distributed parallel processing.

Figure 17:
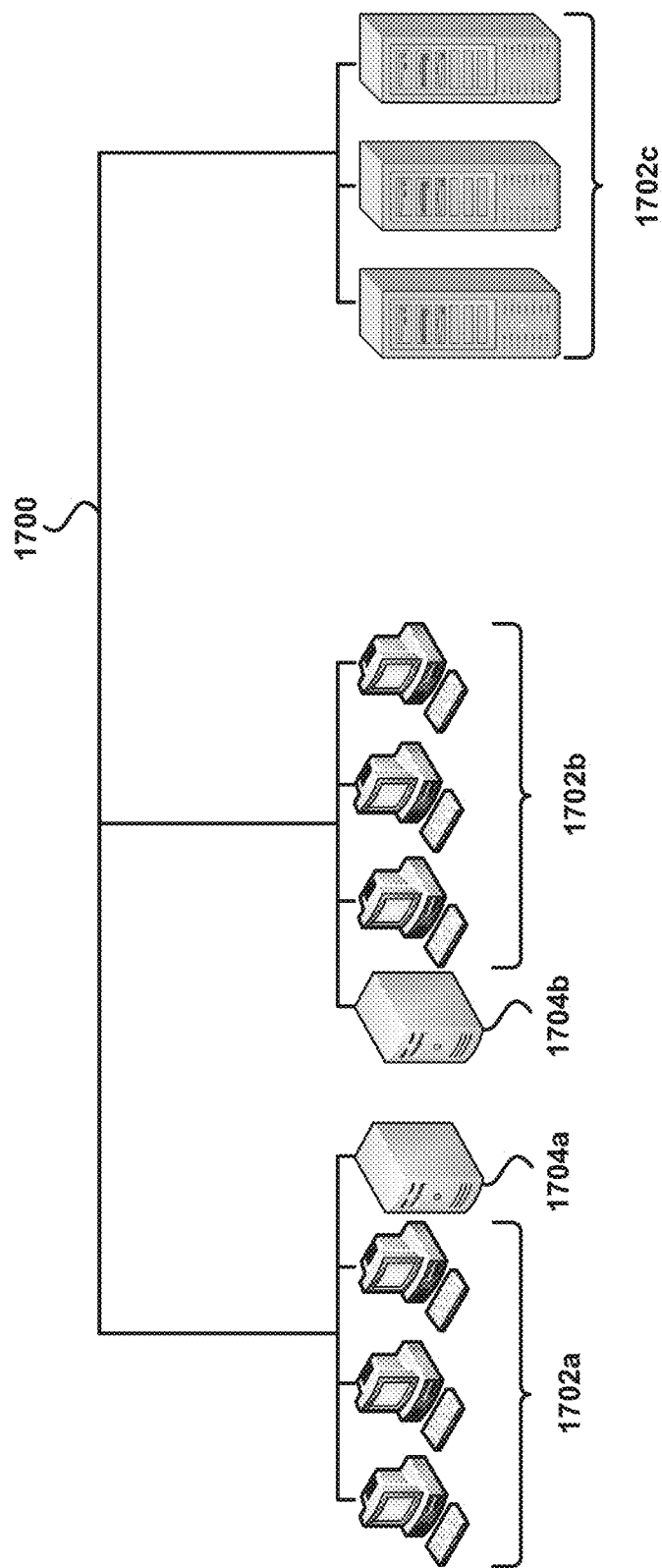
FIG. 17 illustrates a non-limiting exemplary architecture showing a network with a plurality of computer systems suitable for use in the methods of the disclosure.

FIG. 17 illustrates an exemplary diagram showing a network 1700 with a plurality of computer systems 1702a, and 1702b, a plurality of cell phones and personal data assistants 1702c, and Network Attached Storage (NAS)

1704a, and 1704b suitable for use in the methods of the disclosure. In example embodiments, systems 1712a, 1712b, and 1712c can manage data storage and optimize data access for data stored in Network Attached Storage (NAS) 1714a and 1714b. A mathematical model can be used for the data and be evaluated using distributed parallel processing across computer systems 1712a, and 1712b, and cell phone and personal data assistant systems 1712c. Computer systems 1712a, and 1712b, and cell phone and personal data assistant systems 1712c can also provide parallel processing for adaptive data restructuring of the data stored in Network Attached Storage (NAS) 1714a and 1714b. FIG. 17 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

Figure 18:
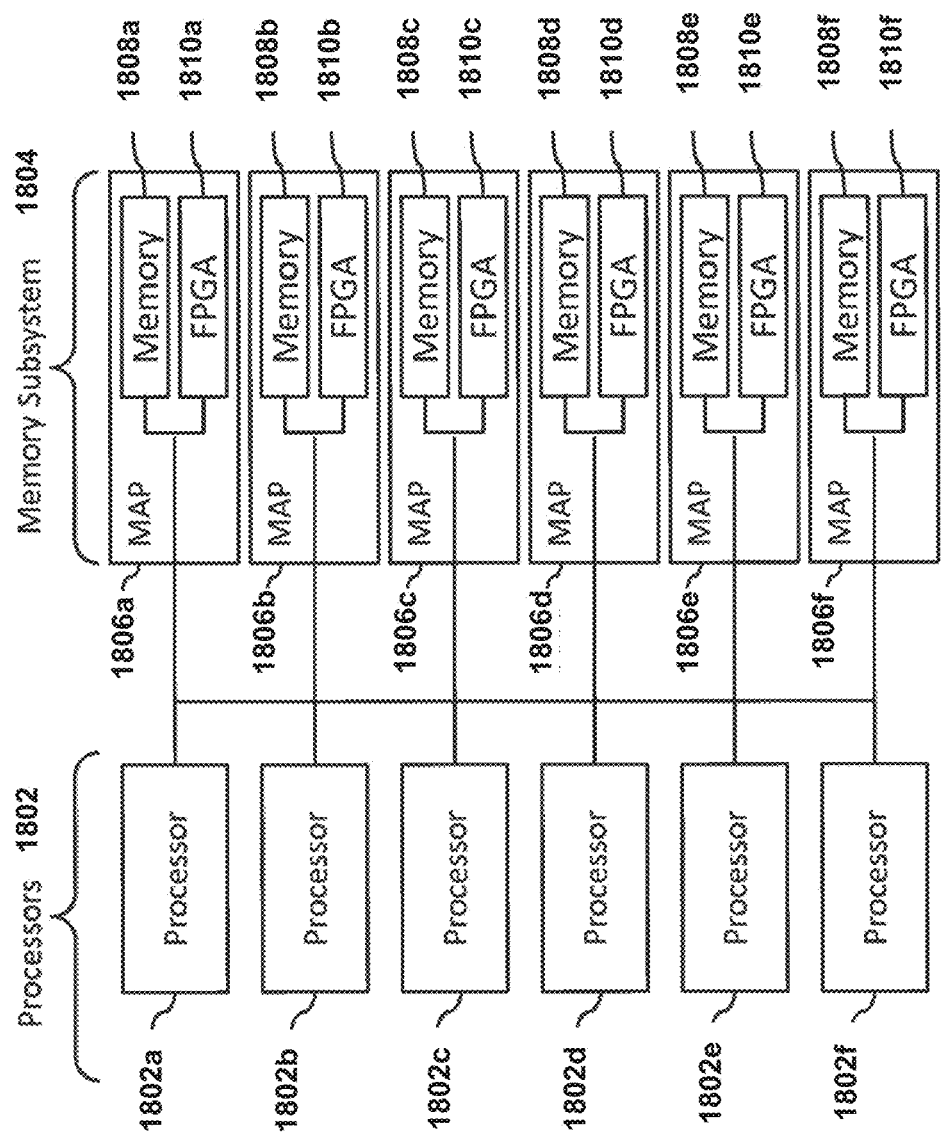
FIG. 18 illustrates a non-limiting exemplary architecture of a multiprocessor computer system using a shared virtual address memory space in accordance with the methods of the disclosure.

FIG. 18 illustrates an exemplary a block diagram of a multiprocessor computer system 1800 using a shared virtual address memory space in accordance with an example embodiment. The system includes a plurality of processors 1802a-f that can access a shared memory subsystem 1804. The system incorporates a plurality of programmable hardware memory algorithm processors (MAPs) 1806a-f in the memory subsystem 1804. Each MAP 1806a-f can comprise a memory 1808a-f and one or more field programmable gate arrays (FPGAs) 1810a-f. The MAP provides a configurable functional unit and particular algorithms or portions of algorithms can be provided to the FPGAs 1810a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 1808a-f, allowing it to execute tasks independently of, and asynchronously from, the respective microprocessor 1802a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer subsystem of the present disclosure can be implemented using software modules executing on any of the above or other computer architectures and systems. In other embodiments, the functions of the system can be implemented partially or completely in firmware, programmable logic devices such as field programmable gate arrays (FPGAs), system on chips (SOLs), application specific integrated circuits (ASICs), or other processing and logic elements. For example, the Set Processor and Optimizer can be implemented with hardware acceleration through the use of a hardware accelerator card, such as accelerator card.

EXAMPLES

Some aspects of the embodiments discussed above are disclosed in further detail in the following examples, which are not in any way intended to limit the scope of the present disclosure.

Example 1

Correcting One-Base Substitution Errors

This example demonstrates correcting PCR or sequencing errors involving one-base substitutions. PCR or sequencing errors involving one-base substitutions were removed by attributing copies of a target with similar molecular labels and with occurrences, i.e. sequencing reads, ≤7 if there were $3^8$ unique stochastic barcodes (17 if there were $4^8$ unique stochastic barcodes) as having the same molecular label for the plurality of targets.

Stochastic barcoding can comprise using a non-depleting pool of $3^8$ (6561) unique stochastic barcodes with oligo(dT) as their target-binding regions to label mRNAs with poly(A) in a sample prior to the RT step. The labelling process can be random, and each target molecule can hybridize to one stochastic barcode. For any target, if the number of target molecules was much smaller than the number of stochastic barcodes, each target molecule may likely hybridize to a different stochastic barcode. So if only a few target molecules were present, the few target molecular may be unlikely to hybridize to stochastic barcodes with similar molecular labels (MLs) during hybridization.

The probability of sampling at least one pair of stochastic barcodes with similar molecular labels from $3^8$ non-depleting unique stochastic barcodes was calculated. Two molecular labels can have similar sequences if they differ by one base. This sampling event can be regarded as sampling with replacement because the stochastic barcodes can be practically non-depleting. This probability can help eliminate stochastic barcodes with similar molecular labels that are most unlikely to be present for a given sample comprising a plurality of targets. The problem can be formulated as the number of stochastic barcodes required so that at least two stochastic barcodes with similar molecular labels can be chosen for a certain probability. This problem can be formulated as the minimum sample size required so that the probability of two stochastic barcodes having similar sequences may be greater than 0.5 given $3^8$ distinct molecular labels. Thus, this problem can be regarded as a generalization of the classical birthday problem. The classical birthday problem can determine the minimum sample size required so that the probability of two persons sharing the same birthday may be greater than 0.5 given 365 distinct birthdays.

To derive this sample size r, the probability of having at least one pair of similar molecular labels given r stochastic barcodes sampled from $3^8$ unique stochastic barcodes was calculated using the probability of its complement event. If only one stochastic barcode was chosen randomly from $3^8$ unique stochastic barcodes, then the probability that its molecular label may not be similar to the molecular labels of other stochastic barcodes, $p_1=1$, because there was only one stochastic barcode. If a second stochastic barcode was also chosen randomly from $3^8$ unique stochastic barcodes, then the probability that its molecular label may not be similar to the molecular label of the first stochastic barcode, $p_2=(3^8-16-1)/3^8$. This was because for a given molecular label, each base position had two possible nucleotide alternatives resulting in a total of 2*8 one-base variants, assuming there were three possible bases for each position in a stochastic barcode. If a third stochastic barcode was continuously drawn randomly from $3^8$ stochastic barcodes with unique molecular labels, then the probability that its molecular label may not be similar to the molecular labels of the previous two, $p_3=(3^8-1-16-1-16)/3^8=(3^8-2*17)/3^8$. Stochastic barcodes can be continuously drawn from $3^8$ unique stochastic barcodes until the rth stochastic barcode. The probability that this last stochastic barcode may not be similar to previous stochastic barcodes, $p_r=(3^8-(r-1)*17)/3^8$. Because all r stochastic barcodes were drawn independent, the probability of drawing all stochastic barcodes not having similar sequences, P (all molecular labels not having similar sequences), $=p_1*p_2*p_3* \ldots *p_r$. Thus the probability of having at least one pair of stochastic barcodes similar amongst r stochastic barcodes from $3^8$ stochastic barcodes with unique molecular labels was P (at least one pair of molecular labels having similar sequences)=1−P (all molecular labels not having similar sequences). The sample size r was then calculated through this equation by setting a desirable value for P (at least one pair of molecular labels having similar sequences)=0.01, 0.05, 0.1, or a desired value.

TABLE 1

Probability of observing stochastic barcodes with similar molecular labels for a given number of unique molecular labels

| N = $3^8$ (6561) | | N = $4^8$ (65536) | |
|---|---|---|---|
| p | r | p | r |
| 0.01 | 4 | 0.01 | 8 |
| 0.05 | 7 | 0.05 | 17 |
| 0.1 | 10 | 0.1 | 25 |
| 0.2 | 14 | 0.2 | 35 |
| 0.5 | 24 | 0.5 | 61 |
| 0.9 | 43 | 0.9 | 111 |

Table 1 shows the probability of having at least one similar pair amongst r molecular labels given $3^8$ or $4^8$ unique molecular labels. If there were $3^8$ unique stochastic barcodes and ≤7 (17 if there were $4^8$ unique stochastic barcodes) stochastic barcodes were selected, the probability of observing a pair of stochastic barcodes with similar molecular labels was less than 0.05, which is negligible. Therefore, as justified by this small probability, similar molecular labels were more likely artifacts than a real chance selection of similar stochastic barcodes and can be corrected.

However, if more than 7 to 24 stochastic barcodes were present, then the probability of observing more than one pair of stochastic barcodes with similar molecular labels would be higher (for example, 0.5). Thus the possibility that these stochastic barcodes were true and not artifacts cannot be confidently ruled out. In contrast, common intuition may have erroneously concluded that if only 24 stochastic barcodes were drawn from a large pool of 6561 unique possibilities, any one-base deviation may be the result of a sequencing error rather than coincidences.

For example, if 115 stochastic barcodes were randomly sampled, then it would be 100% certain that there will be at least one-pair of stochastic barcodes with similar molecular labels because the calculated probability would be one. Suppose that there were 115 targets in the sample, then after the hybridization and reverse transcription processes, two pairs of stochastic barcodes with similar molecular labels and 111 of stochastic barcodes with non-similar molecular labels (in total 115 stochastic barcodes) would be observable. If however in the sequencing data, three pairs of stochastic barcodes with similar molecular labels and 110 of stochastic barcodes with non-similar molecular labels (in total 116 stochastic barcodes) were observed, then the possibility that only two pairs of stochastic barcodes with similar molecular labels were true and the third pair was created by some errors. This 100% probability would indicate that the event of observing at least one-pair of stochastic barcodes with similar molecular labels can occur when 115 stochastic barcodes were randomly sampled during stochastic barcoding; however, this may not mean that all observed pairs of similar molecular labels were true. Stochastic barcodes with similar molecular labels can be generated from stochastic barcoding, real or true molecular labels, or from PCR errors, artifacts, or sequencing errors, error or false molecular labels. Therefore further assessment may be necessary to determine whether a particular pair of molecular labels would be true if similar molecular labels were observed. Also, for each probability, more stochastic barcodes can be required to expect similar pairs of molecular labels when increasing the total molecular labels variety from $3^8$ to $4^8$.

Table 2 and Table 3 show that when ≤7 stochastic barcodes with unique molecular labels were observed, similar molecular labels were very unlikely to occur because the probability of such occurrence was less than 0.05. Accordingly, those similar molecular labels were likely to have been caused by PCR errors, artifacts, or sequencing errors, and these should be removed from the molecular label counts in order to correct or adjust the molecular label counts. Therefore, the total number of true molecular labels in Table 2 and Table 3 can be reduced from 5 to 1, and from 7 to 6 respectively. However, 23 unique barcodes were observed in Table 4, which expects about 50% chance of having at least one pair of stochastic barcodes with similar molecular labels. Accordingly, although 16 pairs of stochastic barcodes with similar molecular labels are likely to be real, each pair of similar molecular label will require further assessment to confirm whether they are be real.

TABLE 2

CD69 raw data from 10 pg input RNA in well H01
(4 pairs of similar molecular labels were observed
from the most abundant barcode)

| Gene ID | ML | SEQ ID NO | Number of Reads Per ML |
|---|---|---|---|
| CD69 | TGTGCGTG | 3 | 261 |
| CD69 | TGTGCGCG | 4 | 2 |
| CD69 | TGTGCGGG | 5 | 2 |

TABLE 2-continued

CD69 raw data from 10 pg input RNA in well H01
(4 pairs of similar molecular labels were observed
from the most abundant barcode)

| Gene ID | ML | SEQ ID NO | Number of Reads Per ML |
|---|---|---|---|
| CD69 | GGTGCGTG | 6 | 1 |
| CD69 | TGGGCGTG | 7 | 1 |

TABLE 3

CD64 raw data from 500 pg input RNA in well A01
(1 pair of similar molecular labels was observed)

| Gene ID | ML | SEQ ID NO | Number of Reads Per ML |
|---|---|---|---|
| CD4 | CGTGTCTG | 8 | 10 |
| CD4 | GGGGGCGA | 9 | 7 |
| CD4 | GCTGCTGG | 10 | 5 |
| CD4 | TCGGGCGA | 11 | 4 |
| CD4 | CGCGTTCA | 12 | 1 |
| CD4 | CGCGTTTA | 13 | 1 |
| CD4 | TGGGCTTG | 14 | 1 |

TABLE 4

TFRC raw data from 10 pg input RNA from well
E11 (16 pairs of similar molecular labels were
observed in total from 4 most abundant stochastic
barcodes)

| Gene ID | ML | SEQ ID NO | Number of Reads Per ML |
|---|---|---|---|
| TFRC | CCGCTCTG | 15 | 369 |
| TFRC | CGGTGTTC | 16 | 363 |
| TFRC | CGGGGGTG | 17 | 335 |
| TFRC | CCCCCTTG | 18 | 22 |
| TFRC | CGGGGGGG | 19 | 6 |
| TFRC | CGGGGGCG | 20 | 5 |
| TFRC | CCGCGCTG | 21 | 4 |
| TFRC | CGGCGTTC | 22 | 3 |
| TFRC | CGGTGTCC | 23 | 2 |
| TFRC | TGGTGTTC | 24 | 2 |
| TFRC | CTGCTCTG | 25 | 2 |
| TFRC | GGCCGTGG | 26 | 2 |
| TFRC | TCGCTCTG | 27 | 2 |
| TFRC | CCGCCCTG | 28 | 2 |
| TFRC | CCCGCTTG | 29 | 1 |
| TFRC | CCGTTCTG | 30 | 1 |
| TFRC | GGGTGTTC | 31 | 1 |
| TFRC | CGTTGTTC | 32 | 1 |
| TFRC | GGGGGTGG | 33 | 1 |
| TFRC | GGGTCCGG | 34 | 1 |
| TFRC | CGGCTCTG | 35 | 1 |
| TFRC | CGGCGTCC | 36 | 1 |
| TFRC | CCGCTCCG | 37 | 1 |

Altogether these data demonstrate that the number of stochastic barcodes with similar molecular labels observed were removed because PCR errors, artifacts, or sequencing errors likely resulted in these stochastic barcodes with similar molecular labels.

Example 2

Determining Quality Status of a Target in Sequencing Data

This example demonstrates determining the quality status of a target in sequencing data to be the complete sequencing quality status, the incomplete sequencing quality status, or the saturated sequencing quality status. The quality status of the target depended on whether all of the true or real molecular labels were observed.

As illustrated in Example 1, the full counting of stochastic barcodes with unique molecular labels present in the library can greatly dependent on the sequencing depth. The deeper the sequencing, the more likely that all true molecular labels were observed. Shallow sequencing would be less expensive but can miss many molecular labels and possibly may also compromise gene detection sensitivity. Complete sequencing can mean all of the true molecular labels of stochastic barcodes used to label the target molecule were observed, and incomplete sequencing can mean that only some of the true molecular labels were observed. Furthermore, it may be possible that more than 48568 target molecules were present in the starting sample (which would be the lower limit of the number of molecules after Poisson correction or adjustment based on seeing 6561–2* standard deviation of distinct stochastic barcodes). Then saturated sequencing can occur when the number of target molecules would be hard to determine due to a limitation on the total molecular label diversity. However, saturated sequencing would be unlikely if a low amount of RNA was used as input for stochastic barcoding.

To define complete or incomplete sequencing mathematically, each was compared with a theoretical model without any error. Under perfect experiment conditions, each copy of a target molecule in the staring sample can generate $(1+C)^j$ copies given j PCR cycles and C efficiency for each cycle. Then for each barcoded molecule in the starting sample, Illumina sequencing can be regarded essentially as a Poisson sampling from $(1+C)^j$ clonal copies amplified from the original barcoded molecules. In theory, for the same target gene, sequencing k stochastically barcoded target molecules can be regarded as repeated Poisson sampling from $(1+C)^j$ copies because all stochastically barcoded molecules can be equally representable after PCR. An important assumption of the Poisson model was that mean equals variance, and sequencing reads should follow equi-dispersion. Dispersion can be defined as variance/mean.

Figures 19A, 19B:
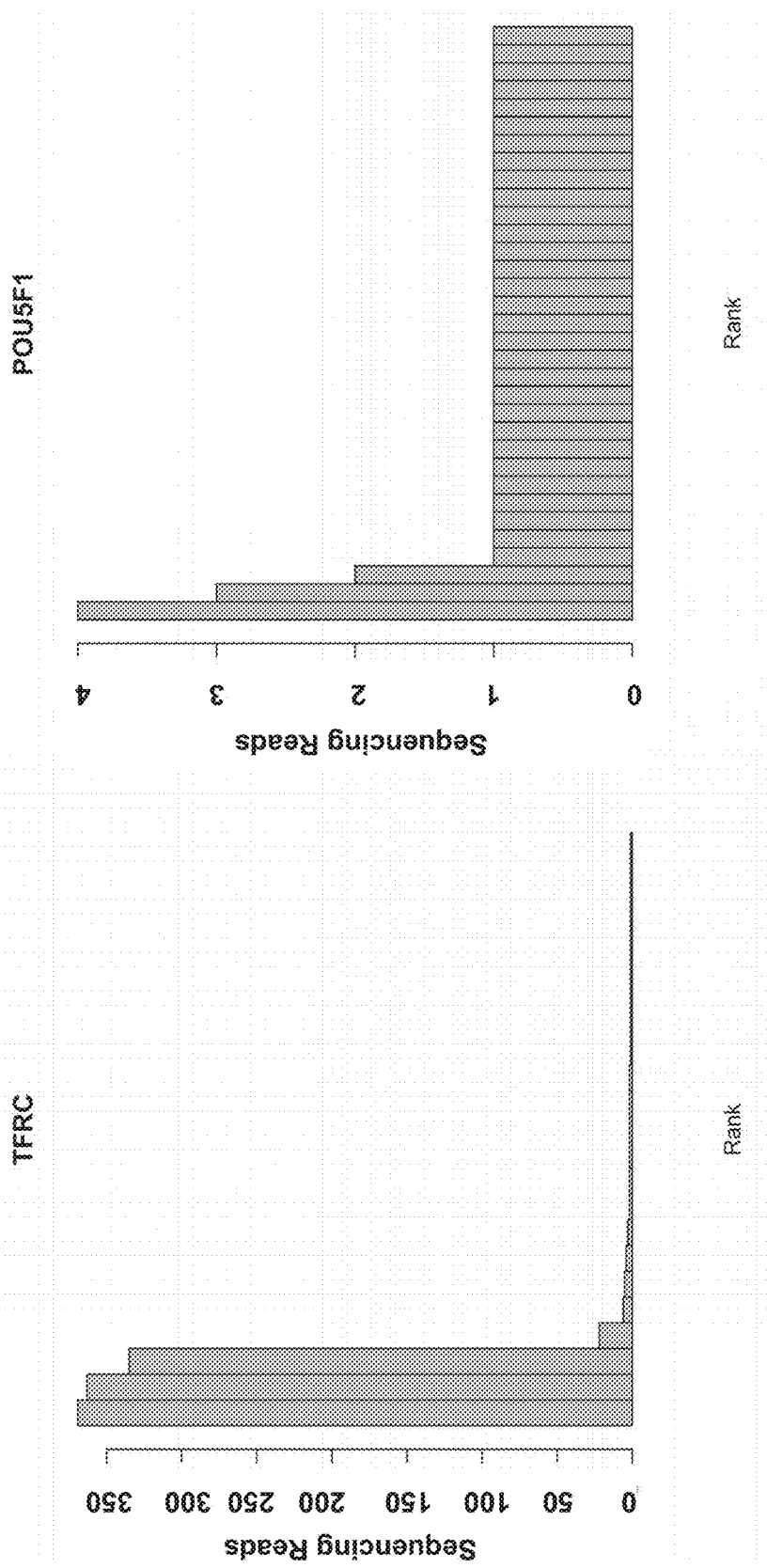
FIGS. 19A-19B show non-limiting examples of completely and incompletely sequenced genes.

In practice, complete sequencing may often be accompanied with errors that usually were clustered at much lower read frequencies because. Unlike true molecular labels, errors would be unlikely to participate in all the PCR cycles and consequently would result in fewer copies leading to variation in read frequency that is much larger compared to Poisson. FIGS. 19A-19B show examples of completely and incompletely sequenced genes. In FIG. 19A, the largest sequencing read was more than 350-folds that of the smallest sequencing read. Therefore, complete sequencing tends to exhibit a bigger dispersion index (>1) relative to Poisson.

In contrast, for incomplete sequencing, only some of the stochastic barcodes with true molecular labels in the library have been sequenced, and thus the variation in sequencing reads would be smaller compared to Poisson. In FIG. 19B, the largest sequencing read was only about 3-folds that of the smallest sequencing read. Therefore, incomplete sequencing would tend to exhibit a smaller dispersion index (<1) relative to Poisson.

In addition to calculating the dispersion index, sequencing read of the most abundant molecule label can be used in deciding if sequencing is complete. For example, the sequencing status can be classified as complete if the read of the most abundant molecular index was 25 and the dispersion index was 5; otherwise, it can be classified as incomplete. A threshold of 25 reads can be used because sequencing can be incomplete until sequencing errors start to appear. Sequencing errors would likely to be generated if any molecular label was seen more than 25 times Under circumstances where the sequencing data for a highly abundant gene was saturated in stochastic barcode, for example exceeding 6557 for $3^8$ stochastic barcodes with unique molecular labels, the sequencing information for other lower expression genes within the same well can be used instead for calculating the dispersion index and the maximum sequencing read of that gene. For example, if the second most abundant gene in the same well had not saturated in stochastic barcodes and is classified as incomplete sequencing, then the saturation of the first gene can be considered as real and the number of molecules cannot be calculated. And if the second most abundant gene was classified as complete sequencing, then the saturation of the first gene may be artificial and the appearance of all the stochastic barcodes might be due to errors. And the Poisson model-based thresholding algorithm can be used to identify the number of true molecular labels.

Altogether, these data demonstrate determining sequencing status to be complete sequencing, incomplete sequencing, or saturated sequencing.

Example 3

Correcting PCR or Sequencing Errors with One-Base Substitutions for Completely Sequenced Genes This example shows correcting PCR or sequencing errors with one-base substitutions for completely sequenced genes, i.e. genes with the quality statutes of complete sequencing in the sequencing data. This example also shows thresholding molecular labels of a target, for example a gene, to determine true molecular labels and false molecular labels associated with the target in the sequencing data.

The sequencing error rate per nucleotide can vary from 0.1-1% and can usually be seen as low frequency reads. As sequencing goes deeper, more sequencing errors would likely to be generated. For example, if the true nucleotide sequencing error was 0.5%, and a molecular label was sequenced 100 times, then the expected number of sequencing errors associated with this molecular label can be about 4, calculated from $100*(1-(1-0.5\%)^8))$ if the molecular label was 8 nucleotides in length. If the molecular label was sequenced 300 times, then the expected number of sequencing errors can be about 12. These sequencing errors can create artificial molecular label sequences that can inflate counts. These molecular labels can be removed to prior to further analysis.

Amongst all the sequencing errors, one-base errors can occur much more frequently than those further than one-base apart. The probability of having one-base sequencing error can be derived from a binomial distribution with sample size 8 and probability of success equaling to the one-base sequencing error rate. One goal was to correct the one-base sequencing errors. The one-base sequencing errors can be regarded as the children of the most abundant and closest (for example, in terms of Hamming distance) molecular label, the parent molecular label. Sequencing errors were identified by finding the true children of the parent molecular label (i.e., children molecular labels that are one-base apart from the parent molecular label).

TABLE 5

Updated TFRC sequencing data after removing one-base sequencing errors from 10 pg input RNA well E11

| Gene ID | ML | SEQ ID NO | Number of Reads Per ML |
|---|---|---|---|
| TFRC | CCGCTCTG | 15 | 378 |
| TFRC | CGGTGTTC | 16 | 374 |
| TFRC | CGGGGGTG | 17 | 335 |
| TFRC | CCCCCTTG | 18 | 23 |
| TFRC | CGGGGGGG | 19 | 6 |
| TFRC | CGGGGGCG | 20 | 5 |
| TFRC | CCGCGCTG | 21 | 4 |
| TFRC | GGCCGTGG | 26 | 2 |
| TFRC | GGGGGTGG | 33 | 1 |
| TFRC | GGGTCCGG | 34 | 1 |
| TFRC | CGGCGTCC | 36 | 1 |

Select Parent and Children Molecular Labels

Parent molecular labels can be required to have >25 sequencing reads and the children molecular labels can be required to have no more than 3 sequencing reads. These requirements were based on the reasoning below. Suppose the sequencing error rate per nucleotide was 0.5%. If a molecular label was sequenced 25 times and 200 nucleotides were generated in total, then it was expected that one nucleotide was an error because 200*0.005=1. Therefore, for each molecular label with a sequencing read of 25, it was expected to have at least one child. It can be assumed the parental molecular label should have a sequencing read of 25. Children molecular labels with sequencing reads of 4 were unlikely to be sequencing errors. This was because the probability of introducing the same sequencing error four times into a molecular label is $8*0.005^4=5*10^{-9}$. If there were 106 sequencing reads in total, then the expected number of sequencing errors which was repeated four times would be $5*10^9*10^6=0.005$, which was negligible. Therefore, children molecular labels should have reads ≤3.

Given a Parental Molecular Label and its Related Children Molecular Labels that are One-Base Apart, how to Determine Children Molecular Labels that are Truly Sequencing Errors of the Parent?

Given a parental molecular label and a set of children molecular labels that were one-base different from the parental molecular label with sequencing reads ($R_{child\ 1}$, $R_{child\ 2}$, ..., $R_{child\ m}$), a multiple binomial test can be used to identify true children molecular labels. Under the null hypothesis, the abundance of the true children molecular labels should be less than or equal to the $R_{par}*p$ (mathematically, $H_0$: $p<e/2$); otherwise, it can be concluded in favor of the alternative hypothesis that the abundance was bigger than $R_{par}*p$ ($H_A$:$p>e/2$) and the hypothesis that the molecular label was a true child molecular label can be rejected. Then the probability of a child molecular label one-base different from its parental molecular label and was observed once would be $p=e/2$. Then mathematically, the probability $p_{child}$ of observing this child molecular label at least $R_{child}$ times out of total abundance ($R_{child}+R_{par}$) would be the following:

$$p_{child} = p(X \le R_{child} \mid R_{child} + R_{par}, p = e/2) = \sum_{R_{par}}^{j=R_{child}} \binom{R_{par}+R_{child}}{j} p^j (1-p)^{R_{par}+R_{child}-j}. \quad \text{Equation (1)}$$

If the child molecular label was indeed a sequencing error of its parent molecular label, then the probability $p_{child}$ should be greater than the critical value at 5%. Because multiple hypotheses are tested simultaneously, the critical value used to reject the null hypothesis can be determined by the False Discovery rates (FDR) controlled at 5% level, and the hypothesis can be accepted if $p_{child}$ is greater than FDR at a 5% level. With FDR controlled at 5% level, the unadjusted p-values can be sorted in an increasing order, such as $p_1 \le p_2 \le \ldots \le p_m$. Next the test with its corresponding rank j can be found. If $p_{child} \le j/m*5\%$, then the null hypothesis that this child molecular label was a one-base sequencing error of the parent molecular label can be accepted.

Altogether, these data demonstrate the steps to correct one-base sequencing errors for a completely sequenced gene: Step (1), select the molecular label with the most abundance sequencing read as the first parent molecular label if its sequencing read is bigger than 25. Step (2), select molecular labels with sequencing reads ≤3, and identify those molecular labels that are one-base apart from the first parent molecular label and call them children molecular labels; if no child molecular label or no one-base children molecular labels are found, go to step (5). Step (3), perform multiple Binomial tests on all children molecular labels and parent molecular labels, and remove those children molecular labels whose null hypothesis is accepted and attributing their sequencing reads to their parents. If none of the null hypotheses was accepted, which would imply that all children molecular labels were not one-base sequencing errors of the parent molecular label, and no read correction would need to be performed. Step (4), update molecular label sequences as well as sequencing reads. Step (5), choose the molecular label with the next largest sequencing read as the parent molecular label and repeat the above steps until no qualified parental molecular label or no qualified child molecular label remain.

Table 5 shows updated TFRC sequencing data after removing one-base sequencing errors using the above analysis. The unique number of molecular labels was reduced from 23 (shown in Table 4) to 11.

Use Poisson Models for Thresholding

Sequencing errors can be more likely to appear under complete sequencing. Some types of errors such as one-base sequencing errors may be correctable, but other errors such as random incorporation of artificial molecular labels cannot be corrected based on sequence similarity. Instead, these types of errors can be identified through modeling. As discussed above, complete sequencing would tend to be over-dispersed relative to Poisson. Therefore two distinctive Poisson models were created featuring the over-dispersion: one can be used to model the sequencing reads for the true molecular labels (i.e. the molecular label sequences used to label target molecules during stochastic barcoding), and the second model can be used for the error molecular labels (i.e. molecular label sequences not used during stochastic barcoding but showed up after sequencing due to errors). The sequencing error rate can be about 0.1-1%, and the PCR error rate can be about 0.001%. PCR errors can occur more in the later cycles of PCR resulting in error molecular labels with low sequencing reads but contribute to a large fraction of all observed molecular label sequences. Accordingly, errors generated through PCR and sequencing can often have lower sequencing reads than true molecular labels. Therefore, it was assumed that the Poisson mean for the sequencing reads of the true molecular labels would be larger than the Poisson mean for the error molecular labels.

Suppose there were k distinctive molecular labels in total, and t of them were true molecular labels such as $BC_1$, $BC_2$, ..., $BC_t$ and the rest of them were error molecular labels such as $BC_{t+1}$, $BC_{t+2}$, ..., $BC_k$. The sequencing reads which were mapped to those true and error molecular labels can be $R_1$, $R_2$, ..., $R_t$ and $R_{t+1}$, $R_{t+2}$, ..., $R_k$. Also assuming the Poisson means using true and error molecular labels were $\mu_t$ and $\mu_n$ with $p_t > \mu_n$, then the likelihood for the whole process would be $$L_1(X;\mu_t,\mu_n) = (X;\mu_t)*(X;\mu_n) = \Pi_{i=1}^t P(X_i=R_i|\mu_t) \Pi_{j=(t+1)}^k P(X_j=R_j|\mu_n), \quad \text{Equation (2)}$$

where $P(X_i=R_i|\mu_t)$ denotes the probability of observing $i^{th}$ molecular with abundance $R_i$ under a Poisson process with mean $\mu_t$.

Figure 20:
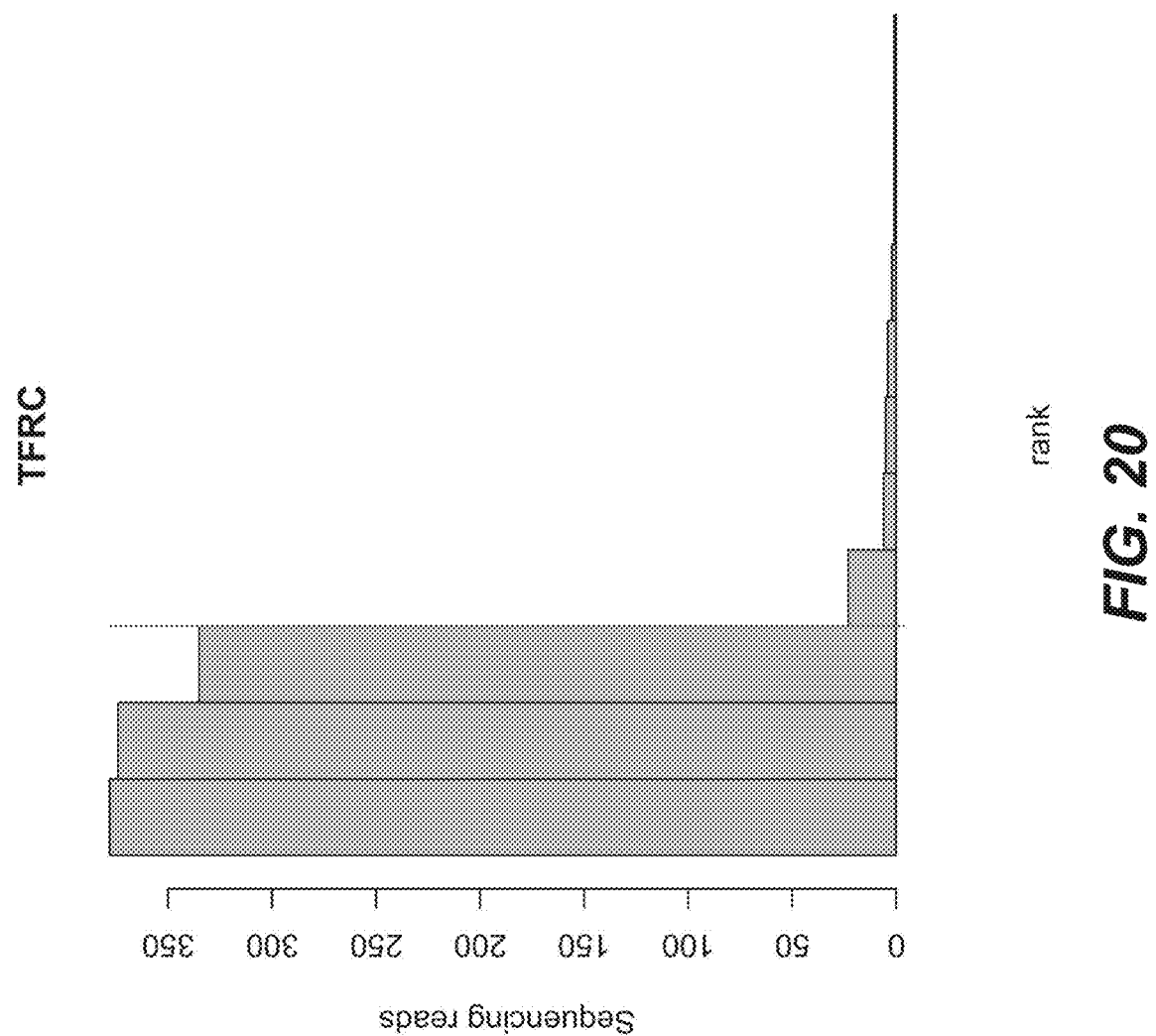
FIG. 20 is a non-limiting exemplary plot of sequencing reads against their ranks after correction on one-base sequencing errors and threshold to separate true and error barcodes.

To determine t the number of true molecular labels, a number of models were considered, starting from the model that assumed all molecular label were true (so l=k); and the second model that assumed the least abundant molecular label was an error and all other molecular label were true (so l=k−1); up to the last model that assumed only the most abundant molecular label was true and all others were error molecular labels (so l=1). At last, the best model would be the one with the highest likelihood amongst all models considered, or equivalent the smallest Akaike Information Criterion (AIC), which can be used in model selection by measuring the relative quality of each possible model for the given data. Mathematically, AIC can be defined as AIC=−2 log L+2p, where p is the number of parameters estimated in the model. So for $L_k$ and $L_1$, p=1, and for other cases p=2. The example in Table 6 shows that only three molecular labels with the largest three sequencing reads were considered to be true molecular labels amongst 8 possible models compared. Also, FIG. 20 shows that the threshold derived from the selected model (largest 3) clearly separated apparent true molecular label reads from those that were more likely errors.

TABLE 6

All possible models together with their log-likelihoods for TFRC from 10 pg input RNA well E11

| Gene ID | ML | Number of Reads Per ML |
|---|---|---|
| TFRC | ALL | −1294 |
| TFRC | largest 8 | −952 |
| TFRC | largest 7 | −813 |
| TFRC | largest 6 | −660 |
| TFRC | largest 5 | −481 |
| TFRC | largest 4 | −263 |
| TFRC | largest 3 | −51 |
| TFRC | largest 2 | −656 |
| TFRC | largest 1 | −1036 |

These data demonstrate the sequencing reads of completely sequenced genes corrected by removing one-base sequencing errors and thresholding using Poisson models.

Example 4

Adjusting Incompletely Sequenced Genes

This example shows adjusting incompletely sequenced genes by removing noisy genes and using a Zero-Truncated Poisson model for estimating the total number of molecular labels expected to be present in the library.

Remove Noisy Genes

In addition to considering the statistics of molecular labels and their sequencing reads, analysis at the gene level can also be informative. A gene can be considered noisy if very few molecular labels were detected and each molecular label has unusually low reads relative to completely sequenced genes. This assumption was based on the reasoning that stochastically barcoded molecules within the same library should be amplified and sequenced at approximately the same frequency. Such an expectation can be affected by PCR or sequencing bias caused by differences in the sequencing of each molecule, but was expected to be small relative to the "noise" created by events such as sample contamination or undesirable molecular recombination during PCR. A gene can be noisy if its amplification rate (average reads per molecular label) was similar to the amplification rate of errors which were derived from completely sequenced genes in the same library.

Specifically, suppose a completely sequenced gene $g_1$ consisted of $t_1$ true molecular labels and $e_1$ error molecular labels in total, such that $R_{g1,1}, R_{g1,2}, \ldots, R_{g1,t1}$ were sequencing reads mapped to the true molecular labels, and $R^*_{g1,1}, R^*_{g1,2}, \ldots, R^*_{g1,e1}$ were sequencing reads mapped to the error molecular labels. Then the amplification rate of error molecular labels (EAMP) for $g_1$ was $EAMP_{g1} = \Sigma_{i=1}^{e1} R^*_{g1,i}/e_1$. Similarly, EAMP can be calculated for $g_2, g_3, \ldots, g_x$ for all other completely sequenced genes. A cutoff can be applied for a potential noisy gene $g'_1$ which has less than 5 molecular labels observed in total and $R_{g'1,1}, R_{g'1,2}, \ldots, R_{g'1,k}$ sequencing reads mapped to each molecular label and determine its amplification rate as $amp_{g'1} = \Sigma_{i=1}^{k} R_{g'1,i}/k$. If $amp_{g'1} <$ median($amp_{g'1}, amp_{g'2}, \ldots, amp_{g'x}$), gene $g'_1$ was considered to be a noisy gene. Otherwise, it can be considered an incomplete gene. Other noisy genes can be tested and removed similarly. The reason for choosing 5 molecular labels as a cutoff was because it may be desirable to treat genes with lower amplification rates into two separate cases: artifacts (with molecular labels observed less than 5) and incomplete sequencing (with molecular labels observed ≥5 due to primer failure of low PCR/sequencing).

Estimations Using the Zero-Truncated Poisson Model

When sequencing was incomplete, errors may still be present in the data but may be difficult to identify due to insufficient sequencing reads overall. When sequencing was shallow and not all of the molecular labels present in the library have been observed, some assumptions may be necessary for meaningful analysis. It can be assumes that all observed molecular labels were true and that unobserved true molecular labels were being truncated at zero, i.e. truncated molecular labels observed zero times. Although not all of the stochastically barcoded transcripts for a given gene have been sampled in sequencing, the frequency of reads of the detected molecular labels can be used to estimate the total diversity of molecular labels present in the full library by applying a Zero-Truncated Poisson model.

Suppose that k distinctive molecular labels with reads $(R_1, R_2, \ldots, R_k)$ were observed and (S−k) molecular labels were unobserved with reads zero. One goal was to estimate S, the total number of molecular labels expected to be present in the library. Assuming frequencies of seeing sequencing read 1, 2, 3, or more as Poisson variates truncated at zero with Poisson mean μ, and sum of all sequencing reads was n, then the likelihood can be expressed as:

$$L(S,\mu) \propto S!/(S-k)! \mu^n \exp(-S\mu). \quad \text{Equation (3)}$$

Figure 21:
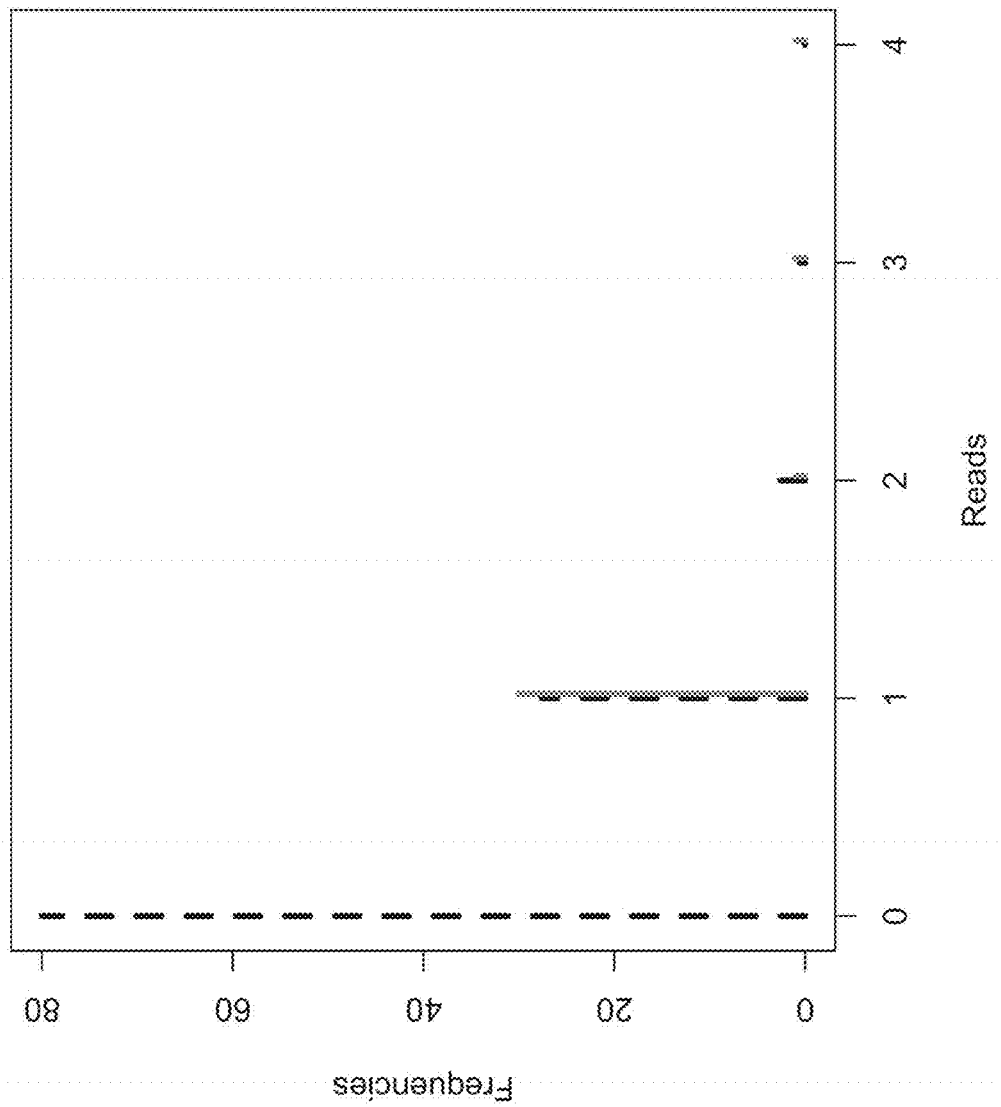
FIG. 21 is a non-limiting exemplary illustration of Zero Truncated Poisson model.

Traditional inference procedures can be applied for estimation of μ, S and their standard errors. Maximum likelihood (MLE) of μ was n/S, and approximations to the MLE of S can be $k/(1-e^{-n/S})$ or $k/(1-(1-1/S)^n)$. FIG. 21 shows the fitted zero truncated Poisson model based on the number of molecular labels and their corresponding sequencing reads. As shown in FIG. 21, 33 unique molecular labels were observed across a total of 39 reads in the partially sequenced library. Based on the frequencies of molecular labels with sequencing reads 1, 2, 3 and 4, a Poisson model was applied to estimate a total of 113 molecular labels in the full library had sequencing proceeded to completion. Inference procedures were applied for estimation of μ, S and their standard errors. MLE of μ can be n/S, and approximations to the MLE of S can be $k/(1-e^{-n/S})$ or $k/(1-(1-1/S)^n)$.

Altogether, these data demonstrate the sequencing reads of incompletely sequenced genes corrected by removing noisy genes and using a Zero-Truncated Poisson model for estimating the total number of molecular labels expected to be present in the library.

Example 5

Adjusting Completely Sequenced Genes and Incompletely Sequenced Genes

This example shows an example of output generated after adjusting the sequencing reads of completely sequenced genes and incompletely sequenced genes.

Table 7 provides an example of output generated after adjusting the sequencing reads of completely sequenced genes and incompletely sequenced genes. Descriptions of column headings were as the follows: "Gene ID" shows the name of gene detected. "Sequencing Status" shows three possible outcomes: complete, incomplete and saturated, which determines further methods for analysis. The classification depended on the dispersion index and the sequencing read mapped to the most abundant molecular label (ML). "Raw ML" shows the count of unique molecular labels observed for that gene ('0' for non-detected genes). "Raw Reads" shows the sum of sequencing reads mapped to Raw ML ('0' for non-detected genes). Corrected ML shows the count of unique molecular labels which were considered as true molecular labels after applying the algorithm (only for complete sequenced genes, 'NA' for incomplete gens, '0' for noisy and non-detected genes). "Corrected Reads" shows the sum of sequencing reads mapped to Corrected ML (only for complete sequenced genes, 'NA' for incomplete genes, '0' for noisy and non-detected genes). "Extrapolated ML" shows the estimated number of unique molecular labels through Zero Truncated Poisson model (only for incomplete sequenced data, 'NA' for complete data, '0' for noisy genes and non-detected genes). "Estimated Mol" shows the number of molecules estimated based on Corrected ML (for complete sequenced genes) or Extrapolated ML (for incomplete sequenced genes), '0' for noisy genes and non-detected genes. "Estimated Mol LB" shows the lower bound for estimated number of molecules. "Estimated Mol UB" shows the upper bound for estimated number of molecules.

In Table 7, Estimated Mol (n), estimated number of starting molecules, was calculated as follows:

$$n = -m \log(1 - k/m), \quad \text{Equation (4)}$$

where m was the total variety of the molecular labels ($3^8$) and k was total number of unique molecular labels observed. Variance of n, var(n), was derived using Taylor expansion: $var(n) = (m/(m-k))^2 var(k)$, where var(k) can be expressed as $m*(1-(1-1/m)^n)(1-1/m)^n + m(m-1)((1-2/m)^n - (1-1/m)^{2n})$. Lower and upper bounds of the estimated number of staring molecules (Estimated Mol LB & Estimated Mol UB) were calculated using $n \pm 2\sqrt{var(n)}$.

Altogether, these data demonstrate adjusting completely sequenced genes and incompletely sequenced genes.

Example 6

Performance of Correcting Completely Sequenced Genes and Incompletely Sequenced Genes This example shows performance of correcting the sequencing reads of completely sequenced genes. The performance was based on the errors and noise in the raw molecular label counting data removed and the sequencing reads that remained.

Several complete sequenced genes were selected to test the performance of the correcting the sequencing reads of completely sequenced genes. Table 8 compares some measures for those genes before and after correcting or adjusting the sequencing reads. Raw ML, Raw reads, Corrected ML, Corrected Reads were imported directly from the output table. Raw-amp (amplification rate using raw data) and Filtered-amp (amplification rate using true molecular label data after corrections) were calculated using (Raw reads/Raw ML) and (Corrected Reads/Corrected ML). The percentage of ML retained compared to the number of true molecular labels after corrections of the observed total number of molecular labels was 100*Corrected ML/Raw ML and % Reads retained was defined similarly as 100*Corrected Reads/Raw Reads. Table 8 shows example genes of different abundance levels with GAPDH and ACTB showing higher molecular label counts and total reads. The number of true molecular labels after applying the corrections accounted for less than 7% of the total molecular labels observed in the raw data, which implies that more than 93% of the molecular label were considered to be error molecular labels and were discarded. Although 93% of the raw molecular labels were eliminated as noise, true molecular labels contribute to at least 72% of the reads, implying that those discarded error molecular label were of much lower reads. Also, amplification rates after applying the algorithm ranged from 137 to 413 which were much higher than those obtained using raw data (6.1 to 29.4). The corrected amplification rates were much more realistic measurements correlating with a PCR efficiency of at least 75%.

TABLE 7

Example of output from 10pg input RNA well A06

| Gene ID | Sequencing Status | Raw Reads | Raw ML | Corrected Reads | Corrected ML | Extrapolated ML | Estimated Mol | Estimated Mol LB | Estimated Mol UB |
|---|---|---|---|---|---|---|---|---|---|
| DAP_PRE LABELED | Incomplete | 1 | 1 | NA | NA | NA | NA | NA | NA |
| PHE_PRE LABELED | Complete | 3129 | 59 | 3059 | 11 | NA | 11.01 | 10.83 | 11.19 |
| KAN_PRE LABELED | Complete | 1418 | 71 | 1259 | 8 | NA | 8 | 7.87 | 8.14 |
| CD4 | Incomplete | 2 | 2 | 0 | 0 | 0 | 0 | 0 | 0 |
| FOXP3 | Incomplete | 0 | 0 | 0 | 0 | 0 | 0 | 0 | 0 |
| STAT5A | Complete | 96 | 4 | 94 | 1 | NA | 1 | 1 | 1 |
| FOXO1 | Incomplete | 1 | 1 | 0 | 0 | 0 | 0 | 0 | 0 |
| FOXO3 | Incomplete | 3 | 3 | 0 | 0 | 0 | 0 | 0 | 0 |
| CD45RA | Incomplete | 0 | 0 | 0 | 0 | 0 | 0 | 0 | 0 |
| CD45RO | Incomplete | 0 | 0 | 0 | 0 | 0 | 0 | 0 | 0 |
| MKI67 | Incomplete | 1 | 1 | 0 | 0 | 0 | 0 | 0 | 0 |
| GAPDH | Complete | 12059 | 709 | 10984 | 38 | NA | 38.11 | 37.45 | 38.77 |
| MYC | Complete | 2842 | 63 | 2765 | 7 | NA | 7 | 6.89 | 7.12 |
| LRRC32 | Incomplete | 0 | 0 | 0 | 0 | 0 | 0 | 0 | 0 |
| IL1R1 | Complete | 177 | 1 | 177 | 1 | NA | 1 | 1 | 1 |
| CCR8 | Incomplete | 10 | 1 | NA | NA | 1 | 1 | 1 | 1 |
| IL-26 | Incomplete | 0 | 0 | 0 | 0 | 0 | 0 | 0 | 0 |

TABLE 8

Comparisons of selected genes from dataset D704 (10pg RNA input) and Customer 1 (single cell, unknown RNA input) before and after using the algorithm

|  |  | Dataset | | | | | |
|---|---|---|---|---|---|---|---|
|  |  | D704 | | | | Customer1 | |
|  |  | Well | | | | | |
|  |  | H01 | H01 | H01 | D01 | H01 | H12 |
|  |  | GeneID | | | | | |
|  |  | GAPDH | MYC | TFRC | LEFTY1 | SOX17 | ACTB |
| Before | Raw ML | 760 | 76 | 45 | 50 | 28 | 2070 |
|  | Raw reads | 11107 | 1710 | 1324 | 434 | 297 | 12625 |
|  | Raw-amp | 14.61 | 22.5 | 29.4 | 8.68 | 10.61 | 6.1 |
| After | Corrected ML | 37 | 4 | 3 | 1 | 1 | 66 |
|  | Corrected Reads | 9351 | 1589 | 1239 | 387 | 226 | 9039 |
|  | % ML retained | 5% | 5% | 7% | 2% | 4% | 3% |
|  | % Reads retained | 84% | 93% | 94% | 89% | 76% | 72% |
|  | Filtered-amp | 252.73 | 397.25 | 413 | 387 | 226 | 137 |

Altogether, these data indicate that correcting sequencing reads of completely sequenced genes significantly reduced the errors and noise in the raw molecular label counting data, while still maintaining the ability to utilize most of the sequencing reads.

Example 7

Tools for Summarizing and Visualizing Counting Data of Stochastically Barcoded Targets This example shows tools for summarizing and visualizing counting data of stochastically barcoded targets illustrated in the previous Examples.

For test data, two plates of single cells were generated for processing through the Precise™ assay (Cellular Research, Inc. (Palo Alto, Calif.)). The experiment used two different cell types at a 4:1 ratio and the identity of the cells deposited into each well was blinded from the researcher performing the experiment. The goal of this study was to identify cell types for each well using gene expression profiles from stochastic barcode counts.

To assess the overall sequencing data quality across wells, the sum of sequencing reads per well were summed. And to assess the performance of the correction method, some statistics measures were before applying and after the correction method were tabulated and compared. Additionally, graphical plots can provide visual displays of the data and detect abnormalities or patterns easily.

Tables 9 and 10 show sum of the sequencing reads per well for Plate 1 with sequencing reads <5000 italicized. For those wells with much lower reads such as reads <5000 might indicate that no single cell was allocated to that well, and further analysis should exclude those wells.

TABLE 9

Sum of sequencing reads per well for plate 1

|  | 1 | 2 | 3 | 4 | 5 | 6 | 7 | 8 | 9 | 10 | 11 | 12 |
|---|---|---|---|---|---|---|---|---|---|---|---|---|
| A | 58346 | 59687 | 141814 | 57269 | 106511 | 26894 | 5908 | 40547 | 16783 | 19896 | 8993 | *3885* |
| B | *3894* | 24164 | 52131 | 40458 | 61725 | 55568 | *3701* | 5189 | *3353* | *2690* | *3799* | *3848* |
| C | 98195 | 175593 | *3627* | *4508* | 22856 | 17253 | *3435* | 49083 | 29189 | 28969 | *4570* | 25593 |
| D | 59960 | 29342 | 27304 | 22649 | 29341 | 55575 | *2861* | *2298* | 78385 | 56112 | *3357* | 15843 |
| E | 18148 | 49333 | 25546 | 40571 | *4190* | 31746 | 111060 | *3956* | 57039 | 12688 | 13917 | 31934 |
| F | 37105 | 34979 | 88619 | 5457 | *3552* | 6499 | *2951* | *2874* | *3127* | *3118* | 166177 | *2848* |
| G | 11930 | 119412 | *2179* | 30913 | 29445 | 6002 | *4260* | 41497 | 16535 | 48453 | 15058 | 17844 |
| H | 29988 | 28987 | *3414* | *2548* | 74279 | *4609* | *4164* | *4043* | 35764 | *2911* | *3276* | 38723 |

TABLE 10

Sum of sequencing reads per well for plate 2

|  | 1 | 2 | 3 | 4 | 5 | 6 | 7 | 8 | 9 | 10 | 11 | 12 |
|---|---|---|---|---|---|---|---|---|---|---|---|---|
| A | *2291* | 45737 | 124283 | 95919 | 50637 | *3822* | *2770* | *4147* | 20528 | 93362 | 24443 | 29416 |
| B | 26870 | 26126 | *3350* | 42649 | 63897 | *2960* | 71319 | 13673 | 40682 | 28120 | *2439* | *3387* |
| C | 52029 | 51582 | *232* | 20538 | 28556 | 18871 | 49769 | 24187 | 43879 | 17136 | 106123 | 17861 |
| D | 41845 | 124785 | 26143 | *4836* | *2740* | 18416 | 37201 | 90892 | 87375 | 21552 | 29307 | 31768 |
| E | 22866 | 29578 | 8506 | 76852 | 15211 | 18138 | 4087 | 19625 | 17151 | 22380 | 15928 | *2242* |
| F | 16868 | 46605 | 21848 | 53195 | *3391* | 94041 | 29196 | 19468 | 38771 | *2801* | 5703 | *2735* |
| G | 22187 | 30552 | 20213 | *3010* | *3143* | *4578* | *1901* | *2873* | 163669 | 34898 | 60463 | 19940 |
| H | 30216 | 25110 | 112489 | 34535 | *3976* | 32726 | 17868 | 9807 | 58375 | 22972 | 38446 | 18290 |

Tables 10 and 11 compare several measures before and after using the correction method. From these tables, the huge variations in 'Raw Reads' (sum of sequencing reads per well) and 'Raw ML' (total number of molecular label counts per well) was notice. The huge variations may be because their standard deviations (SD) were bigger than the mean, which again flagging the presence of low reads wells. After using the method, about 47% of genes per well were classified as complete sequenced genes amongst all the genes present. If most of the genes were classified as incomplete genes (such as 0%), then the current method may not remove the noise in the data. For each well, only 15% of molecular labels were retained after correction for complete genes, but those molecular labels mapped to 95% of sequencing reads on average. A higher value of % Reads retained indicates the correction method can effectively capture signals (reads which were contributed from true molecular labels) while removing noise. Also, amplification rate for each molecular label retained as true molecular label was 163.32, much higher than 22.76 before applying the correction method.

labels (the percentage of molecular labels were regarded as true molecular labels after applying the correction method relative to observed molecular labels before the applying the correction method, the top row for each well); and the level of noise per well using sequencing reads (percentage of reads mapped to true molecular labels relative to total raw reads, the middle row for each well). As shown, the % of completely sequenced genes varied with wells, but much lower at wells A12, B01, V07-B12, C03, C04, C07, D07, D08, D11, E05, E08, F04, F07-F10, F12, G03, G07, H03, H06, H07, H10-H11, which corresponded to those wells with much lower reads. The % ML retained denoted by the top row was generally under 20% for all wells, whilst % Reads retained denoted by the middle row exceeded 90% overall for all wells. This type of plot can provide a general idea about how effective the correction method was in removing noise but meanwhile maximizing its signal for each well.

Figure 24:
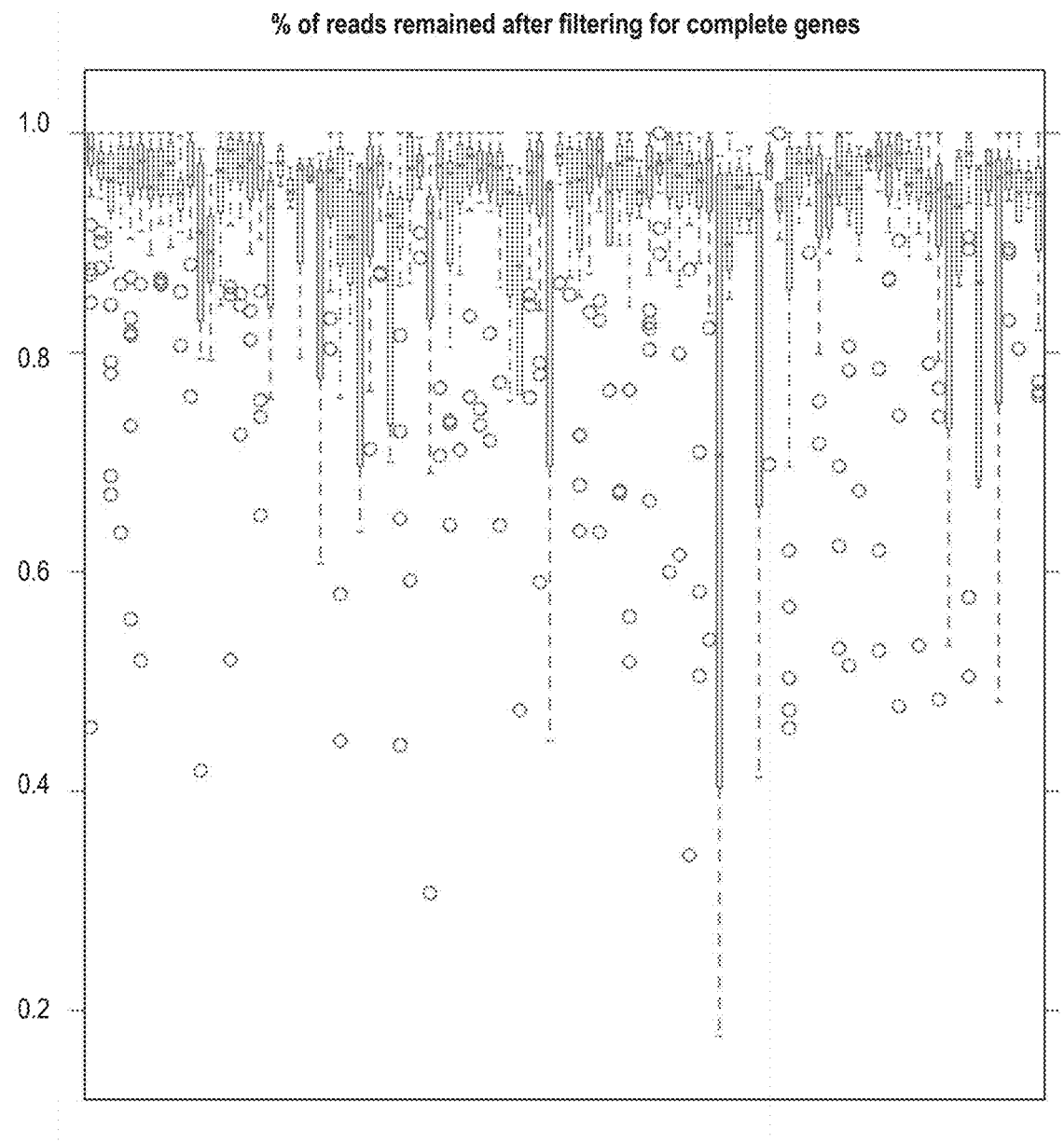
FIG. 24 shows boxplots of % Reads retained varied by genes for each well.

FIG. 24 show boxplots of % Reads retained varied by genes for each well. The box plots at gene level revealed detailed information such as how well the correction method

TABLE 11

Summary statistics using different measures before and after applying algorithm using data from plate 1

| | Measure/Statistics | Mean | SD | Median | Min | Max |
|---|---|---|---|---|---|---|
| Before | Genes | 35.31 | 11.41 | 35.5 | 16 | 60 |
| | Raw ML | 1184.54 | 1202.71 | 837 | 137 | 5617 |
| | Reads Raw | 31110.6 | 35808.4 | 21272.5 | 2179 | 175593 |
| | Amp | 22.76 | 7.42 | 24.08 | 4.45 | 35.53 |
| After | % Complete genes | 0.47 | 0.2 | 0.54 | 0.1 | 0.79 |
| | % MI retained | 0.15 | 0.03 | 0.16 | 0.07 | 0.22 |
| | % Reads retained | 0.95 | 0.02 | 0.96 | 0.86 | 0.98 |
| | Corrected Amp | 163.32 | 19.36 | 165.47 | 116.96 | 194.86 |

TABLE 12

Summary statistics using different measures before and after applying algorithm using data from plate 2

| | Measure/Statistics | Mean | SD | Median | Min | Max |
|---|---|---|---|---|---|---|
| Before | Genes | 36.52 | 9.92 | 37.5 | 16 | 57 |
| | Raw ML | 1159.13 | 1050.72 | 851.5 | 79 | 5303 |
| | Reads Raw | 32602.8 | 32144.1 | 22919 | 232 | 163669 |
| | Amp | 25.25 | 6.44 | 27.72 | 2.94 | 34.09 |
| After | % Complete genes | 0.53 | 0.2 | 0.6 | 0.05 | 0.78 |
| | % MI retained | 0.17 | 0.04 | 0.17 | 0.11 | 0.5 |
| | % Reads retained | 0.95 | 0.01 | 0.95 | 0.89 | 0.98 |
| | Corrected Amp | 161.63 | 24.06 | 163.88 | 27 | 195.74 |

Figure 22:
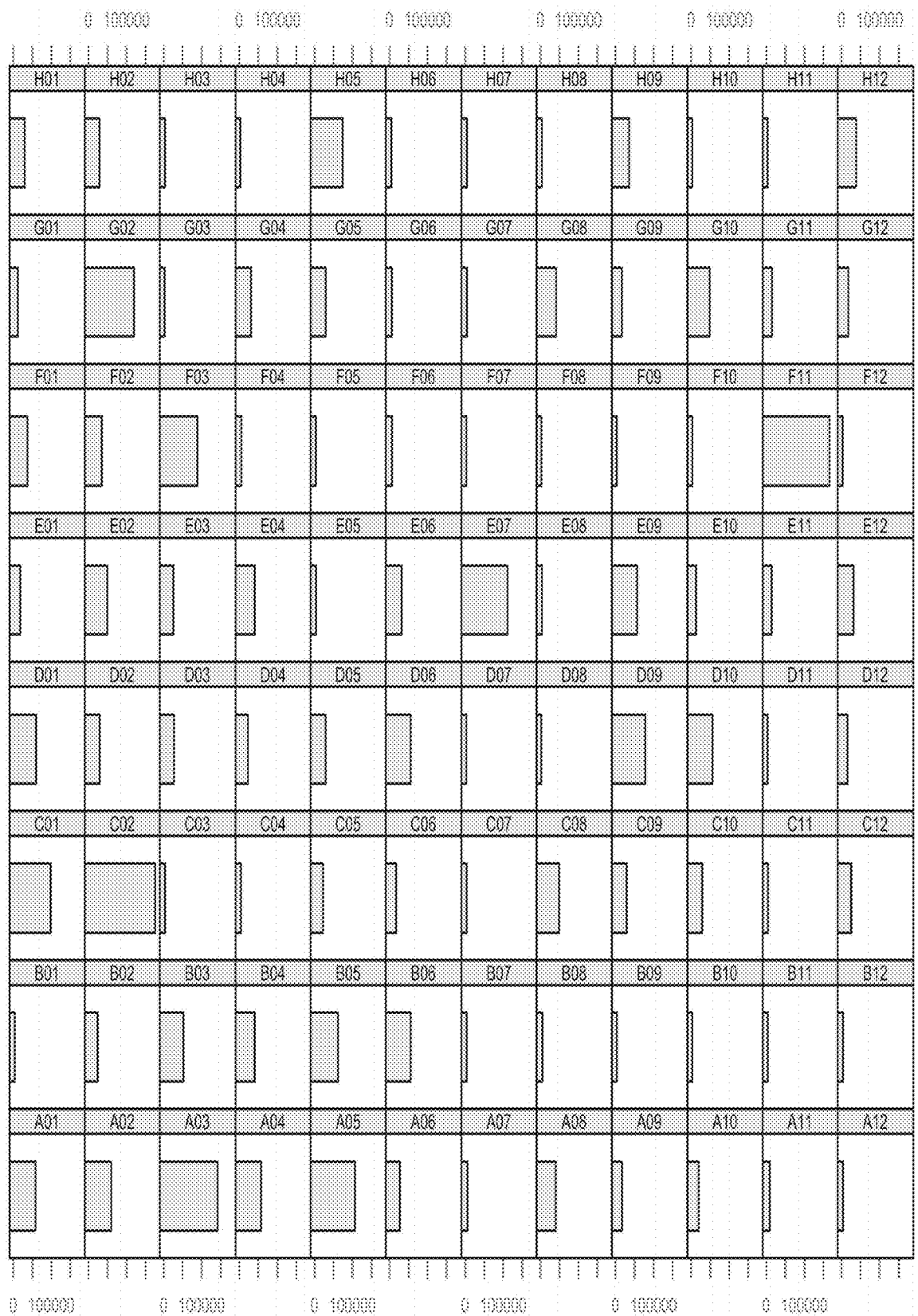
FIG. 22 shows bar charts of total sequencing reads per well.

FIG. 22 show bar charts of total sequencing reads per well. FIG. 22 provides a direct visualization of relative input across 96 wells. This Figure shows wells C02 and F11 had higher reads compared to others, which might indicate multiple cells for those wells. Wells A12, B01, B07-B12, C03, C04, C07, C11, D07, D08, D11, E05, E08, F04-F10, F12, G03, G07, H03, H04, H07-H09, H10-H11 had much lower reads relative to other wells, which might indicate cells were not placed in those wells.

Figure 23:
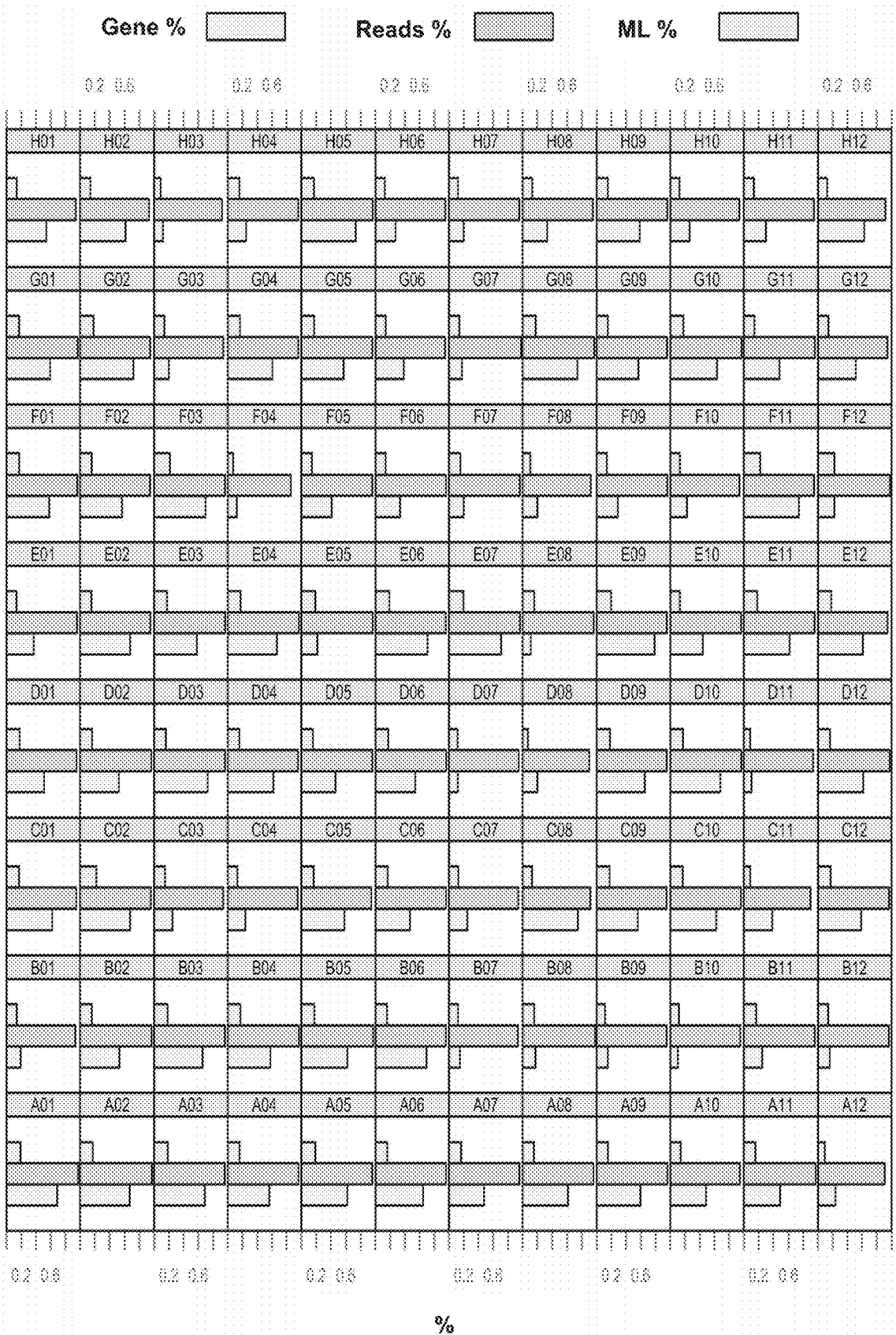
FIG. 23 shows bar charts of % Completely Sequenced genes, % molecular label (ML) retained as true barcodes and % Reads Retained mapped to those ML retained for each well.

FIG. 23 show bar charts of % Completely Sequenced genes, % molecular label (ML) retained as true molecular labels and % Reads Retained mapped to those ML retained for each well. FIG. 23 illustrates the percentage of genes per well which were classified as complete and the correction method can be applied to remove the noise (the lower row for each well); the level of noise per well using molecular worked for each gene in a well, which may not be reflected through bar chart at well level. Boxplot of % reads retained for all the completely sequenced genes per well in FIG. 24 revealed that variations amongst genes can be substantial, such as for well D11, F4, F8, H3 and H8 which had whiskers extended beyond 0.6. But those five wells corresponded to much lower total sequencing reads, 3357, 5457, 2874, 3414 and 4043.

Clustering can be used in the analysis of gene expression data. Principal component analysis (PCA) can be used for dimension reduction by reducing multi-dimensionality and possibly correlated variables into few linearly uncorrelated variables through orthogonal transformation. The leading principal components from PCA can be used in searching clusters in the data.

Figures 25A, 25B:
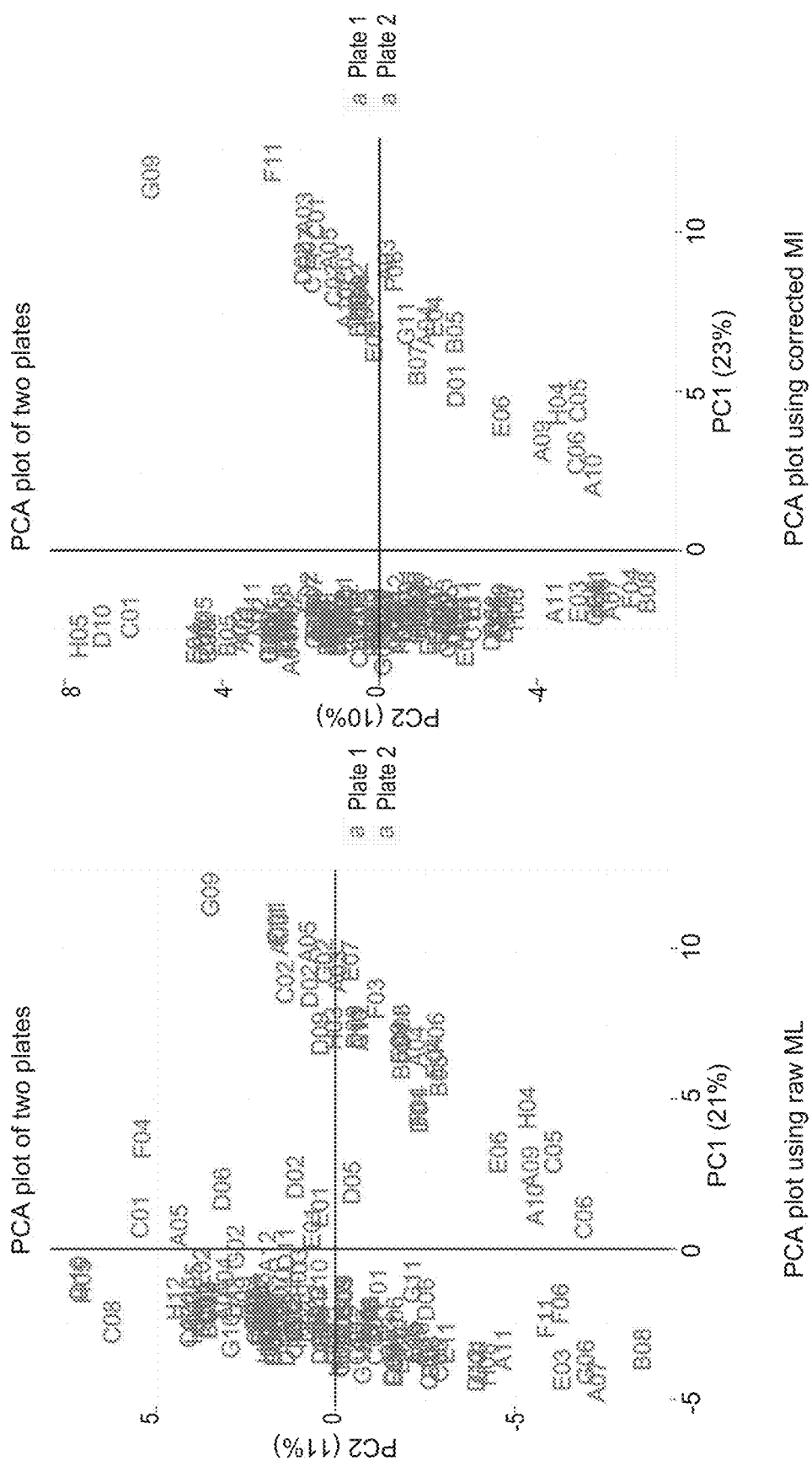
FIGS. 25A-25B show principal component analysis (PCA) plots of using raw ML vs. corrected MI after applying algorithm from two plates.

FIGS. 25A-25B show PCA plots of using raw ML vs. corrected MI after applying algorithm from two plates. FIG.

25A shows PCA plot of using raw ML per gene per well for wells with total sequencing reads >5000. This PCA plot was generated by first removing wells having total sequencing reads <5000 (resulting in 139 wells, and 107 genes excluding 3 controlled genes); second, removing genes with zero raw ML across 139 wells (85 genes remained); third, taking of logarithm of raw ML plus one to incorporate zeros in the dataset, then applying PCA on the log data after centering and scaling. The PCA plot shows apparent two clusters, but for wells such as D02, D05, and F06, roughly equal distance from both clusters, the cell types were difficult to determine. The results of clustering may be corrupted because of the addition of noise, even a few noise variables can corrupt a clear cluster structure. Thus clustering can benefit from a preprocessing step of feature/variable selection or from a filtering or de-noising step. By applying the correction method on the complete sequenced data, a clear cluster structure resulted as shown in FIG. 25B. The PCA plot in FIG. 25B was generated similarly as the previous PCA plot in FIG. 25A except using corrected ML (counts of true molecular labels for complete sequenced genes after applying the correction method) rather than raw ML (counts of molecular labels for all detected genes before applying the algorithm), which used 75 genes across 139 wells in total. Two distinctive clusters were observed, which were well separated by y-axis (PC2). Compared to FIG. 25A, clusters in FIG. 25B were more compacted in size, and cells in each well were assigned to a cluster clearly. In addition, the smaller cluster on the right hand of y-axis of FIG. 25B consist of 31 wells, about 22% of the total wells and quite close to 20% expected.

Altogether, these data demonstrate several tools useful for summarizing and visualizing of counting data of stochastically barcoded targets.

Example 8

ML Coverage of Each ML Across a Plate for a High Expressor Gene-ACTB

This example demonstrates distinct distributions of ML errors derived during sequencing or PCR generally have distinct distributions from true MLs.

Figure 27:
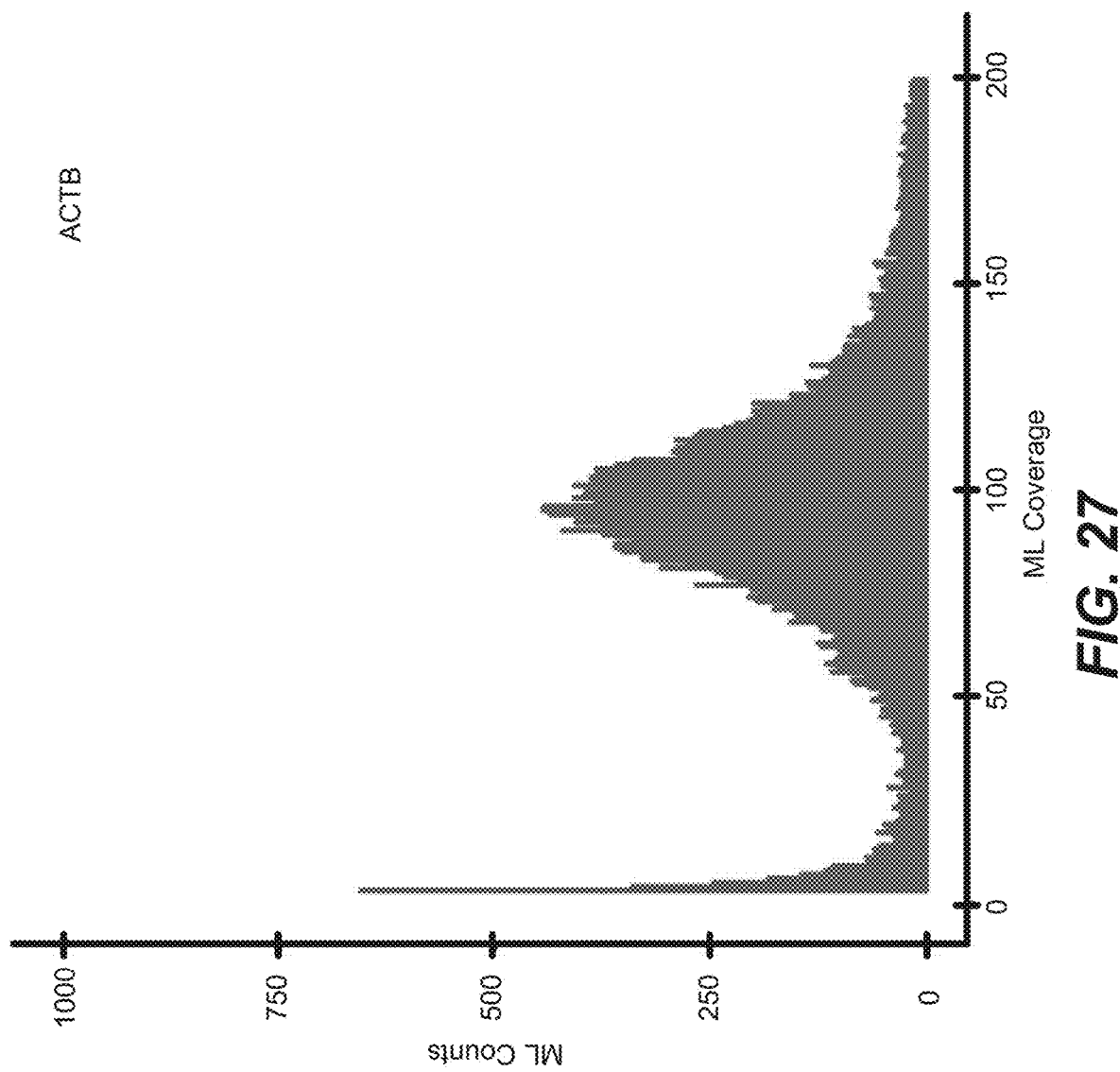
FIG. 27 is an exemplary plot showing molecular label coverage of each molecular label across a microwell plate for a high expressor gene-ATCB, where distinct distributions were observed between error molecular labels and real molecular labels.
Figure 28:
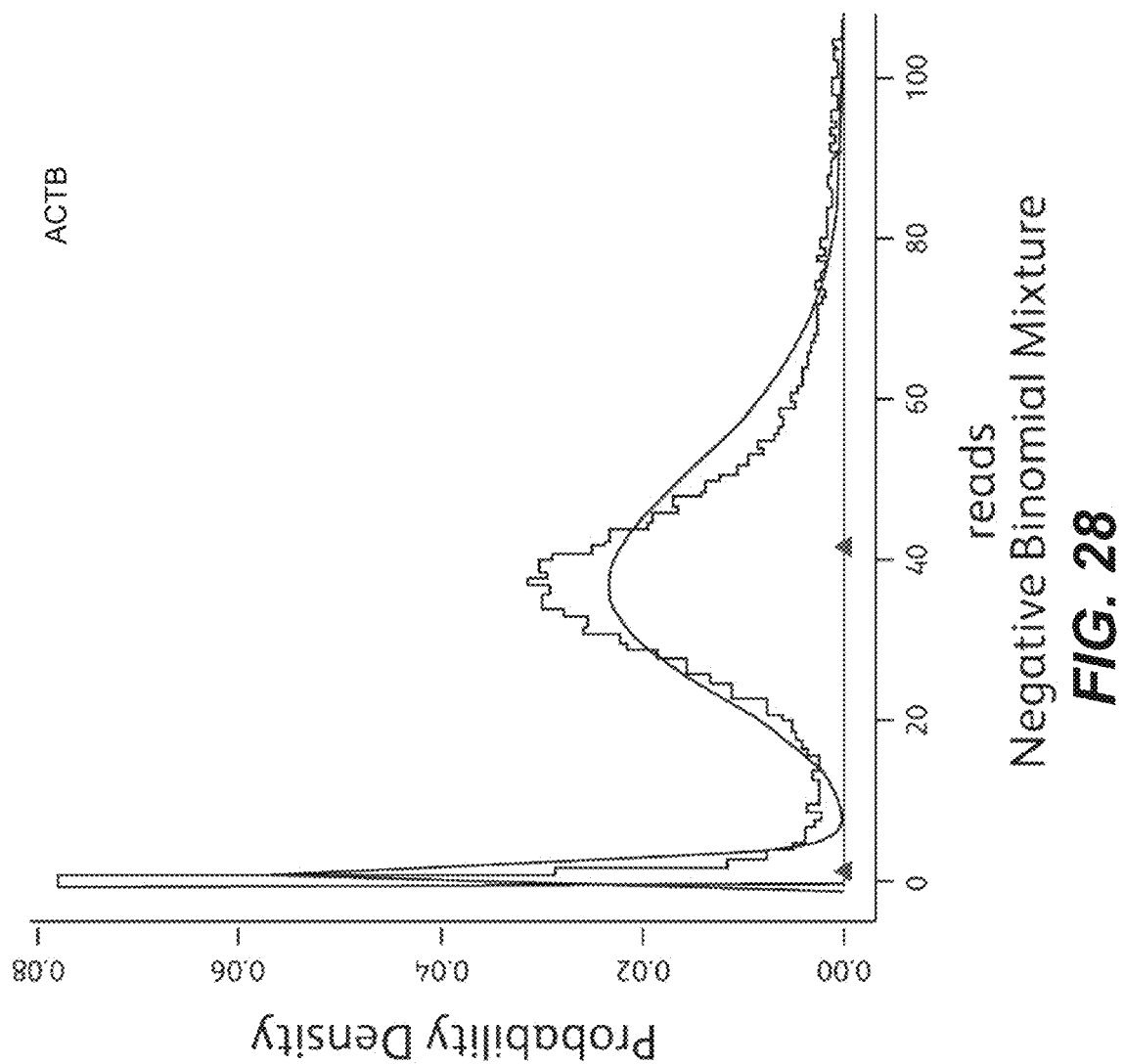
FIG. 28 is an exemplary plot showing fitting two negative binomial distributions to molecular label coverage of each molecular label across a microwell plate for a high expressor gene-ATCB. The fitting of two negative binomial distributions demonstrates that molecular label errors with lower molecular label depth and true molecular label with higher molecular label depth can be statistically distinguished. The x axis is the molecular depth.

In addition to absolute gene expression counting and PCR bias correction, MLs can provide a better understanding of the statistical quality of the library preparation procedure and sequencing data. When looking at the number of reads presenting the same gene ML—referred to as ML coverage—it is possible to detect for sequencing erroneous base calls or PCR errors generated during library preparation. For example, a gene ML from a given SL that is represented by multiple reads is likely an accurate measurement compared to a gene ML from a given SL that is represented by only a single read. Low ML coverage barcodes in the presence of high ML coverage barcodes in the same library are often artifacts or errors generated during the sequencing run or PCR steps during library preparation. The ML errors derived during sequencing or PCR generally have distinct distributions from the true MLs. FIG. 27 is an exemplary plot showing molecular label coverage of each molecular label across a microwell plate for a high expressor gene-ATCB, where distinct distributions were observed between error molecular labels and real molecular labels. FIG. 28 is an exemplary plot showing fitting two negative binomial distributions to molecular label coverage of each molecular label across a microwell plate for a high expressor gene-ATCB. The fitting of two negative binomial distributions demonstrates that molecular label errors with lower molecular label depth and true molecular label with higher molecular label depth can be statistically distinguished. The x axis is the molecular depth.

Altogether, these data demonstrate the ML errors derived during sequencing or PCR generally have distinct distributions from the true MLs.

Example 9

Correcting Molecular Labels Due to PCR or Sequencing Substitution Errors

This example demonstrates a method for correcting molecular labels due to PCR and sequencing substitution errors that can be applied to whole transcriptome assays without the assumption of uniform coverage and without requiring high sequencing coverage for the complete sequencing status.

Deduplication was performed on the first mapping coordinate and unique molecular labels (UMI) of each read, and reads were assumed to be identical given the same start coordinate, UML, and strand. After deduplication, UMLs with the highest counts per cluster were retained (Table 13).

Figure 29:
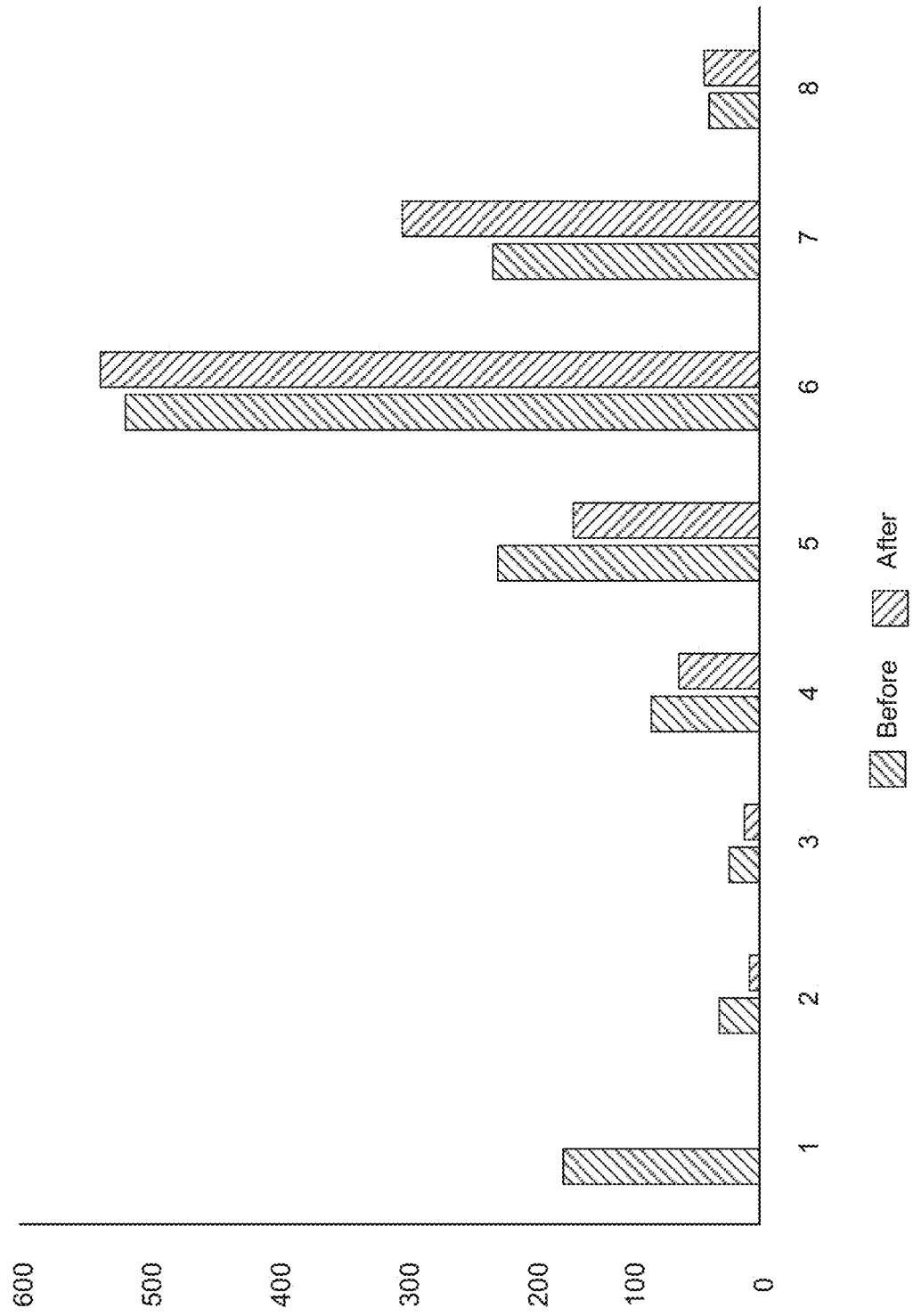
FIG. 29 shows molecular label correction, where pairwise Hamming distance of 1 was overrepresented. After molecular label correction, molecular labels with Hamming distance of one apart were clustered and collapsed to the same parent molecular label.
Figure 30:
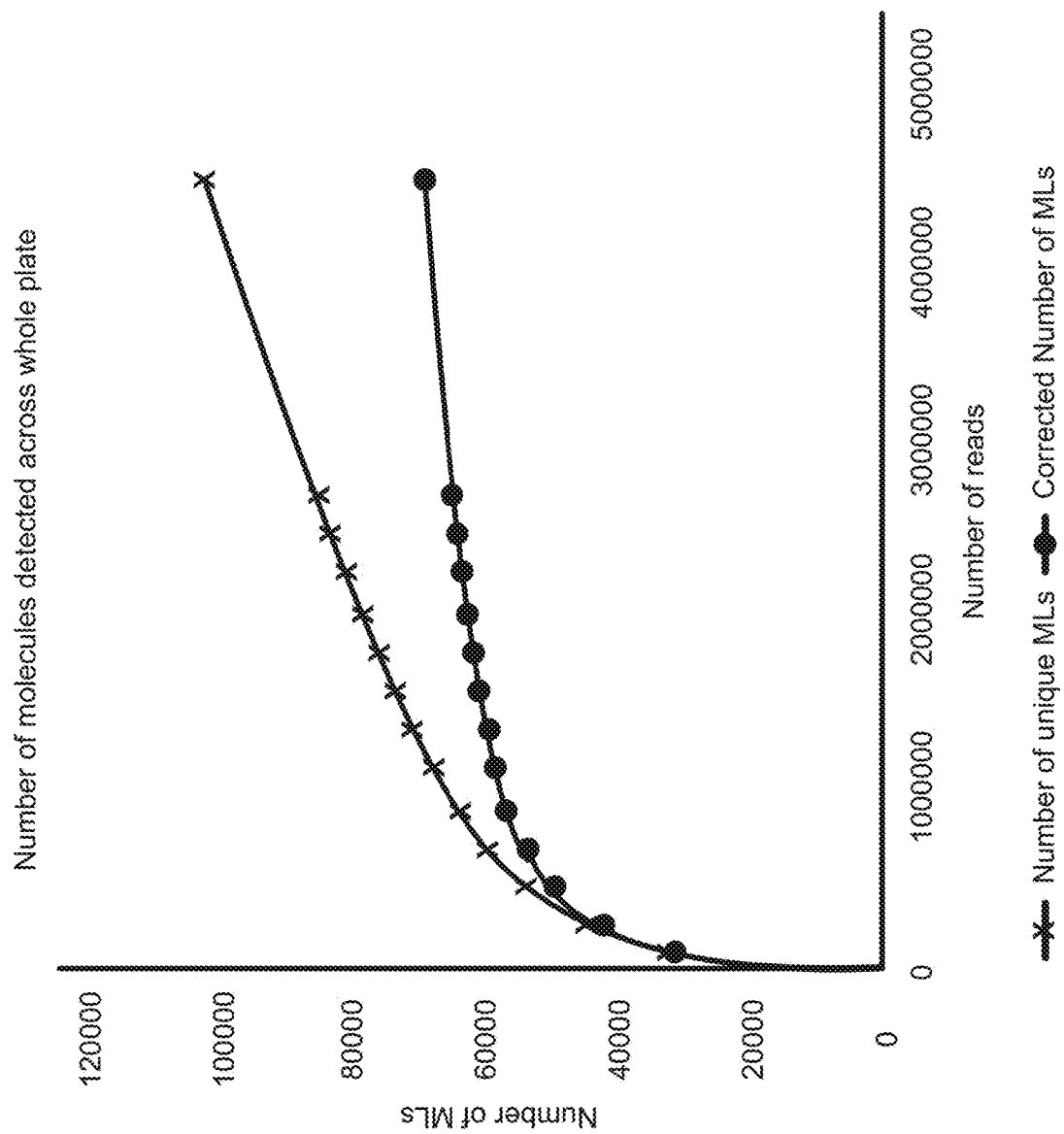
FIG. 30 shows the curve of corrected number of molecular labels vs. corrected number of reads coverages.

Molecular labels (MLs) were corrected on a per gene basis. For each gene, clusters of MLs were identified with directional adjacency. The directional adjacency method clustered MLs if the MLs were within a Hamming distance of 1 and a parent ML count ≥2*(child MI count)−1. All MLs within the same cluster were considered to originate from the same parent ML, and children ML counts were collapsed to the parent ML. FIG. 29 shows molecular label correction, where pairwise Hamming distance of 1 was overrepresented. After molecular label correction, molecular labels with Hamming distance of one apart were clustered and collapsed to the same parent molecular label. FIG. 30 shows that the curve of the corrected number of MLs vs. the number of reads converge. Because all the reads were retained, this method can also be used to remove one-base PCR or sequencing errors.

TABLE 13

After deduplicating molecular labels, only an insufficient number, given a whole transcriptome assay, of unique molecular labels were considered as errors

| | | Raw Counts | | Deduplicate UMLs | |
|---|---|---|---|---|---|
| Sample | Well | Number of Reads | Number of Unique MI | Number of Reads | Number of Unique MI |
| Plate 2 | A02 | 234646 | 3079 | 28925 | 2335 |
| Plate 3 | A02 | 773050 | 14126 | 95023 | 11410 |

Altogether, these data demonstrate a correction method which can be applied to correct or adjust data of whole transcriptome assays because all the reads were retrained.

Example 10

Molecular Label Counting for High Input Samples

This example describes unique molecular labels used as input molecules increase.

Figure 26:
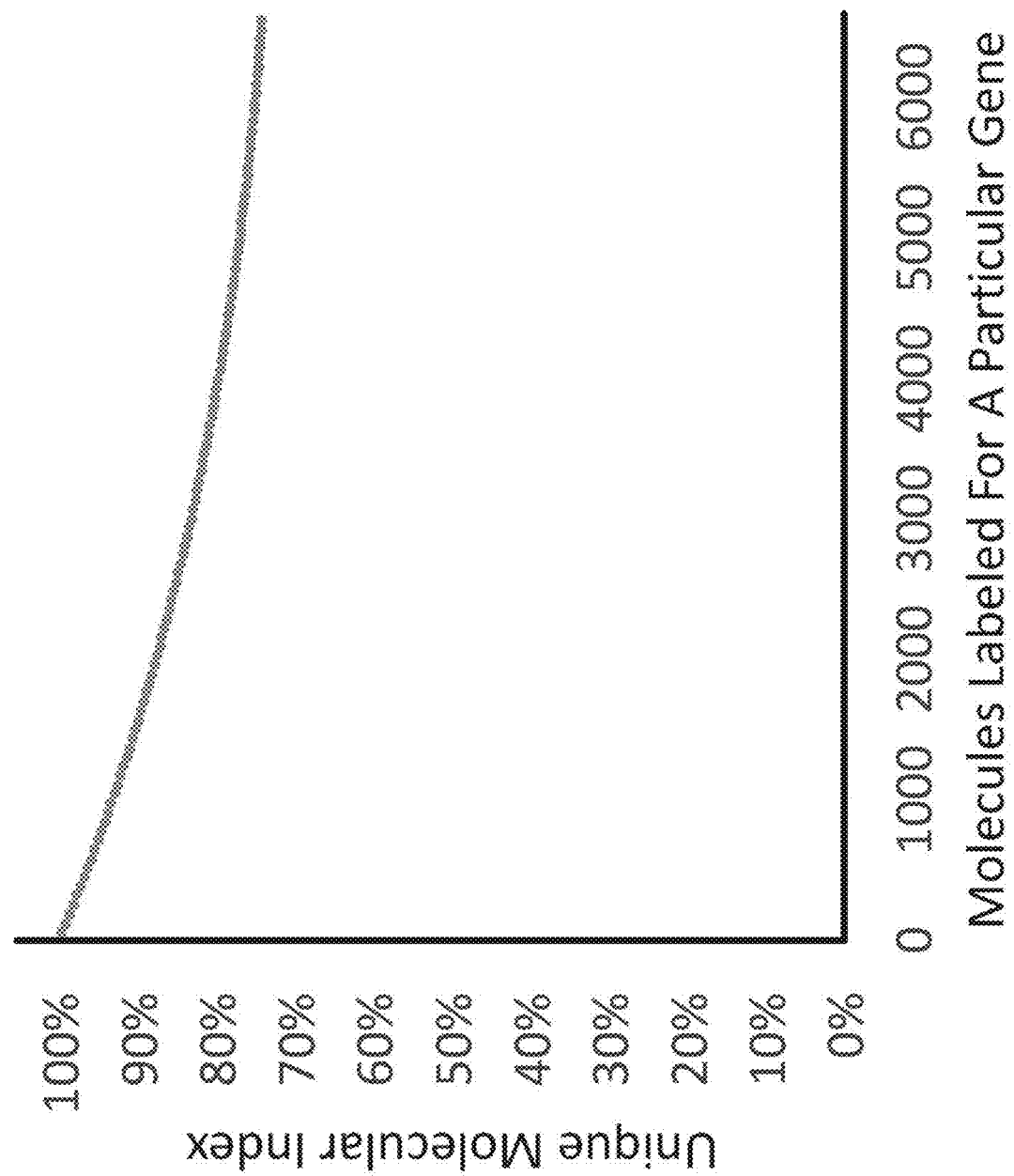
FIG. 26 is an exemplary plot of theoretical calculation of unique molecular labels used as input molecules increases.

The BD Precise™ Targeted Assay may be the most suitable when used in small sample input—such as in single cells—to allow for stochastic and unique labeling of mRNAs. As the number of transcripts increases relative to the barcode pool in high RNA/cell input experiments, the percentage of MLs being recycled to label the same gene increases and was theoretically calculated using a Poisson distribution (FIG. 26). In these situations, without statistical correction, quantifying gene expression using MLs would underestimate the number of molecules that are initially present without any Poisson corrections or corrections based on two negative binomial distributions.

At extremely high input samples where the number of mRNAs per gene is beyond the entire collection of 6561 barcodes, a Poisson correction or a correction based on two negative binomial distributions is no longer possible. For example, regardless of 65000 or 100000 input molecules, a maximum of 6561 saturated barcodes is expected in either case. Hence, genes and samples that appear to have high sample input can be altered, whereby ML counts would likely be underestimated.

Altogether, these data demonstrate the need to adjust raw data when quantifying gene expression using MLs.

Example 11

Recursive Substitution Error Correction (RSEC)

This example demonstrates recursive substitution error correction.

Two collaborative methods can be employed in the BD Precise™ Targeted Assay analysis pipeline to remove ML errors. In brief, ML errors that are derived from sequencing base calls substitution errors are identified and adjusted to the true ML barcode using Recursive Substitution Error Correction (RSEC). Subsequently, ML errors that are derived from library preparation steps or sequencing base deletion errors are adjusted using Distribution-Based Error Correction (DBEC).

The RSEC algorithm can adjust ML errors that are derived from PCR or sequencing substitution. These rare erroneous events have been observed when examining the ML coverage. For example, the ML coverage for error MLs can be significantly lower than true MLs in adequately sequenced samples (FIG. 27); in cases where two very similar MLs are used during the initial Molecular Indexing (reverse transcription) steps, they would generally have similar ML coverage and do not need to be eliminated. As sequencing depth increases, more ML errors appear, hence RSEC can be crucial for adjusting the ML count for highly sequenced barcoded libraries.

In brief, RSEC considers two factors in error correction: 1) Similarity in ML sequence; and 2) and their ML coverage. For each target gene, MLs are connected when both of their ML sequence is within 1 base (Hamming distance=1) with each other. For each connection between ML x and y, if:

$$\text{Coverage}(y) > 2*\text{Coverage}(x) + 1, \quad \text{Equation (5)}$$

where y denotes "Parent ML," and x denotes "Child ML."

Based on this assignment, child MLs can be collapsed to their parent ML. This process is recursive until there are no more identifiable parent/child MLs for the gene.

Figure 31:
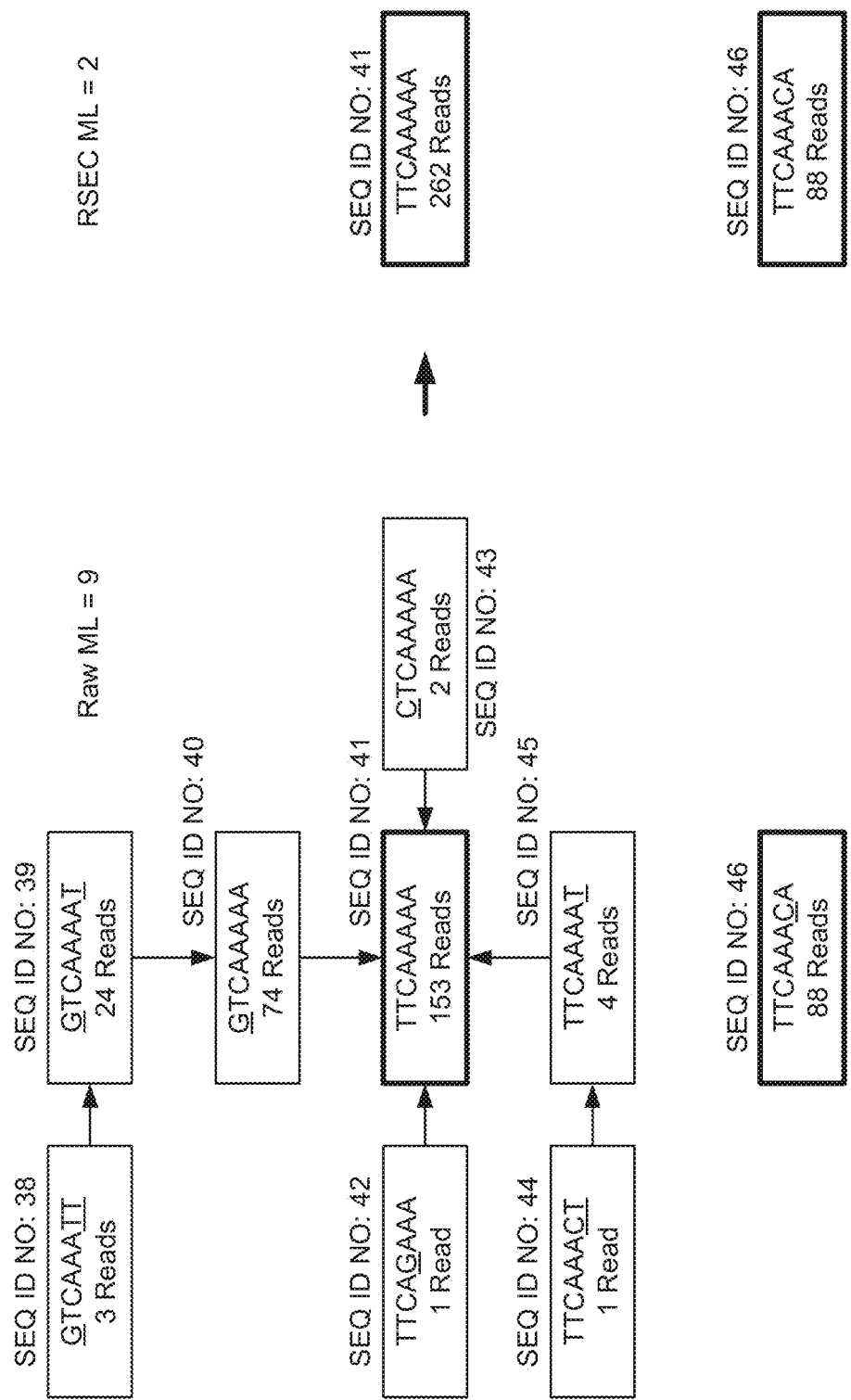
FIG. 31 shows a schematic illustration of an example of recursive substitution error correction.

FIG. 31 shows a schematic illustration of an example of recursive substitution error correction outline above. The MLs in the raw data prior to the RSEC correction includes nine unique MLs: GTCAAATT, GTCAAAAT, GTCAAAAA, TTCAAAAA, TTCAGAAA, CTCAAAAA, TTCAAACT, TTCAAAAT, and TTCAAACA (SEQ ID NO: 38-46). By applying RSEC, GTCAAA<u>TT</u> (SEQ ID NO: 38) can be collapsed into GTCAAA<u>A</u>T (SEQ ID NO: 39) because the two MLs differ by one nucleotide (underlined) and the ML GTCAAATT (SEQ ID NO: 38) has a lower ML count than that of GTCAAAAT (SEQ ID NO: 39). In turn, the ML GTCAAAA<u>T</u> (SEQ ID NO: 39) can be collapsed into the ML GTCAAAA<u>A</u> (SEQ ID NO: 40) (the difference in ML sequences is underlined), which has a higher ML count than that of GTCAAAAT (SEQ ID NO: 39). Similarly, the MLs TTCAGAAA (SEQ ID NO: 42) and CTCAAAAA (SEQ ID NO: 43) can be collapsed into the ML TTCAAAAA (SEQ ID NO: 41). The ML TTCAAACT (SEQ ID NO: 44) can be collapsed into the ML TTCAAAAT (SEQ ID NO: 45), which can be in turn collapsed into ML TTCAAAAA (SEQ ID NO: 41). The ML TTCAAACA (SEQ ID NO: 46) differs from all other MLs by more than one nucleotide, and thus is not collapsed into any of the other eight MLs. Before RSEC correction, the raw ML count number was nine. After RSEC correction, the ML count number was two: MLs TTCAAAAA (SEQ ID NO: 41) and TTCAAACA (SEQ ID NO: 46).

Altogether, these data demonstrate using RSEC to correct raw ML counts.

Example 12

ML Coverage Calculations

This example describes ML coverage calculation.

After RSEC, gene ML counts per well are evaluated to determine their suitability for further correction. Genes with low ML coverage (<4 Reads Per ML) bypass subsequent correction steps and are reported in the final ML data table and is logged to be "Low Depth" in the bioinformatics pipeline. For genes with extremely high inputs whereby at least 6557 out of the possible 6561 barcodes are observed, where it becomes challenging to determine the number of molecules due to barcode diversity and genes are flagged as "Saturated." For gene MLs that do not meet either of the 2 decision points move forward to the subsequent DBEC algorithm and are marked as "Pass" in the output log file. In addition, genes with higher than an average of 650 MLs per well are logged to be 'High Input' as >5% of these MLs are recycled based on a Poisson distribution (FIG. 27).

Altogether, this example describes ML coverage calculation.

Example 13

Distribution-Based Error Correction (DBEC)

This example describes distribution-based error correction.

Unlike RSEC, DBEC algorithm is a method to discriminate whether a ML is an error or true signal regardless of its ML sequence. While RSEC both ML sequence and ML coverage information to correct for errors, DBEC relies primarily on ML coverage only to correct for non-substitution errors. As aforementioned, error barcodes generally have low ML coverage that is distinct from true barcodes ML coverage; this difference in ML coverage can be observed in a histogram plot of the ML coverage as distinct distributions (FIG. 27). Given this difference, DBEC fits two negative binomial distributions to statistically distinguish between ML errors (with lower ML coverage), and one for true signal with higher ML coverage.

Removal of Recycled MLs for Optimal Distribution Fitting

For a given gene, as ML detected increases, the percentage of recycled ML (i.e. the same ML is used to label 2 or more mRNAs from the same gene) increases and can be estimated. Using a Poisson distribution ($\lambda_{non-unique}$), the number of recycled MLs for well i ($n_{non-unique, i}$) is estimated from the ML recycling rate equation (Equation (6)). If the estimated recycled ML is greater than 5% of total ML for the given gene in well i, this gene in well i is flagged as "High Input." For these "High Input" data, the top ML coverage MLs would be eliminated from distribution fitting—but preserved for later counting steps—to obtain a better negative binomial distribution.

$$P(X>1|\lambda_{non-unique}), \lambda_{non-unique} = \text{Number of } ML/6561. \quad \text{Equation (6)}$$

$$n_{non-unique} = \Sigma_{i=i}^{n\ wells} n_{non-unique,i}. \quad \text{Equation (7)}$$

Addition of Pseudopoints for Low Expressing Genes

If the unique number of ML is less than 10, it is often more challenging for fitting distributions due to the sparseness of the data. To alleviate this problem, DBEC adds pseudopoints at 1% signal counts are used for assisting the distribution fitting, yet does not affect the data.

Estimation of Parameters

To fit two negative binomial distributions to separate the error from the signal ML, two sets of starting values for parameter estimation are approximated. The error distribution is assumed to be negative binomial with mean and dispersion of 1.

Error/Signal Probability Estimation

Assume the signal and error distributions as NegativeBinomial($\mu_{signal}$, $size_{signal}$) and NegativeBinomial($\mu_{error}$, $size_{error}$), respectively. To determine the number of signal ML, in ascending order, the probabilities that the number of reads from a given ML are from the signal and error distributions are calculated until Equation (8) is satisfied where all preceding ML are considered as error ML.

$$P(X=r|\mu=\mu_{error}, size=size_{error}) < P(X=r|\mu=\mu_{signal}, size=size_{signal}). \quad \text{Equation (8)}$$

Altogether, this example shows calculations for performing distribution-based error correction.

Example 14

Adjusting for SL Errors Based on Second Derivatives

This example demonstrates adjusting for SL errors based on second derivatives.

Figure 32:
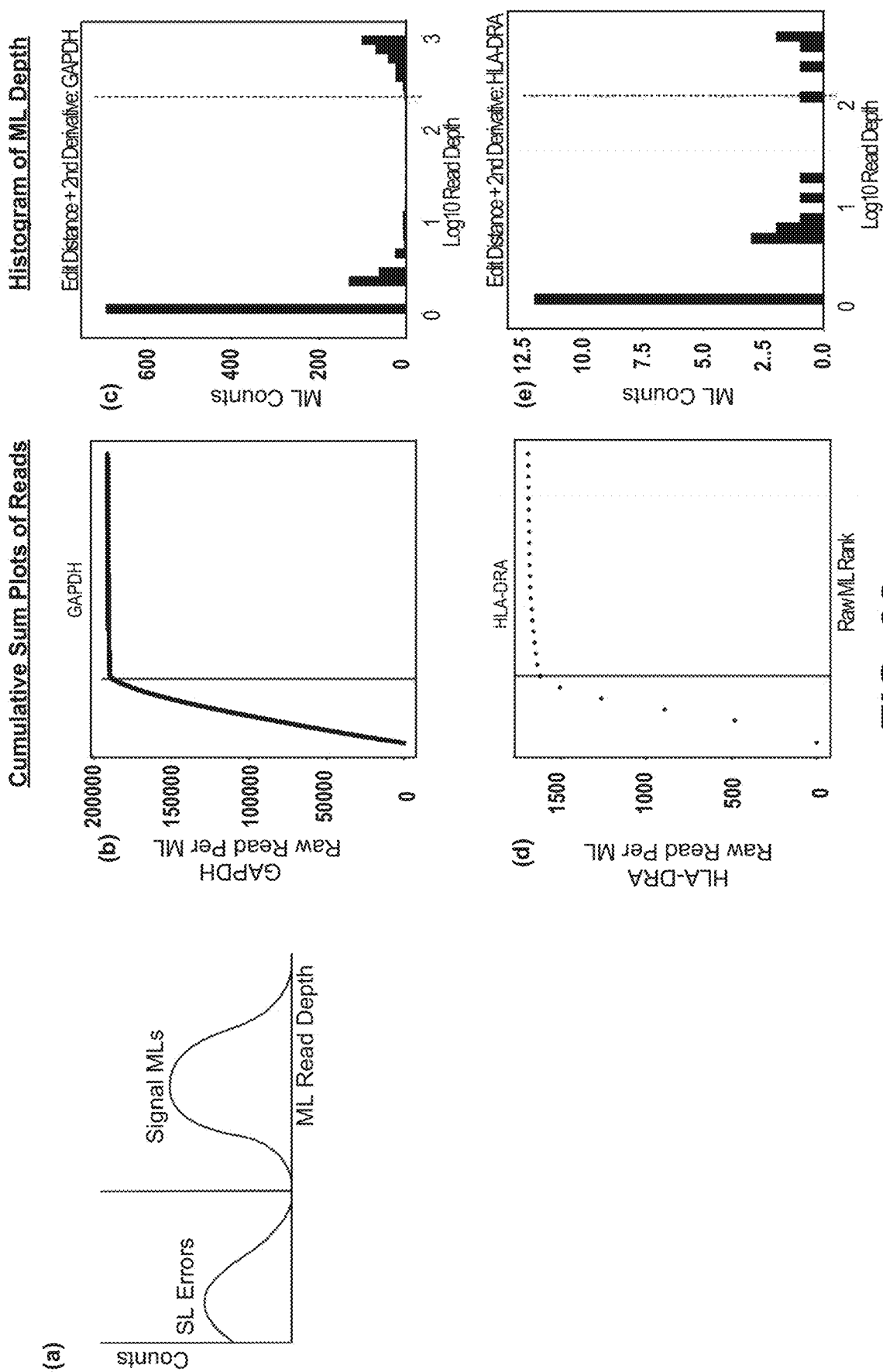
FIG. 32, panels (a)-(e) show exemplary results of correcting PCR and sequencing errors based on second derivatives of molecular label depth change.

FIG. 32, panels (a)-(e) show exemplary results of correcting PCR and sequencing errors based on second derivatives of molecular label depth change. FIG. 32, panel (a) shows that SL errors and signal MLs can be well separated. FIG. 32, panels (b) and (d) show cumulative sum plots of molecular label counts from ML counts shown in FIG. 32, panels (c) and (e), respectively. The vertical lines in FIG. 32, panels (b) and (d) show the positions of maxima of the second derivatives. The dotted lines in FIG. 32, panels (c) and (e) show that the positions of the maxima of the second derivatives can separate ML in the plots of ML counts vs. ML read depth.

Altogether, these data show that maxima of second derivatives of molecular label depth change can be used to separate SL errors from ML signals.

Example 15

Correcting PCR and Sequencing Errors Based on DBEC

This example demonstrates correcting PCR and sequencing errors based on two negative binomial distributions.

Figure 33:
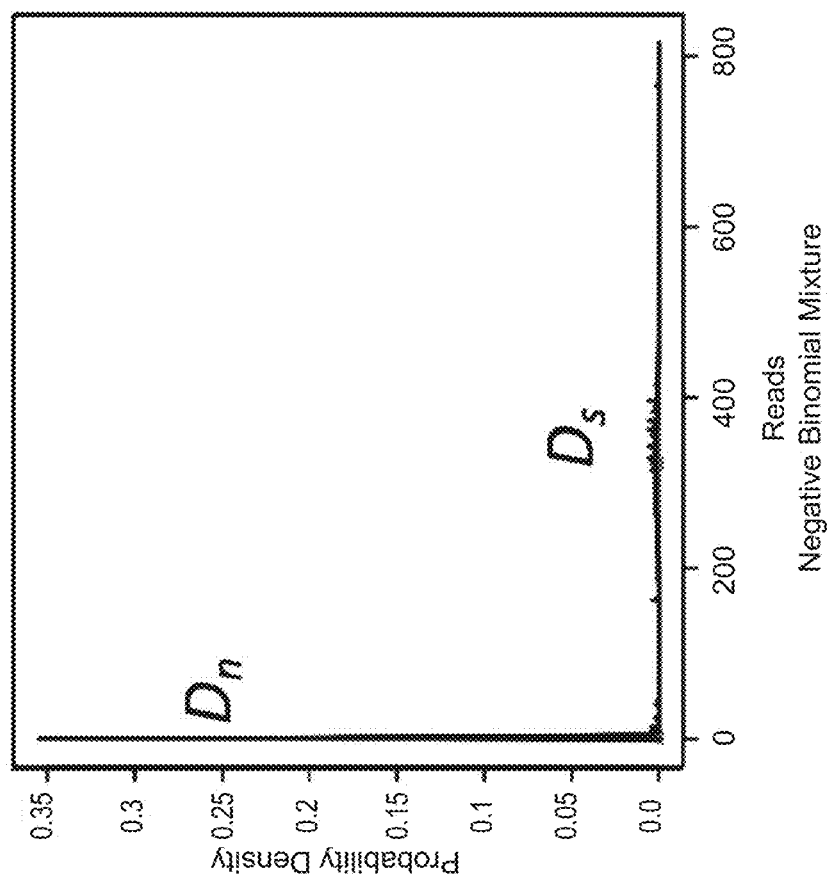
FIG. 33, panels (a)-(c) show exemplary results of correcting PCR and sequencing errors based on two negative binomial distributions for CD69.
Figure 33:
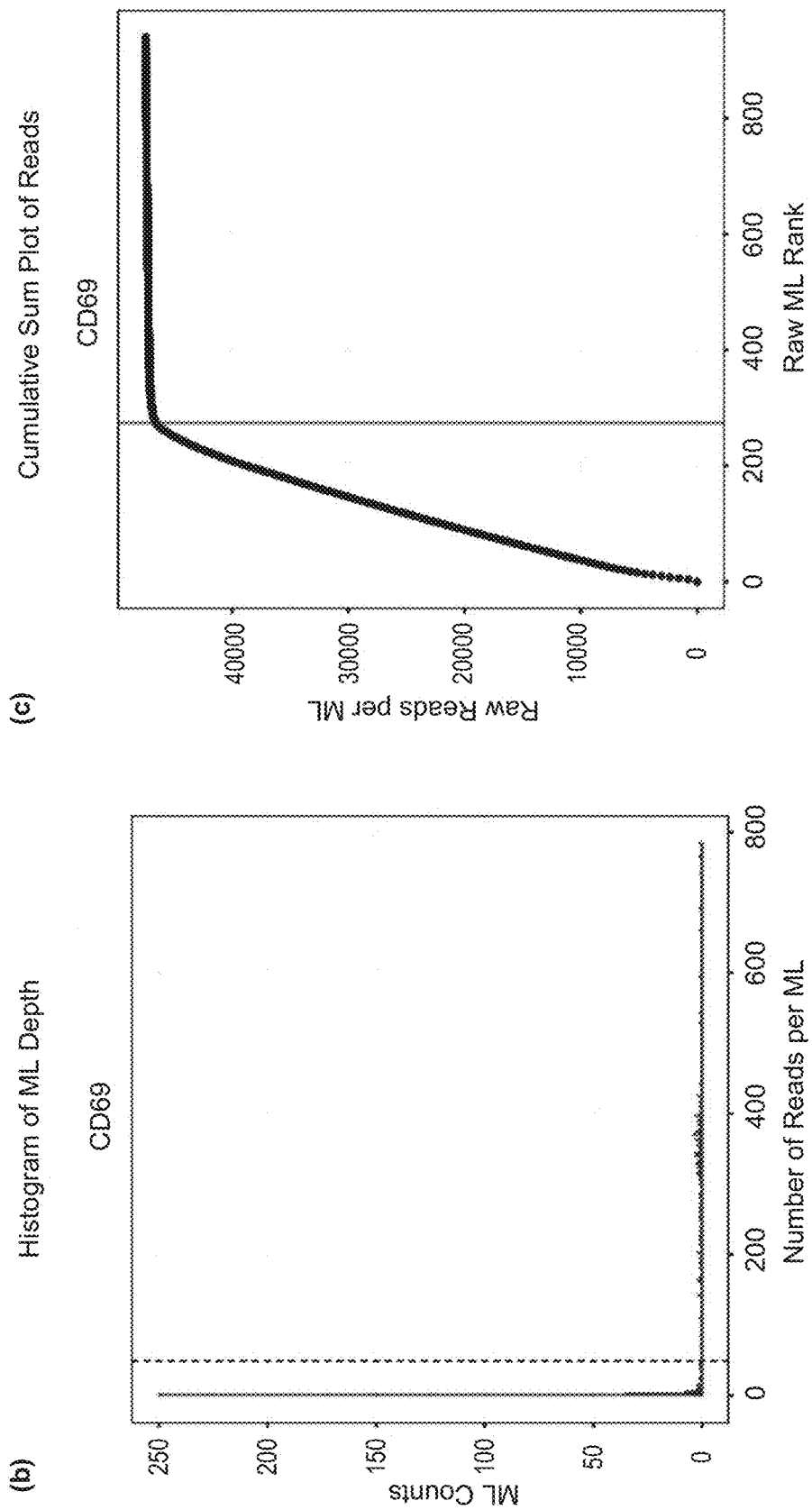
Figure 34:
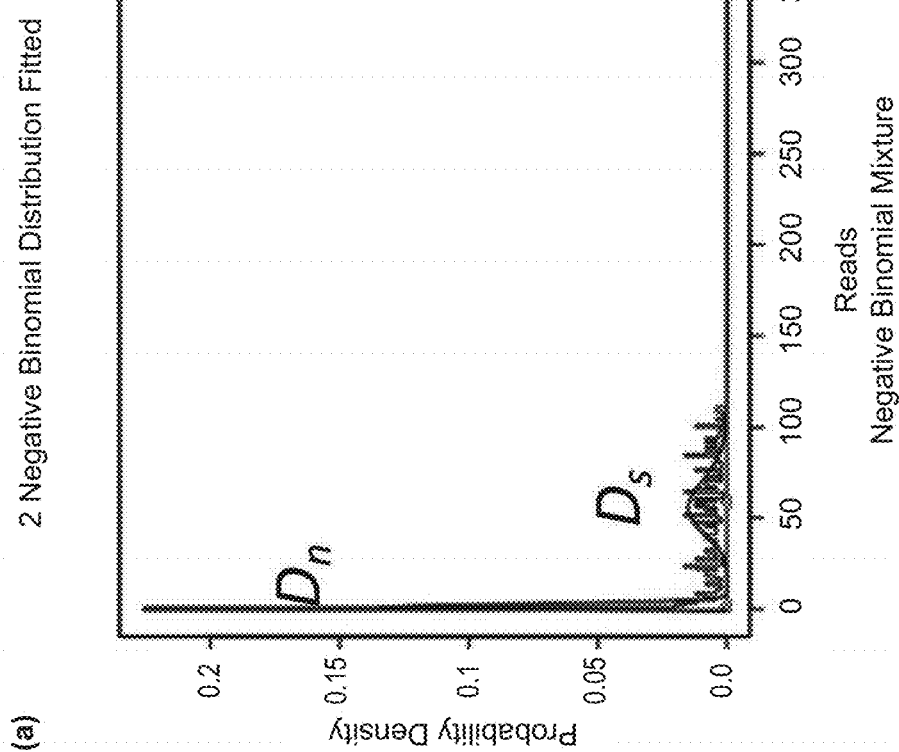
FIG. 34, panels (a)-(c) show exemplary results of correcting PCR and sequencing errors based on two negative binomial distributions for CD3E.
Figure 34:
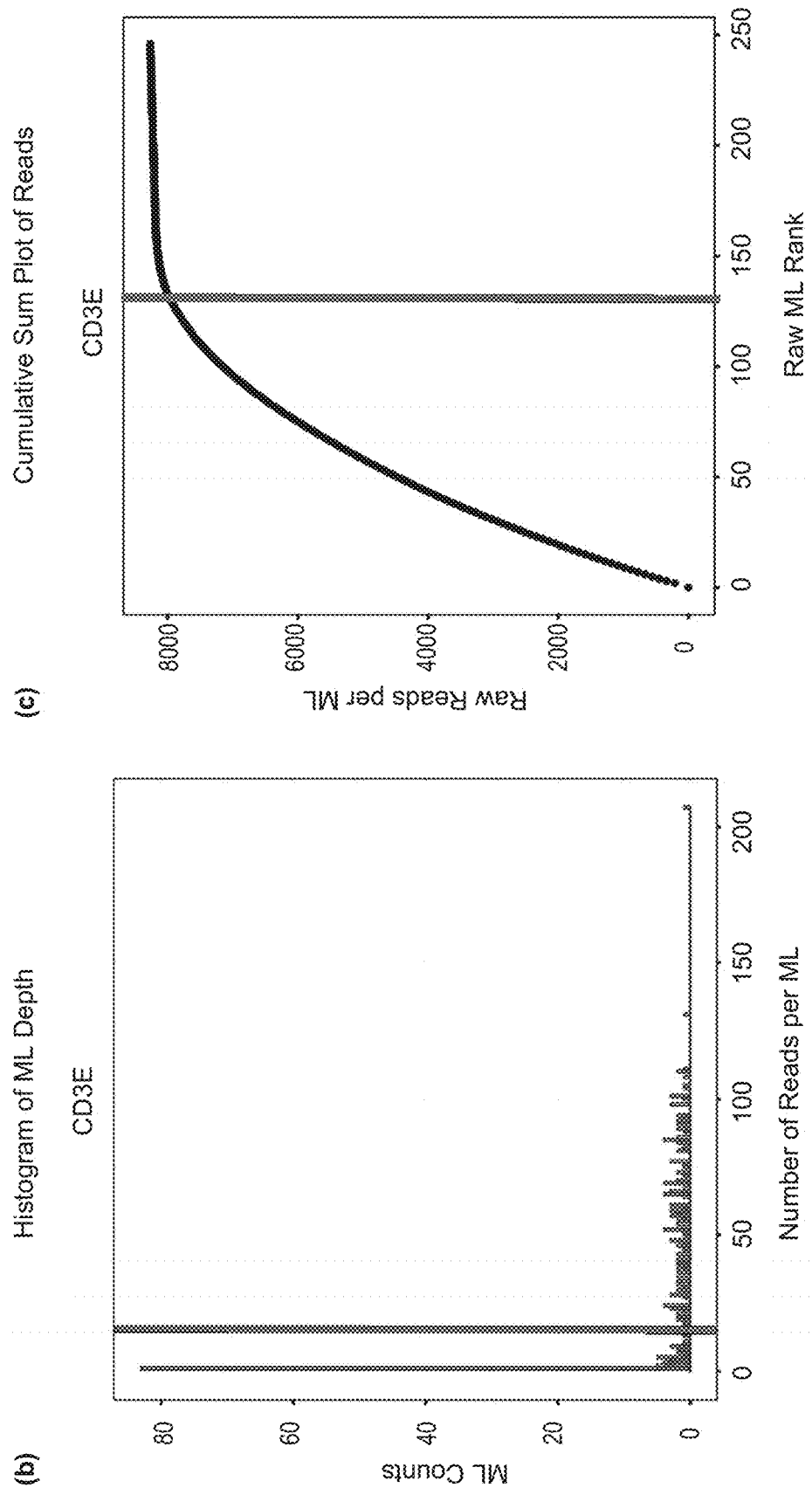

FIG. 33, panels (a)-(c) show exemplary results of correcting PCR and sequencing errors based on two negative binomial distributions for CD69. FIG. 33, panel (a) shows the fitting of two negative binomial distributions ($D_n$ for the noise negative binomial distribution and $D_s$ for the signal binomial distribution) for CD69 on the ML count data shown in the histogram of ML depth in FIG. 33, panel (b). The dotted line in 33, panel (b) shows the separation of ML signals and SL errors determined by the two negative binomial distributions shown in FIG. 33, panel (a). The vertical line in FIG. 33, panel (c) shows the local maximum of second derivatives as determined based on the cumulative sum plot of reads. Similar to FIG. 33, FIG. 34, panels (a)-(c) show exemplary results of correcting PCR and sequencing errors based on two negative binomial distributions for CD3E.

Altogether, these data show that DBEC can be used to correct for PCR and sequencing errors.

Example 16

ML Recycling

This example demonstrates ML recycling for high expressor genes and need for adjusting input data for high expressor genes prior to distribution fitting.

Figure 35:
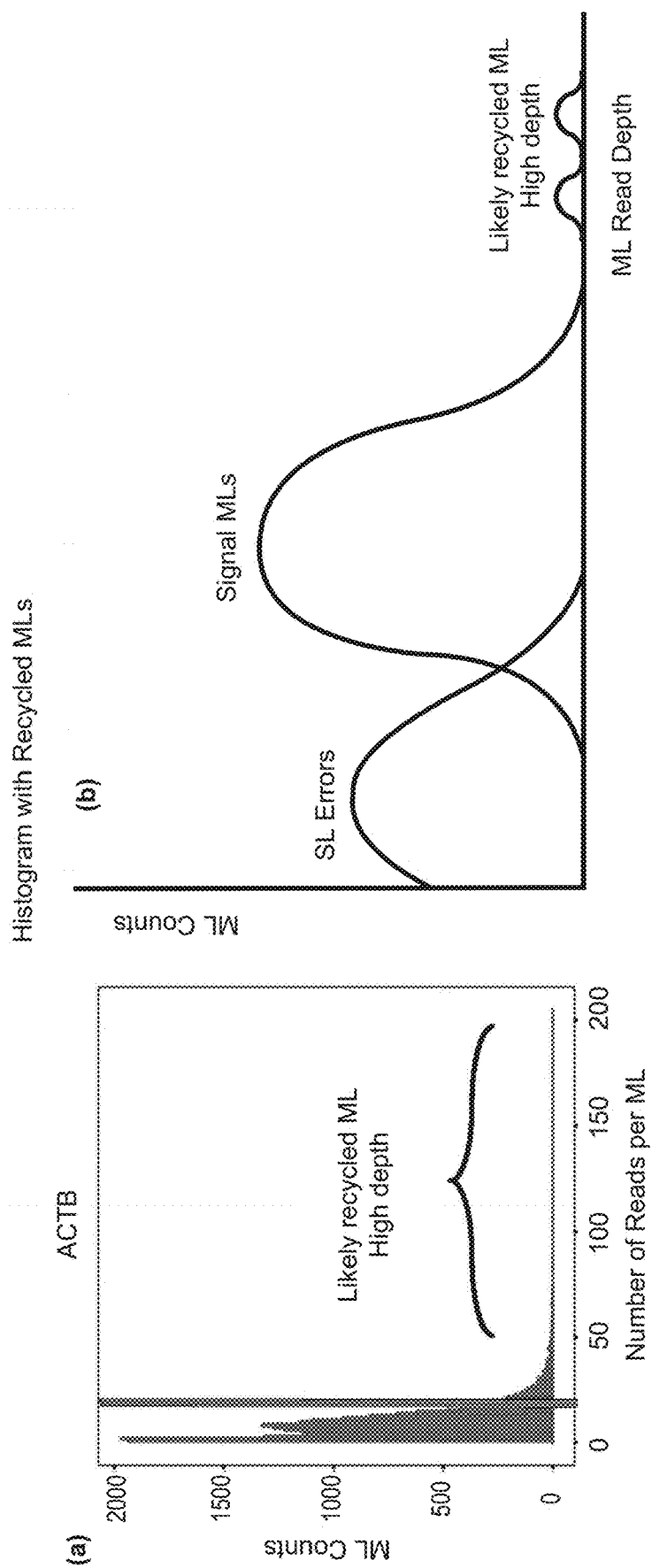
FIG. 35, panels (a)-(c) shows exemplary results of correcting PCR and sequencing errors based on two negative binomial distributions for high expressor genes.
Figure 35:
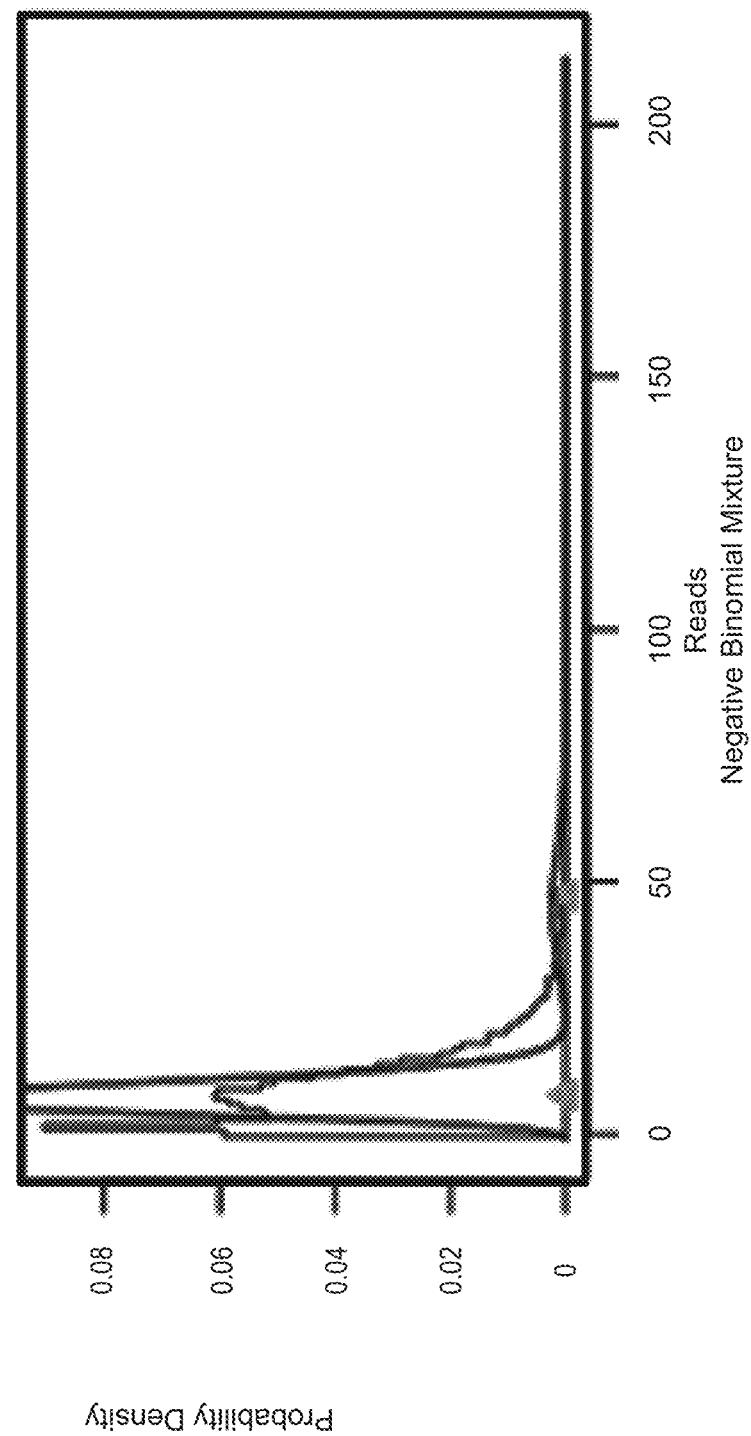

FIG. 35, panels (a)-(c) show exemplary results of correcting PCR and sequencing errors based on two negative binomial distributions for an high expressor gene-ACTB. A high expressor gene can have the over sequencing status (for example, with a ML coverage of 100 or more). In some embodiments, a high expressor gene may be determined using other criteria. In FIG. 35, panel (a) the molecular labels to the right of the vertical line corresponded to likely recycled ML based on their high depths. FIG. 35, panel (b) schematically illustrates that molecular labels can be divided into three categories (in addition to the ML errors): SL errors, signal MLs, and likely recycled MLs. FIG. 35, panel (c) demonstrates that, without adjusting for likely recycled MLs, two negative binomial distributions fitted was non-ideal.

FIG. 36 shows exemplary results of recycling of G-rich molecular labels for high expressor genes. FIG. 36 shows top 20 high depth MLs for high expressor genes GAPDH, ACTB, and HSP90AB1. These high depth MLs had high G's and T's, which were more likely to be recycled and barcoding was not stochastic. ML doublets occurred sooner than theoretical calculation which assumes stochastic labeling. For ACTB, the actual doublets was around four percent even though theoretically, there would be 2.7% doublets if there were 350 MLs per well.

Figure 37:
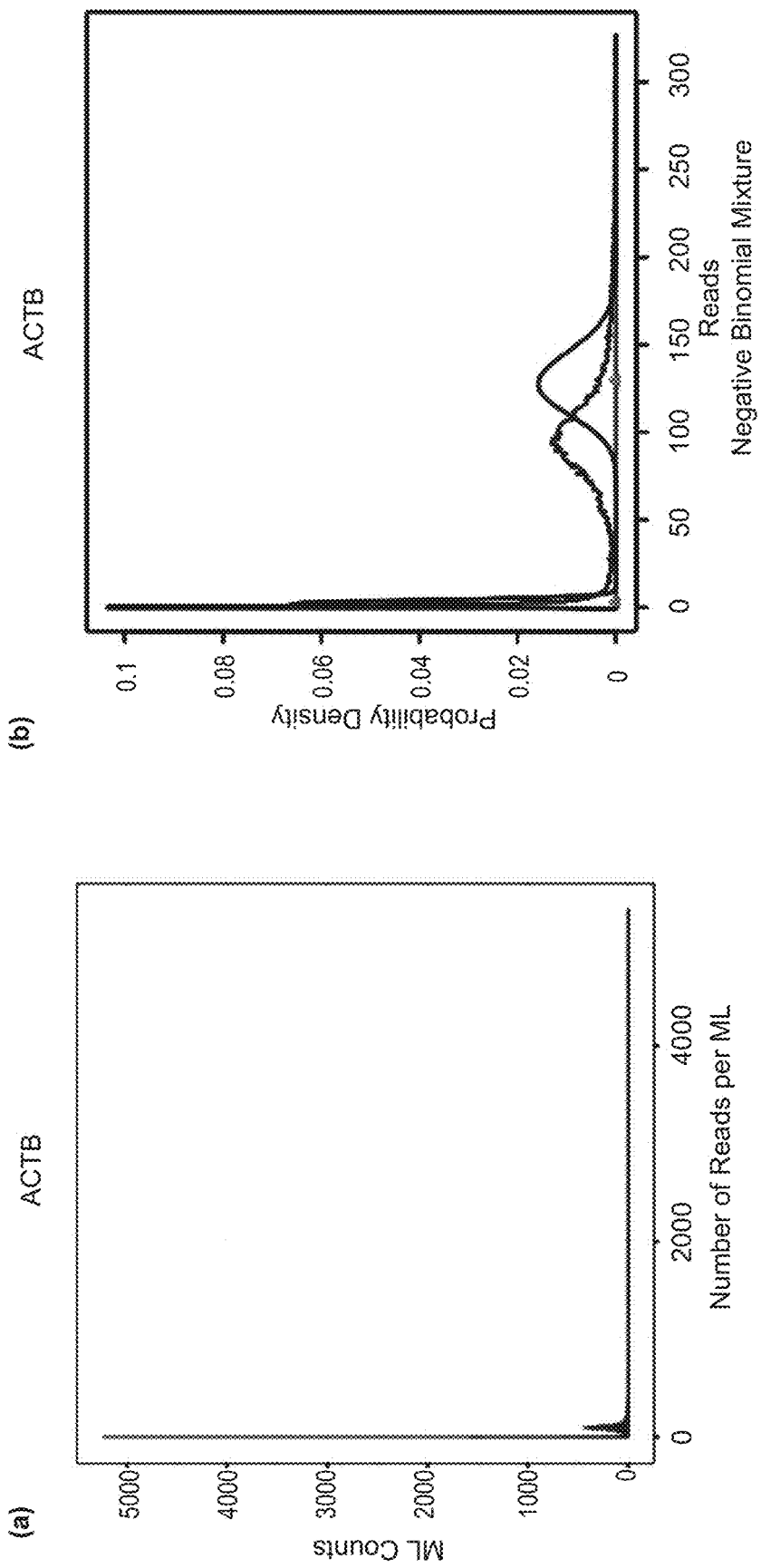
FIG. 37, panels (a)-(b) show exemplary results of adjusting input data for high expressor genes before fitting two negative binomial distributions.

FIG. 37, panels (a)-(b) show exemplary results of adjusting input data for high expressor genes before fitting two negative binomial distributions. FIG. 37, panel (a) shows the input data in FIG. FIG. 35, panel (a) adjusted for high expressor genes. In contrast to the non-ideal distribution fittings in FIG. 35, panel (c), FIG. 37, panel (b) shows two negative binomial distributions fitted.

Altogether, these data show that prior to fitting of two negative binomial distributions, recycled MLs may need to be removed from sequencing data for high expressor genes.

Example 17

ML Counts Correction Using Two Negative Binomial Distributions

This example demonstrates ML counts of ten targets corrected using two negative binomial distributions.

Figure 38:
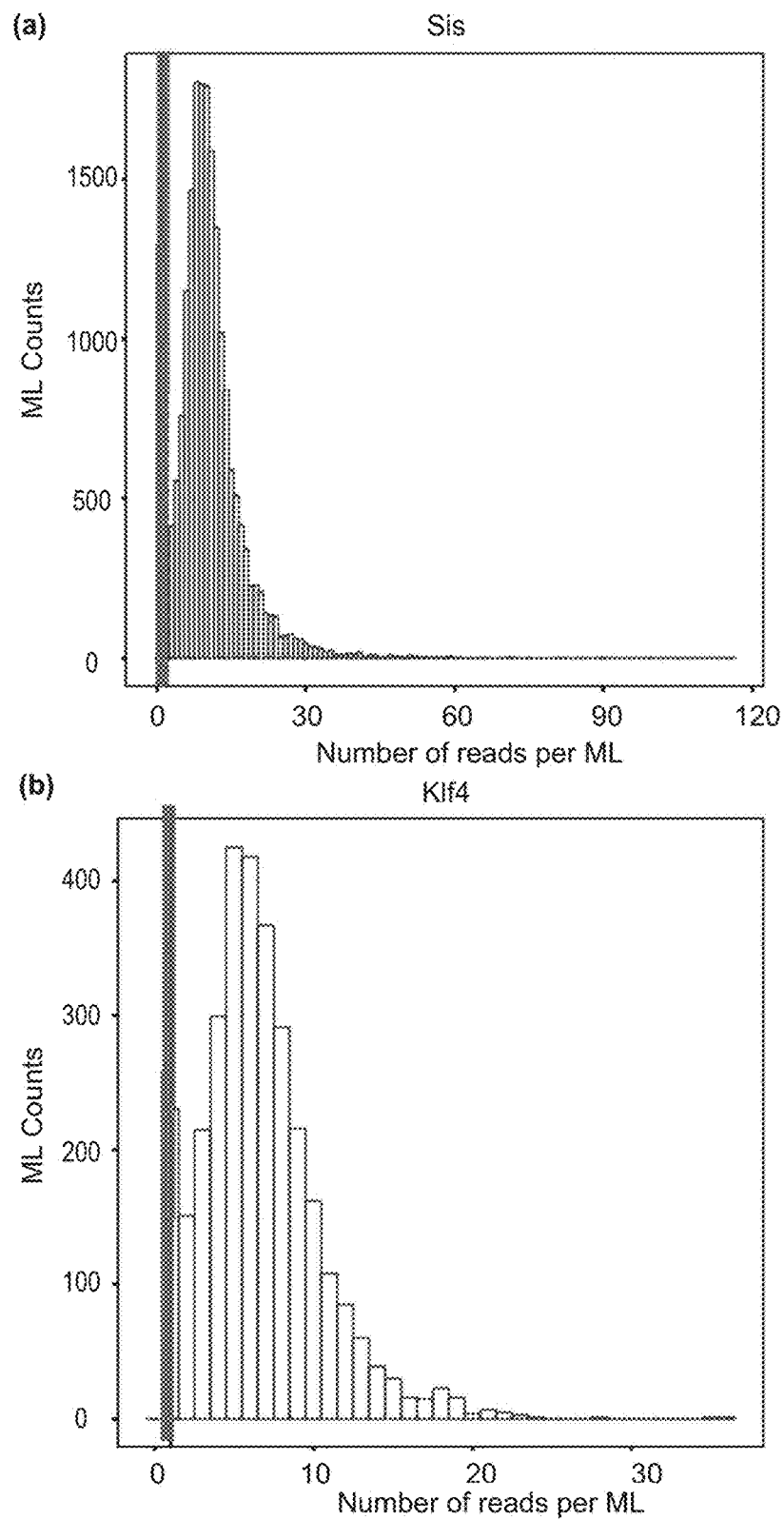
FIG. 38, panels (a)-(j) show non-limiting exemplary validation of dataset corrected using two negative binomial distributions.
Figure 38:
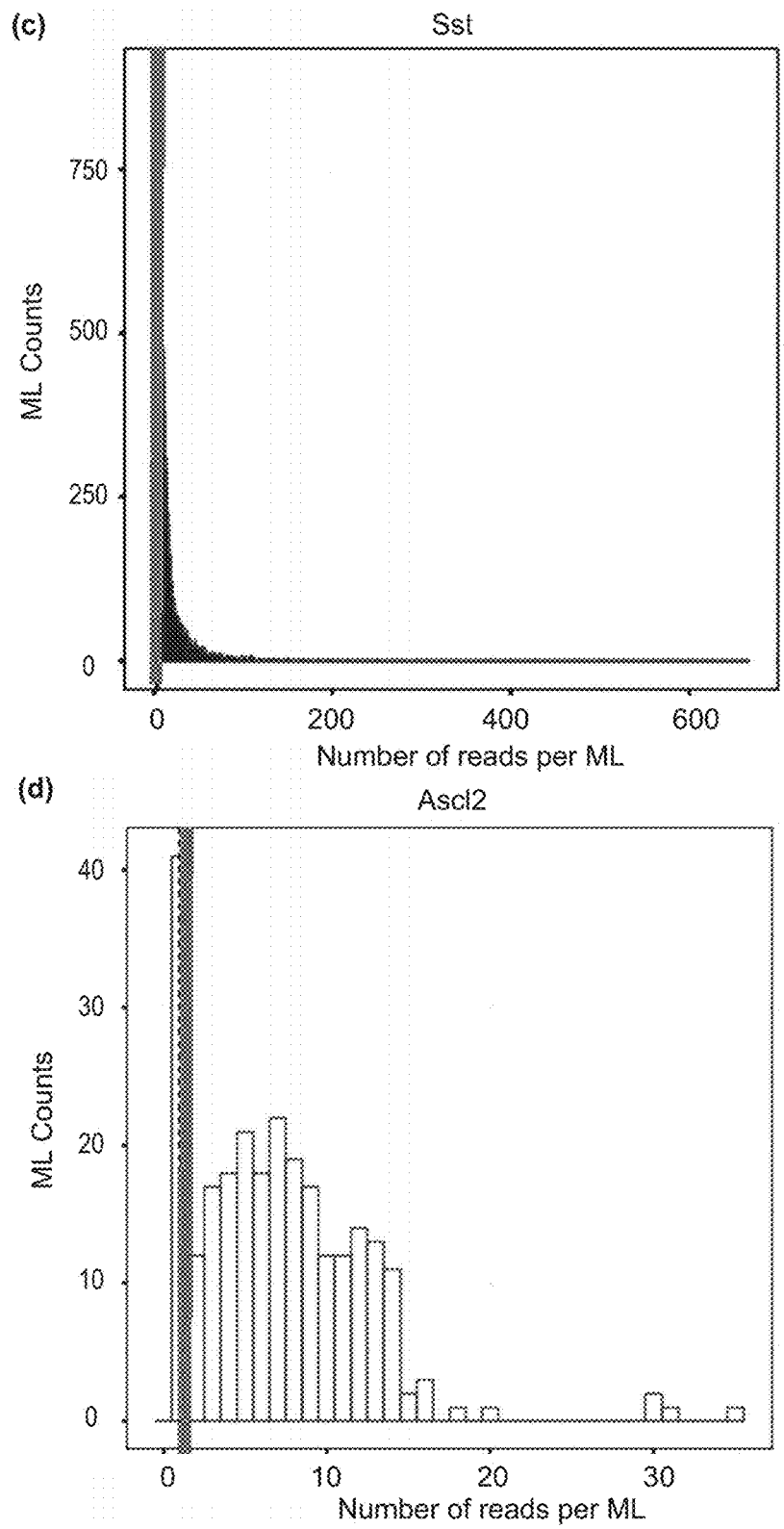
Figure 38:
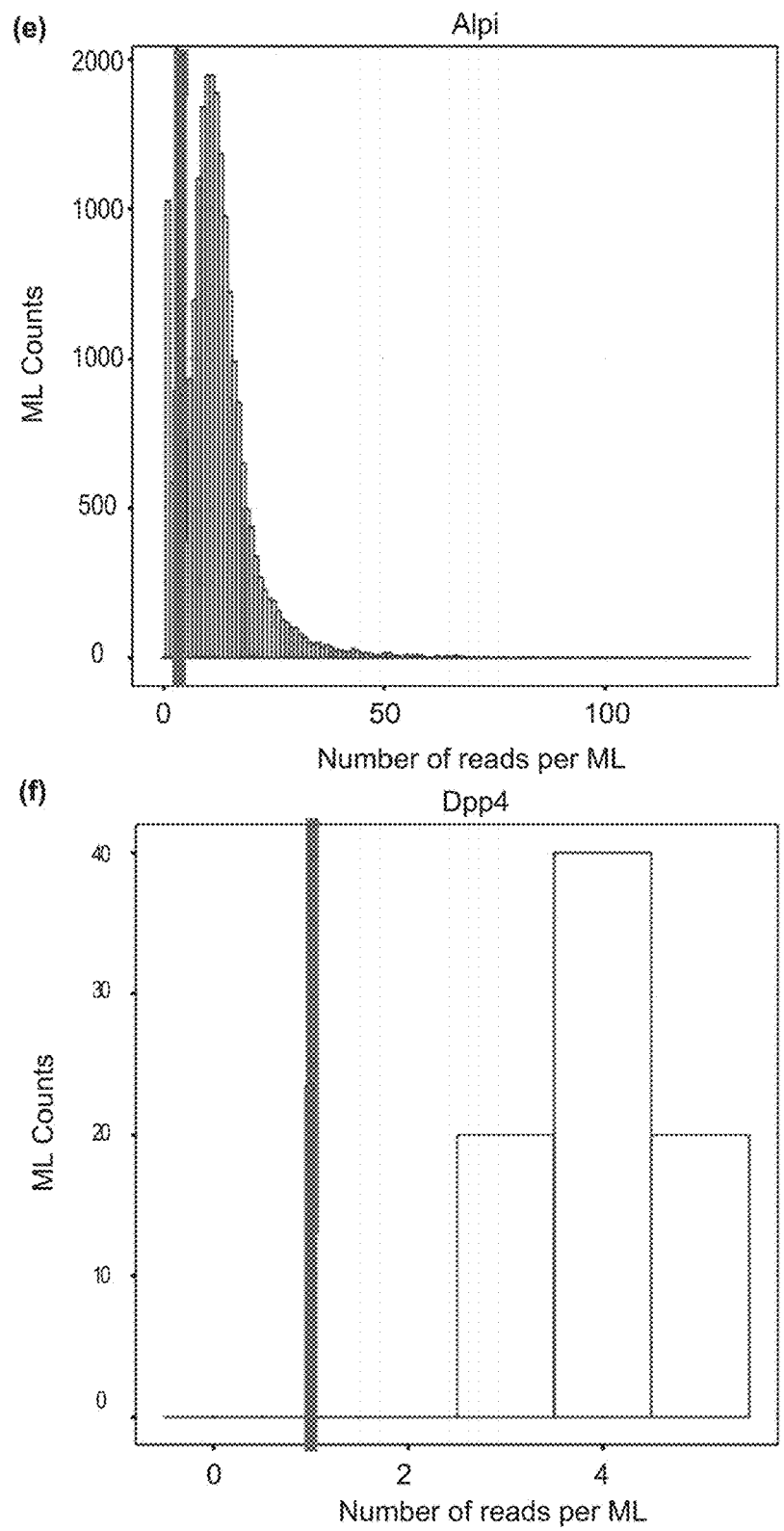
Figure 38:
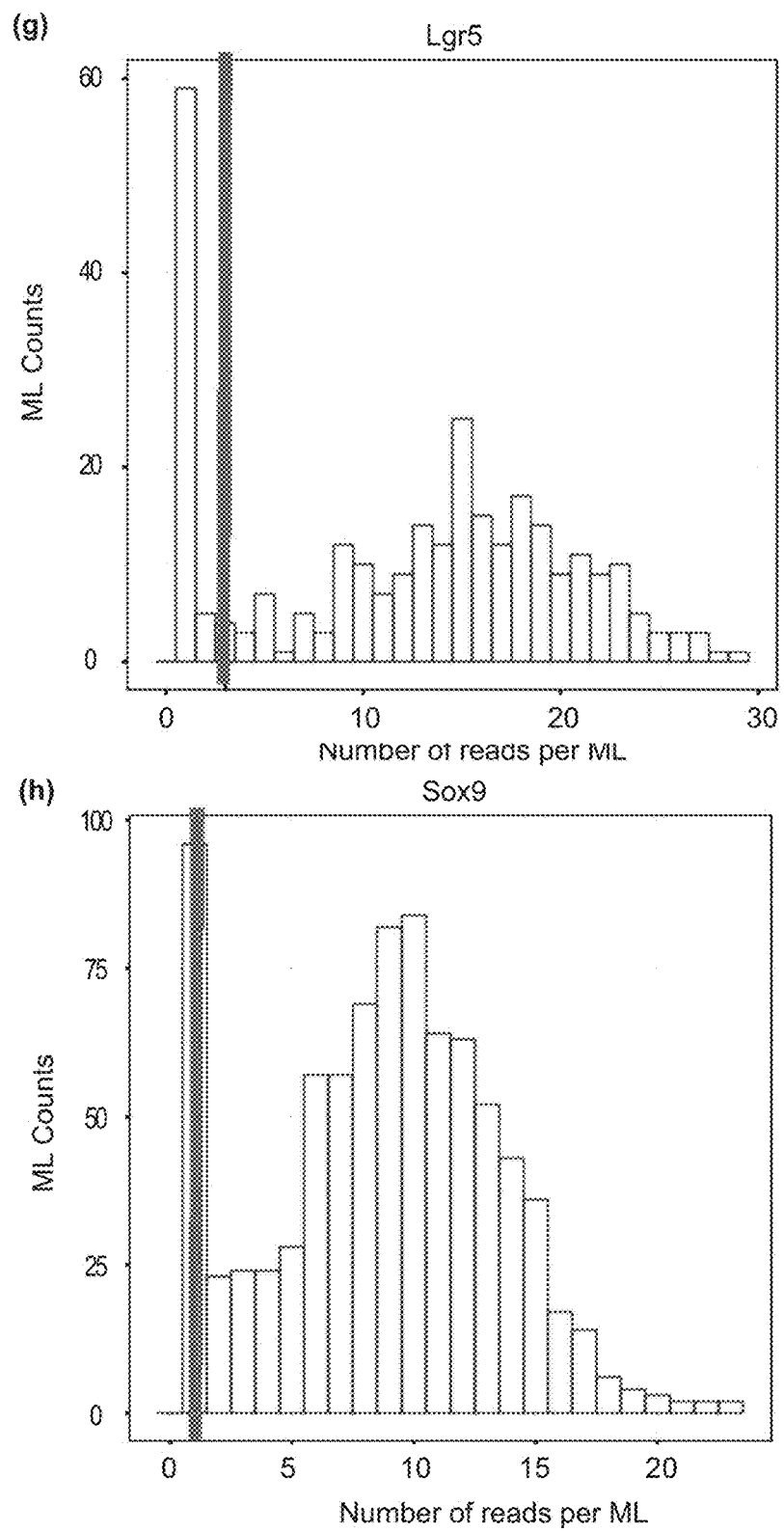
Figure 38:
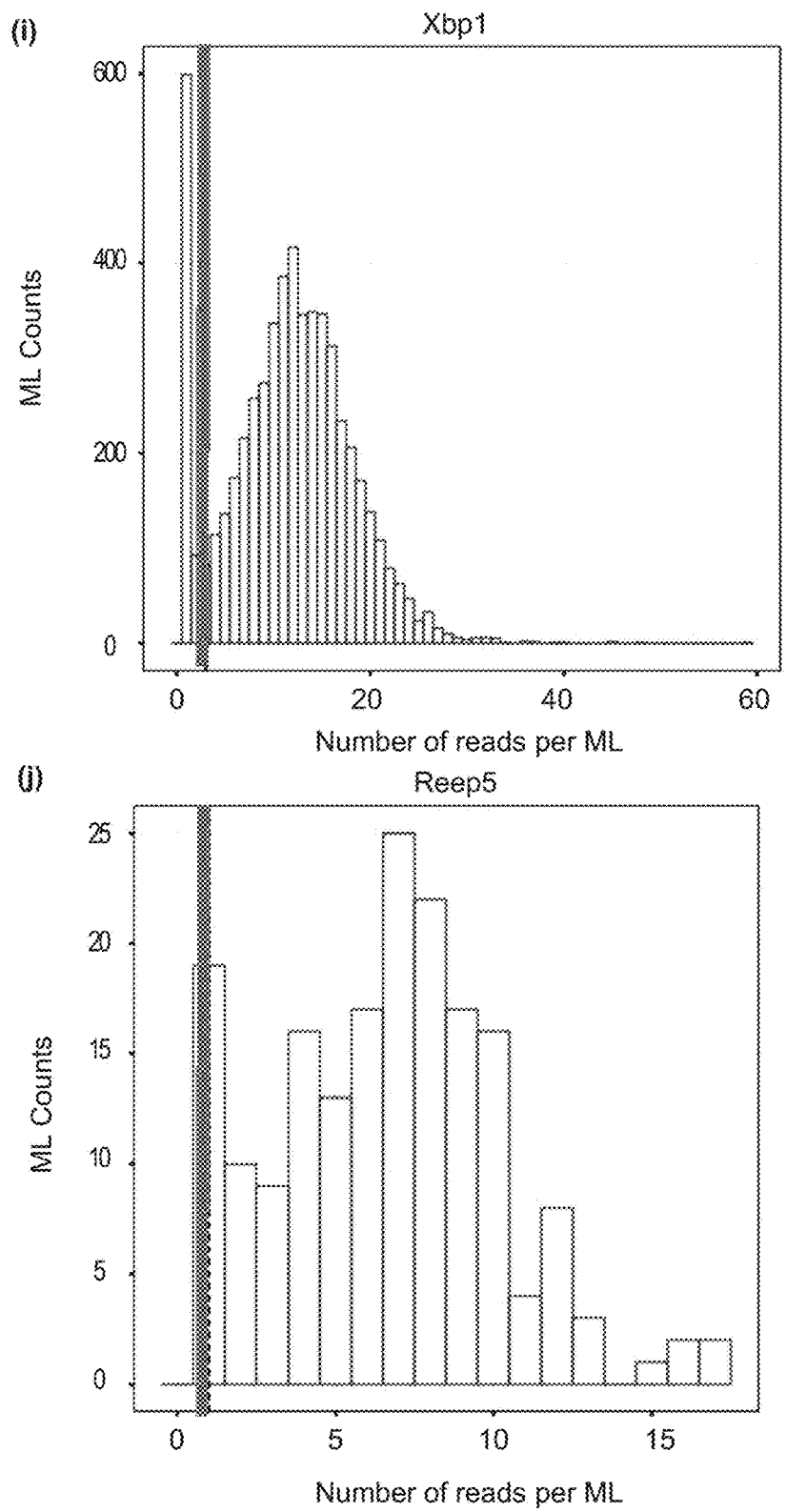

FIG. 38, panels (a)-(j) show non-limiting exemplary validation of dataset corrected using two negative binomial distributions. ML counts of ten targets were corrected as shown in FIG. 38. The vertical line in each panel of FIG. 38 shows the separation of ML signals and SL errors for a target determined using two negative binomial distributions.

Altogether, these data validate ML counts correction using two negative binomial distributions.

Example 18 t-Stochastic Neighbor Embedding Visualization of a BD Precise™ Targeted Assay from a 96-Well of Mixed Jurkat and Breast Cancer (BrCa) Single Cells This example demonstrates a method for correcting PCR and sequencing errors based on recursive substitution error correction and distribution-based error correction for mixed Jurkat and breast cancer (BrCa) single cells.

Figure 39:
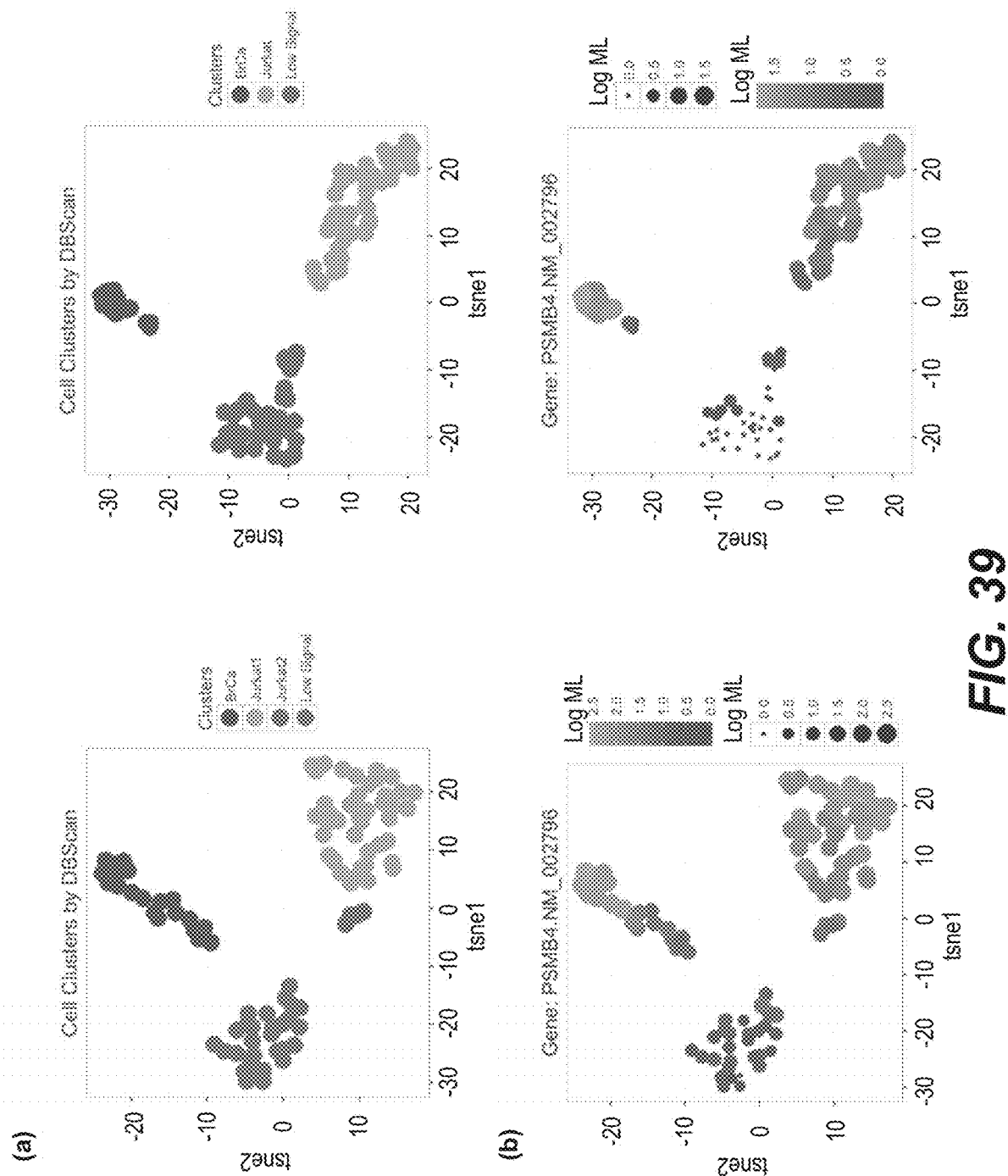
FIG. 39, panels (a)-(d) show exemplary t-stochastic neighbor embedding (t-SNE) visualizations of Precise™ targeted assay from a 96-well of mixed Jurkat and breast cancer (BrCa) single cells (86 genes examined).
Figure 39:
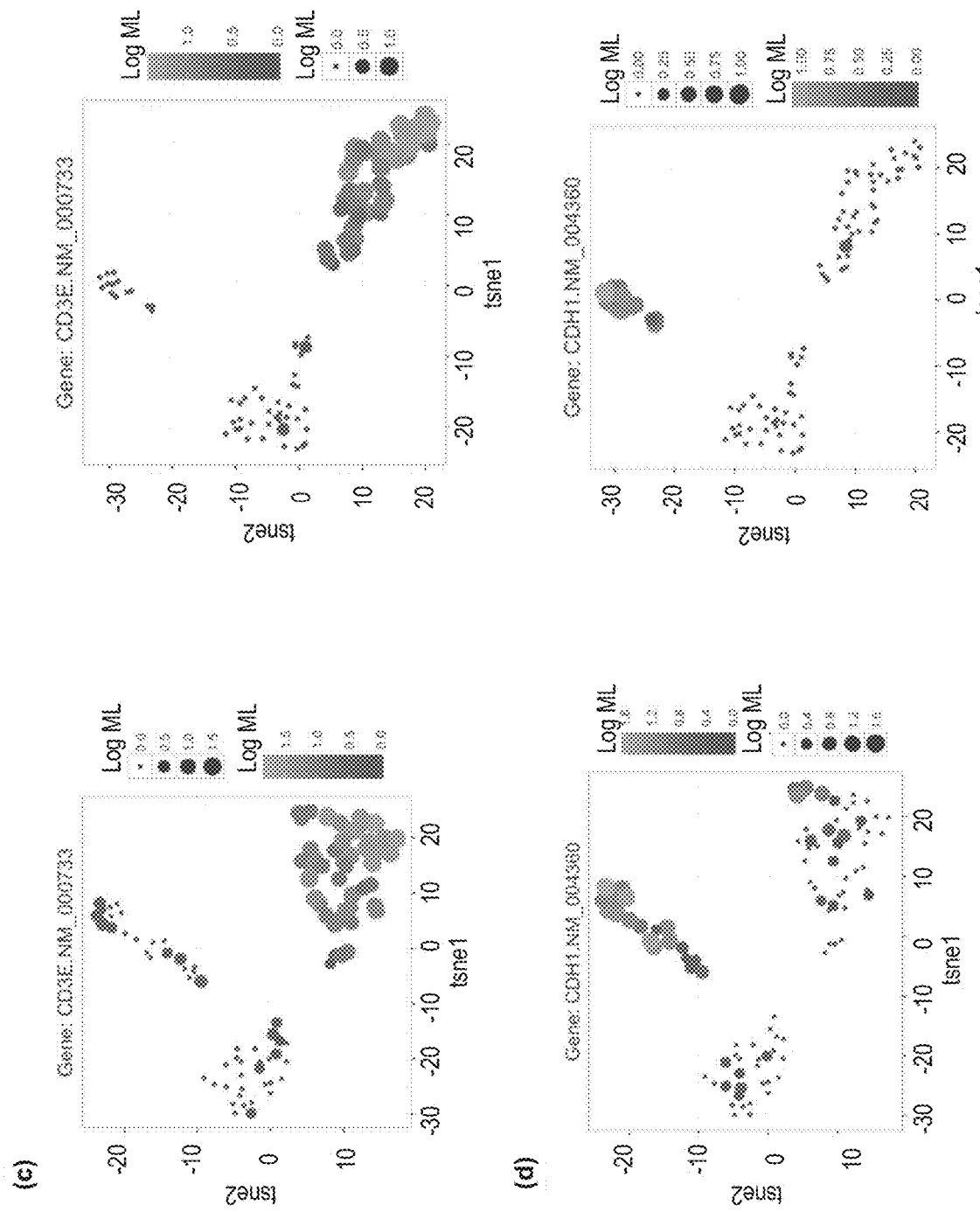

FIG. 39, panels (a)-(d) show exemplary t-stochastic neighbor embedding (t-SNE) visualizations of Precise™ targeted assay from a 96-well of mixed Jurkat and breast cancer (BrCa) single cells (86 genes examined). FIG. 39, panel (a) shows that cell clusters were identified using DBScan with the same parameters before and after ML adjustments. FIG. 39, panels (b)-(d) show individual marker expression scaled both by color and point size. FIG. 39, panel (b) shows PSMB4, a housekeeping gene that is present in both cell types and after ML adjustments, the lack of PSMB4 signal is highlighted further in the 'Low Signal' cluster. FIG. 39, panel (c) shows CD3E, a lymphocyte marker that highlights Jurkat cell clusters. FIG. 39, panel (d) shows CDH1, an epithelial cell marker that highlights the BrCa cluster.

Altogether, these data demonstrate that ML adjustment removed ML noise which allowed for clear differentiation of gene expression between cell clusters.

Example 19

Differential Expression Analysis Between Cell Clusters

This example demonstrates a method of correcting PCR and sequencing errors based on recursive substitution error correction and distribution-based error correction for low signal cells and breast cancer (BrCa) cells.

Figure 40:
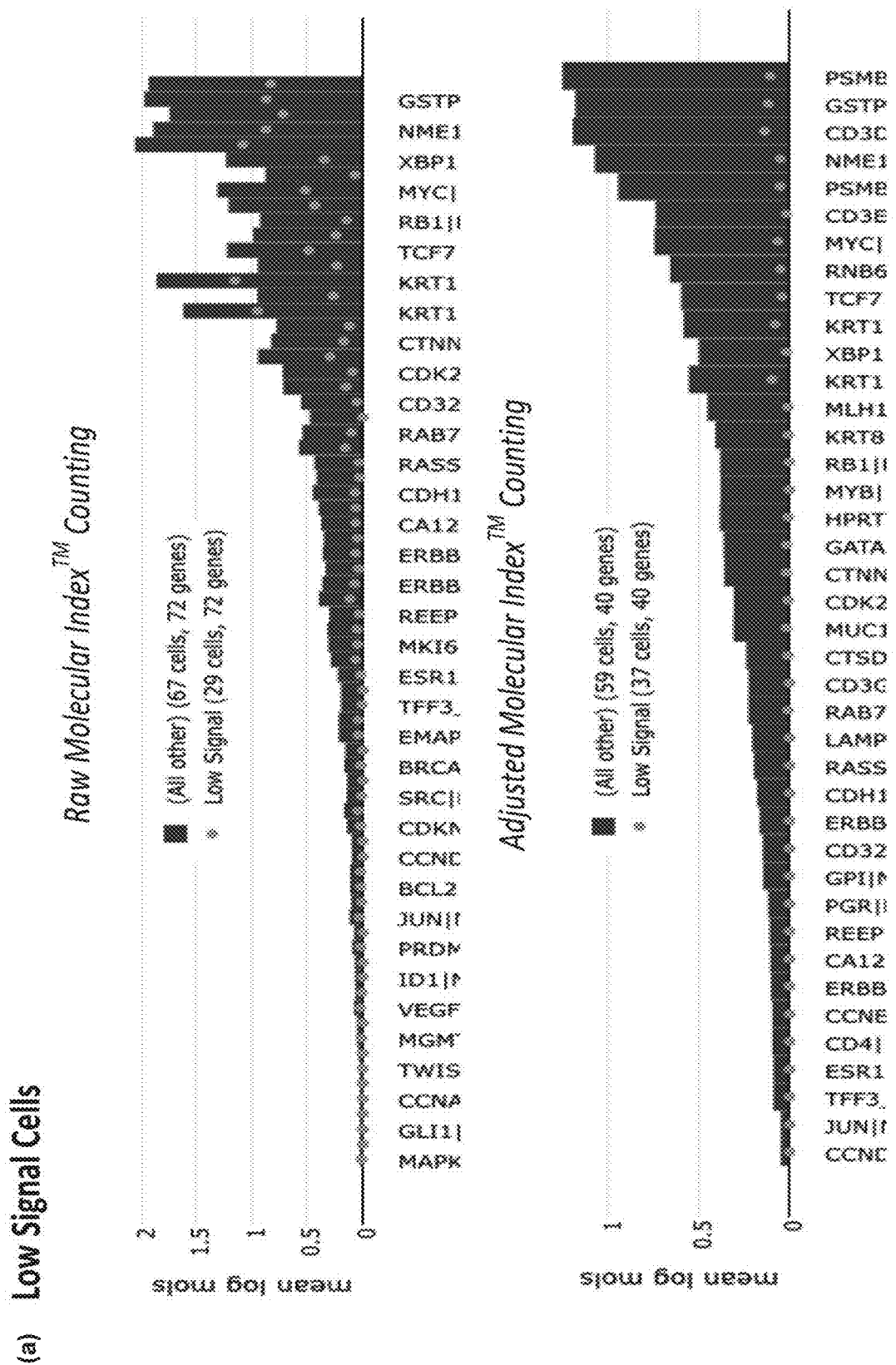
FIG. 40, panels (a)-(b) are non-limiting exemplary plots showing differential expression analysis between cell clusters for genes with >0 ML in both selected clusters calculated by DBScan and determined by gene marker level in each cluster.
Figure 40:
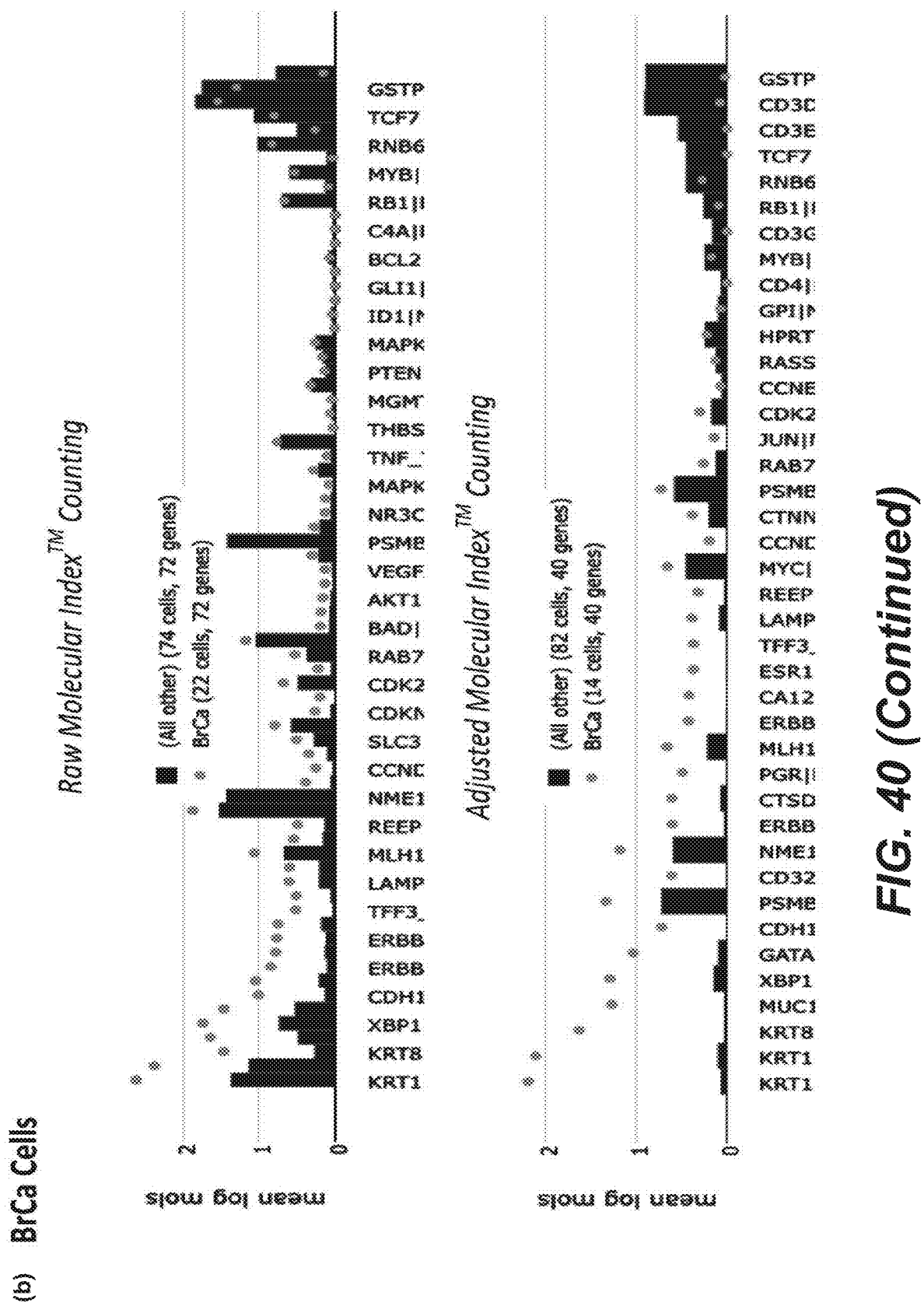

FIG. 40, panels (a)-(b) are non-limiting exemplary plots showing differential expression analysis between cell clusters for genes with >0 ML in both selected clusters calculated by DBScan and determined by gene marker level in each cluster. FIG. 40, panel (a) shows 'Low Signal' cluster gene expression compared to the rest of the cells. FIG. 40, top of panel (a) shows raw ML comparison showing that ML noise was generally higher for genes with higher average expression in other cells. FIG. 40, bottom of panel (a) shows that after ML adjustments using RSEC and DBEC, ML noise detected in 'Low Signal' cluster was reduced, allowing clearer distinction of gene expression between clusters. FIG. 40, panel (b) shows 'BrCa' cluster gene expression compared to the rest of the cells. FIG. 40 top of panel (b) shows raw ML in non-BrCa cells also had a significant ML count of BrCa markers, such as KRT1, MUC1. FIG. 40, bottom of panel (b) shows adjusted MLs of BrCa markers were highly enriched in BrCa cluster than the rest of the cells.

Altogether, these data demonstrate that PCR and sequencing errors can be corrected based on recursive substitution error correction and distribution-based error correction for cells, such as low signal cells and breast cancer cells.

Example 20

Adjusting Molecular Label Counts for Mixed Jurkat and T47D Cells

This example demonstrates a method of adjusting molecular label counts for mixed Jurkat and T47D cells.

Figure 41:
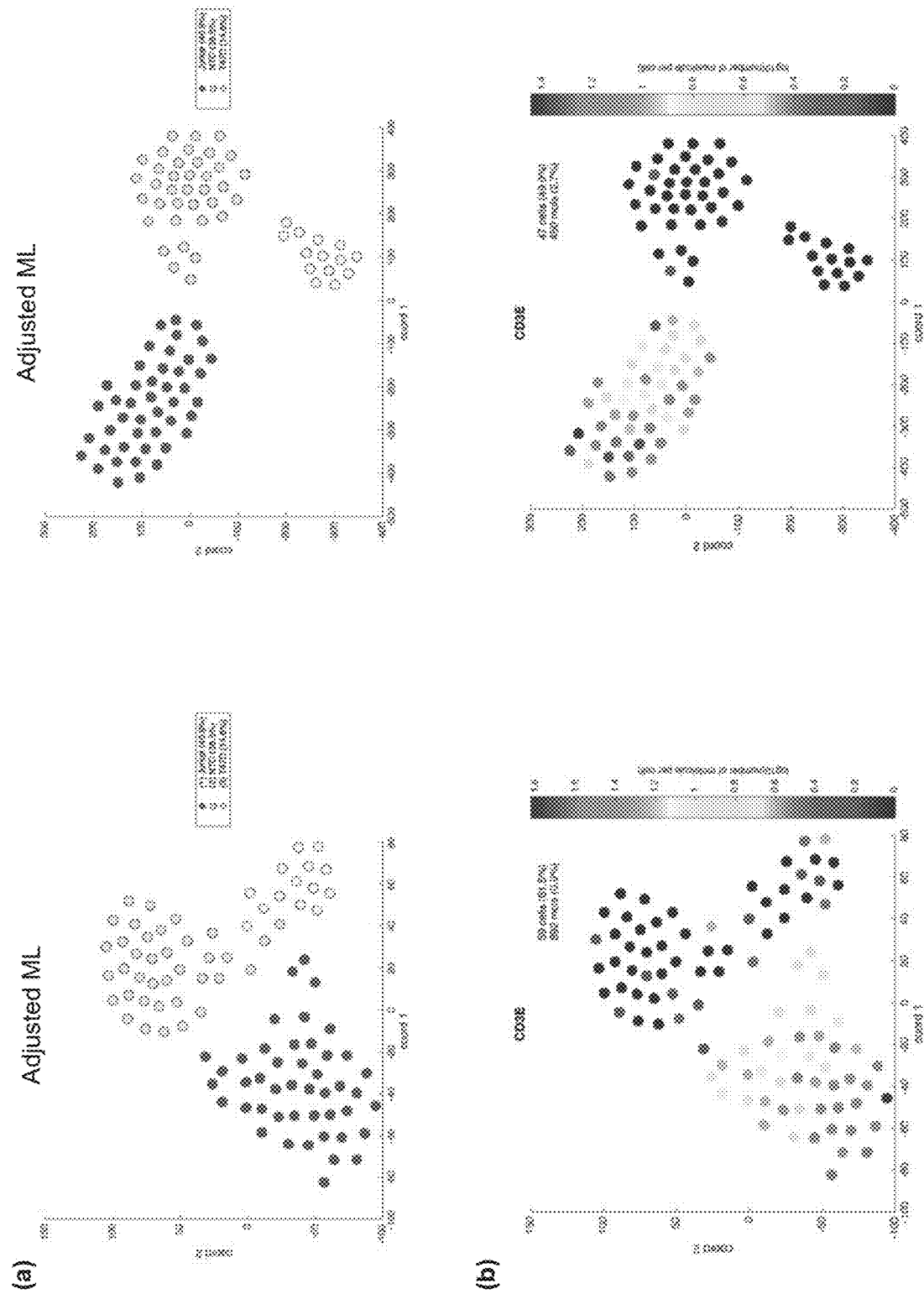
FIG. 41, panels (a)-(d) are non-limiting exemplary plots showing t-stochastic neighbor embedding (t-SNE) visualization of a BD Precise™ targeted assay from a 96-well plate of mixed Jurkat and breast cancer (T47D) single cells with 86 genes examined.
Figure 41:
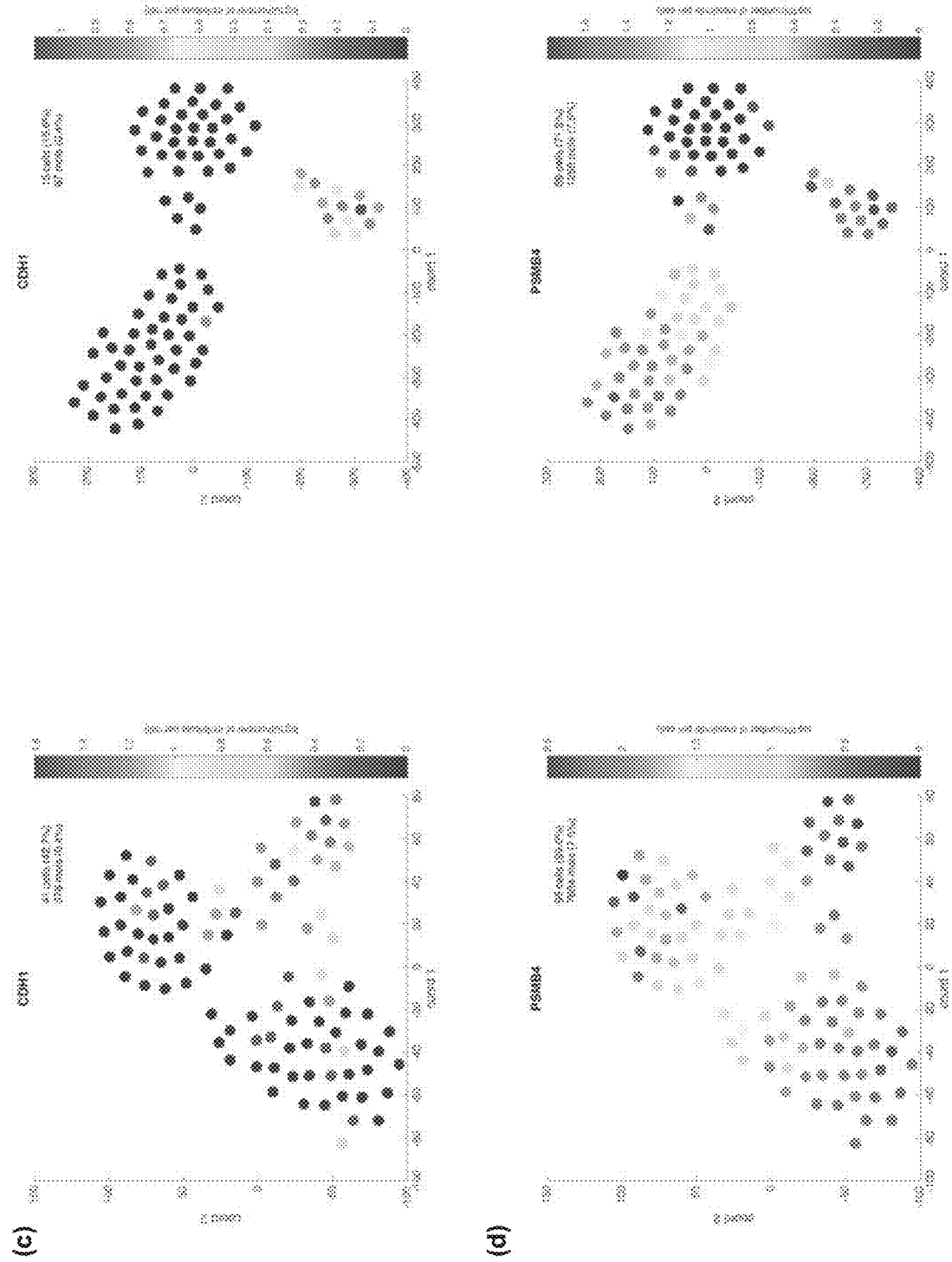

FIG. 41, panels (a)-(d) are non-limiting exemplary plots showing t-stochastic neighbor embedding (t-SNE) visualization of a BD Precise™ targeted assay from a 96-well plate of mixed Jurkat and breast cancer (T47D) single cells with 86 genes examined. FIG. 41, panel (a) show that cell clusters were identified using DBScan with the same parameters before and after ML adjustments. FIG. 41, panels (b)-(d) show that individual marker expression scaled both by color and point size. FIG. 41, panel (b) shows the scaling of PSMB4, a housekeeping gene that was present in both cell types and after ML adjustments. The lack of PSMB4 signal is highlighted further in the no-template control (NTC) cluster. FIG. 41, panel (c) shows the scaling of CD3E, a lymphocyte marker that highlights Jurkat cell clusters. FIG. 41, panel (d) shows the scaling of CDH1, an epithelial cell marker that highlights the T47D cluster.

Figure 42:
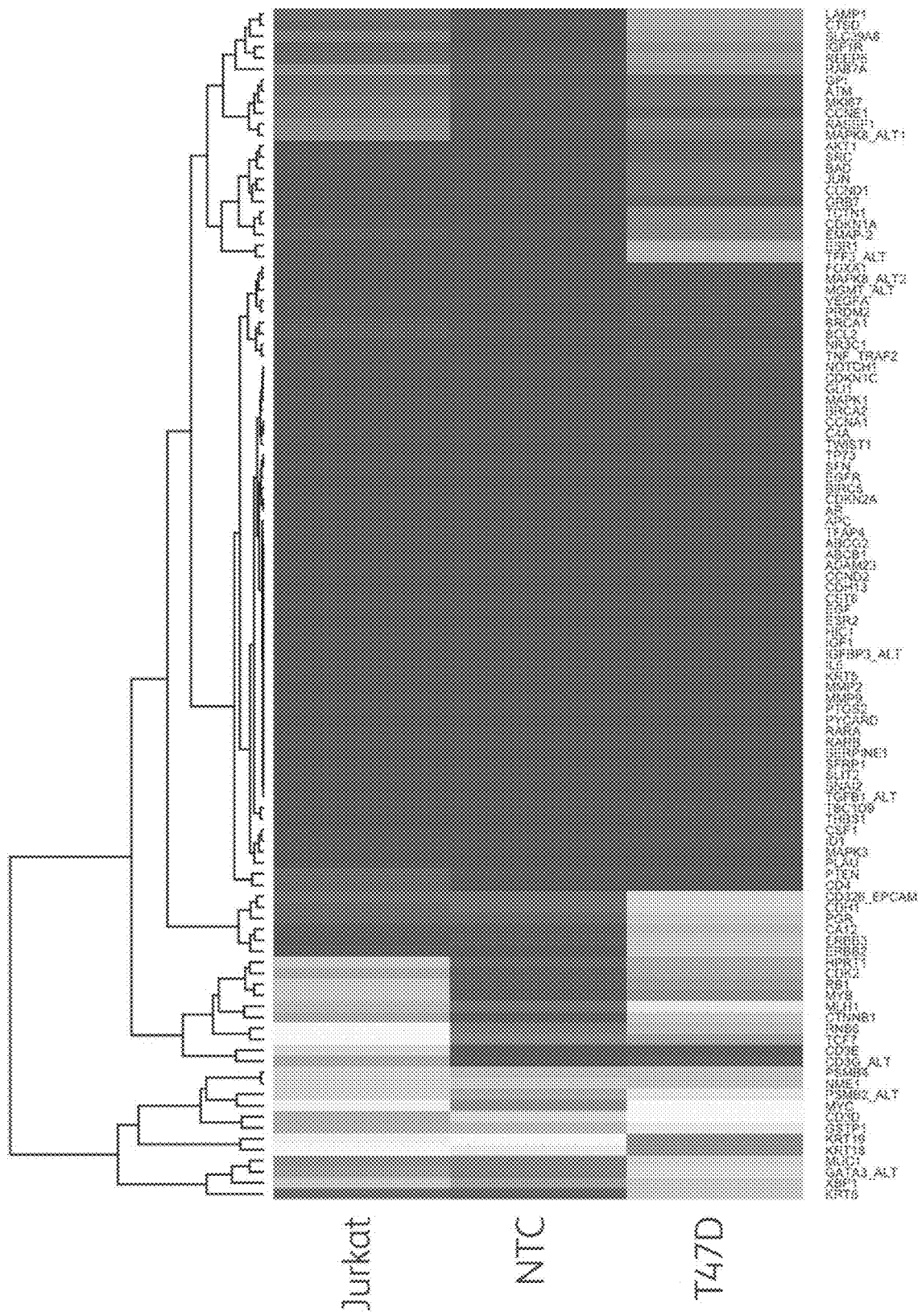
FIG. 42, panels (a)-(b) are non-limiting exemplary heat maps displaying differential gene expression by molecular label counts between different cell clusters identified in FIG. 41 before any error correction steps (Raw ML shown in FIG. 42, panel (a)) and after RSEC and DBEC correction (Adjusted ML shown in FIG. 42, panel (b)).
Figure 42:
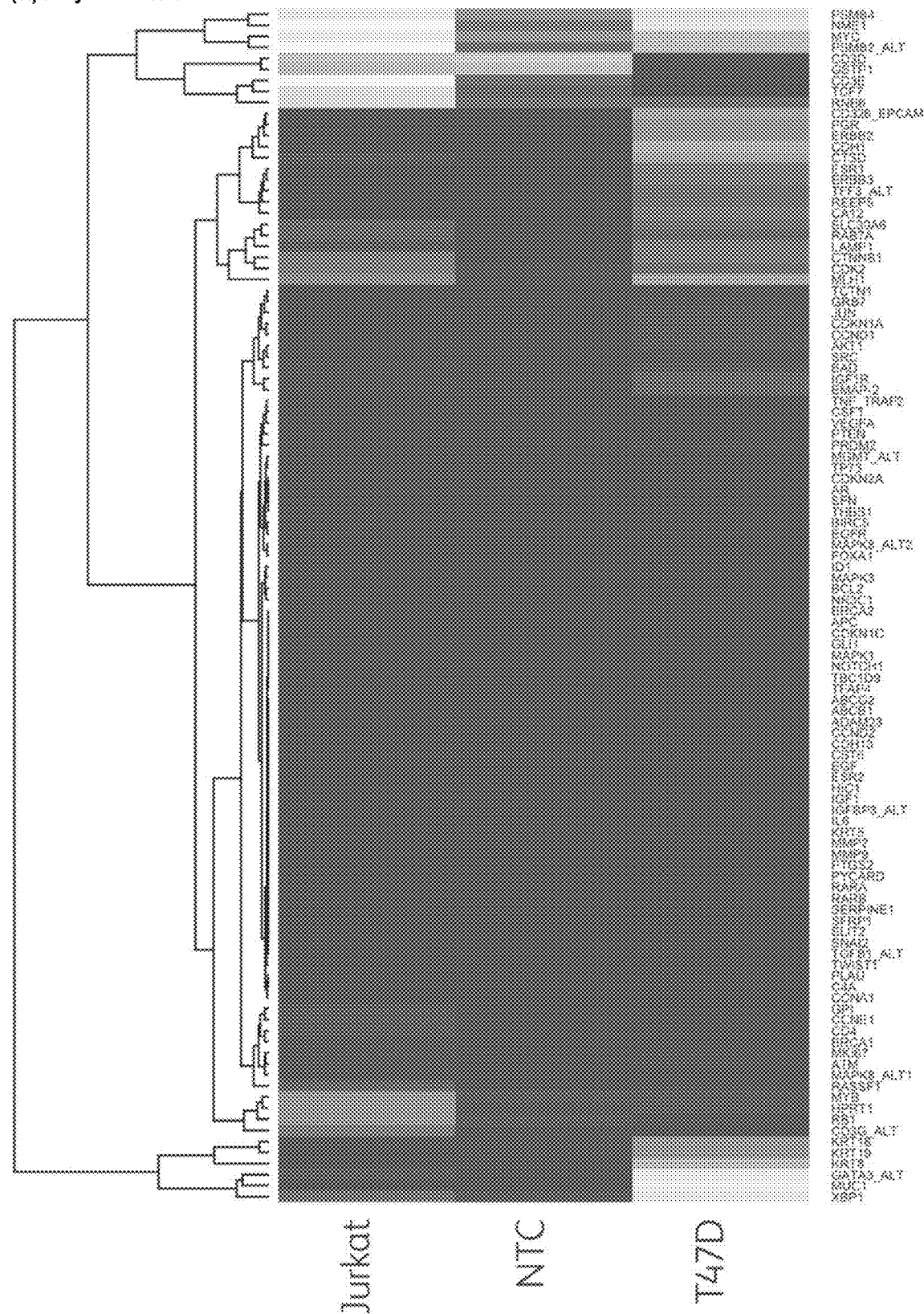

FIG. 42, panels (a)-(b) are non-limiting exemplary heat maps displaying differential gene expression by molecular label counts between different cell clusters identified in FIG. 41 before any error correction steps (Raw ML shown in FIG. 42, panel (a)) and after RSEC and DBEC correction (Adjusted ML shown in FIG. 42, panel (b)). Genes that were low in expression is in blue, and genes that are high in expression is orange. Genes that are similar in gene expression pattern between these cell types are clustered together. Without error correction, NTC had noise from high expressing genes such as CD3E and KRT18, which are Jurkat and T47D markers, respectively. Moreover, error correction revealed distinct gene expression patterns between Jurkat and T47D.

Altogether, these data demonstrate that ML adjustment can remove MI noise which allows for clear differentiation of gene expression between cell clusters.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of identifying cell types in a sample, comprising:
(a) for each cell of a plurality of cells in a sample, using a plurality of stochastic barcodes to stochastically barcode a plurality of nucleic acid targets and thereby generate a plurality of stochastically barcoded nucleic acid targets from RNA from the cell, wherein each stochastic barcode of the plurality of stochastic barcodes comprises a molecular label;
(b) obtaining sequencing data of the plurality of stochastically barcoded nucleic acid targets, wherein the sequencing data comprises one or more errors that inflate the number of molecular labels with distinct sequences associated with at least one of the plurality of nucleic acid targets;
(c) for one or more of the plurality of stochastically barcoded nucleic acid targets, correcting for the one or more errors in the sequencing data by:
   (i) counting the number of molecular labels with distinct sequences associated with the nucleic acid target in the sequencing data;
   (ii) identifying clusters of molecular labels of the nucleic acid target using directional adjacency, wherein the identifying comprises:
      determining, recursively for all molecular labels with distinct sequences, whether a child molecular label belongs to a cluster comprising one or more parent molecular labels, wherein the molecular labels of the nucleic acid target within the cluster comprise one or more parent molecular labels and children molecular labels of the one or more parent molecular labels, and wherein the occurrence of the parent molecular label is greater than or equal to twice the occurrence of a child molecular label less one;
   (iii) collapsing the sequencing data obtained in (b) using the clusters of molecular labels identified in (ii) by attributing the occurrence of the child molecular label to the parent molecular label, thereby reducing the number of molecular labels with distinct sequences associated with the at least one of the plurality of nucleic acid targets; and
   (iv) estimating the number of the nucleic acid target, wherein the estimated number correlates with the number of molecular labels with distinct sequences associated with the nucleic acid target in the sequencing data counted in (i) after collapsing the sequencing data in (iii);
(d) generating an RNA expression profile of each of the plurality of cells based on the number of the nucleic acid targets estimated in (c); and
(e) identifying a cell type of each of the plurality of cells based on the RNA expression profile by correlating the number of the nucleic acid target(s) estimated in (c) with the cell type.

2. The method of claim 1, wherein molecular labels of the nucleic acid target within a cluster are within a predetermined directional adjacency threshold of one another.

3. The method of claim 1, further comprising:
determining a sequencing depth of the nucleic acid target.

4. The method of claim 3, wherein estimating the number of the nucleic acid target comprises adjusting the sequencing data counted in (i), wherein the sequencing depth of the nucleic acid target is above a predetermined sequencing depth threshold.

5. The method of claim 4, wherein adjusting the sequencing data counted in (i) comprises:
thresholding molecular labels of the nucleic acid target to determine true molecular labels and false molecular labels associated with the nucleic acid target in the sequencing data obtained in (b).

6. The method of claim 5, wherein thresholding the molecular labels of the nucleic acid target comprises performing a statistical analysis on the molecular labels of the nucleic acid target.

7. The method of claim 6, wherein performing the statistical analysis comprises:
fitting the distribution of the molecular labels of the nucleic acid target and their occurrences to two negative binomial distributions;
determining the number of true molecular labels n using the two negative binomial distributions; and
removing the false molecular labels from the sequencing data obtained in (b), wherein the false molecular labels comprise molecular labels with occurrences lower than the occurrence of the nth most abundant molecular label, and wherein the true molecular labels comprise molecular labels with occurrences greater than or equal to the occurrence of the nth most abundant molecular label.

8. The method of claim 7, wherein the two negative binomial distributions comprise a first negative binomial distribution corresponding for the true molecular labels and a second negative binomial distribution for the false molecular labels.

9. The method of claim 1, wherein the plurality of stochastically barcoded nucleic acid targets are generated from mRNA, microRNA, or tRNA.

10. The method of claim 2, wherein the directional adjacency threshold is a Hamming distance of one.

11. The method of claim 1, wherein the plurality of stochastically barcoded nucleic acid targets comprises nucleic acid targets of the whole transcriptome of a cell.

12. A computer-implemented method of identifying cell types from sequencing data, comprising:
(a) obtaining sequencing data of a plurality of stochastically barcoded nucleic acid targets, wherein each stochastically barcoded nucleic acid target of the plurality of stochastically barcoded nucleic acid targets:

corresponds to an RNA target of a plurality of RNA targets of a cell of a plurality of cells in a sample; and comprises a stochastic barcode of a plurality of stochastic barcodes, wherein each stochastic barcode comprises a molecular label, wherein the sequencing data comprises one or more errors that inflate the number of molecular labels with distinct sequences associated with at least one of the plurality of nucleic acid targets;

(b) for one or more of the plurality of stochastically barcoded nucleic acid targets, correcting for the one or more errors in the sequencing data by:
  (i) counting the number of molecular labels with distinct sequences associated with the nucleic acid target in the sequencing data;
  (ii) identifying clusters of molecular labels of the nucleic acid target using directional adjacency, wherein the identifying comprises:
    determining, recursively for all molecular labels with distinct sequences, whether a child molecular label belongs to a cluster comprising one or more parent molecular labels, wherein the molecular labels of the target within the cluster comprise one or more parent molecular labels and children molecular labels of the one or more parent molecular labels, and wherein the occurrence of the parent molecular label is greater than or equal to twice the occurrence of a child molecular label less one;
  (iii) collapsing the sequencing data obtained in (b) using the clusters of molecular labels identified in (ii) by attributing the occurrence of the child molecular label to the parent molecular label, thereby reducing the number of molecular labels with distinct sequences associated with the at least one of the plurality of nucleic acid targets; and
  (iv) estimating the number of the nucleic acid target, wherein the estimated number correlates with the number of molecular labels with distinct sequences associated with the nucleic acid target in the sequencing data counted in (i) after collapsing the sequencing data in (iii);
(c) generating an RNA expression profile of each of the plurality of cells based on the number of the nucleic acid targets estimated in (b); and
(d) identifying a cell type of each of the plurality of cells based on the RNA expression profile by correlating the number of the nucleic acid target(s) estimated in (b) with the cell type.

13. A computer system for generating single-cell RNA expression profiles from sequencing data, comprising:
  a hardware processor; and
  non-transitory memory having instructions stored thereon, which when executed by the hardware processor cause the processor to perform the method of claim 12.

14. The method of claim 1, wherein the sequencing data comprises sequencing reads of the stochastically barcoded nucleic acid targets, and wherein all the sequencing reads are retained in (c).

15. The method of claim 12, wherein the sequencing data comprises sequencing reads of the stochastically barcoded nucleic acid targets, and wherein all the sequencing reads are retained in (b).

16. The method of claim 1, further comprising determining a sequencing depth of the nucleic acid target, wherein the sequencing depth of the nucleic acid target is above a predetermined sequencing depth threshold, and wherein estimating the number of the nucleic acid target comprises adjusting the sequencing data by:
  thresholding molecular labels of the nucleic acid target to determine true molecular labels and false molecular labels associated with the target in the sequencing data obtained in (b), wherein the thresholding comprises:
    fitting the distribution of the molecular labels of the nucleic acid target and their occurrences to two negative binomial distributions, wherein the two negative binomial distributions comprise a first negative binomial distribution corresponding for the true molecular labels and a second negative binomial distribution for the false molecular labels; and
    determining the number of true molecular labels n using the two negative binomial distributions; and
  removing the false molecular labels from the sequencing data, wherein the false molecular labels comprise molecular labels with occurrences lower than the occurrence of the nth most abundant molecular label, and wherein the true molecular labels comprise molecular labels with occurrences greater than or equal to the occurrence of the nth most abundant molecular label.

* * * * *